United States Patent
Takaku et al.

(10) Patent No.: US 9,653,686 B2
(45) Date of Patent: May 16, 2017

(54) ORGANIC FILM TRANSISTOR, ORGANIC SEMICONDUCTOR FILM, ORGANIC SEMICONDUCTOR MATERIAL AND APPLICATION OF THESE

(71) Applicant: FUJIFILM Corporation, Tokyo (JP)

(72) Inventors: Koji Takaku, Kanagawa (JP); Akihiro Kaneko, Kanagawa (JP); Hiroki Sugiura, Kanagawa (JP); Kensuke Masui, Kanagawa (JP); Yasunori Yonekuta, Kanagawa (JP); Yuki Hirai, Kanagawa (JP); Masashi Koyanagi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/993,371

(22) Filed: Jan. 12, 2016

(65) Prior Publication Data

US 2016/0126459 A1   May 5, 2016

Related U.S. Application Data

(63) Continuation of application No. PCT/JP2014/068797, filed on Jul. 15, 2014.

(30) Foreign Application Priority Data

| Jul. 19, 2013 | (JP) | ................................. | 2013-150768 |
| Jul. 19, 2013 | (JP) | ................................. | 2013-150769 |
| Feb. 18, 2014 | (JP) | ................................. | 2014-028173 |

(51) Int. Cl.
  *C08G 59/00*    (2006.01)
  *H01L 51/00*   (2006.01)
  (Continued)

(52) U.S. Cl.
  CPC ........ *H01L 51/0036* (2013.01); *C07C 49/697* (2013.01); *C08G 61/02* (2013.01);
  (Continued)

(58) Field of Classification Search
  CPC ......... C07C 17/12; C07C 25/02; C07C 45/46; C07C 49/697; C07C 49/665
  (Continued)

(56) References Cited

FOREIGN PATENT DOCUMENTS

| JP | 2010-535270 A | 11/2010 |
| JP | 2012-177104 A | 9/2012 |
| WO | 2009/017798 A1 | 2/2009 |

OTHER PUBLICATIONS

International Search Report and Written Opinion—PCT/JP2014/068797 mailed Aug. 26, 2014.
(Continued)

*Primary Examiner* — Shane Fang
(74) *Attorney, Agent, or Firm* — Studebaker & Brackett PC

(57) ABSTRACT

An organic film transistor containing a compound, which is composed of n repeating units represented by Formula (1-1), (1-2), or (101), in a semiconductor active layer is an organic film transistor using a compound that results in high carrier
(Continued)

mobility when being used in the semiconductor active layer of the organic film transistor and exhibits high solubility in an organic solvent;

Formula (1-1)

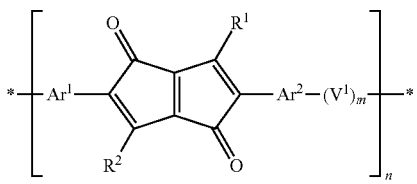

Formula (1-2)

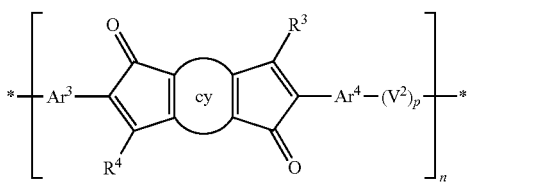

Formula (101)

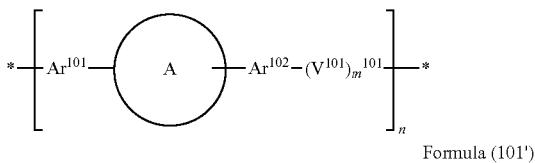

Formula (101')

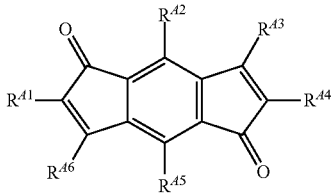

(Each of $R^1$ $R^2$ represents a hydrogen atom or a substituent; each of $Ar^1$ and $Ar^2$ independently represents a heteroarylene group or an arylene group; $V^1$ represents a divalent linking group; m represents an integer of 0 to 6; cy represents a naphthalene ring or an anthracene ring; each of $R^3$ and $R^4$ represents a hydrogen atom or a substituent; each of $Ar^3$ and $Ar^4$ represents a heterocyclic aromatic ring or an aromatic ring; $V^2$ represents a divalent linking group; p represents an integer of 0 to 6; n represents an integer of equal to or greater than 2; A is a divalent linking group represented by Formula (101'); each of $R^{41}$ to $R^{46}$ represents a hydrogen atom, a substituent, or a direct bond with $Ar^{101}$ or $Ar^{102}$ in Formula (101); and among the groups represented by $R^{41}$ to $R^{46}$, two different groups are direct bonds with $Ar^{101}$ and $Ar^{102}$ in Formula (101) respectively.)

47 Claims, 1 Drawing Sheet

(51) Int. Cl.
  *C08G 61/12* (2006.01)
  *C07C 49/697* (2006.01)
  *C08G 61/02* (2006.01)
  *H01L 51/05* (2006.01)

(52) U.S. Cl.
  CPC ........... *C08G 61/12* (2013.01); *C08G 61/126* (2013.01); *H01L 51/0043* (2013.01); *C07C 2103/10* (2013.01); *C08G 2261/148* (2013.01); *C08G 2261/149* (2013.01); *C08G 2261/1412* (2013.01); *C08G 2261/18* (2013.01); *C08G 2261/314* (2013.01); *C08G 2261/3142* (2013.01); *C08G 2261/3223* (2013.01); *C08G 2261/3241* (2013.01); *C08G 2261/3242* (2013.01); *C08G 2261/332* (2013.01); *C08G 2261/3325* (2013.01); *C08G 2261/342* (2013.01); *C08G 2261/344* (2013.01); *C08G 2261/364* (2013.01); *C08G 2261/414* (2013.01); *C08G 2261/92* (2013.01); *H01L 51/0007* (2013.01); *H01L 51/0545* (2013.01); *H01L 51/0558* (2013.01)

(58) Field of Classification Search
  USPC ......................................................... 528/403
  See application file for complete search history.

(56) References Cited

OTHER PUBLICATIONS

Yavari et al., "An ab initio molecular orbital study of quinones of pentalene", Journal of Molecular Structure (THEOCHEM), 2002, 589-590, pp. 459-464.
Communication pursuant to Rules 164(1) EPC issued by the European Patent Office on Jul. 5, 2016, which corresponds to European Patent Application No. 14827004.4-1302 and is related to U.S. Appl. No. 14/993,371.
Chunchang Zhao et al.; "4,9-Dihydro-s-indaceno[1,2-b:5,6-b']dithiophene-4, 9-dione Functionalized Copolymers for Organic Photovoltaic Devices"; Journal of Polymer Science: Part A: Polymer Chemistry; 2008, pp. 2680-2688; John Wiley & Sons, Inc. XP-002550805; Wiley InterScience (www.interscience.wiley.com).
Hakan Usta et al.; "Design, Synthesis, and Characterization of Ladder-Type Molecules and Polymers. Air-Stable, Solution-Processable n-Channel and Ambipolar Semiconductors for Thin-Film Transistors via Experiment and Theory"; Journal of the American Chemical Society; 2009; pp. 5586-5608; vol. 131; No. 15; American Chemical Society.
F.Kehrer et al.; "230. IR.-spektroskopische Untersuchungen in der Chinophtalon-Reihe"; Helvetica Chimica Acta; 1969; pp. 2200-2211; vol. 50; No. 8.
F.Kehrer et al.; "230. IR.-spektroskopische Untersuchungen in der Chinophtalon-Reihe"; Helvetica Chimica Acta; 1969; pp. 2200-2211; vol. 50; No. 8; with English language summary.
Translation of International Preliminary Report on Patentability in Corresponding Application No. PCT/JP2014/068797 mailed Jan. 28, 2016.
The extended European search report issued by the European Patent Office on Nov. 8, 2016, which corresponds to European Patent Application No. 14827004.4-1302 and is related to U.S. Appl. No. 14/993,371.
Mahboubeh Rostami et al.; "A simple conversion of azlactones into indenones via H3PW12O40/Al2O3 catalyzed intramolecular Friedel-Crafts reaction"; Tetrahedron Letters; Oct. 28, 2011; pp. 7149-7152; vol. 52; No. 52; Elsevier.
Xinhong Gu et al.; "Iodine-Induced Transannular Coupling of 1,6-Cyclodecadiyne"; Tetrahedron Letters; Mar. 4, 1966; pp. 1571-1574; vol. 37; No. 10; Pergamon; GB.
Bradley D. Rose et al.; "Synthesis, Crystal Structures, and Photophysical Properties of Electron-Accepting Diethynylindenofluorenediones"; Organic Letters; Apr. 15, 2011; pp. 2106-2109; vol. 13; No. 8; American Chemical Society.

(56) References Cited

OTHER PUBLICATIONS

Yasuo Miyata et al.; "Synthesis of fluorinated anti-fluorenacenedione and the structural, electronic, and field-effect properties"; Organic & Biomolecular Chemistry; Jan. 1, 2007; pp. 2592-2598; vol. 5; No. 16; The Royal Socierty of Chemistry.
An Office Action; "Notification of Reasons for Refusal," issued by the Japanese Patent Office on Dec. 20, 2016, which corresponds to Japanese Patent Application No. 2014-028173 and is related to U.S. Appl. No. 14/993,371; with English language translation.

US 9,653,686 B2

ORGANIC FILM TRANSISTOR, ORGANIC SEMICONDUCTOR FILM, ORGANIC SEMICONDUCTOR MATERIAL AND APPLICATION OF THESE

CROSS-REFERENCE TO RELATED APPLICATIONS

This application is a Continuation of PCT International Application No. PCT/JP2014/068797, filed on Jul. 15, 2014, which claims priority under 35 U.S.C. Section 119(a) to Japanese Patent Application No. 2013-150768 filed on Jul. 19, 2013, Japanese Patent Application No. 2013-150769 filed on Jul. 19, 2013 and Japanese Patent Application No. 2014-028173 filed on Feb. 18, 2014. Each of the above applications is hereby expressly incorporated by reference, in its entirety, into the present application.

BACKGROUND OF THE INVENTION

1. Field of the Invention

The present invention relates to an organic film transistor, an organic semiconductor film, an organic semiconductor material, and the like. Specifically, the present invention relates to a compound having a repeating unit composed of a linking group which can form a hydrogen bond with at least two cyclopentadienone ring-condensed structures, an organic film transistor containing the compound, a composition containing the compound, an organic semiconductor material for a non-light-emitting organic semiconductor device containing the compound, a material for an organic film transistor containing the compound, a coating solution for a non-light-emitting organic semiconductor device containing the compound, and an organic semiconductor film for a non-light-emitting organic semiconductor device containing the compound.

2. Description of the Related Art

The devices using an organic semiconductor material are drawing great attention because they are expected to be superior to devices using a conventional inorganic semiconductor material such as silicon in many ways. Examples of the devices using an organic semiconductor material include a photoelectric conversion element, such as an organic film solar cell or a solid-state imaging element using an organic semiconductor material as a photoelectric conversion material, and a non-light-emitting organic transistor. The devices using an organic semiconductor material are likely to make it possible to prepare a large-area element at a lower temperature and lower cost compared to the devices using an inorganic semiconductor material. Furthermore, because the characteristics of the material can be easily changed by varying the molecular structure thereof, the material shows high variation, and it is possible to realize functions or elements which cannot be obtained from the inorganic semiconductor material.

For example, JP2012-177104A describes a polycyclic ring-condensed polymer in which a 5-membered ring is condensed on a terminal of linear polyacene. The document describes that by using the polymer in an organic light-emitting element, high charge transporting properties and solvent solubility can be realized.

Furthermore, THEOCHEM, (2002), 589-590, 459-464 describes that as a result of calculating molecular orbitals of various isomers of pentalenedione which is a low-molecular weight compound, a 1,5-dione isomer is found to be the most stable.

In addition, JP2010-535270A describes a semiconductor material having an indacenedione skeleton. The document describes that the semiconductor material exhibits bipolar semiconductor activity, high solvent treatability, and high atmospheric stability.

SUMMARY OF THE INVENTION

JP2012-177104A describes a polycyclic ring-condensed polymer in which a 5-membered ring is condensed on a terminal of linear polyacene. The polycyclic ring-condensed polymer, in which a 5-membered ring is condensed on a terminal of linear polyacene as described in JP2012-177104A, does not interact with the ring linked thereto, and thus the planarity is reduced. Therefore, the overlapping of HOMO does not sufficiently occur, and sufficient transistor characteristics (low carrier mobility) are not obtained. Actually, the inventors of the present invention manufactured an organic film transistor element having a bottom gate•bottom contact structure by using the polycyclic ring-condensed polymer described in Examples of JP2012-177104A. As a result, the obtained transistor characteristics were about $10^{-3}$, so the inventors found that the carrier mobility is low.

Although THEOCHEM, (2002), 589-590, 459-464 describes a low-molecular weight compound having condensed cyclopentadienone rings, the document does not disclose an example in which the low-molecular weight compound is used in an organic transistor. In addition, the inventors of the present invention used the low-molecular weight compound described in the same document, but sufficient transistor characteristics (low carrier mobility) were not obtained.

JP2010-535270A describes a semiconductor material having an indacenedione skeleton. In the semiconductor material having an indacenedione skeleton as described in the document, thiophene or bithiophene is used as a linking group, and thus the conjugation length is short. Accordingly, sufficient solubility and low HOMO are not obtained. The inventors of the present invention found that as a result, the semiconductor material described in the document has low hole mobility such as $10^{-5}$ $cm^2/Vs$ to $10^{-3}$ $cm^2/Vs$.

In order to solve the problems of the related art, the inventors of the present invention conducted an investigation. An object of the present invention is to provide a compound, which results in high carrier mobility when being used in a semiconductor active layer of an organic film transistor and exhibits high solubility in an organic solvent, and an organic film transistor which uses the compound.

In order to achieve the aforementioned object, the inventors of the present invention conducted an intensive investigation. As a result, they obtained the following knowledge. Due to the structure of the repeating unit, which is formed by introducing a heteroarylene group or an arylene group as a linking group into a position adjacent to a carbonyl group on two cyclopentadienone ring-condensed structures or two cyclopentadienone ring-condensed structures condensed on a terminal of polyacene, an intramolecular hydrogen bond is formed between the carbonyl group of the cyclopentadienone ring-condensed structures and an atom of a ring of the heteroarylene group or the arylene group adjacent to the carbonyl group, and thus the planarity is increased. Consequently, the overlapping of HOMO sufficiently occurs, and the carrier mobility increases. The inventors also obtained the following knowledge. Generally, a compound having high planarity and high carrier mobility is known to have low solubility, but the aforementioned compound exhibits unexpectedly high solubility in a solvent, and accordingly, high carrier mobility and high solubility can be achieved simultaneously. Based on the above knowledge, the inventors accomplished the present invention.

The present invention which is specific means for achieving the aforementioned object is constituted as below.

[1] An organic film transistor containing a compound, which is composed of n repeating units represented by the following Formula (1-1), (1-2), or (101), in a semiconductor active layer.

Formula (1-1)

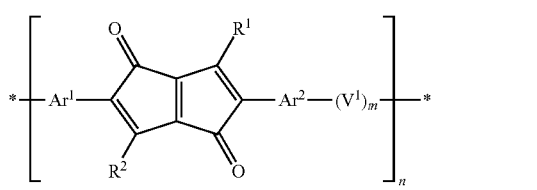

In Formula (1-1), each of $R^1$ and $R^2$ independently represents a hydrogen atom or a substituent; each of $Ar^1$ and $Ar^2$ independently represents a heteroarylene group or an arylene group; $V^1$ represents a divalent linking group; m represents an integer of 0 to 6; when m is equal to or greater than 2, two or more groups represented by $V^1$ may be the same as or different from each other; and n represents an integer of equal to or greater than 2;

Formula (1-2)

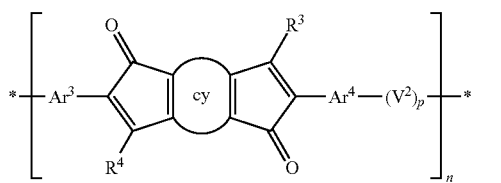

in Formula (1-2), cy represents a naphthalene ring or an anthracene ring; each of $R^3$ and $R^4$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2;

Formula (101)

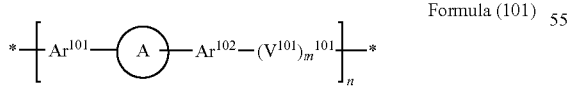

in Formula (101), each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; n represents an integer of equal to or greater than 2; and A represents a divalent linking group represented by the following Formula (101'); and Formula (101')

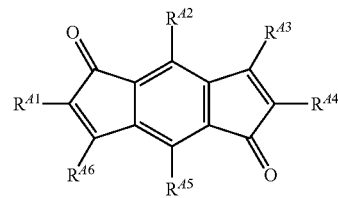

in Formula (101'), each of $R^{A1}$ to $R^{A6}$ independently represents a hydrogen atom, a substituent, or a direct bond with $Ar^{101}$ or $Ar^{102}$ in Formula (101); and among the groups represented by $R^{A1}$ to $R^{A6}$, two different groups represent direct bonds with $Ar^{101}$ and $Ar^{102}$ in Formula (101) respectively.

[2] The organic film transistor described in [1], in which the compound composed of n repeating units represented by the following Formula (1-1) or (1-2) is preferably contained in the semiconductor active layer.

Formula (1-1)

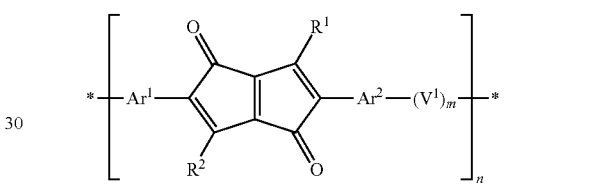

(In Formula (1-1), each of $R^1$ and $R^2$ independently represents a hydrogen atom or a substituent; each of $Ar^1$ and $Ar^2$ independently represents a heteroarylene group or an arylene group; $V^1$ represents a divalent linking group; m represents an integer of 0 to 6; when m is equal to or greater than 2, two or more groups represented by $V^1$ may be the same as or different from each other; and n represents an integer of equal to or greater than 2.)

Formula (1-2)

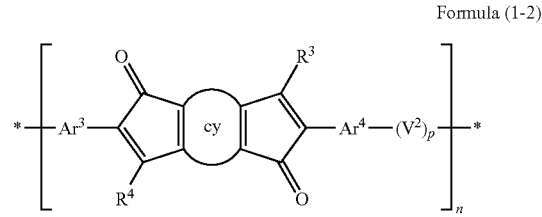

(In Formula (1-2), cy represents a naphthalene ring or an anthracene ring; each of $R^3$ and $R^4$ independently represents a hydrogen atom or a substituent; each of Ara and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2.)

[3] The organic film transistor described in [1] or [2], in which Formula (1-2) represents a compound composed of n repeating units represented by the following Formula (2-1), (2-2), (2-3), (2-4), or (2-5).

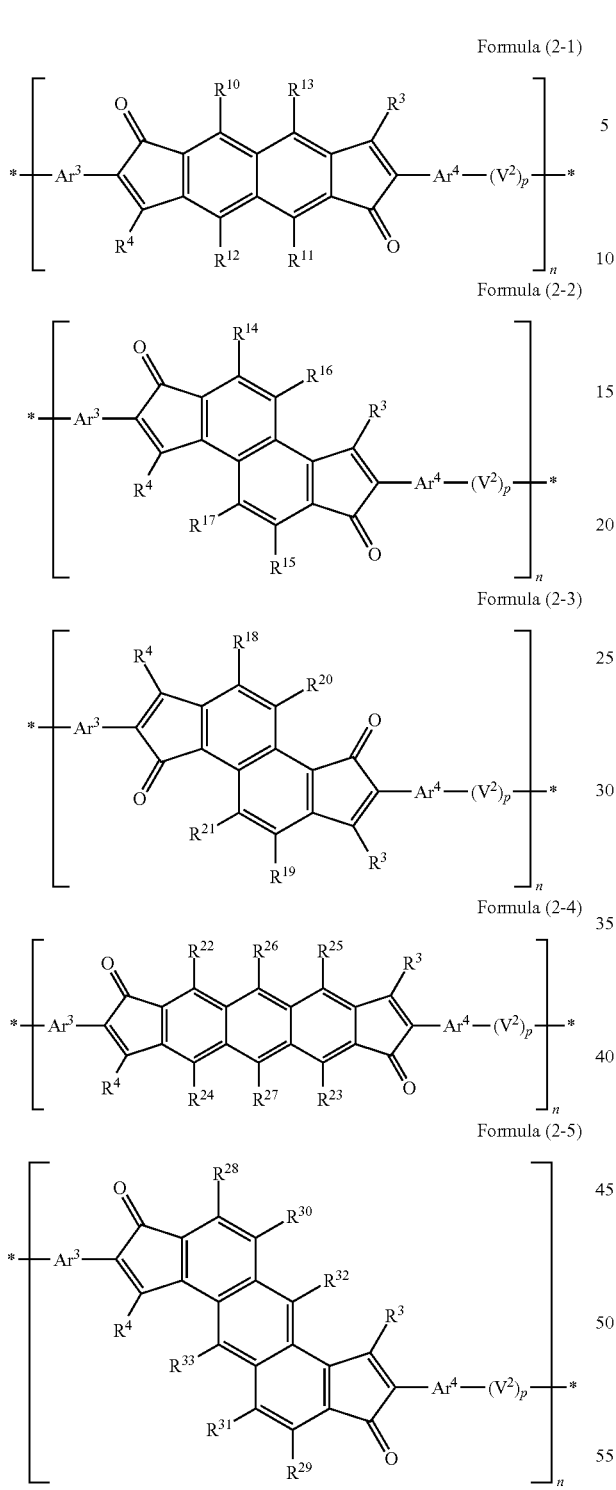

(In Formulae (2-1) to (2-5), each of $R^3$, $R^4$, and $R^{10}$ to $R^{33}$ independently represents a hydrogen atom or a substituent; each of Ara and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2.)

[4] The organic film transistor described in any one of [1] to [3], in which in Formulae (1-1), (1-2), and (2-1) to (2-5), each of $V^1$ and $V^2$ is independently a divalent linking group represented by any of the following Formulae (V-1) to (V-17).

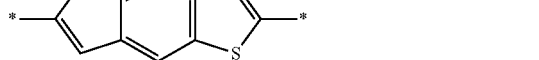

-continued

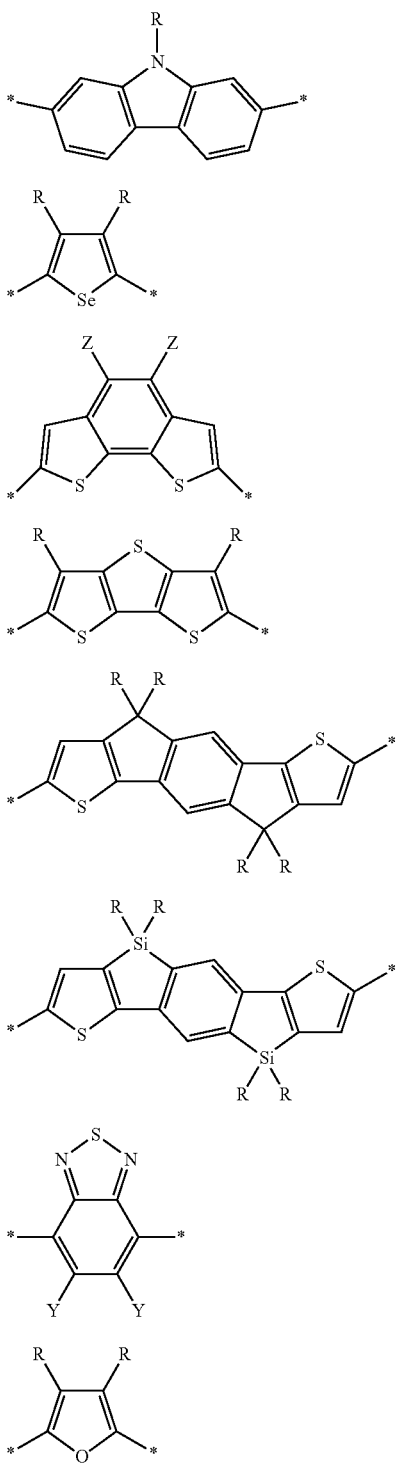

(In Formulae (V-1) to (V-17), * represents a position where the divalent linking group is bonded to any of $Ar^1$ to $Ar^4$ when p is 1, and represents a position where the divalent linking group is bonded to any of $Ar^1$ to $Ar^4$ and the divalent linking groups represented by Formulae (V-1) to (V-17) when m or p is equal to or greater than 2; each R in Formulae (V-1), (V-2), (V-5), (V-6), (V-9) to (V-11), (V-13) to (V-15), and (V-17) independently represents a hydrogen atom or an alkyl group; the groups adjacent to each other represented by R may form a ring by being bonded to each other; each Z in Formulae (V-4), (V-7), (V-8), and (V-12) independently represents a hydrogen atom, an alkyl group, or an alkoxy group; the groups adjacent to each other represented by Z may form a ring by being bonded to each other; each Y in Formula (V-16) independently represents a hydrogen atom, an alkyl group, an alkoxy group, a CN group, or a F atom; and the groups adjacent to each other represented by Y may form a ring by being bonded to each other.)

[5] The organic film transistor described in [4], in which in Formulae (1-1), (1-2), and (2-1) to (2-5), each of $V^1$ and $V^2$ is a divalent linking group represented by any of Formulae (V-1) to (V-8) and (V-11) to (V-15).

[6] The organic film transistor described in any one of [1] to [5], in which in Formulae (1-1), (1-2), and (2-1) to (2-5), each of $Ar^1$ to $Ar^4$ is independently a divalent linking group represented by the following Formula (4-1), (4-2), or (4-3).

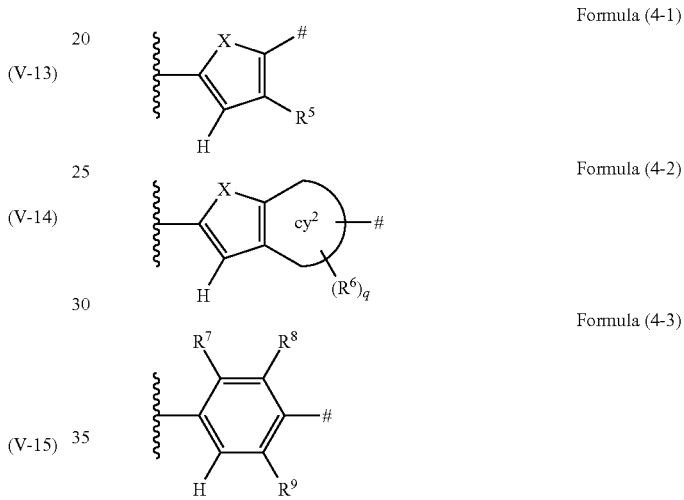

(In Formulae (4-1) to (4-3), X represents a S atom, an O atom, or a Se atom; $cy^2$ represents a structure in which 1 to 4 rings are condensed; each of $R^5$ to $R^9$ independently represents a hydrogen atom or a substituent; q represents an integer of 0 to 6; when q is equal to or greater than 2, two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^1$ or $V^2$.)

[7] The organic film transistor described in [6], in which in Formulae (1-1), (1-2), and (2-1) to (2-5), each of $Ar^1$ to $Ar^4$ is independently a divalent linking group represented by Formula (4-1) or (4-2).

[8] The organic film transistor described in [6] or [7], in which the divalent linking group represented by Formula (4-2) is a divalent linking group represented by any of the following Formulae (5-1) to (5-8).

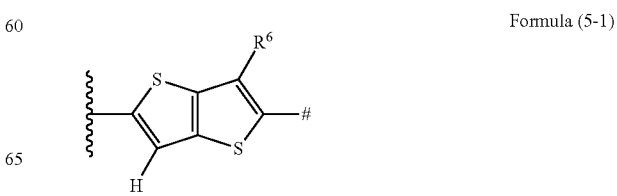

-continued

Formula (5-2)
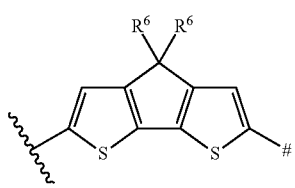

Formula (5-3)
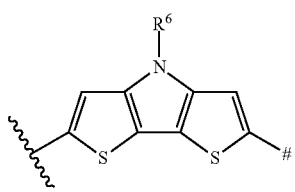

Formula (5-4)
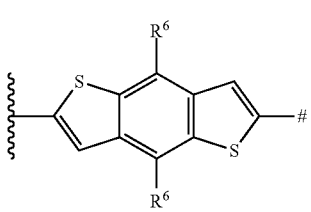

Formula (5-5)
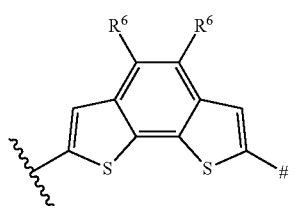

Formula (5-6)
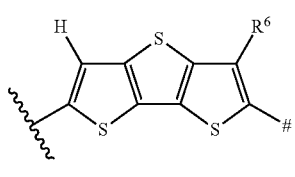

Formula (5-7)
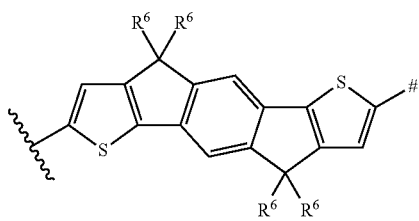

Formula (5-8)
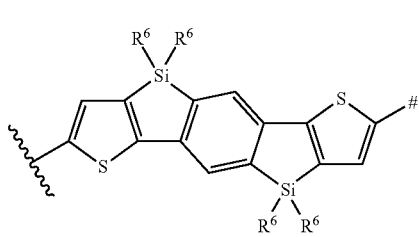

(In Formulae (5-1) to (5-8), each $R^6$ independently represents a hydrogen atom or a substituent; two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^1$ or $V^2$.)

[9] The organic film transistor described in any one of [1] to [8], in which each of at least one of $R^1$ and $R^2$ in Formula (1-1), at least one of $R^3$ and $R^4$ in Formula (1-2), at least one of $R^3$, $R^4$, $R^{10}$, $R^{11}$, $R^{12}$, and $R^{13}$ in Formula (2-1), at least one of $R^3$, $R^4$, $R^{14}$, $R^{15}$, $R^{16}$, and $R^{17}$ in Formula (2-2), at least one of $R^3$, $R^4$, $R^{18}$, $R^{19}$, $R^{20}$, and $R^{21}$ in Formula (2-3), at least one of $R^3$, $R^4$, $R^{22}$, $R^{23}$, $R^{24}$, $R^{25}$, $R^{26}$, and $R^{27}$ in Formula (2-4), and at least one of $R^3$, $R^4$, $R^{28}$, $R^{29}$, $R^{30}$, $R^{31}$, $R^{32}$, and $R^{33}$ in Formula (2-5) is a group represented by the following Formula (W).

-L-R    Formula (W)

(In Formula (W), L represents a divalent linking group represented by any of the following Formulae (L-1) to (L-12) or a divalent linking group formed by bonding of two or more divalent linking groups represented by any of the following Formulae (L-1) to (L-12); R represents a substituted or unsubstituted alkyl group, an oligo-oxyethylene group in which a repetition number v of an oxyethylene unit is equal to or greater than 2, an oligosiloxane group having two or more silicon atoms, or a substituted or unsubstituted silyl group; and R represents a substituted or unsubstituted silyl group only when L adjacent to R is a divalent linking group represented by any of the following Formulae (L-1) to (L-3).)

(L-1)

(L-2)

(L-3)

(L-4)

(L-5)

(L-6)

(L-7)

(L-8)

-continued

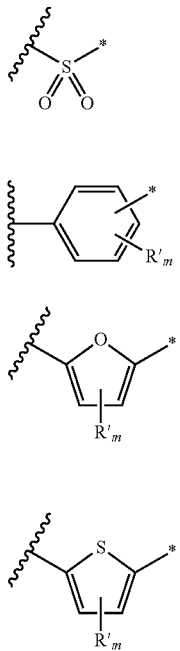

(In Formulae (L-1) to (L-12), the portion of a wavy line represents a position where the divalent linking group is bonded to a cyclopentadienone skeleton; * represents a position where the divalent linking group is bonded to any of the divalent linking groups represented by (L-1) to (L-12) and R; m in Formula (L-10) is 4; m in Formulae (L-11) and (L-12) is 2; and each R' in Formulae (L-1), (L-2), (L-10), (L-11), and (L-12) independently represents a hydrogen atom or a substituent.)

[10] The organic film transistor described in [9], in which in Formula (W), L is a divalent linking group represented by any of Formulae (L-1), (L-4), and (L-8) or a divalent linking group formed by bonding of two or more divalent linking groups described above.

[11] The organic film transistor described in any one of [1] to [10], in which in Formulae (1-1), (1-2), and (2-1) to (2-5), n is equal to or greater than 10.

[12] The organic film transistor described in [1], containing a compound, which is composed of n repeating units represented by the following Formula (101), in the semiconductor active layer;

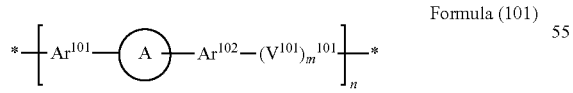

Formula (101)

in Formula (101), each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; n represents an integer of equal to or greater than 2; and A represents a divalent linking group represented by the following Formula (101'); and

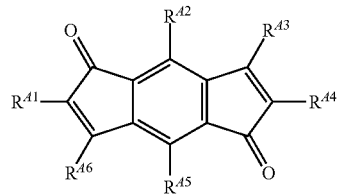

Formula (101')

in Formula (101'), each of $R^{A1}$ to $R^{A6}$ independently represents a hydrogen atom, a substituent, or a direct bond with $Ar^{101}$ or $Ar^{102}$ in Formula (101); and among the groups represented by $R^{A1}$ to $R^{A6}$, two different groups represent direct bonds with $Ar^{101}$ and $Ar^{102}$ in Formula (101) respectively.

[13] The organic film transistor described in [1] or [12], in which the compound composed of n repeating units represented by Formula (101) is a compound composed of n repeating units represented by any of the following Formulae (101-1) to (101-3);

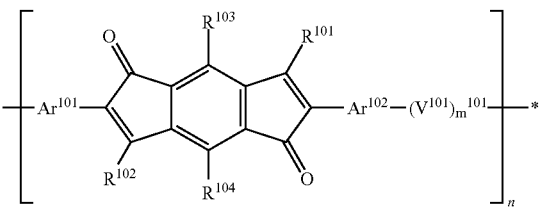

Formula (101-1)

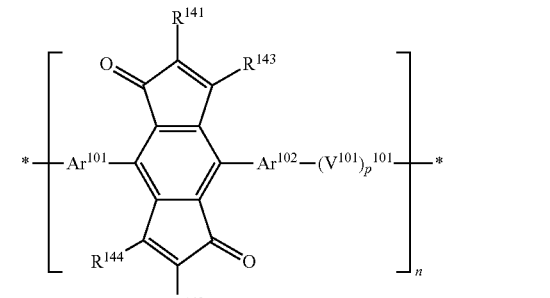

Formula (101-2)

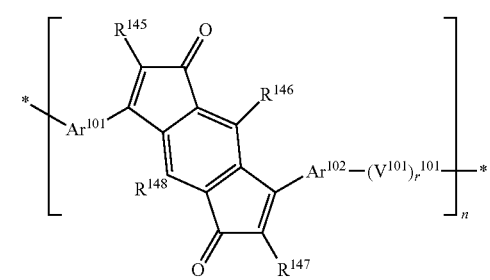

Formula (101-3)

in Formulae (101-1), (101-2), and (101-3), each of $R^{101}$ to $R^{104}$ and $R^{141}$ to $R^{148}$ independently represents a hydrogen atom or a substituent; each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; each of $p^{101}$ and $r^{101}$ represents an integer of 0 to 6; when each of $p^{101}$ and $r^{101}$ is equal to or greater than 2, two or more groups represented by $V^{101}$ may be the same as or different from each other; and n represents an integer of equal to or greater than 2.

[14] The organic film transistor described in any one of [1], [12], and [13], in which the compound composed of n repeating units represented by Formula (101) is a compound composed of n repeating units represented by the following Formula (101-1);

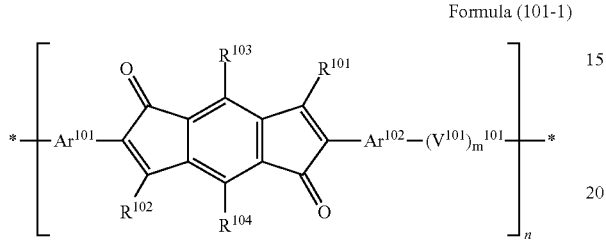

Formula (101-1)

in Formula (101-1), each of $R^{101}$ to $R^{104}$ independently represents a hydrogen atom or a substituent; each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; and n represents an integer of equal to or greater than 2.

[15] The organic film transistor described in [13] or [14], in which in Formulae (101-1) to (101-3), $V^{101}$ is a divalent linking group represented by any of the following Formulae (V-101) to (V-117);

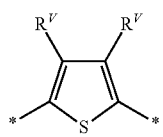
(V-101)

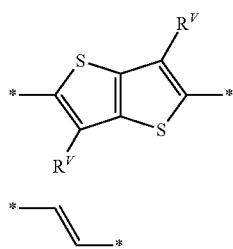
(V-102)

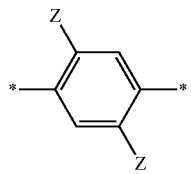
(V-103)

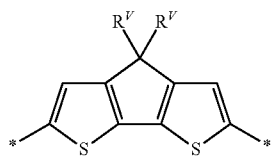
(V-104)

(V-105)

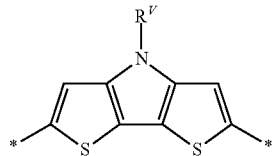
(V-106)

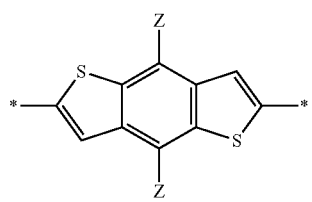
(V-107)

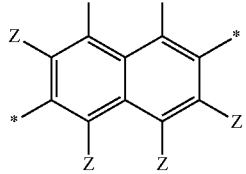
(V-108)

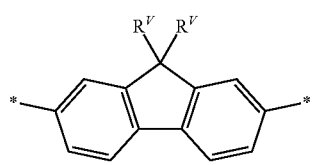
(V-109)

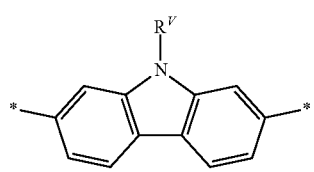
(V-110)

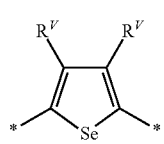
(V-111)

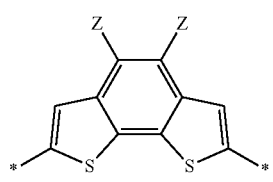
(V-112)

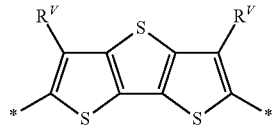
(V-113)

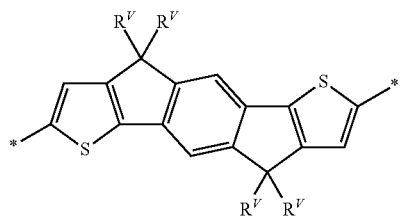
(V-114)

-continued

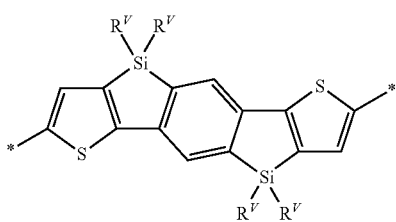
(V-115)

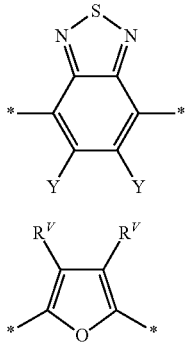
(V-116)

(V-117)

in Formulae (V-101) to (V-117), * represents a position where the divalent linking group is bonded to any of $Ar^{101}$ and $Ar^{102}$ when $m^{101}$, $p^{101}$, or $r^{101}$ is 1 and represents a position where the divalent linking group is bonded to any of $Ar^{101}$, $Ar^{102}$, and divalent linking groups represented by the following Formulae (V-101) to (V-117) when $m^{101}$, $p^{101}$, or $r^{101}$ is equal to or greater than 2; each $R^V$ in Formulae (V-101), (V-102), (V-105), (V-106), (V-109) to (V-111), (V-113) to (V-115), and (V-117) independently represents a hydrogen atom or an alkyl group; the groups adjacent to each other represented by $R^V$ may form a ring by being bonded to each other; Z in Formulae (V-104), (V-107), (V-108), and (V-112) independently represents a hydrogen atom, an alkyl group, or an alkoxy group; the groups adjacent to each other represented by Z may form a ring by being bonded to each other; each Y in Formula (V-116) independently represents a hydrogen atom, an alkyl group, an alkoxy group, a CN group, or a F atom; and the groups adjacent to each other represented by Y may form a ring by being bonded to each other.

[16] The organic film transistor described in [15], in which in Formulae (101-1) to (101-3), $V^{101}$ is a divalent linking group represented by any of Formulae (V-101) to (V-108) and (V-111) to (V-115).

[17] The organic film transistor described in any one of [13] to [16], in which in Formulae (101-1) to (101-3), each of $Ar^{101}$ and $Ar^{102}$ is a divalent linking group represented by the following Formula (102-1), (102-2), or (102-3);

Formula (102-1)

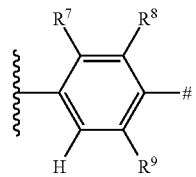

Formula (102-2)

Formula (102-3)

in Formulae (102-1) to (102-3), X represents a S atom, an O atom, or a Se atom; $cy^2$ represents a structure in which 1 to 4 rings are condensed; each of $R^5$ to $R^9$ independently represents a hydrogen atom or a substituent; q represents an integer of 0 to 6; when q is equal to or greater than 2, two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^{101}$.

[18] The organic film transistor described in [17], in which in Formula (101-1), each of $Ar^{101}$ and $Ar^{102}$ is a divalent linking group represented by Formula (102-1), and $V^{101}$ is a divalent linking group represented by any of Formulae (V-102) to (V-107).

[19] The organic film transistor described in [17], in which in Formulae (101-1) to (101-3), each of $Ar^{101}$ and $Ar^{102}$ is independently a divalent linking group represented by Formula (102-1) or (102-2).

[20] The organic film transistor described in [17] or [19], in which the divalent linking group represented by Formula (102-2) is a divalent linking group represented by any of the following Formulae (5-1) to (5-8);

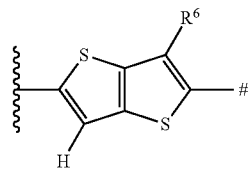
Formula (5-1)

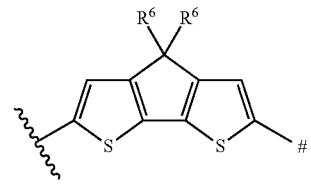
Formula (5-2)

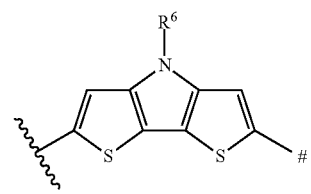
Formula (5-3)

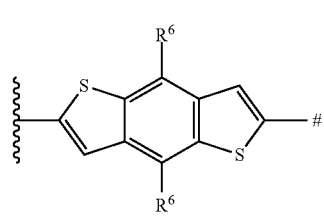
Formula (5-4)

Formula (5-5)
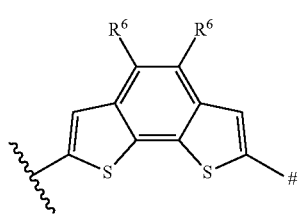

Formula (5-6)
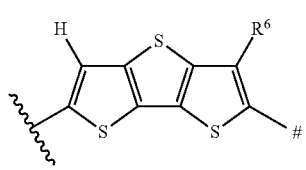

Formula (5-7)
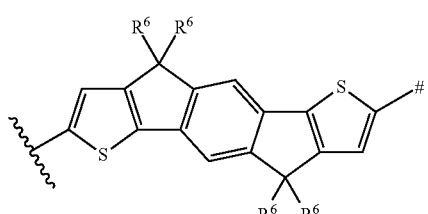

Formula (5-8)
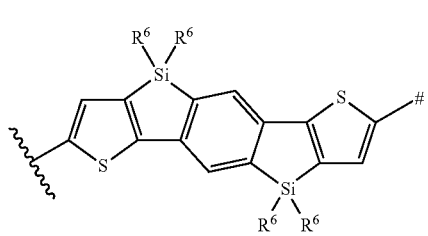

in Formulae (5-1) to (5-8), each $R^6$ independently represents a hydrogen atom or a substituent; two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^{101}$.

[21] The organic film transistor described in any one of [13] to [20], in which at least one of $R^{101}$, $R^{102}$, $R^{103}$, and $R^{104}$ in Formulae (101-1) to (101-3), at least one of $R^{141}$, $R^{142}$, $R^{143}$, and $R^{144}$ in the same formulae, or at least one of $R^{145}$, $R^{146}$, $R^{147}$, and $R^{148}$ in the same formulae is a group represented by the following Formula ($W^{101}$);

-$L^{101}$-$R^{101}$      Formula ($W^{101}$)

in Formula ($W^{101}$), $L^{101}$ represents a divalent linking group represented by any of the following Formulae (L-101) to (L-125) or a divalent linking group formed by bonding of two or more divalent linking groups represented by any of the following Formulae (L-101) to (L-125); $R^{101}$ represents a substituted or unsubstituted alkyl group, an oligo-oxyethylene group in which a repetition number v of an oxyethylene unit is equal to or greater than 2, an oligosiloxane group having two or more silicon atoms, or a substituted or unsubstituted silyl group; and $R^{101}$ represents a substituted or unsubstituted silyl group only when $L^{101}$ adjacent to $R^{101}$ is a divalent linking group represented by any of the following Formulae (L-101) to (L-103);

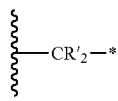 (L-101)

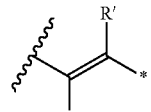 (L-102)

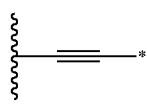 (L-103)

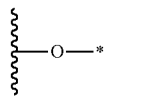 (L-104)

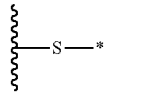 (L-105)

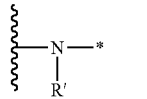 (L-106)

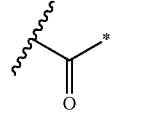 (L-107)

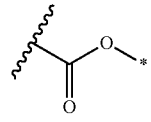 (L-108)

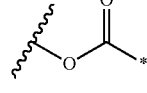 (L-109)

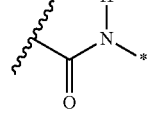 (L-110)

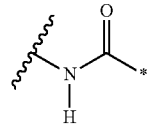 (L-111)

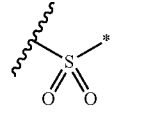 (L-112)

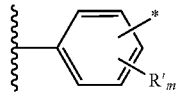 (L-113)

-continued (L-114) 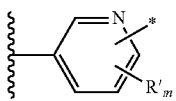

(L-115) 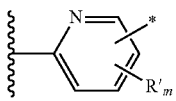

(L-116) 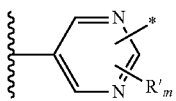

(L-117) 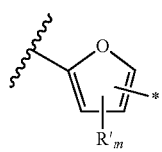

(L-118) 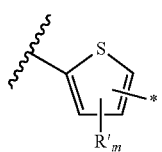

(L-119) 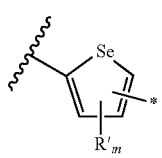

(L-120) 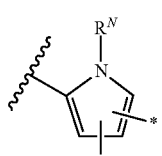

(L-121) 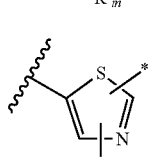

(L-122) 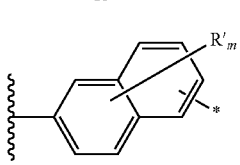

(L-123) 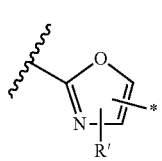

(L-124) 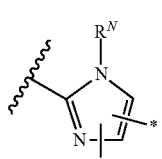

(L-125) 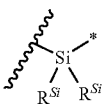

in Formulae (L-101) to (L-125), the portion of a wavy line represents a position where the divalent linking group is bonded to a cyclopentadienone skeleton; * represents a position where the divalent linking group is bonded to any of divalent linking groups represented by (L-101) to (L-125) and $R^{101}$; m in Formula (L-113) is 4; m in Formulae (L-114) and (L-115) is 3; m in Formulae (L-116) to (L-120) is 2; m in Formula (L-122) is 6; each R' in Formulae (L-101), (L-102), (L-106), and (L-113) to (L-124) independently represents a hydrogen atom or a substituent; $R^N$ represents a hydrogen atom or a substituent; and each $R^{si}$ independently represents a hydrogen atom, an alkyl group, an alkenyl group, or an alkynyl group.

[22] The organic film transistor described in [21], in which in Formula ($W^{101}$), $L^{101}$ is a divalent linking group represented by any of Formulae (L-101), (L-104), and (L-109) or a divalent linking group formed by bonding of two or more divalent linking groups described above.

[23] The organic film transistor described in any one of [1] and [12] to [22], in which the weight average molecular weight of the compound composed of n repeating units represented by Formula (101) is equal to or greater than 2,000.

[24] A compound composed of n repeating units represented by the following Formula (1-1), (1-2), or (101);

Formula (1-1)

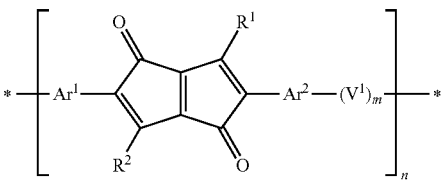

in Formula (1-1), each of R1 and $R^2$ independently represents a hydrogen atom or a substituent; each of $Ar^1$ and $Ar^2$ independently represents a heteroarylene group or an arylene group; $V^1$ represents a divalent linking group; m represents an integer of 0 to 6; when m is equal to or greater than 2, two or more groups represented by $V^1$ may be the same as or different from each other; and n represents an integer of equal to or greater than 2;

Formula (1-2)

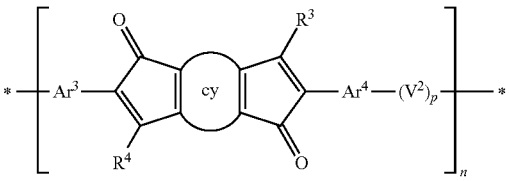

in Formula (1-2), cy represents a naphthalene ring or an anthracene ring; each of $R^3$ and $R^4$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2;

Formula (101)

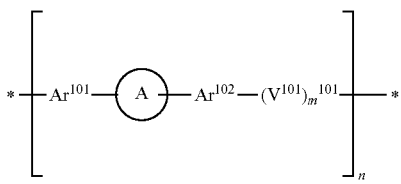

in Formula (101), each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; n represents an integer of equal to or greater than 2; and A represents a divalent linking group represented by the following Formula (101'); and Formula (101')

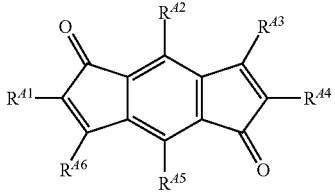

in Formula (101'), each of $R^{A1}$ to $R^{A6}$ independently represents a hydrogen atom, a substituent, or a direct bond with $Ar^{101}$ or $Ar^{102}$ in Formula (101); and among the groups represented by $R^{A1}$ to $R^{A6}$, two different groups represent direct bonds with $Ar^{101}$ and $Ar^{102}$ in Formula (101) respectively.

[25] The compound described in [24] that is a compound composed of n repeating units represented by the following Formula (1-1) or (1-2).

Formula (1-1)

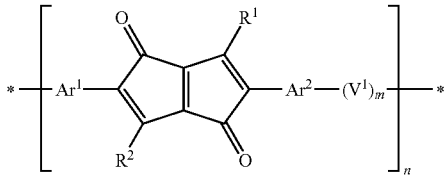

(In Formula (1-1), each of $R^1$ and $R^2$ independently represents a hydrogen atom or a substituent; each of $Ar^1$ and $Ar^2$ independently represents a heteroarylene group or an arylene group; $V^1$ represents a divalent linking group; m represents an integer of 0 to 6; when m is equal to or greater than 2, two or more groups represented by $V^1$ may be the same as or different from each other; and n represents an integer of equal to or greater than 2.)

Formula (1-2)

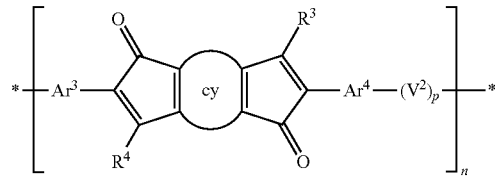

(In Formula (1-2), cy represents a naphthalene ring or an anthracene ring; each of $R^3$ and $R^4$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2.)

[26] The compound described in [24] or [25] in which Formula (1-2) represents a compound composed of n repeating units represented by the following Formula (2-1), (2-2), (2-3), (2-4), or (2-5).

Formula (2-1)

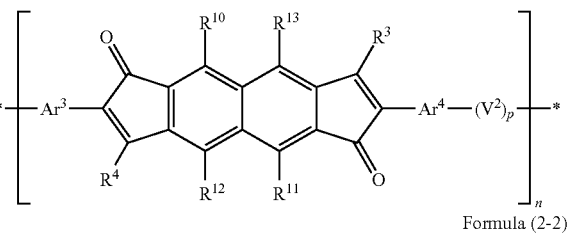

Formula (2-2)

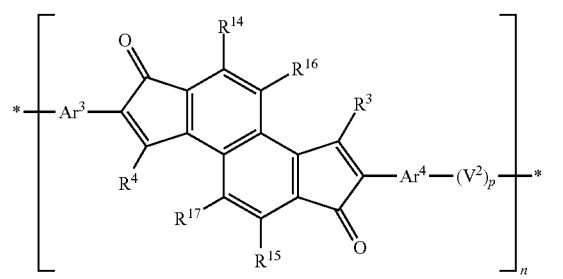

Formula (2-3)

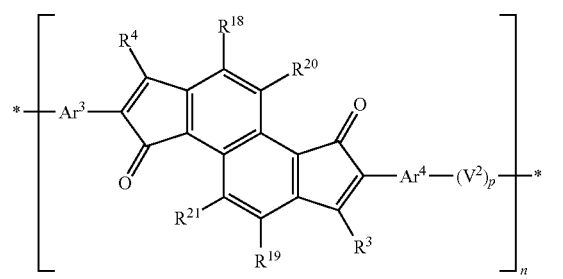

Formula (2-4)

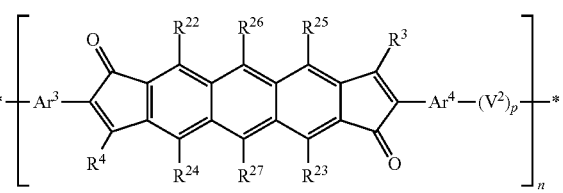

Formula (2-5)

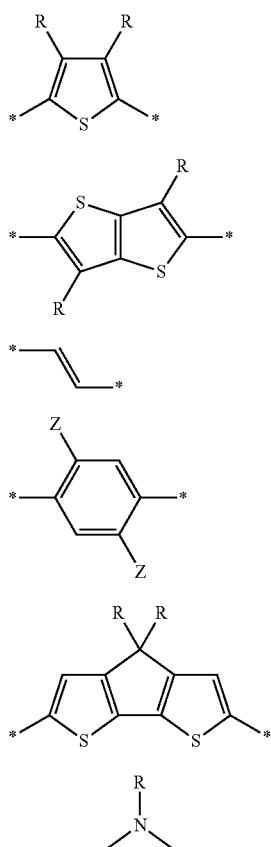

(In Formulae (2-1) to (2-5), each of $R^3$, $R^4$, and $R^{10}$ to $R^{33}$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2.)

[27] The compound described in any one of [24] to [26], in which in Formulae (1-1), (1-2), and (2-1) to (2-5), each of $V^1$ and $V^2$ is independently a divalent linking group represented by any of the following Formulae (V-1) to (V-17).

(V-1)

(V-2)

(V-3)

(V-4)

(V-5)

(V-6)

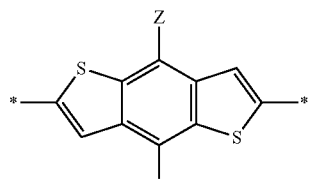 (V-7)

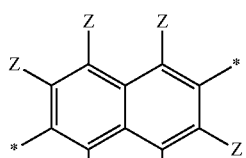 (V-8)

(V-9)

(V-10)

(V-11)

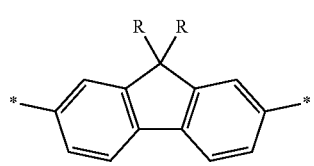 (V-12)

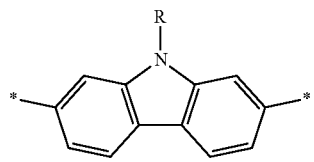 (V-13)

(V-14)

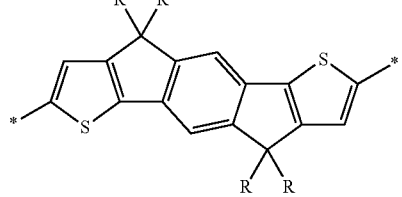 (V-15)

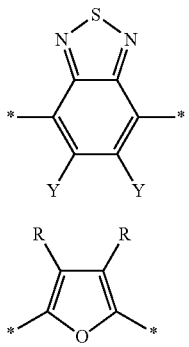
(V-16)

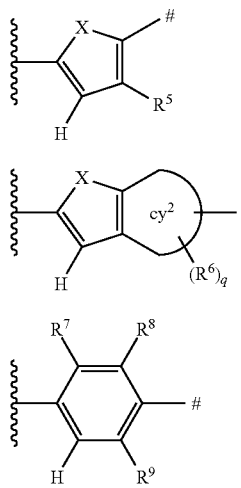
(V-17)

(In Formulae (V-1) to (V-17), * represents a position where the divalent linking group is bonded to any of $Ar^1$ to $Ar^4$ when p is 1, and represents a position where the divalent linking group is bonded to any of $Ar^1$ to $Ar^4$ and the divalent linking groups represented by Formulae (V-1) to (V-17) when m or p is equal to or greater than 2; each R in Formulae (V-1), (V-2), (V-5), (V-6), (V-9) to (V-11), (V-13) to (V-15), and (V-17) independently represents a hydrogen atom or an alkyl group; the groups adjacent to each other represented by R may form a ring by being bonded to each other; each Z in Formula (V-4), (V-7), (V-8), and (V-12) independently represents a hydrogen atom, an alkyl group, or an alkoxy group; the groups adjacent to each other represented by Z may form a ring by being bonded to each other; each Y in Formula (V-16) independently represents a hydrogen atom, an alkyl group, an alkoxy group, a CN group, or a F atom; and the groups adjacent to each other represented by Y may form a ring by being bonded to each other.)

[28] The compound described in [27], in which in Formulae (1-1), (1-2), and (2-1) to (2-5), each of $V^1$ and $V^2$ is a divalent linking group represented by any of Formulae (V-1) to (V-8) and (V-11) to (V-15).

[29] The compound described in any one of [24] to [28], in which in Formulae (1-1), (1-2), and (2-1) to (2-5), each of $Ar^1$ to $Ar^4$ is independently a divalent linking group represented by the following Formula (4-1), (4-2), or (4-3).

Formula (4-1)

Formula (4-2)

Formula (4-3)

(In Formulae (4-1) to (4-3), X represents a S atom, an O atom, or a Se atom; $cy^2$ represents a structure in which 1 to 4 rings are condensed; each of $R^5$ to $R^9$ independently represents a hydrogen atom or a substituent; q represents an integer of 0 to 6; when q is equal to or greater than 2, two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^1$ or $V^2$.)

[30] The compound described in [29], in which in Formulae (1-1), (1-2), and (2-1) to (2-5), each of $Ar^1$ to $Ar^4$ is independently a divalent linking group represented by Formula (4-1) or (4-2).

[31] The compound described in [29] or [30], in which the divalent linking group represented by Formula (4-2) is a divalent linking group represented by any of the following Formulae (5-1) to (5-8).

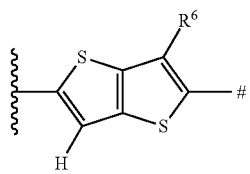
Formula (5-1)

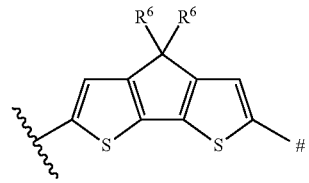
Formula (5-2)

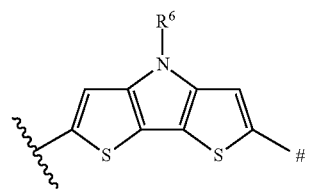
Formula (5-3)

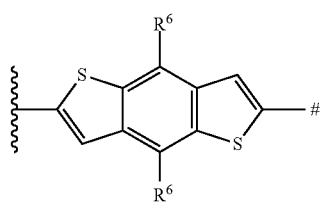
Formula (5-4)

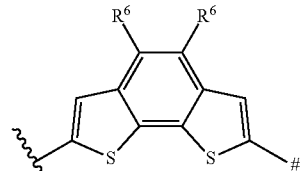
Formula (5-5)

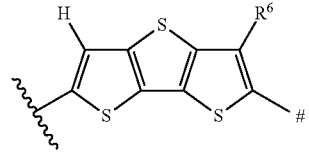
Formula (5-6)

Formula (5-7)

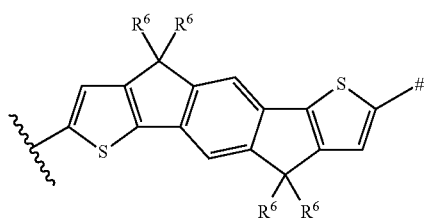

Formula (5-8)

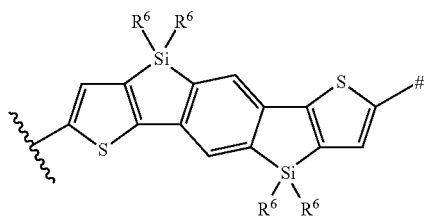

(In Formulae (5-1) to (5-8), $R^6$ represents a hydrogen atom or a substituent; two or more groups represented by $R^6$ may be the same as or different from each other; the wavy line represents a position where the divalent linking group is bonded to a cyclopentadienone ring-condensed site; and # represents a position where the divalent linking group is bonded to $V^1$ or $V^2$.)

[32] The compound described in any one of [24] to [31], in which each of at least one of R' and $R^2$ in Formula (1-1), at least one of $R^3$ and $R^4$ in Formula (1-2), at least one of $R^3$, $R^4$, $R^{10}$, $R^{11}$, $R^{12}$, and $R^{13}$ in Formula (2-1), at least one of $R^3$, $R^4$, $R^{14}$, $R^{15}$, $R^{16}$, and $R^{17}$ in Formula (2-2), at least one of $R^3$, $R^4$, $R^{18}$, $R^{19}$, $R^{20}$, and $R^{21}$ in Formula (2-3), at least one of $R^3$, $R^4$, $R^{22}$, $R^{23}$, $R^{24}$, $R^{25}$, $R^{26}$, and $R^{27}$ in Formula (2-4), and at least one of $R^3$, $R^4$, $R^{28}$, $R^{29}$, $R^{30}$, $R^{31}$, $R^{32}$, and $R^{33}$ in Formula (2-5) is a group represented by the following Formula (W).

-L-R　　　　Formula (W)

(In Formula (W), L represents a divalent linking group represented by any of the following Formulae (L-1) to (L-12) or a divalent linking group formed by bonding of two or more divalent linking groups represented by any of the following Formulae (L-1) to (L-12); R represents a substituted or unsubstituted alkyl group, an oligo-oxyethylene group in which a repetition number v of an oxyethylene unit is equal to or greater than 2, an oligosiloxane group having two or more silicon atoms, or a substituted or unsubstituted silyl group; and R represents a substituted or unsubstituted silyl group only when L adjacent to R is a divalent linking group represented by any of the following Formulae (L-1) to (L-3).)

(L-1)

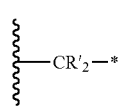

(L-2)

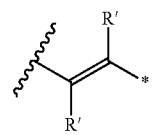

(L-3)

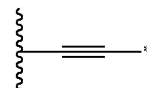

(L-4)

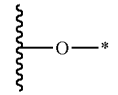

(L-5)

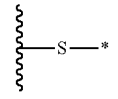

(L-6)

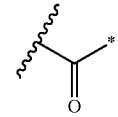

(L-7)

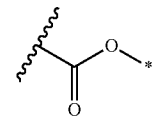

(L-8)

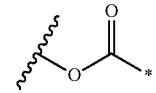

(L-9)

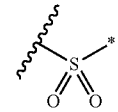

(L-10)

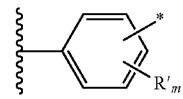

(L-11)

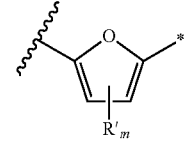

(L-12)

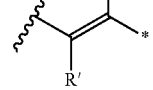

(In Formulae (L-1) to (L-12), the portion of a wavy line represents a position where the divalent linking group is bonded to a cyclopentadienone skeleton; * represents a position where the divalent linking group is bonded to any of the divalent linking groups represented by (L-1) to (L-12) and R; m in Formula (L-10) is 4; m in Formulae (L-11) and (L-12) is 2; and each R' in Formulae (L-1), (L-2), (L-10), (L-11), and (L-12) independently represents a hydrogen atom or a substituent.)

[33] The compound described in [32], in which in Formula (W), L is a divalent linking group represented by any of Formulae (L-1), (L-4), and (L-8) or a divalent linking group formed by bonding of two or more divalent linking groups described above.

[34] The compound described in any one of [24] to [33], in which in Formulae (1-1), (1-2), and (2-1) to (2-5), n is equal to or greater than 10.

[35] The organic film transistor described in [24], containing a compound, which is composed of n repeating units represented by the following Formula (101), in the semiconductor active layer;

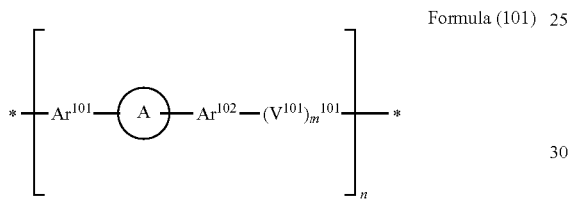

Formula (101)

in Formula (101), each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; n represents an integer of equal to or greater than 2; and A represents a divalent linking group represented by the following Formula (101'); and

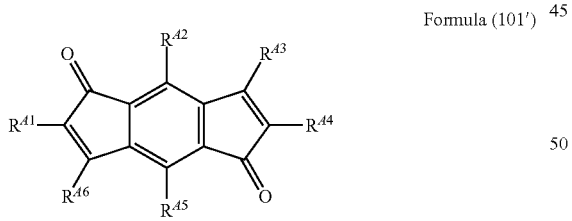

Formula (101')

in Formula (101'), each of $R^{41}$ to $R^{46}$ independently represents a hydrogen atom, a substituent, or a direct bond with $Ar^{101}$ or $Ar^{102}$ in Formula (101); and among the groups represented by $R^{41}$ to $R^{46}$, two different groups represent direct bonds with $Ar^{101}$ and $Ar^{102}$ in Formula (101) respectively.

[36] The organic film transistor described in [24] or [35], in which the compound composed of n repeating units represented by Formula (101) is a compound composed of n repeating units represented by any of the following Formulae (101-1) to (101-3);

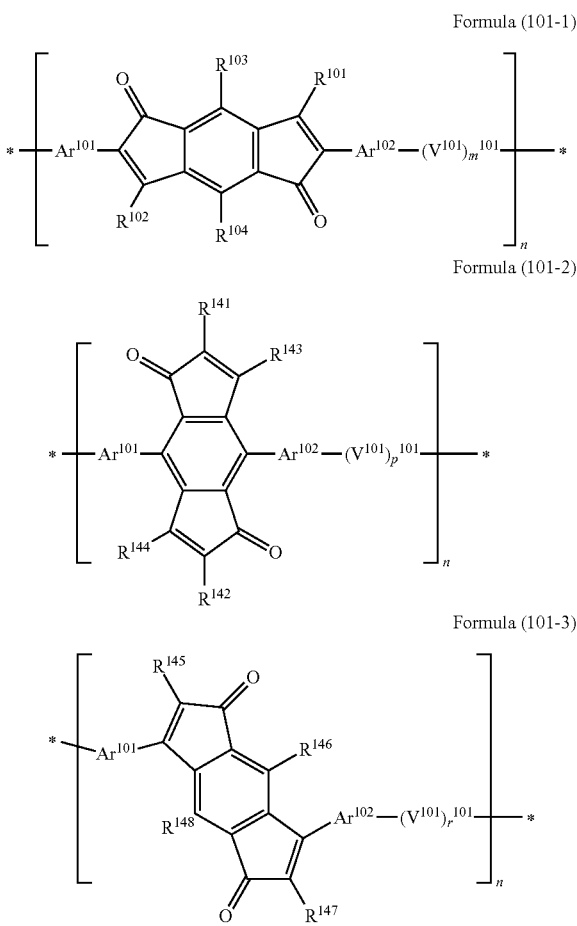

In Formulae (101-1), (101-2), and (101-3), each of $R^{101}$ to $R^{104}$ and $R^{141}$ to $R^{148}$ independently represents a hydrogen atom or a substituent; each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; each of $p^{101}$ and $r^{101}$ represents an integer of 0 to 6; when each of $p^{101}$ and $r^{101}$ is equal to or greater than 2, two or more groups represented by $V^{101}$ may be the same as or different from each other; and n represents an integer of equal to or greater than 2.

[37] The organic film transistor described in any one of [24], [35], and [36], in which the compound composed of n repeating units represented by Formula (101) is a compound composed of n repeating units represented by the following Formula (101-1);

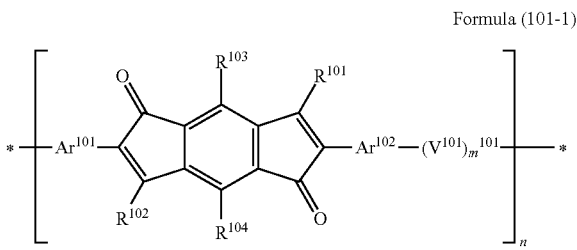

Formula (101-1)

in Formula (101-1), each of $R^{101}$ to $R^{104}$ independently represents a hydrogen atom or a substituent; each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; and n represents an integer of equal to or greater than 2.

[38] The organic film transistor described in [36] or [37], in which in Formulae (101-1) to (101-3), $V^{101}$ is a divalent linking group represented by any of the following Formulae (V-101) to (V-117);

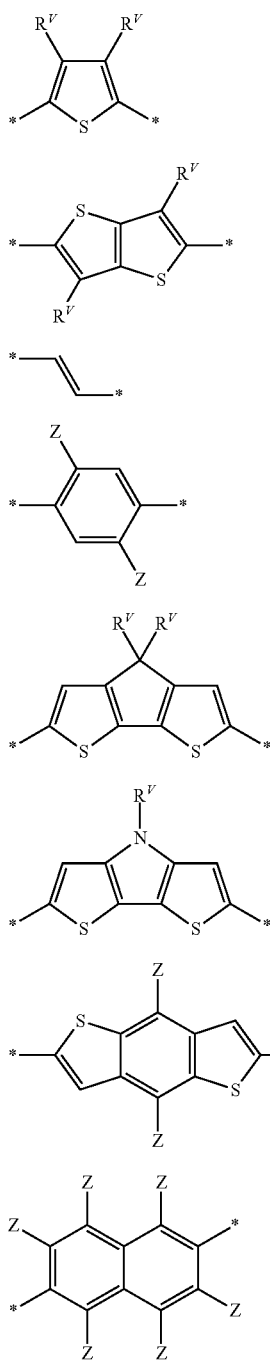

(V-101)

(V-102)

(V-103)

(V-104)

(V-105)

(V-106)

(V-107)

(V-108)

-continued

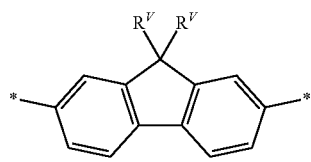

(V-109)

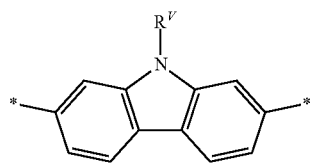

(V-110)

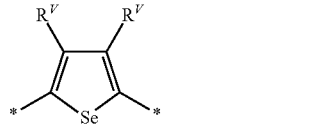

(V-111)

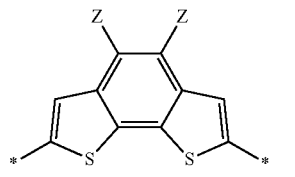

(V-112)

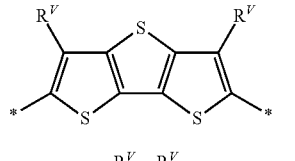

(V-113)

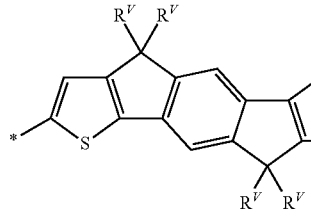

(V-114)

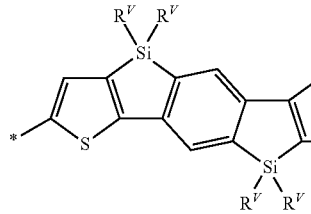

(V-115)

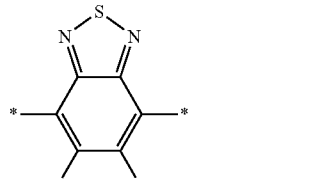

(V-116)

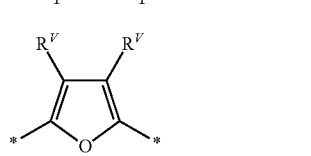

(V-117)

in Formulae (V-101) to (V-117), * represents a position where the divalent linking group is bonded to any of $Ar^{101}$ and $Ar^{102}$ when $m^{101}$, $p^{101}$, or $r^{101}$ is 1 and represents a position where the divalent linking group is bonded to any of $Ar^{101}$, $Ar^{102}$, and divalent linking groups represented by Formulae (V-101) to (V-117) when $m^{101}$, $p^{101}$, or $r^{101}$ is equal to or greater than 2; each $R^V$ in Formulae (V-101), (V-102), (V-105), (V-106), (V-109) to (V-111), (V-113) to (V-115), and (V-117) independently represents a hydrogen atom or an alkyl group; the groups adjacent to each other represented by $R^V$ may form a ring by being bonded to each other; each Z in Formulae (V-104), (V-107), (V-108), and (V-112) independently represents a hydrogen atom, an alkyl group, or an alkoxy group; the groups adjacent to each other represented by Z may form a ring by being bonded to each other; each Y in Formula (V-116) independently represents a hydrogen atom, an alkyl group, an alkoxy group, a CN group, or a F atom; and the groups adjacent to each other represented by Y may form a ring by being bonded to each other.

[39] The organic film transistor described in [38], in which in Formulae (101-1) to (101-3), $V^{101}$ is a divalent linking group represented by any of Formulae (V-101) to (V-108) and (V-111) to (V-115).

[40] The organic film transistor described in any one of [36] to [39], in which in Formulae (101-1) to (101-3), each of $Ar^{101}$ and $Ar^{102}$ is a divalent linking group represented by the following Formula (102-1), (102-2), or (102-3);

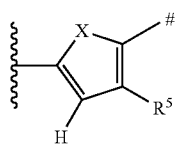

Formula (102-1)

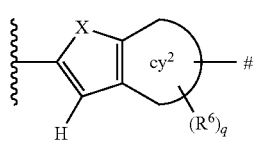

Formula (102-2)

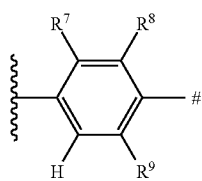

Formula (102-3)

in Formulae (102-1) to (102-3), X represents a S atom, an O atom, or a Se atom; $cy^2$ represents a structure in which 1 to 4 rings are condensed; each of $R^5$ to $R^9$ independently represents a hydrogen atom or a substituent; q represents an integer of 0 to 6; when q is equal to or greater than 2, two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^{101}$.

[41] The organic film transistor described in [40], in which in Formula (101-1), each of $Ar^{101}$ and $Ar^{102}$ is a divalent linking group represented by Formula (102-1), and $V^{101}$ is a divalent linking group represented by any of Formulae (V-102) to (V-107).

[42] The organic film transistor described in [40], in which in Formulae (101-1) to (101-3), each of $Ar^{101}$ and $Ar^{102}$ is independently a divalent linking group represented by Formula (102-1) or (102-2).

[43] The organic film transistor described in [40] or [42], in which the divalent linking group represented by Formula (102-2) is a divalent linking group represented by any of the following Formulae (5-1) to (5-8);

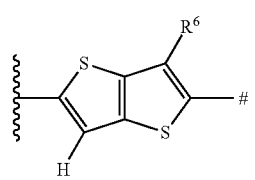

Formula (5-1)

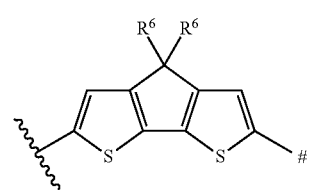

Formula (5-2)

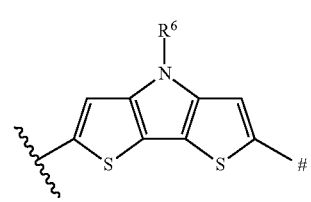

Formula (5-3)

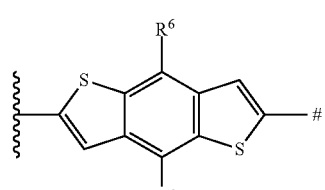

Formula (5-4)

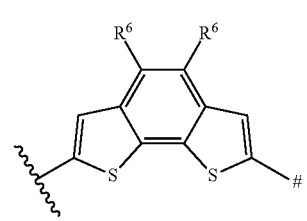

Formula (5-5)

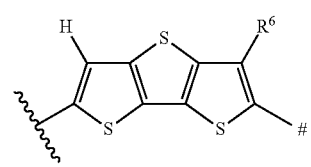

Formula (5-6)

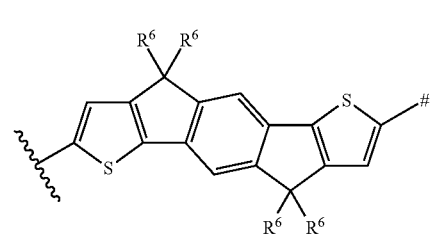

Formula (5-7)

Formula (5-8)

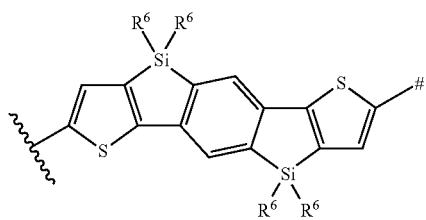

in Formulae (5-1) to (5-8), each $R^6$ independently represents a hydrogen atom or a substituent; two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^{101}$.

[44] The organic film transistor described in any one of [36] to [43], in which at least one of $R^{101}$, $R^{102}$, $R^{103}$, and $R^{104}$ in Formulae (101-1) to (101-3), at least one of $R^{141}$, $R^{142}$, $R^{143}$ and $R^{144}$ in the same formulae, or at least one of $R^{145}$, $R^{146}$, $R^{147}$, and $R^{148}$ in the same formulae is a group represented by the following Formula ($W^{101}$);

$$-L^{101}-R^{101} \qquad \text{Formula } (W^{101})$$

in Formula (W101), $L^{101}$ represents a divalent linking group represented by any of the following Formulae (L-101) to (L-125) or a divalent linking group formed by bonding of two or more divalent linking groups represented by any of the following Formulae (L-101) to (L-125); $R^{101}$ represents a substituted or unsubstituted alkyl group, an oligo-oxyethylene group in which a repetition number v of an oxyethylene group is equal to or greater than 2, an oligosiloxane group having two or more silicon atoms, or a substituted or unsubstituted silyl group; and $R^{101}$ represents a substituted or unsubstituted silyl group only when $L^{101}$ adjacent to $R^{101}$ is a divalent linking group represented by any of the following Formulae (L-101) to (L-103);

(L-101)

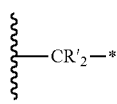

(L-102)

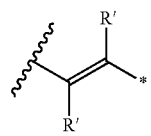

(L-103)

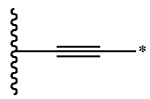

(L-104)

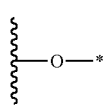

(L-105)

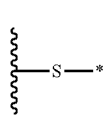

(L-106)

(L-107)

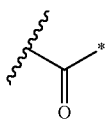

(L-108)

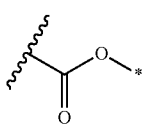

(L-109)

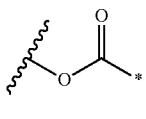

(L-110)

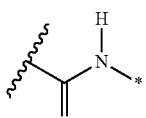

(L-111)

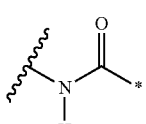

(L-112)

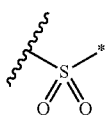

(L-113)

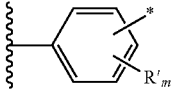

(L-114)

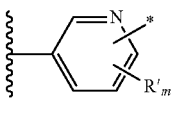

(L-115)

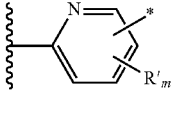

(L-116)

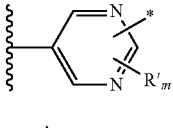

(L-117)

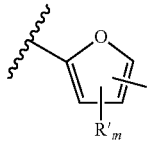

-continued (L-118) 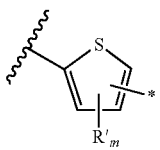

(L-119) 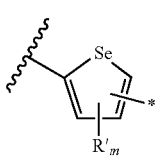

(L-120) 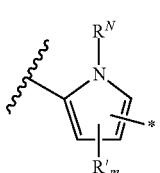

(L-121) 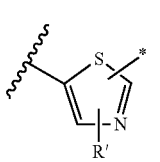

(L-122) 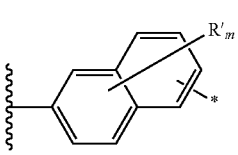

(L-123) 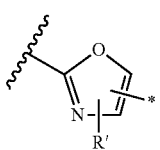

(L-124) 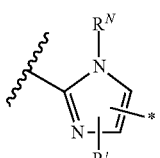

(L-125) 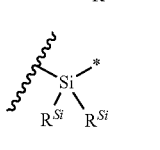

in Formulae (L-101) to (L-125), the portion of a wavy line represents a position where the divalent linking group is bonded to a cyclopentadienone skeleton; * represents a position where the divalent linking group is bonded to any of divalent linking groups represented by (L-101) to (L-125) and $R^{101}$; m in Formula (L-113) is 4; m in Formulae (L-114) and (L-115) is 3; m in Formulae (L-116) to (L-120) is 2; m in Formula (L-122) is 6; each R' in Formulae (L-101), (L-102), (L-106), and (L-113) to (L-124) independently represents a hydrogen atom or a substituent; $R^N$ represents a hydrogen atom or a substituent; and each $R^{si}$ independently represents a hydrogen atom, an alkyl group, an alkenyl group, or an alkynyl group.

[45] The organic film transistor described in [44], in which in Formula ($W^{101}$), $L^{101}$ is a divalent linking group represented by any of Formulae (L-101), (L-104), and (L-109) or a divalent linking group formed by bonding of two or more divalent linking groups described above.

[46] The organic film transistor described in any one of [24] and [35] to [45], in which the weight average molecular weight of the compound composed of n repeating units represented by Formula (101) is equal to or greater than 2,000.

[47] A compound represented by the following Formula (6);

Formula (6)

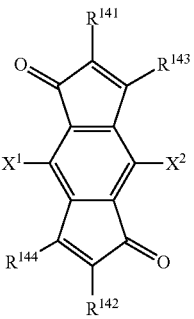

in Formula (6), each of to $R^{141}$ to $R^{144}$ independently represents a hydrogen atom or a substituent; each of $X^1$ and $X^2$ independently represents a halogen atom, $-OSO_2R^i$, $-Sn(R^J)_3$, $-Si(R^J)_3$, or $-B(R^k)_s$; $R^i$ represents a substituted or unsubstituted alkyl group or a hydrogen atom; $R^J$ represents a substituted or unsubstituted alkyl group; $R^k$ represents a substituted or unsubstituted alkoxy group, a hydroxyl group, or a halogen atom; s represents an integer of 2 or 3; the groups represented by $R^k$ may form a ring by being bonded to each other; and when s is 3, $-B(R^k)_s$ is accompanied by a cation $(X^3)^+$ and represents a salt of $-B^-(R^k)_s(X^3)^+$.

[48] A compound represented by the following Formula (7);

Formula (7)

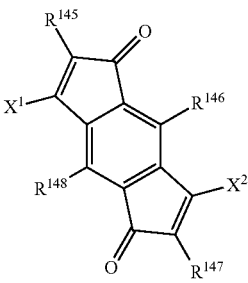

in Formula (7), each of $R^{145}$ to $R^{148}$ independently represents a hydrogen atom or a substituent; each of $X^1$ and $X^2$ independently represents a halogen atom, $-OSO_2R^i$, $-Sn(R^J)_3$, $-Si(R^J)_3$, or $-B(R^k)_s$; $R^i$ represents a substituted or unsubstituted alkyl group or a hydrogen atom; $R^J$ represents a substituted or unsubstituted alkyl group; $R^k$ represents a substituted or unsubstituted alkoxy group, a hydroxyl group, or a halogen atom; s represents an integer of 2 or 3; the groups represented by $R^k$ may form a ring by being bonded to each other; and when s is 3, $-B(R^k)_s$ is accompanied by a cation $(X^3)^+$ and represents a salt of $-B^-(R^k)_s(X^3)^+$.

[49] The compound described in [47] or [48] that is a synthetic intermediate compound of the compound described in any one of [35] to [46].

[50] A composition containing the compound described in any one of [24] to [46] and an organic solvent.

[51] The composition described in [50], in which the organic solvent is an aromatic hydrocarbon-based solvent, an ether-based solvent, or a ketone-based solvent.

[52] An organic semiconductor material for a non-light-emitting organic semiconductor device, containing the compound described in any one of [24] to [46] or the composition described in [50] or [51].

[53] A material for an organic film transistor, containing the compound described in any one of [24] to [46] or the composition described in [50] or [51].

[54] A coating solution for a non-light-emitting organic semiconductor device, containing the compound described in any one of [24] to [46] or the composition described in [50] or [51].

[55] A coating solution for a non-light-emitting organic semiconductor device, containing the compound described in any one of [24] to [46] or the composition described in [50] or [51] and a polymer binder.

[56] An organic semiconductor film for a non-light-emitting organic semiconductor device, containing the compound described in any one of [24] to [46] or the composition described in [50] or [51].

[57] An organic semiconductor film for a non-light-emitting organic semiconductor device, containing the compound described in any one of [24] to [46] or the composition described in [50] or [51] and a polymer binder.

[58] The organic semiconductor film for a non-light-emitting organic semiconductor device described in [56] or [57] that is prepared by a solution coating method.

According to the present invention, it is possible to provide a compound, which results in high carrier mobility when being used in a semiconductor active layer of an organic film transistor and exhibits high solubility in an organic solvent, and an organic film transistor which uses the compound.

DESCRIPTION OF THE PREFERRED EMBODIMENTS

Figure 1:
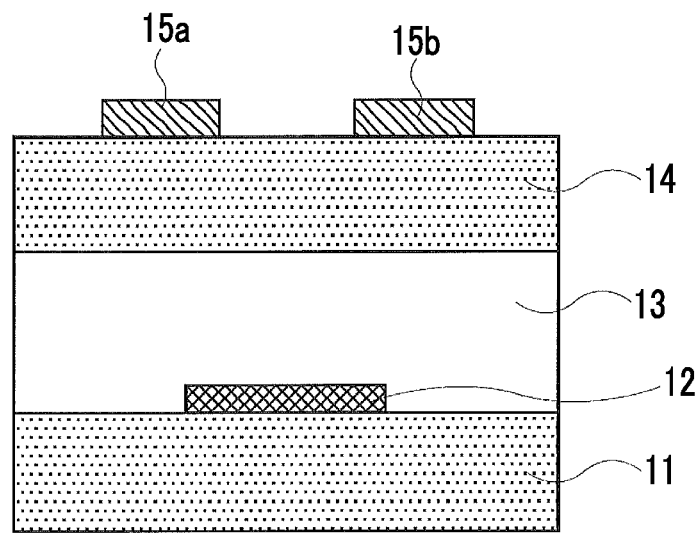
FIG. 1 is a schematic view showing the cross-section of an exemplary structure of an organic film transistor of the present invention.

Hereinafter, the present invention will be specifically described. The following constituents are described based on typical embodiments or specific examples in some cases, but the present invention is not limited to such embodiments. In the present specification, a range of numerical values represented by using "to" means a range which includes the numerical values listed before and after "to" as a lower limit and an upper limit In the present invention, in a case in which hydrogen atoms are used in describing each formula without being particularly differentiated from each other, the hydrogen atoms include isotopes (a deuterium atom and the like). Furthermore, atoms constituting a substituent also include isotopes thereof.

In the present specification, a compound composed of n repeating units represented by Formula (1-1), (1-2), or (101) has the same definition as a compound represented by Formula (1-1), (1-2), or (101). In Formulae (1-1) and (1-2), Formulae (2-1) to (2-5) which will be described later, Formula (101), and Formulae (101-1) to (101-3) which will be described later, * represents a linking group linked to a hydrogen atom or a substituent. In the compound composed of n repeating units represented by any of Formulae (1-1) and (1-2), Formula (2-1) to (2-5) which will be described later, Formula (101), and Formulae (101-1) to (101-3) which will be described later, * on a molecular terminal may be a hydrogen atom or any substituent, and the molecular terminal is preferably a hydrogen atom, a trialkyltin group, a halogen atom, a perfluoroalkanesulfonyloxy group, $-B(OH)_2$, $-B(OR^x)_2$, a trialkylsilyl group, an aryl group, a heteroaryl group, or the like. Herein, $R^x$ represents an alkyl group, and a plurality of alkyl groups represented by $R^x$ may form a ring by being bonded to each other.

[Organic Film Transistor]

The organic film transistor of the present invention contains a compound, which is composed of n repeating units represented by the following Formula (1-1), (1-2), or (101), in a semiconductor active layer.

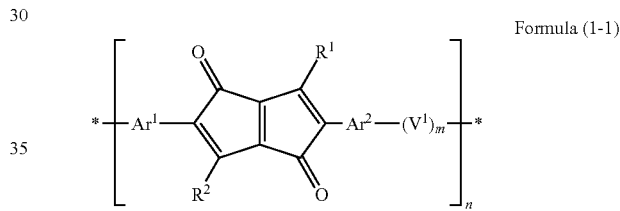

Formula (1-1)

(In Formula (1-1), each of $R^1$ and $R^2$ independently represents a hydrogen atom or a substituent; each of $Ar^1$ and $Ar^2$ independently represents a heteroarylene group or an arylene group; $V^1$ represents a divalent linking group; m represents an integer of 0 to 6; when m is equal to or greater than 2, two or more groups represented by $V^1$ may be the same as or different from each other; and n represents an integer of equal to or greater than 2.)

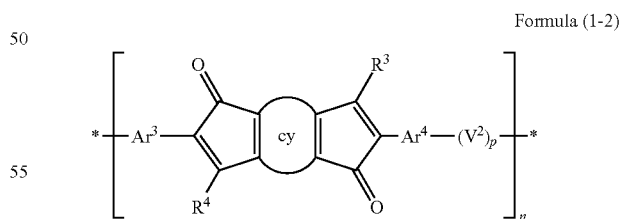

Formula (1-2)

(In Formula (1-2), cy represents a naphthalene ring or an anthracene ring; each of $R^3$ and $R^4$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2.)

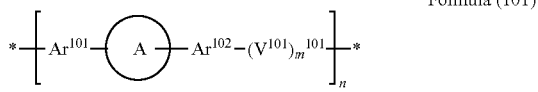

Formula (101)

In Formula (101), each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; n represents an integer of equal to or greater than 2; and A represents a divalent linking group represented by the following Formula (101');

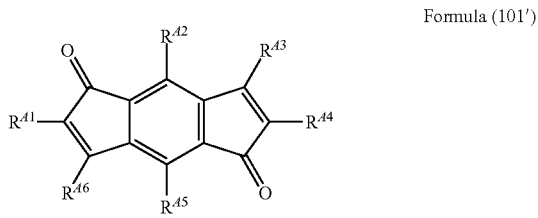

Formula (101')

in Formula (101'), each of $R^{41}$ to $R^{46}$ independently represents a hydrogen atom, a substituent, or a direct bond with $Ar^{101}$ or $Ar^{102}$ in Formula (101); and among the groups represented by $R^{41}$ to $R^{46}$, two different groups represent direct bonds with $Ar^{101}$ and $Ar^{102}$ in Formula (101) respectively.

A first preferred embodiment of the organic film transistor of the present invention contains the compound represented by Formula (1-1) or (1-2) in the semiconductor active layer.

A second preferred embodiment of the organic film transistor of the present invention contains the compound represented by Formula (101) in the semiconductor active layer.

When being used in the semiconductor active layer of the organic film transistor, the compound composed of n repeating units represented by Formula (1-1), (1-2), or (101) results in high carrier mobility and exhibits high solubility in an organic solvent. Therefore, by containing the compound in the semiconductor layer, the organic film transistor of the present invention exhibits high carrier mobility.

In the compound composed of n repeating units represented by Formula (1-1), (1-2), or (101), a ring-condensed cyclopentadienone skeleton has a carbonyl group, and thus the overlapping of HOMO sufficiently occurs. Accordingly, an organic film transistor having high carrier mobility can be obtained. Furthermore, the compound brings about an effect of obtaining unexpectedly high solubility in an organic solvent. Such an effect is considered to be obtained by the following mechanism. The compound composed of n repeating units represented by Formula (1-1), (1-2), or (101) has a hydrogen bond between a double-bonded oxygen atom of the ring-condensed cyclopentadienone skeleton, which will be a mother skeleton, and a hydrogen atom of arylene groups or heteroarylene groups adjacent to each other on both sides of the ring-condensed cyclopentadienone skeleton. In a film, the hydrogen bond is maintained, and thus the planarity is improved. As a result, the distance between polymer molecules is shortened, and hence the carrier mobility can be improved. In a solution, the hydrogen bond is dissociated and freely rotates, and thus the solubility in an organic solvent can be improved.

Conventionally, a polycyclic ring-condensed compound having an aromatic heterocyclic ring is known to be useful as an organic EL element material. However, the usefulness of the compound as an organic EL element material does not necessarily mean that the compound is also useful as a semiconductor material for an organic film transistor. This is because the characteristics required for an organic compound vary between the organic EL element and the organic film transistor. Generally, in the organic EL element, a charge needs to be transported in the film thickness direction (usually, several nm to hundreds of nm) of the film. In contrast, in the organic film transistor, a charge (carrier) needs to be transported through a long distance between electrodes (usually, several μm to hundreds of μm) in the film surface direction, and hence extremely high carrier mobility is required. Therefore, as the semiconductor material for an organic film transistor, an organic compound which has high regularity of molecular arrangement and high crystallinity is required. Furthermore, in order to achieve high carrier mobility, a π conjugation plane is preferably perpendicular to a substrate. In contrast, in the organic EL element, in order to improve light emitting efficiency, an element which has high light emitting efficiency and uniformly emits light within a plane is required. Generally, an organic compound having high crystallinity results in defectiveness in emitting light, such as uneven field intensity within a plane, uneven light emission, and emission quenching. Accordingly, as the material for an organic EL element, a material which has low crystallinity and high amorphousness is desirable. Therefore, even if an organic compound constituting the organic EL element material is directly used as the organic semiconductor material, excellent transistor characteristics are not necessarily obtained.

In addition, it is preferable that the organic film transistor of the present invention using the compound composed of n repeating units represented by Formula (1-1), (1-2), or (101) shows a slight threshold voltage shift after repeated driving. In order to make the organic film transistor show a slight threshold voltage shift after repeated driving, HOMO of the organic semiconductor material needs not to be too shallow or too deep. Furthermore, the chemical stability (particularly, resistance against air oxidation and stability against oxidation and reduction) of the organic semiconductor material, the heat stability of the film state, the high film density which makes it difficult for air or moisture to permeate the film, the film quality in which the film has small defectiveness such that charge accumulation does not easily occur, and the like are required. It is considered that because the compound composed of n repeating units represented by Formula (1-1), (1-2), or (101) satisfies the aforementioned requirements, the organic film transistor shows a slight threshold voltage shift after repeated driving. That is, in the organic film transistor showing a slight threshold voltage shift after repeated driving, the semiconductor active layer has high chemical resistance, high film density, and the like, and thus the organic film transistor can effectively function as a transistor over a long period of time.

Hereinafter, preferred embodiments of the compound of the present invention, the organic film transistor of the present invention, and the like will be described.

<Compound Composed of n Repeating Units Represented by Formula (1-1) or (1-2)>

The compound of the present invention is preferably composed of n repeating units represented by the following Formula (1-1) or (1-2). The compound of the present invention is contained in a semiconductor active layer, which will be described later, in the organic film transistor of the present invention. That is, the compound of the present invention can be used as a material for an organic film transistor.

Hereinafter, the compound composed of n repeating units represented by Formula (1-1) or (1-2) will be described.

<<Compound Composed of n Repeating Units Represented by Formula (1-1)>>

The compound composed of n repeating units represented by Formula (1-1) is represented by the following formula.

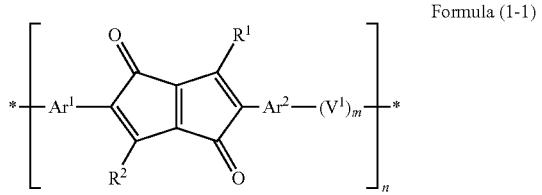

Formula (1-1)

(In Formula (1-1), each of $R^1$ and $R^2$ independently represents a hydrogen atom or a substituent; each of $Ar^1$ and $Ar^2$ independently represents a heteroarylene group or an arylene group; $V^1$ represents a divalent linking group; m represents an integer of 0 to 6; when m is equal to or greater than 2, two or more groups represented by $V^1$ may be the same as or different from each other; and n represents an integer of equal to or greater than 2.)

In Formula (1-1), each of $R^1$ and $R^2$ independently represents a hydrogen atom or a substituent. The substituent which can be adopted as $R^1$ and $R^2$ is not particularly limited, and examples thereof include the same substituents as exemplified as a group represented by the following Formula (W) or as a substituent which can be adopted as $R^5$ to $R^9$ which will be described later. The substituent which can be adopted as $R^1$ and $R^2$ is preferably the group represented by the following Formula (W). More preferably, at least one of $R^1$ and $R^2$ is the group represented by the following Formula (W).

-L-R    Formula (W)

(In Formula (W), L represents a divalent linking group represented by any of the following Formulae (L-1) to (L-12) or a divalent linking group formed by bonding of two or more divalent linking groups represented by any of the following Formulae (L-1) to (L-12); R represents a substituted or unsubstituted alkyl group, an oligo-oxyethylene group in which a repetition number v of an oxyethylene unit is equal to or greater than 2, an oligosiloxane group having two or more silicon atoms, or a substituted or unsubstituted silyl group; and R represents a substituted or unsubstituted silyl group only when L adjacent to R is a divalent linking group represented by any of the following Formulae (L-1) to (L-3).)

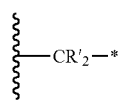

(L-1)

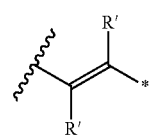

(L-2)

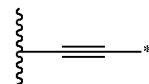

(L-3)

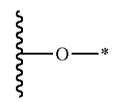

(L-4)

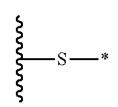

(L-5)

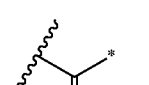

(L-6)

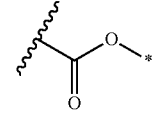

(L-7)

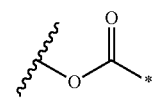

(L-8)

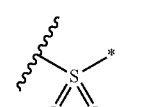

(L-9)

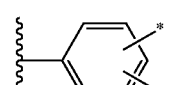

(L-10)

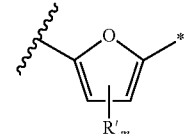

(L-11)

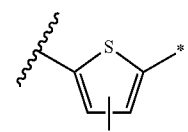

(L-12)

(In Formulae (L-1) to (L-12), the portion of a wavy line represents a position where the divalent linking group is bonded to a cyclopentadienone skeleton; * represents a position where the divalent linking group is bonded to any of the divalent linking groups represented by (L-1) to (L-12) and R; m in Formula (L-10) is 4; m in Formulae (L-11) and (L-12) is 2; and each R' in Formulae (L-1), (L-2), (L-10), (L-11), and (L-12) independently represents a hydrogen atom or a substituent.)

In Formula (W), L represents a divalent linking group represented by any of the following Formulae (L-1) to (L-12) or a divalent linking group formed by bonding of two or more divalent linking groups represented by any of Formulae (L-1) to (L-12). When L represents a linking group in which divalent linking groups represented by any of Formula (L-1) to (L-12) are bonded to each other, the number of the bonded divalent linking groups represented by any of Formula (L-1) to (L-12) is preferably 2 to 4, and more preferably 2 or 3.

Each R' in Formulae (L-1), (L-2), (L-10), (L-11), and (L-12) independently represents a hydrogen atom or a substituent. Examples of the substituent which can be adopted as R' include an alkyl group having 5 to 15 carbon atoms (preferably an alkyl group having 6 to 15 carbon atoms) and an alkoxy group having 5 to 15 carbon atoms (preferably an alkoxy group having 6 to 15 carbon atoms).

m in Formula (L-10) represents 4, and m in Formulae (L-11) and (L-12) represents 2.

L is preferably a divalent linking group represented by any of Formulae (L-1), (L-4), and (L-8) or a divalent linking group formed by bonding of two or more divalent linking groups described above, more preferably a divalent linking group represented by any of Formula (L-1) and (L-4) or a divalent linking group formed by bonding of two or more divalent linking groups described above, and particularly preferably a divalent linking group represented by Formula (L-1) or a divalent linking group formed by bonding of two or more divalent linking groups described above.

In Formula (W), R represents a hydrogen atom, a substituted or unsubstituted alkyl group, an oligo-oxyethylene group in which a repetition number v of an oxyethylene unit is equal to or greater than 2, an oligosiloxane group having two or more silicon atoms, or a substituted or unsubstituted silyl group. Here, R represents a substituted or unsubstituted silyl group only when L adjacent to R is a divalent linking group represented by Formula (L-3), and represents a hydrogen atom only when L adjacent to R is a divalent linking group represented by any of Formulae (L-1) to (L-3).

When L is represented by Formula (L-1), the substituted or unsubstituted alkyl group which can be adopted as R is preferably an alkyl group having 3 or more carbon atoms, more preferably an alkyl group having 3 to 40 carbon atoms, even more preferably an alkyl group having 10 to 30 carbon atoms from the viewpoint of the chemical stability and the carrier transport properties, and particularly preferably an alkyl group having 15 to 30 carbon atoms. Furthermore, when L is represented by Formula (L-1), the substituted or unsubstituted alkyl group which can be adopted as R is preferably a linear or branched alkyl group, and more preferably a branched alkyl group from the viewpoint of improving the carrier mobility and the solubility in a solvent without deteriorating the intramolecular hydrogen bonding properties.

When L is represented by any of Formulae (L-2) and (L-3), the alkyl group which can be adopted as R is preferably an alkyl group having 2 or more carbon atoms, more preferably an alkyl group having 3 to 18 carbon atoms, even more preferably an alkyl group having 3 to 12 carbon atoms, and particularly preferably an alkyl group having 4 to 10 carbon atoms.

When L is represented by any of Formulae (L-4) to (L-12), the alkyl group which can be adopted as R is preferably an alkyl group having 4 or more carbon atoms, more preferably an alkyl group having 4 to 18 carbon atoms, even more preferably an alkyl group having 4 to 12 carbon atoms, and particularly preferably an alkyl group having 4 to 10 carbon atoms.

When -L-R in Formula (W) contains an alkyl group, if the number of carbon atoms of the alkyl group represented by R is equal to or greater than the lower limit of the aforementioned range, the carrier mobility is improved. Furthermore, when L contains an alkylene group represented by Formula (L-1) adjacent to R, if the number of carbon atoms of the alkyl group formed by bonding of the alkylene group represented by Formula (L-1) and the alkyl group represented by R is equal to or greater than the lower limit of the aforementioned range, the carrier mobility is improved.

When R is an alkyl group having a substituent, examples of the substituent include a halogen atom and the like, and as the halogen atom, a fluorine atom is preferable. When R is an alkyl group having a fluorine-atom, a perfluoroalkyl group may be formed by substituting all the hydrogen atoms of the alkyl group with fluorine atoms.

In the present specification, when R is an oligo-oxyethylene group in which a repetition number v of an oxyethylene unit is equal to or greater than 2, the "oxyethylene group" represented by R is a group represented by $-(CH_2CH_2)_vOY$ (the repetition number v of an oxyethylene unit represents an integer of equal to or greater than 2, and Y on the terminal represents a hydrogen atom or a substituent). When Y on the terminal of the oligo-oxyethylene group is a hydrogen atom, the terminal becomes a hydroxy group. The repetition number v of an oxyethylene unit is preferably 2 to 4, and more preferably 2 or 3. It is preferable that the hydroxy group on the terminal of the oligo-oxyethylene group is blocked. That is, Y preferably represents a substituent. In this case, the hydroxy group is preferably blocked by an alkyl group having 1 to 3 carbon atoms. That is, Y is preferably an alkyl group having 1 to 3 carbon atoms, more preferably a methyl group or an ethyl group, and particularly preferably a methyl group.

When R is an oligosiloxane group having 2 or more silicon atoms, the repetition number of the siloxane unit is preferably 2 to 4, and more preferably 2 or 3. Furthermore, the Si atom is preferably bonded to a hydrogen atom or an alkyl group. When the Si atom is bonded to an alkyl group, the number of carbon atoms of the alkyl group is preferably 1 to 3. For example, the Si atom is preferably bonded to a methyl group or an ethyl group. The Si atom may be bonded to the same alkyl groups or may be bonded to different alkyl groups or hydrogen atoms. The siloxane units constituting the oligosiloxane group may be the same as or different from each other, but it is preferable that they are the same as each other.

When R is a substituted or unsubstituted silyl group, as the silyl group which can be adopted as R, a trialkylsilyl group having 3 to 15 carbon atoms and silyl groups substituted with 1 to 3 trialkylsilyloxy groups (a monoalkyl di(trialkylsilyloxy)silyl group, a dialkyl mono(trialkylsilyloxy)silyl group, and a tri(trialkylsilyloxy)silyl group) are preferable.

Examples of the group represented by Formula (W) include a 2,6-dimethyloctyl group, a 2-decyltetradecyl group, a 2-hexyldodecyl group, a 2-ethyloctyl group, a 2-butyldecyl group, a 2-octylnonyl group, a 2-octyltetradecyl group, a 2-hexyldecyloxy group, a ditrimethylsiloxy methylbutoxy group, a hexyl group, a heptyl group, an octyl group, a nonyl group, a decyl group, an undecyl group, a dodecyl group, a tridecyl group, a tetradecyl group, a pentadecyl group, and the like.

The substituent which can be adopted as $R^1$ and $R^2$ is preferably a branched substituent in which a linear substituent further has a substituent.

Each of $Ar^1$ and $Ar^2$ independently represents a heteroarylene group or an arylene group. From the viewpoint of improving the solubility, it is preferable that $Ar^1$ and $Ar^2$ do not form a condensed ring by being bonded to each other. Furthermore, from the viewpoint of improving the solubility, it is preferable that $Ar^2$ and $R^1$ do not form a condensed ring by being bonded to each other. The heteroarylene group or the arylene group which can be adopted as $Ar^1$ and $Ar^2$ is not particularly limited, and examples thereof include a heteroarylene group having 4 to 30 carbon atoms and an arylene group having 6 to 30 carbon atoms. The heteroarylene group or the arylene group which can be adopted as $Ar^1$ and $Ar^2$ is preferably a divalent linking group represented by the following Formula (4-1), (4-2), or (4-3), and more preferably a divalent linking group represented by the following Formula (4-1) or (4-2). Furthermore, it is preferable that $Ar^1$ and $Ar^2$ represent the same heteroarylene groups or arylene groups.

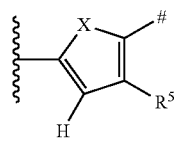

Formula (4-1)

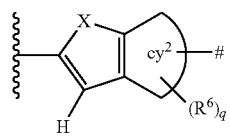

Formula (4-2)

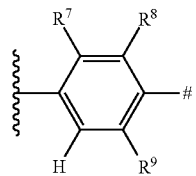

Formula (4-3)

(In Formulae (4-1) to (4-3), X represents a S atom, an O atom, or a Se atom; $cy^2$ represents a structure in which 1 to 4 rings are condensed; each of $R^5$ to $R^9$ independently represents a hydrogen atom or a substituent; q represents an integer of 0 to 6; when q is equal to or greater than 2, two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^1$ or $V^2$.)

In Formulae (4-1) to (4-3), X represents a S atom, an O atom, or a Se atom. X is preferably a S atom or a Se atom, and more preferably a S atom.

In Formulae (4-1) to (4-3), each of $R^5$ to $R^9$ independently represents a hydrogen atom or a substituent. The substituent which can be adopted as $R^5$ to $R^9$ is not particularly limited, and examples thereof include a halogen atom, an alkyl group (including an alkyl group having 1 to 40 carbon atoms such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, or a pentadecyl group (preferably an alkyl group having 3 to 40 carbon atoms and more preferably an alkyl group having 10 to 30 carbon atoms), a 2,6-dimethyloctyl group, a 2-decyltetradecyl group, a 2-hexyldodecyl group, a 2-ethyloctyl group, a 2-butyldecyl group, a 1-octylnonyl group, a 2-octyltetradecyl group, and the like), an alkenyl group (including a 1-pentenyl group, a cycloalkenyl group, a bicycloalkenyl group, and the like), an alkynyl group (including a 1-pentynyl group, a trimethylsilylethynyl group, a triethylsilylethynyl group, a tri-i-propylsilylethynyl group, a 2-p-propylphenylethynyl group, and the like), an aryl group (including an aryl group having 6 to 20 carbon atoms such as a phenyl group, a naphthyl group, a p-pentylphenyl group, a 3,4-dipentylphenyl group, a p-heptoxyphenyl group, a 3,4-diheptoxyphenyl group, and the like), a hetero ring group (may also be referred to as a heterocyclic group, including a 2-hexylfuranyl group and the like), a cyano group, a hydroxyl group, a nitro group, an acyl group (including a hexanoyl group, a benzoyl group, and the like), an aryloxy group, a silyloxy group, a heterocyclic oxy group, an acyloxy group, a carbamoyloxy group, an amino group (including an anilino group), an acylamino group, an aminocarbonylamino group (including a ureide group), an alkoxy group (including an alkoxy group having 1 to 40 carbon atoms such as a methoxy group, an ethoxy group, a propoxy group, a butoxy group, a pentoxy group, a hexyloxy group, a heptoxy group, an octoxy group, a nonyloxy group, a decyloxy group, a 2-hexyldecyloxy group, an undecyloxy group, a dodecyloxy group, a tridecyloxy group, a tetradecyloxy group, and a pentadecyloxy group (preferably an alkoxy group having 3 to 40 carbon atoms and more preferably an alkoxy group having 10 to 30 carbon atoms)), an aryloxycarbonylamino group, alkyl and aryl sulfonylamino groups, a mercapto group, alkyl and arylthio groups (including a methylthio group, an octylthio group, and the like), a heterocyclic thio group, a sulfamoyl group, a sulfo group, alkyl and aryl sulfinyl groups, alkyl and aryl sulfonyl groups, alkyloxy and aryloxy carbonyl groups, a carbamoyl group, an arylazo group, a heterocyclic azo group, an imide group, a phosphino group, a phosphinyl group, a phosphinyloxy group, a phosphinylamino group, a phosphono group, a silyl group (a ditrimethylsiloxy methylbutoxy group), a hydrazino group, and other known substituents. Among these, an alkyl group and an alkoxy group are preferable.

The alkyl group which can be adopted as $R^5$ to $R^9$ is more preferably an alkyl group having 3 to 40 carbon atoms, even more preferably an alkyl group having 10 to 30 carbon atoms from the viewpoint of the chemical stability and the carrier transport properties, and particularly preferably an alkyl group having 15 to 30 carbon atoms. Furthermore, the alkyl group which can be adopted as $R^5$ to $R^9$ is preferably a linear or branched alkyl group, and more preferably a branched alkyl group from the viewpoint of improving the carrier mobility and the solubility in a solvent without deteriorating the intramolecular hydrogen bonding properties.

The alkoxy group which can be adopted as $R^5$ to $R^9$ is more preferably an alkoxy group having 3 to 40 carbon atoms, even more preferably an alkoxy group having 10 to 30 carbon atoms from the viewpoint of the chemical stability and the carrier transport properties, and particularly preferably an alkoxy group having 15 to 30 carbon atoms. Furthermore, the alkoxy group which can be adopted as $R^5$ to $R^9$ is preferably a linear or branched alkoxy group, and more preferably a branched alkoxy group from the viewpoint of improving the carrier mobility and the solubility in a solvent without deteriorating the intramolecular hydrogen bonding properties.

These substituents may further have a substituent.

In addition, these substituents may have a group derived from a polymerizable group.

In Formula (4-2), q represents an integer of 0 to 6. q is preferably an integer of 0 to 3, more preferably an integer of 0 to 2, and even more preferably an integer of 0 or 1.

In Formula (4-2), $cy^2$ represents a structure in which 1 to 4 rings are condensed. $cy^2$ is preferably a structure in which 1 to 4 aromatic rings or heterocyclic aromatic rings are condensed, more preferably a structure in which 1 to 4 aromatic rings having 6 to 10 carbon atoms or 1 to 4 heterocyclic aromatic rings having 4 to 6 carbon atoms are condensed, and particularly preferably a structure in which 1 to 4 benzene rings or thiophene rings are condensed.

The divalent linking group represented by Formula (4-2) is preferably a divalent linking group represented by any of the following Formulae (5-1) to (5-8), and more preferably a divalent linking group represented by Formula (5-1).

Formula (5-1)
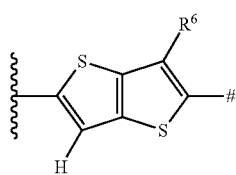

Formula (5-2)
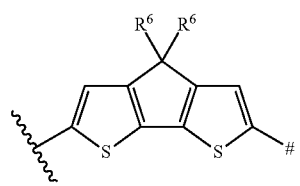

Formula (5-3)
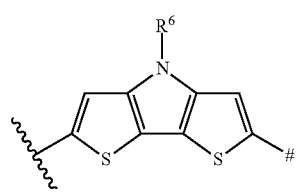

Formula (5-4)
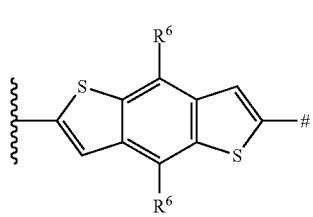

Formula (5-5)
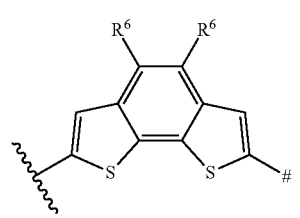

Formula (5-6)
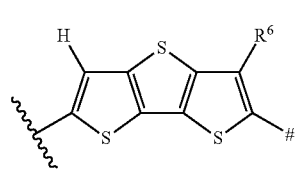

Formula (5-7)
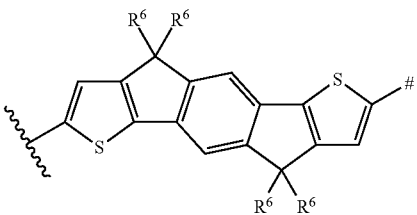

Formula (5-8)
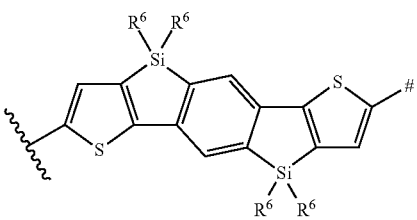

(In Formulae (5-1) to (5-8), each $R^6$ independently represents a hydrogen atom or a substituent; two or more groups represented by $R^6$ may be the same as or different from each other; the wavy line represents a position where the divalent linking group is bonded to a cyclopentadienone ring-condensed site; and # represents a position where the divalent linking group is bonded to $V^1$ or $V^2$.)

In Formulae (5-1) to (5-8), each $R^6$ independently represents a hydrogen atom or a substituent, and two or more groups represented by $R^6$ may be the same as or different from each other. Examples of the substituent which can be adopted as $R^6$ include those exemplified above as substituents which can be adopted as $R^5$ to $R^9$ in Formulae (4-1) to (4-3), and the preferred range thereof is also the same.

In Formula (1-1), $V^1$ represents a divalent linking group. From the viewpoint of improving the solubility, it is preferable that $V^1$ does not form a condensed ring together with $Ar^1$ or $Ar^2$. The divalent linking group which can be adopted as $V^1$ is not particularly limited, but is preferably represented by any of the following Formulae (V-1) to (V-17).

(V-1)

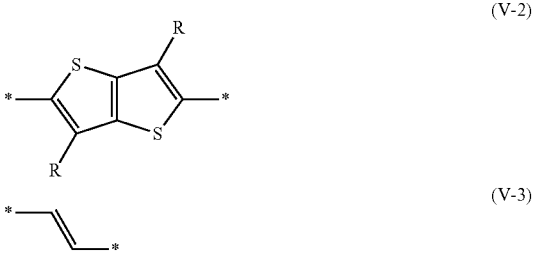
(V-2)

(V-3)

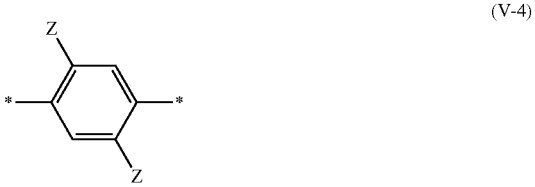
(V-4)

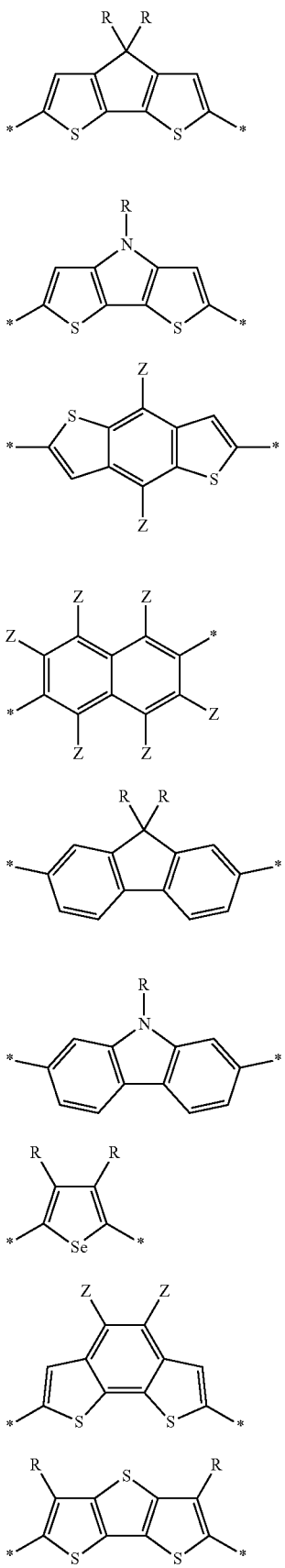
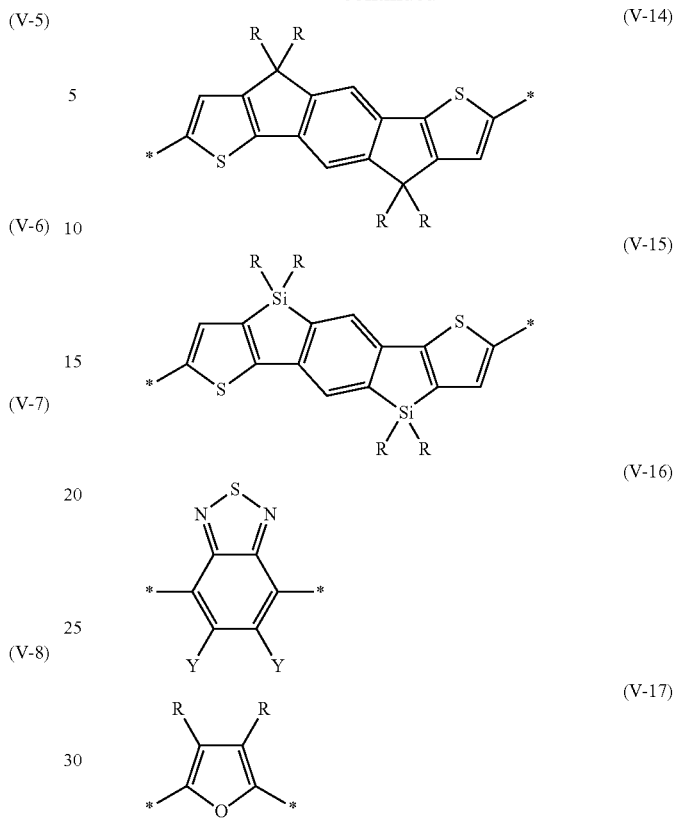

(In Formulae (V-1) to (V-17), * represents a position where the divalent linking group is bonded to any of Ar¹ and Ar² when p is 1, and represents a position where the divalent linking group is bonded to any of Ar¹, Ar², and the divalent linking groups represented by Formulae (V-1) to (V-17) when m or p is equal to or greater than 2; each R in Formulae (V-1), (V-2), (V-5), (V-6), (V-9) to (V-11), (V-13) to (V-15), and (V-17) independently represents a hydrogen atom or an alkyl group; the groups adjacent to each other represented by R may form a ring by being bonded to each other; each Z in Formulae (V-4), (V-7), (V-8), and (V-12) independently represents a hydrogen atom, an alkyl group, or an alkoxy group; the groups adjacent to each other represented by Z may form a ring by being bonded to each other; each Y in Formula (V-16) independently represents a hydrogen atom, an alkyl group, an alkoxy group, a CN group, or an F atom; and the groups adjacent to each other represented by Y may form a ring by being bonded to each other.)

Each R in Formulae (V-1), (V-2), (V-5), (V-6), (V-9) to (V-11), (V-13) to (V-15), and (V-17) independently represents a hydrogen atom or an alkyl group, and the groups adjacent to each other represented by R may form a ring by being bonded to each other. Examples of the alkyl group which can be adopted as R include the alkyl group which can be adopted as $R^5$ to $R^9$ in Formulae (4-1) to (4-3). Furthermore, the preferred range of the alkyl group which can be adopted as R is the same as the preferred range of the alkyl group which can be adopted as $R^5$ to $R^9$.

Each Z in Formulae (V-4), (V-7), (V-8), and (V-12) independently represents a hydrogen atom, an alkyl group, or an alkoxy group, and the groups adjacent to each other represented by Z may form a ring by being bonded to each other. Examples of the alkyl group or the alkoxy group which can be adopted as Z include the alkyl group and the alkoxy group which can be adopted as $R^5$ to $R^9$ in Formulae (4-1) to (4-3). Furthermore, the preferred range of the alkyl group and the alkoxy group which can be adopted as Z is the same as the preferred range of the alkyl group and the alkoxy group which can be adopted as $R^5$ to $R^9$.

Each Y in Formula (V-16) independently represents a hydrogen atom, an alkyl group, an alkoxy group, a CN group, or an F atom, and the groups adjacent to each other represented by Y may form a ring by being bonded to each other. Y is preferably an alkyl group or an alkoxy group. Examples of the alkyl group or the alkoxy group which can be adopted as Y include the alkyl group and the alkoxy group exemplified above as the substituent which can be adopted as $R^5$ to $R^9$ in Formulae (4-1) to (4-3), and the preferred range thereof is also the same.

Among the divalent linking groups represented by Formulae (V-1) to (V-17), the divalent linking groups represented by Formulae (V-1) to (V-8) and (V-11) to (V-15) are preferable, and the divalent linking groups represented by Formulae (V-1) to (V-3) are more preferable.

In Formula (1-1), m represents an integer of 0 to 6. When m is equal to or greater than 2, two or more groups represented by $V^1$ may be the same as or different from each other. m is preferably an integer of 0 to 5, and more preferably 0 to 3.

In Formula (1-1), n represents an integer of equal to or greater than 2. n is preferably equal to or greater than 10, more preferably equal to or greater than 30, and particularly preferably equal to or greater than 50. The greater the value of n, the further the interaction between π-conjugated polymer chains can be improved, and thus the carrier mobility can be improved. The upper limit of n is not particularly limited, but it is preferably equal to or less than 1,000 and more preferably equal to or less than 500.

<<Compound Composed of n Repeating Units Represented by Formula (1-2)>>

The compound composed of n repeating units represented by Formula (1-2) is represented by the following formula.

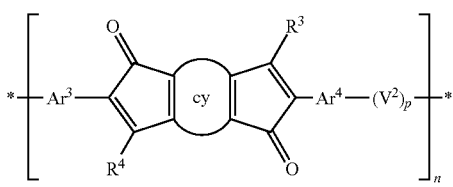

Formula (1-2)

(In Formula (1-2), cy represents a naphthalene ring or an anthracene ring; each of $R^3$ and $R^4$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2.)

In Formula (1-2), each of $R^3$ and $R^4$ independently represents a hydrogen atom or a substituent. The substituent which can be adopted as $R^3$ and $R^4$ is the same as the substituent which can be adopted as $R^1$ and $R^2$ in Formula (1-1). Each of $R^3$ and $R^4$ is independently preferably any of a hydrogen atom, an alkyl group, an aryl group, an alkenyl group, an alkynyl group, a hetero ring group, an alkoxy group, an alkylthio group, and a group represented by Formula (W), more preferably any of a hydrogen atom, an alkyl group having 1 to 12 carbon atoms, and an alkoxy group having 1 to 11 carbon atoms, particularly preferably any of a hydrogen atom, an alkyl group having 1 to 3 carbon atoms, and an alkoxy group having 1 to 3 carbon atoms from the viewpoint of obtaining high carrier mobility by suppressing bulkiness of $R^3$ and $R^4$ without deteriorating the intermolecular interaction, further particularly preferably any of a hydrogen atom, a methyl group, and an ethoxy group, and most preferably a hydrogen atom.

In Formula (1-2), each of $Ar^3$ and $Ar^4$ independently represents a heteroarylene group or an arylene group. From the viewpoint of improving the solubility, it is preferable that $Ar^3$ and $R^4$ do not form a condensed ring by being bonded to each other. In addition, from the viewpoint of improving the solubility, it is preferable that $Ar^4$ and $R^3$ do not form a condensed ring by being bonded to each other. The heteroarylene group or the arylene group which can be adopted as $Ar^3$ and $Ar^4$ is the same as the heteroarylene group or the arylene group which can be adopted as $Ar^1$ and $Ar^2$ in Formula (1-1), and the preferred range thereof is also the same.

In Formula (1-2), $V^2$ represents a divalent linking group. From the viewpoint of improving the solubility, it is preferable that $V^2$ does not form a condensed ring together with $Ar^3$ or $Ar^4$. The divalent linking group which can be adopted as $V^2$ is the same as the divalent linking group which can be adopted as $V^1$ in Formula (1-1), and the preferred range thereof is also the same. Here, when m or p is 1, * in Formulae (V-1) to (V-17) represents a position where the divalent linking group is bonded to any of $Ar^3$ and $Ar^4$, and when m or p is equal to or greater than 2, * in Formulae (V-1) to (V-17) represents a position where the divalent linking group is bonded to any of $Ar^3$, $Ar^4$, and the divalent linking groups represented by Formulae (V-1) to (V-17).

In Formula (1-2), p represents an integer of 0 to 6. When p is equal to or greater than 2, two or more groups represented by $V^2$ may be the same as or different from each other. p has the same definition as m in Formula (1-1), and the preferred range thereof is also the same.

In Formula (1-2), n represents an integer of equal to or greater than 2. n has the same definition as n in Formula (1-1), and the preferred range thereof is also the same.

In Formula (1-2), cy represents a naphthalene ring or an anthracene ring. The site where the naphthalene ring and the anthracene ring are condensed with a cyclopentadienone ring is not particularly limited. Specifically, it is preferable that the naphthalene ring or the anthracene ring is condensed such that the compound composed of n repeating units represented by Formula (1-2) has a rotationally symmetric skeleton. It is more preferable that the naphthalene ring or the anthracene ring is condensed so as to form a compound composed of n repeating units represented by the following Formula (2-1), (2-2), (2-3), (2-4), or (2-5).

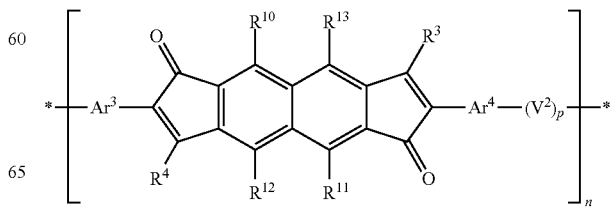

Formula (2-1)

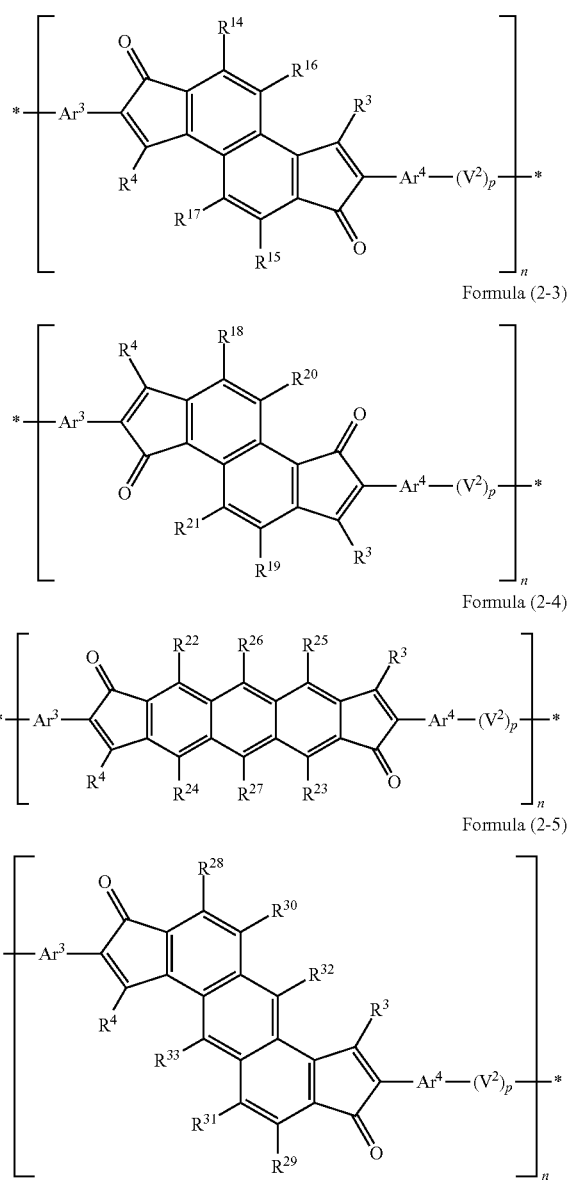

Formula (2-2)

Formula (2-3)

Formula (2-4)

Formula (2-5)

(In Formulae (2-1) to (2-5), each of $R^3$, $R^4$, and $R^{10}$ to $R^{33}$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2.)

In Formulae (2-1) to (2-5), each of $R^3$, $R^4$, and $R^{10}$ to $R^{33}$ independently represents a hydrogen atom or a substituent.

The substituent which can be adopted as $R^3$ and $R^4$ in Formulae (2-1) to (2-5) is the same as the substituent which can be adopted as $R^3$ and $R^4$ in Formula (1-2), and the preferred range thereof is also the same.

The substituent which can be adopted as $R^{10}$ to $R^{33}$ in Formulae (2-1) to (2-5) is the same as the substituent which can be adopted as $R^1$ and $R^2$ in Formula (1-1). Each of $R^{10}$ to $R^{33}$ is independently preferably any of a hydrogen atom, an alkyl group, an aryl group, an alkenyl group, an alkynyl group, an alkoxy group, a hetero ring group, an alkylthio group, an amino group, and a group represented by Formula (W), and more preferably any of a hydrogen atom, an alkyl group having 3 to 40 carbon atoms, an aryl group having 6 to 20 carbon atoms, an alkenyl group having 2 to 12 carbon atoms, an alkynyl group having 2 to 12 carbon atoms, an alkoxy group having 3 to 40 carbon atoms, a hetero ring group having 5 to 12 carbon atoms, an alkylthio group having 1 to 12 carbon atoms, an amino group substituted with an alkyl group having 1 to 12 carbon atoms, and a group represented by Formula (W). Furthermore, each of $R^{10}$ to $R^{33}$ is preferably a branched substituent in which a linear substituent further has a substituent.

The alkyl group which can be adopted as $R^{10}$ to $R^{33}$ is more preferably an alkyl group having 3 to 40 carbon atoms, even more preferably an alkyl group having 10 to 30 carbon atoms from the viewpoint of the chemical stability and the carrier transport properties, and particularly preferably an alkyl group having 15 to 30 carbon atoms. Furthermore, the alkyl group which can be adopted as $R^{10}$ to $R^{33}$ is preferably a linear or branched alkyl group, and more preferably a branched alkyl group from the viewpoint of improving the carrier mobility and the solubility in a solvent without deteriorating the intramolecular hydrogen bonding properties.

The alkoxy group which can be adopted as $R^{10}$ to $R^{33}$ is preferably an alkoxy group having 3 to 40 carbon atoms, more preferably an alkoxy group having 10 to 30 carbon atoms from the viewpoint of the chemical stability and the carrier transport properties, and particularly preferably an alkoxy group having 15 to 30 carbon atoms. Furthermore, the alkoxy group which can be adopted as $R^{10}$ to $R^{33}$ is preferably a linear or branched alkoxy group, and more preferably a branched alkoxy group from the viewpoint of improving the carrier mobility and the solubility in a solvent without deteriorating the intramolecular hydrogen bonding properties.

It is preferable that at least one of $R^3$, $R^4$, $R^{10}$, $R^{11}$, $R^{12}$, and $R^{13}$ in Formula (2-1) is a group represented by Formula (W). More preferably, at least one of $R^{10}$, $R^{11}$, $R^{12}$, and $R^{13}$ is a group represented by Formula (W) while none of $R^3$ and $R^4$ are groups represented by Formula (W). Even more preferably, one or two out of $R^{10}$, $R^{11}$, $R^{12}$, and $R^{13}$ are groups represented by Formula (W) while none of $R^3$ and $R^4$ are groups represented by Formula (W). Particularly preferably, two out of $R^{10}$, $R^{11}$, $R^{12}$, and $R^{13}$ are groups represented by Formula (W) while none of $R^3$ and $R^4$ are groups represented by Formula (W).

It is preferable that at least one of $R^3$, $R^4$, $R^{14}$, $R^{15}$, $R^{16}$, and $R^{17}$ in Formula (2-2) is a group represented by Formula (W). More preferably, at least one of $R^{14}$, $R^{15}$, $R^{16}$, and $R^{17}$ is a group represented by Formula (W) while none of R3 and R4 are groups represented by Formula (W). Even more preferably, at least one or two out of $R^{14}$, $R^{15}$, $R^{16}$, and $R^{17}$ are groups represented by Formula (W) while none of R3 and R4 are groups represented by Formula (W). Particularly preferably, at least two out of $R^{14}$, $R^{15}$, $R^{16}$, and $R^{17}$ are groups represented by Formula (W) while none of R3 and R4 are groups represented by Formula (W).

It is preferable that at least one of $R^3$, $R^4$, $R^{18}$, $R^{19}$, $R^{20}$, and $R^{21}$ in Formula (2-3) is a group represented by Formula (W). More preferably, at least one of $R^{18}$, $R^{19}$, $R^{20}$, and $R^{21}$ is a group represented by Formula (W) while none of $R^3$ and $R^4$ are groups represented by Formula (W). Even more preferably, at least one or two out of $R^{18}$, $R^{19}$, $R^{20}$, and $R^{21}$ are groups represented by Formula (W) while none of $R^3$ and $R^4$ are groups represented by Formula (W). Particularly preferably, at least two out of $R^{18}$, $R^{19}$, $R^{20}$, and $R^{21}$ are groups represented by Formula (W) while none of $R^3$ and $R^4$ are groups represented by Formula (W).

It is preferable that at least one of $R^3$, $R^4$, $R^{22}$, $R^{23}$, $R^{24}$, $R^{25}$, $R^{26}$, and $R^{27}$ in Formula (2-4) is a group represented by Formula (W). More preferably, at least one of $R^{22}$, $R^{23}$, $R^{24}$, $R^{25}$, $R^{26}$, and $R^{27}$ is a group represented by Formula (W) while none of $R^3$ and $R^4$ are groups represented by Formula (W). Even more preferably, at least two to four out of $R^{22}$, $R^{23}$, $R^{24}$, $R^{25}$, $R^{26}$, and $R^{27}$ are groups represented by Formula (W) while none of $R^3$ and $R^4$ are groups represented by Formula (W). Particularly preferably, at least two out of $R^{22}$, $R^{23}$, $R^{24}$, $R^{25}$, $R^{26}$, and $R^{27}$ are groups represented by Formula (W) while none of $R^3$ and $R^4$ are groups represented by Formula (W).

It is preferable that at least one of $R^3$, $R^4$, $R^{28}$, $R^{29}$, $R^{30}$, $R^{31}$, $R^{32}$, and $R^{33}$ in Formula (2-5) is a group represented by Formula (W). More preferably, at least one of $R^{28}$, $R^{29}$, $R^{39}$, $R^{31}$, $R^{32}$, and $R^{33}$ is a group represented by Formula (W) while none of $R^3$ and $R^4$ are groups represented by Formula (W). Even more preferably, two to four out of $R^{28}$, $R^{29}$, $R^{30}$, $R^{31}$, $R^{32}$, and $R^{33}$ are groups represented by Formula (W) while none of $R^3$ and $R^4$ are groups represented by Formula (W). Particularly preferably, at least two out of $R^{28}$, $R^{29}$, $R^{39}$, $R^{31}$, $R^{32}$, and $R^{33}$ are groups represented by Formula (W) while none of $R^3$ and $R^4$ are groups represented by Formula (W).

In Formulae (2-1) to (2-5), each of $Ar^3$ and $Ar^4$ independently represents a heteroarylene group or an arylene group. The heteroarylene group or the arylene group which can be adopted as $Ar^3$ and $Ar^4$ is the same as the heteroarylene group or the arylene group which can be adopted as $Ar^3$ and $Ar^4$ in Formula (1-2), and the preferred range thereof is also the same.

In Formulae (2-1) to (2-5), $V^2$ represents a divalent linking group. The divalent linking group which can be adopted as $V^2$ is the same as the divalent linking group which can be adopted as $V^2$ in Formula (1-2), and the preferred range thereof is also the same.

In Formulae (2-1) to (2-5), p represents an integer of 0 to 6. When p is equal to or greater than 2, two or more groups represented by $V^2$ may be the same as or different from each other. p in Formulae (2-1) to (2-5) has the same definition as p in Formula (1-2), and the preferred range thereof is also the same.

In Formulae (2-1) to (2-5), n represents an integer of equal to or greater than 2. n has the same definition as n in Formula (1-2), and the preferred range thereof is also the same.

From the viewpoint of high carrier mobility and high solubility in a solvent, the compound composed of n repeating units represented by Formula (1-2) is preferably a compound composed of n repeating units represented by any of Formulae (2-1) and (2-2).

Specific examples of the compound composed of n repeating units represented by Formula (1-1) or (1-2) will be shown below. However, the compound composed of n repeating units represented by Formula (1-1) or (1-2) that can be used in the present invention is not limited to the specific examples. In the following specific examples of the compound, the number n of the repeating unit is not described, and only the repeating unit is illustrated.

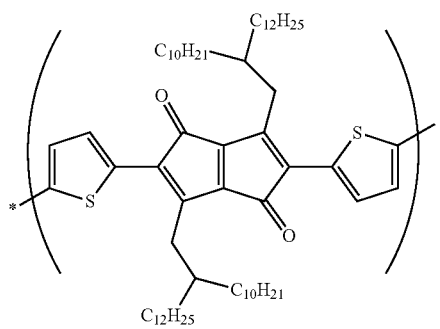

Compound 1

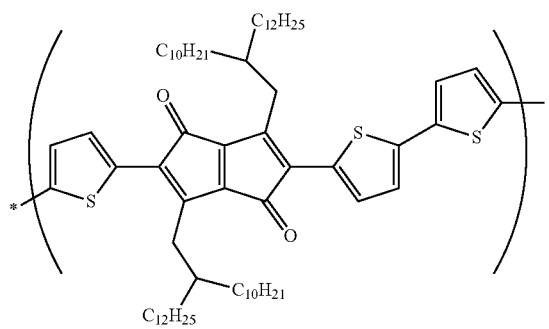

Compound 2

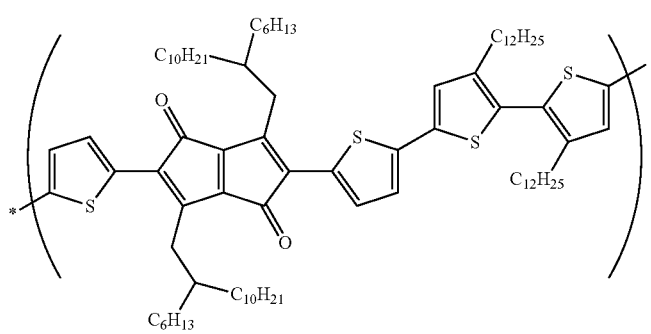

Compound 3

-continued
Compound 4
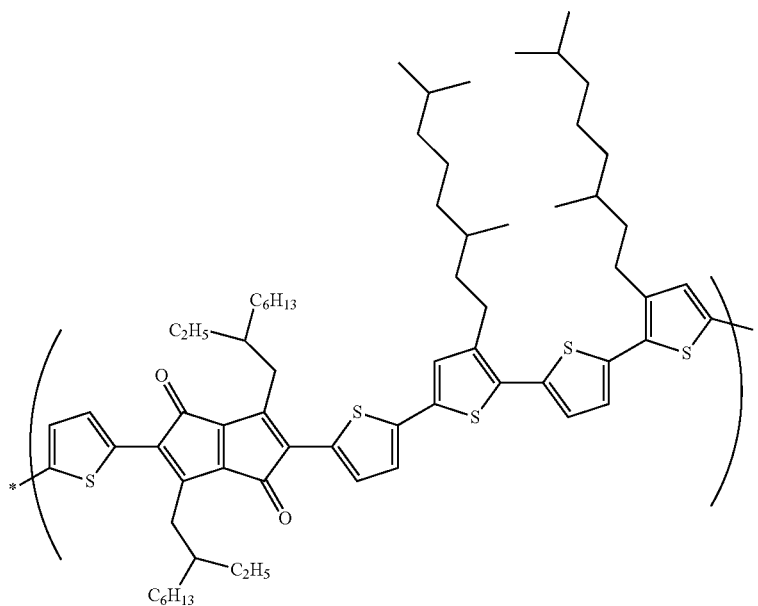
Compound 5
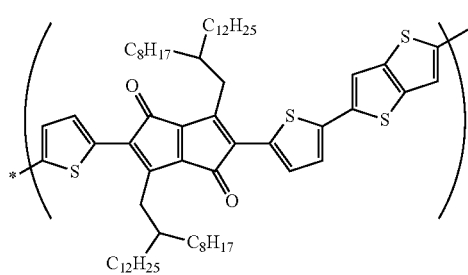
Compound 6
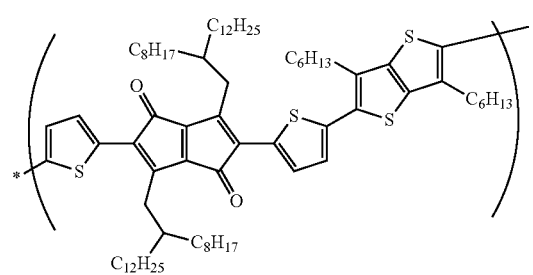
Compound 7
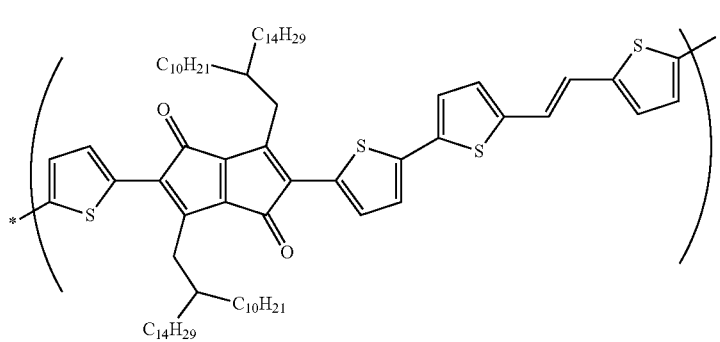
Compound 8
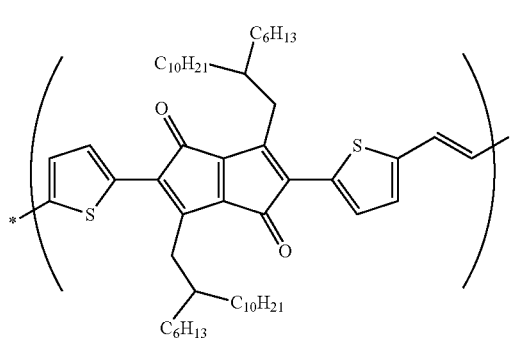

-continued
Compound 9
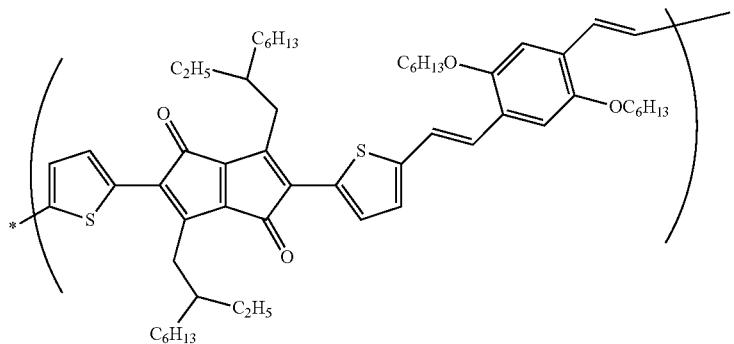
Compound 10
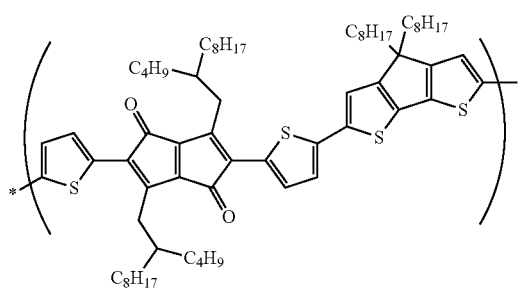
Compound 11
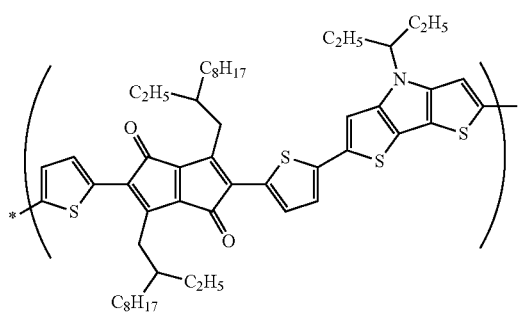
Compound 12
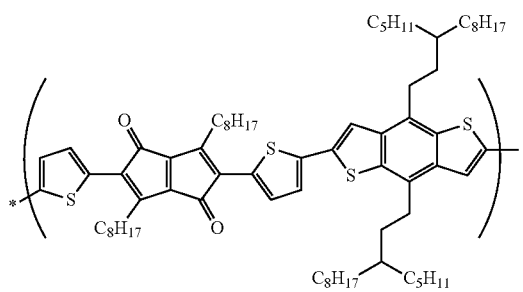
Compound 13
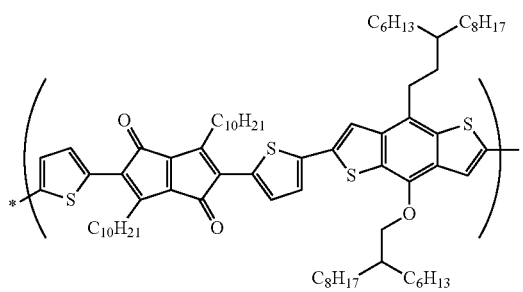
Compound 14
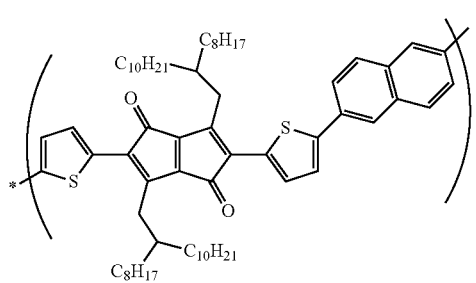
Compound 15
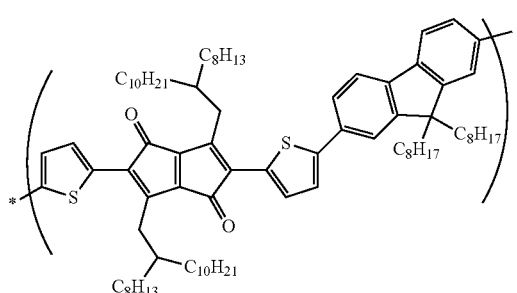
Compound 16
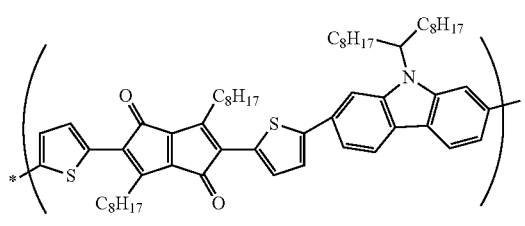
Compound 17
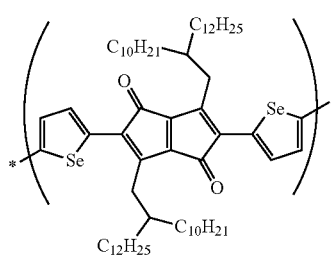

-continued
Compound 18
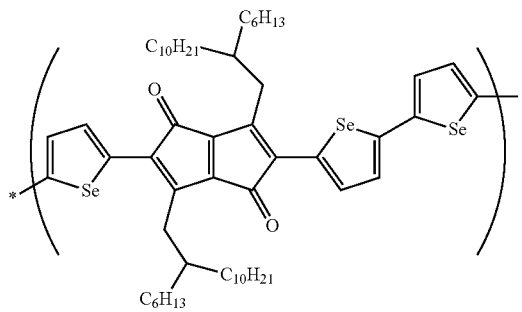
Compound 19
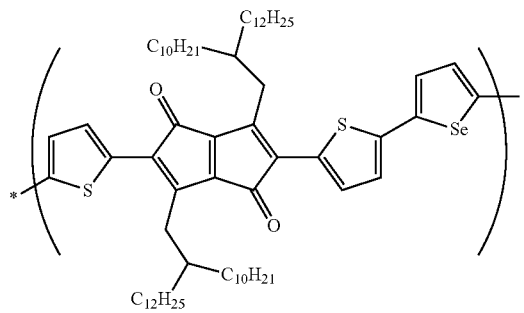
Compound 20
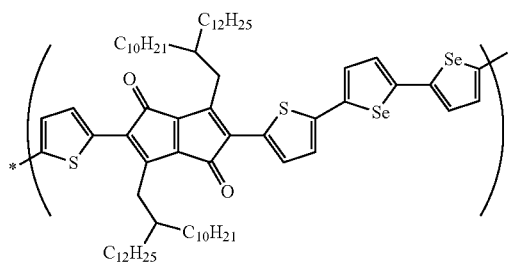
Compound 21
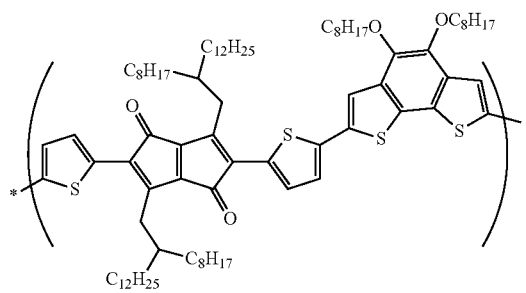
Compound 22
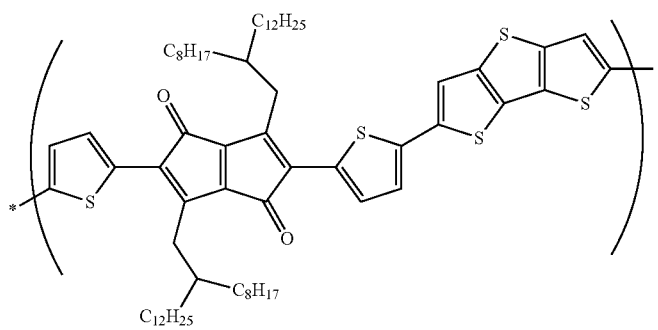
Compound 23
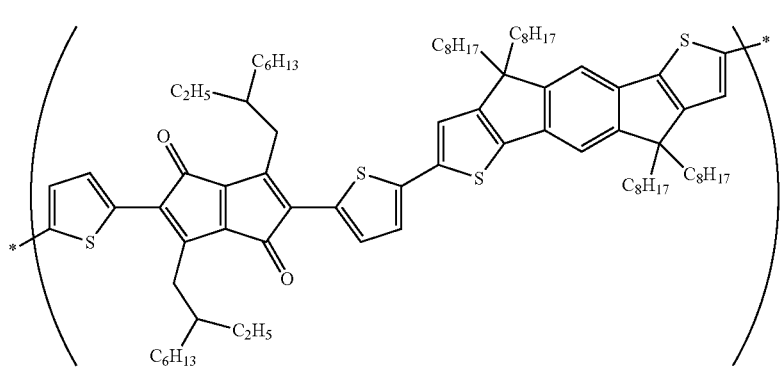

-continued
Compound 24
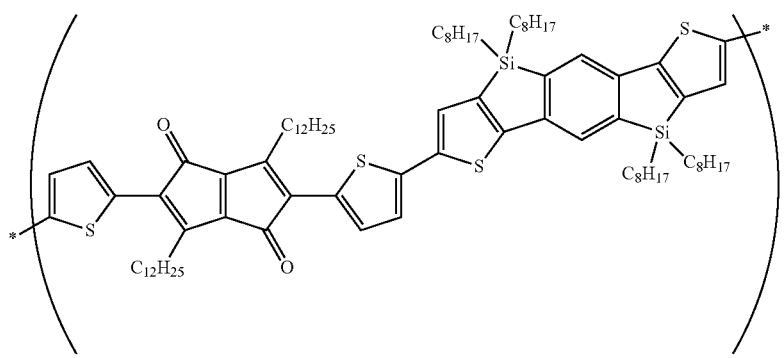
Compound 25
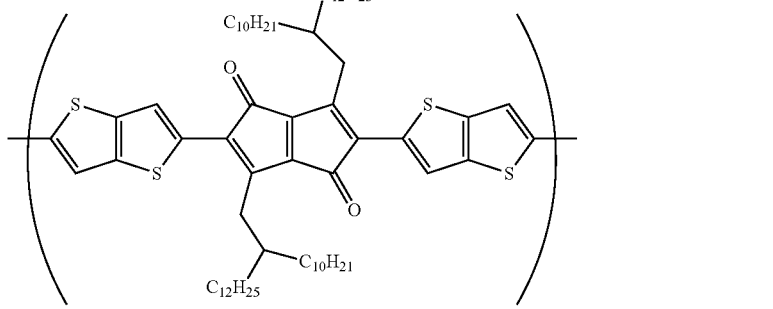
Compound 26
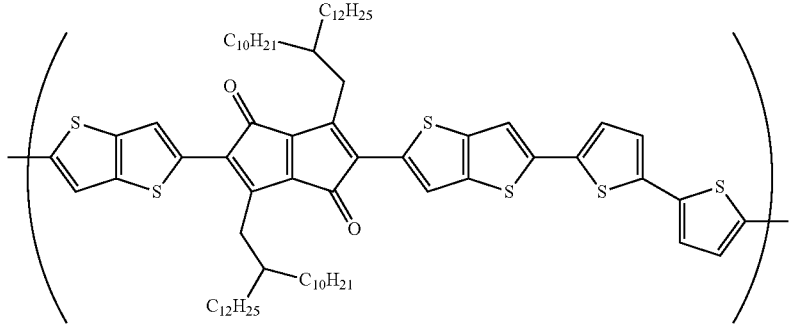
Compound 27
Compound 28
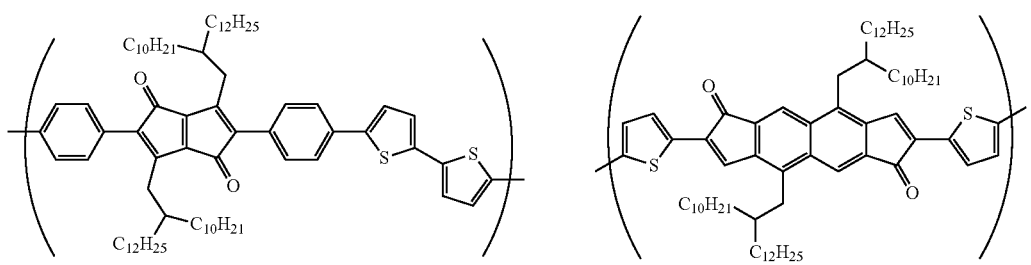
Compound 29
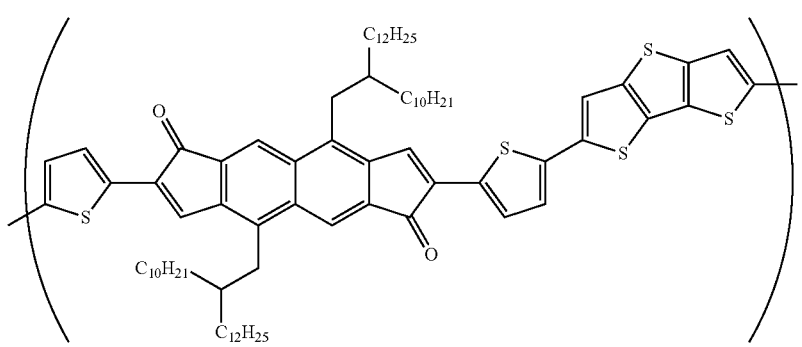

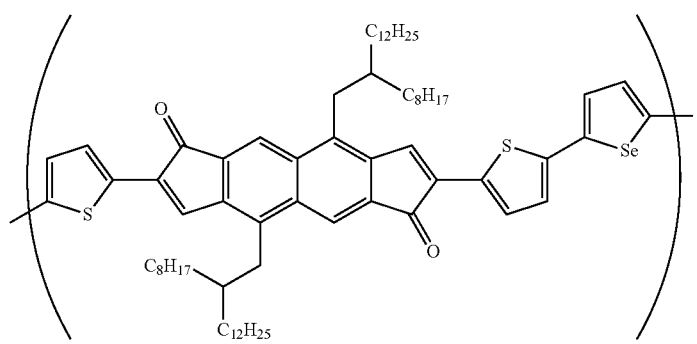
Compound 30
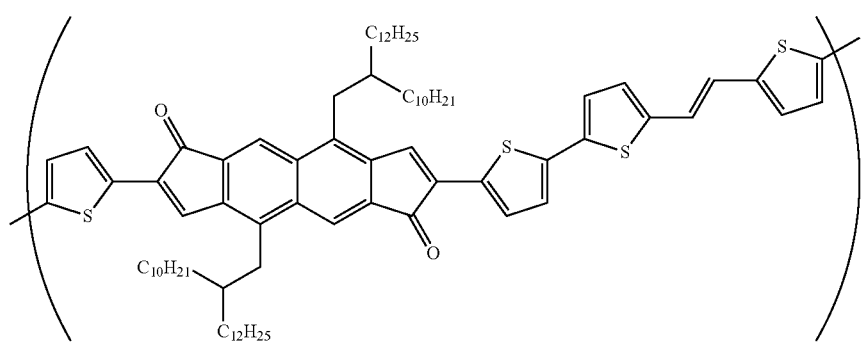
Compound 31
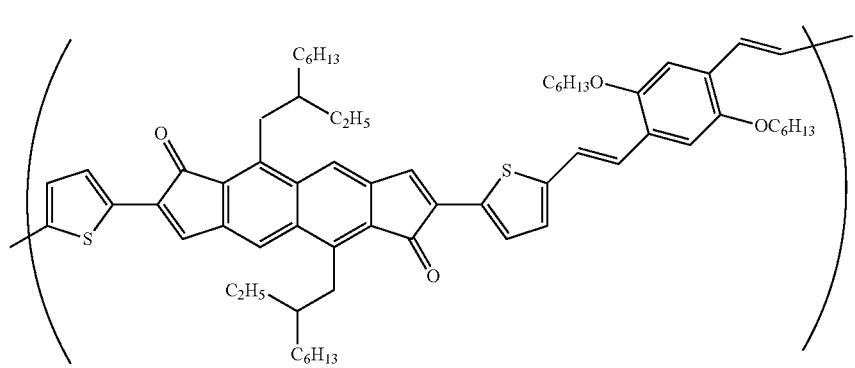
Compound 32
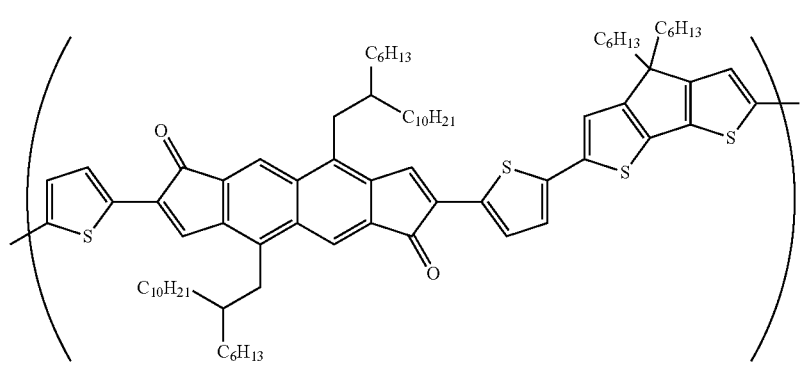
Compound 33

Compound 34
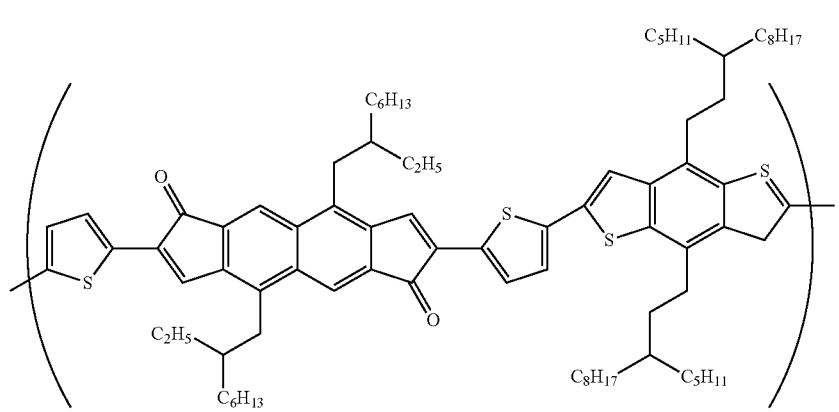
Compound 35
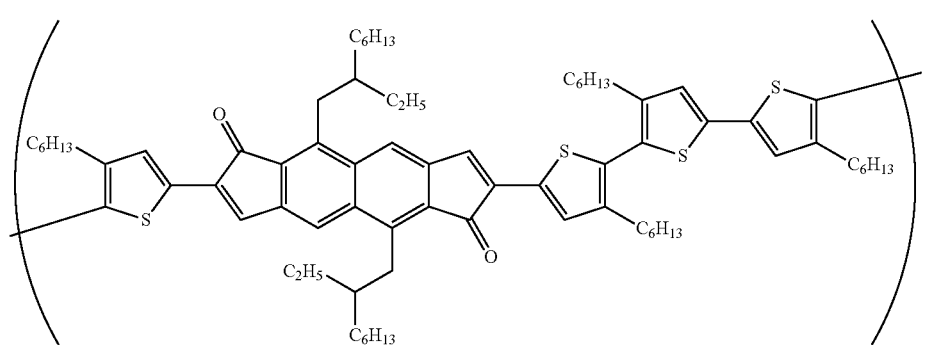
Compound 36
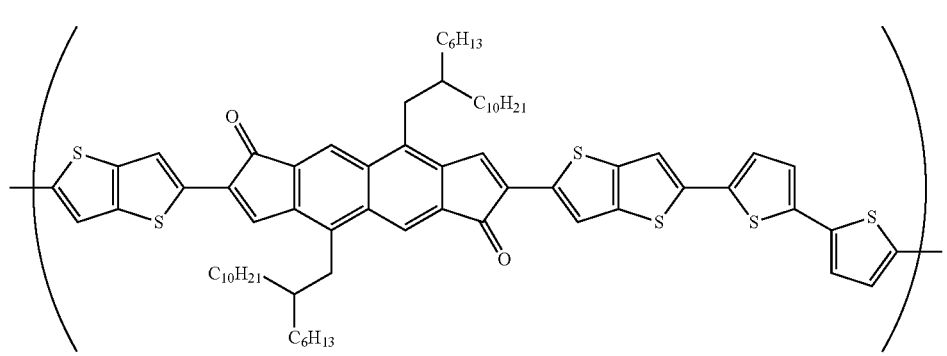
Compound 37
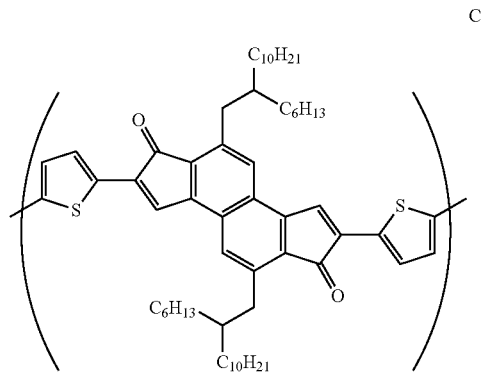
Compound 38
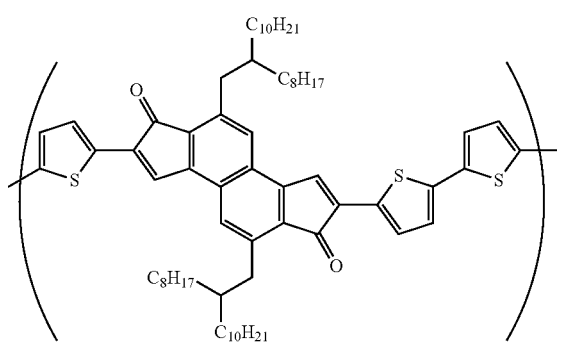

Compound 39
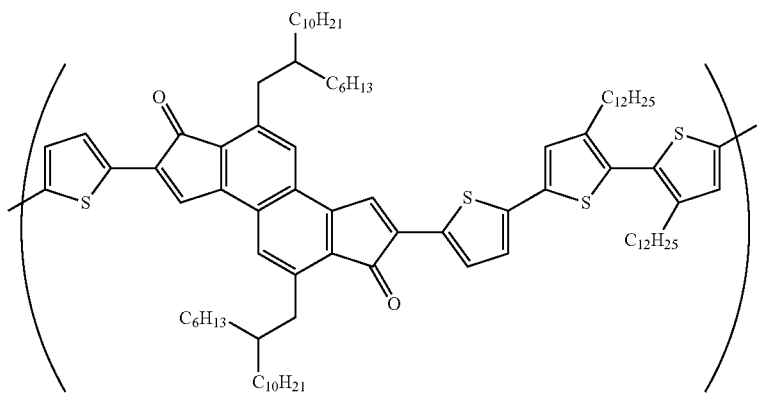
Compound 40
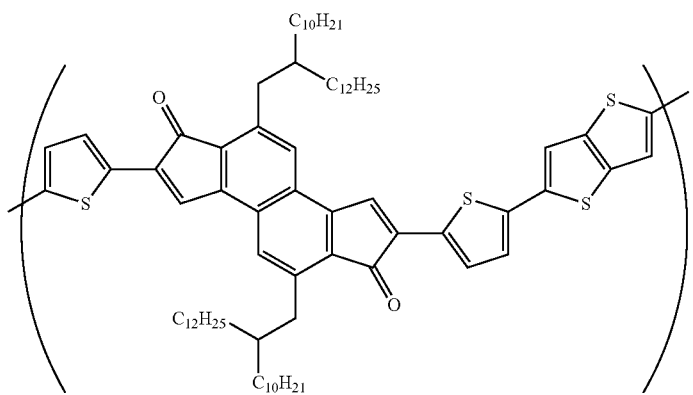
Compound 41
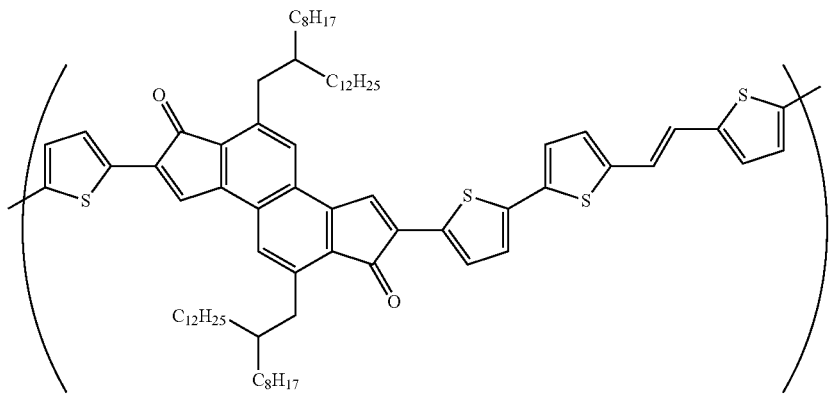
Compound 42
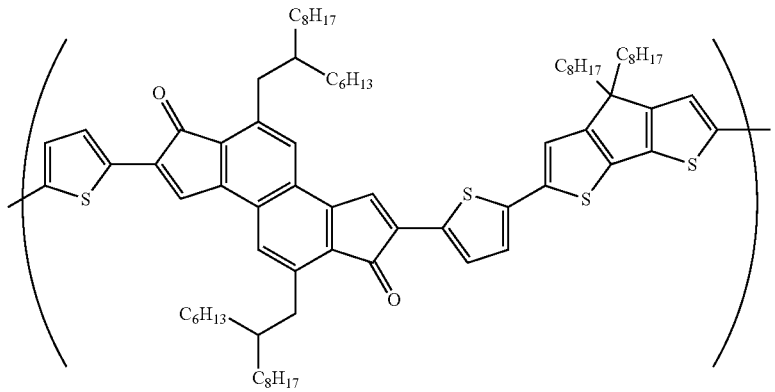

-continued
Compound 43
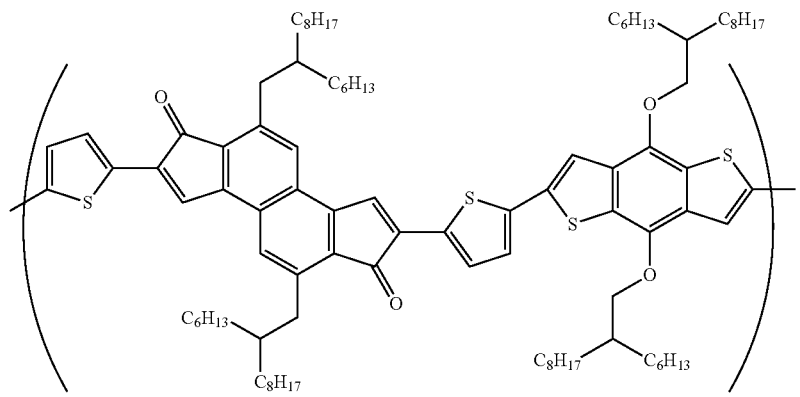
Compound 44
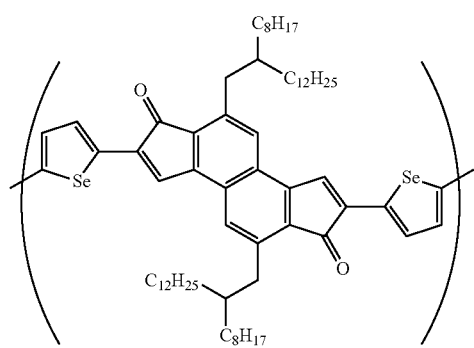
Compound 45
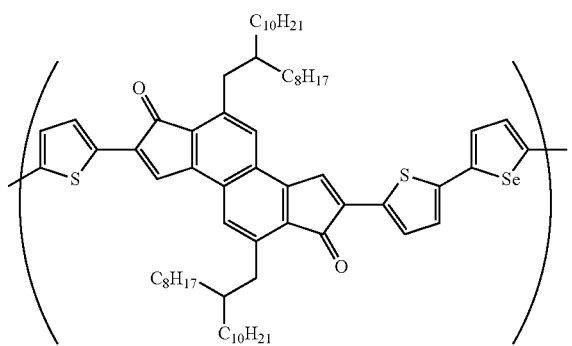
Compound 46
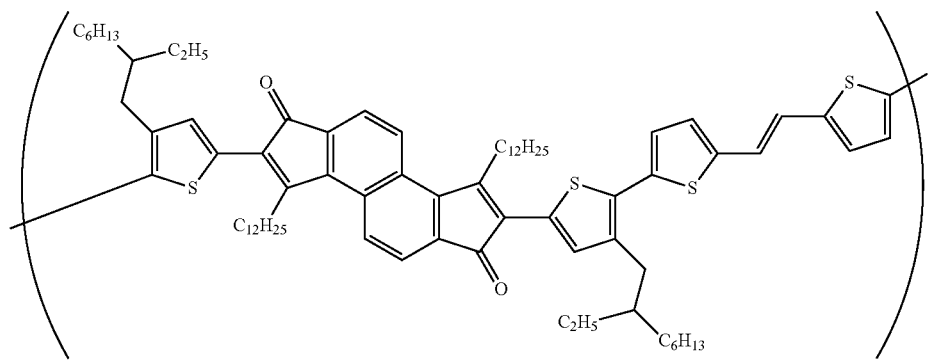
Compound 47
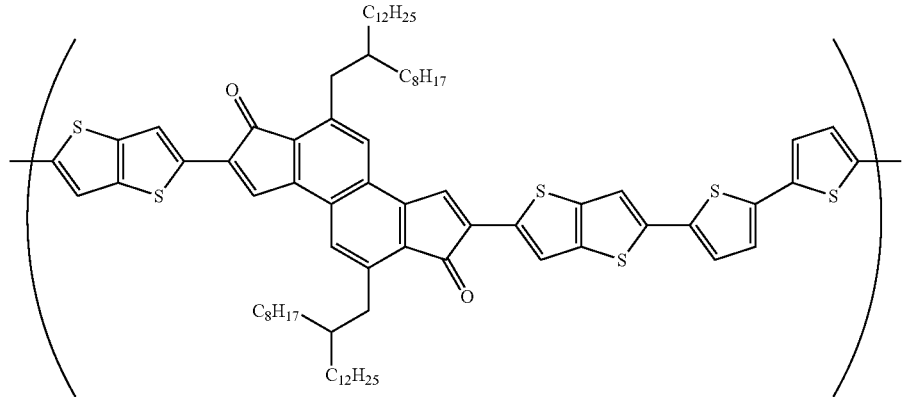

-continued
Compound 48
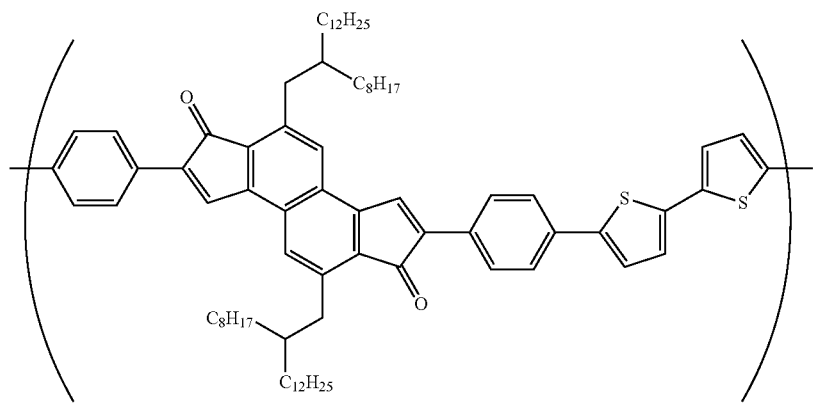
Compound 49
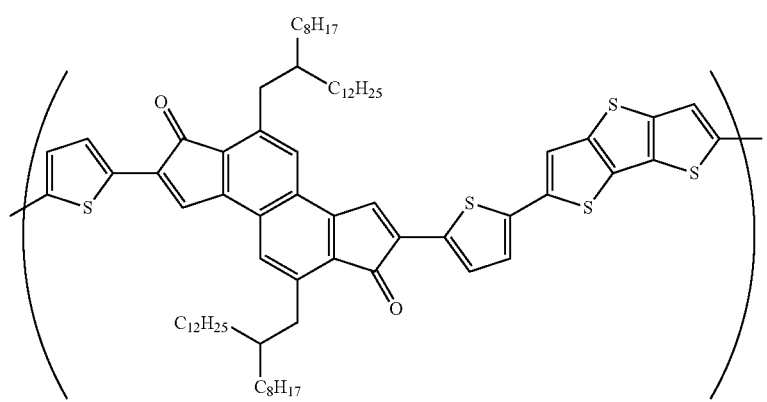
Compound 50
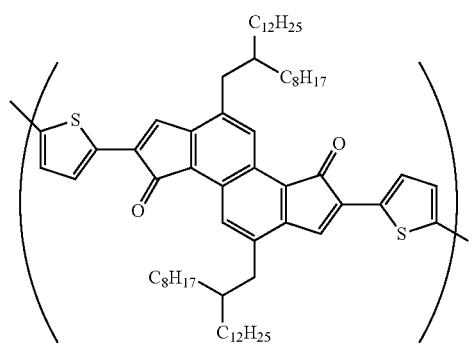
Compound 51
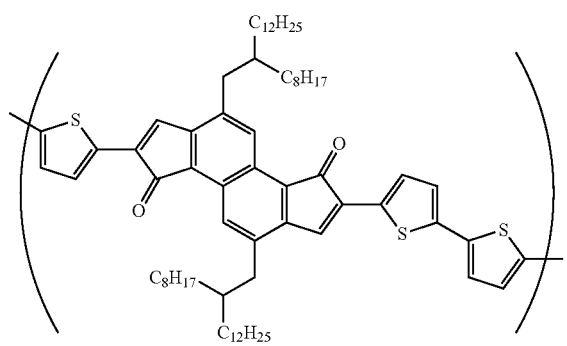
Compound 52
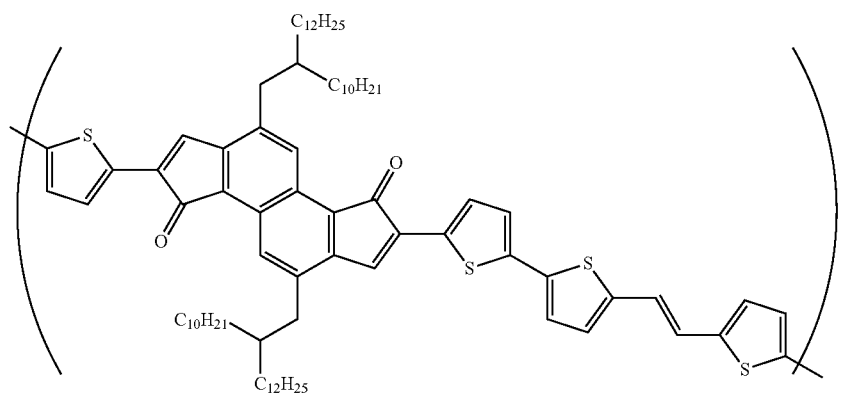

-continued
Compound 53
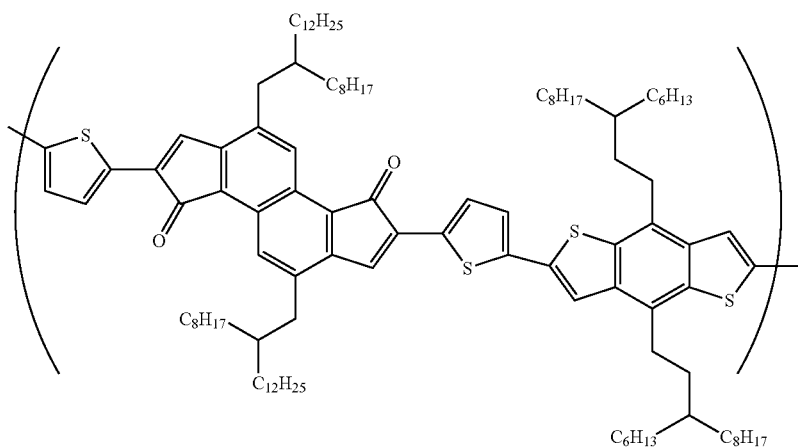
Compound 54
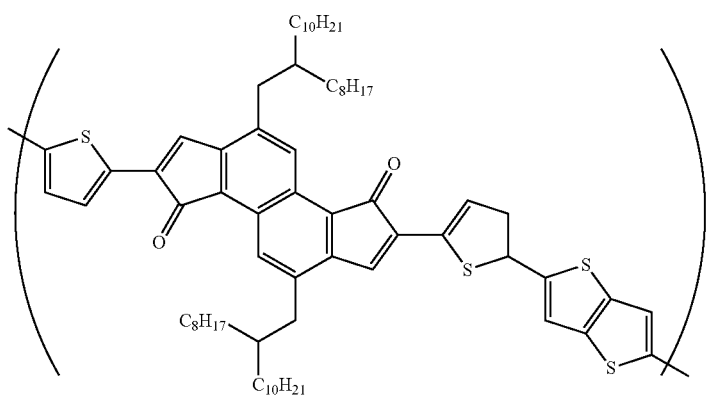
Compound 55
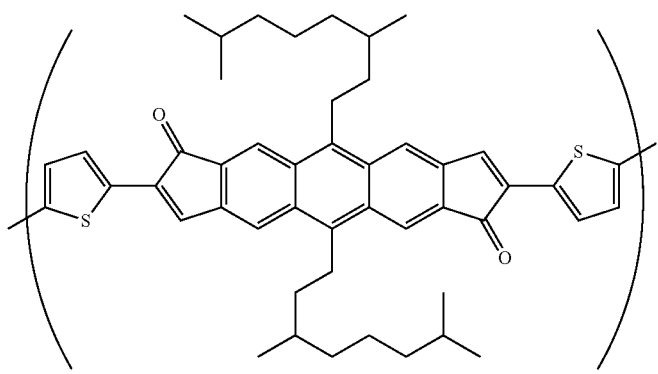
Compound 56
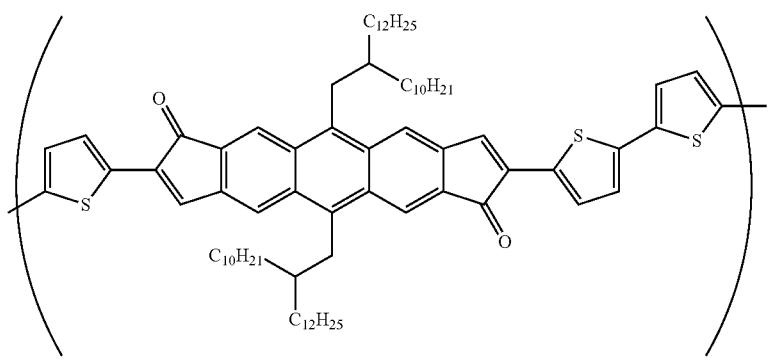

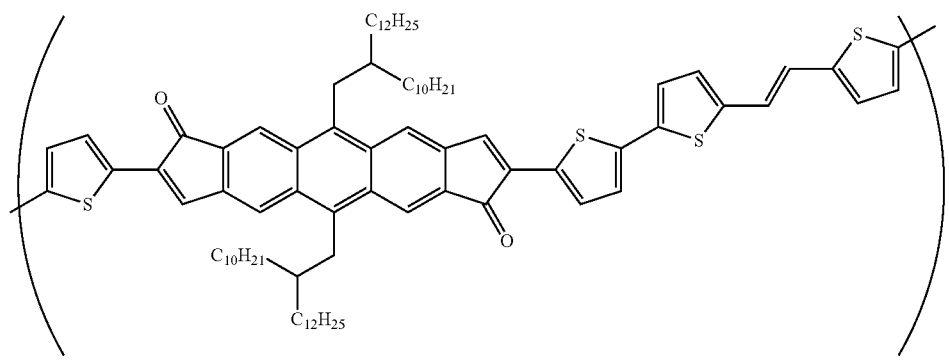
Compound 57
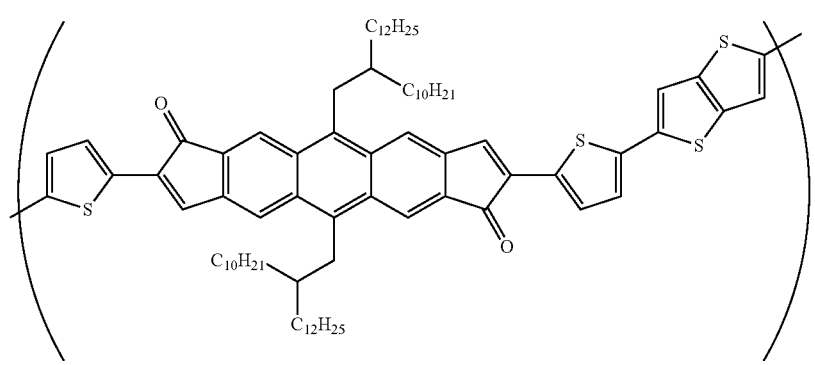
Compound 58
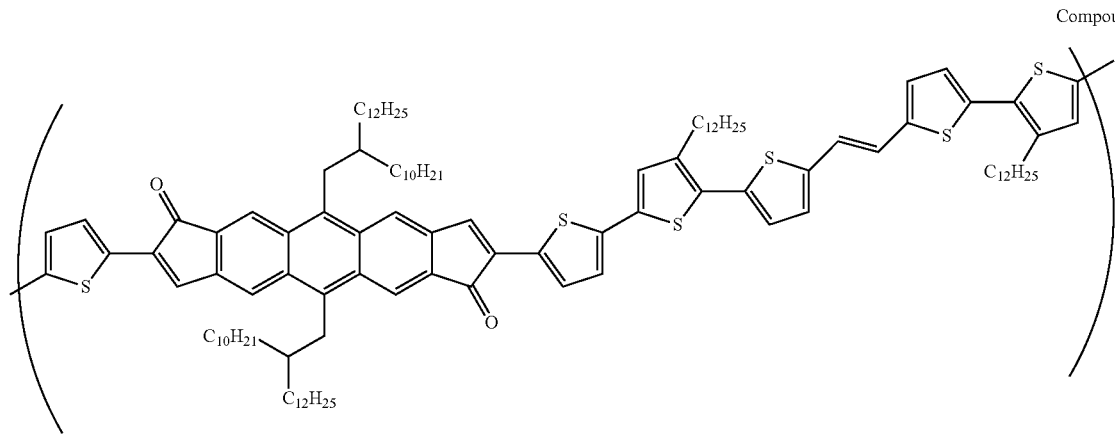
Compound 59
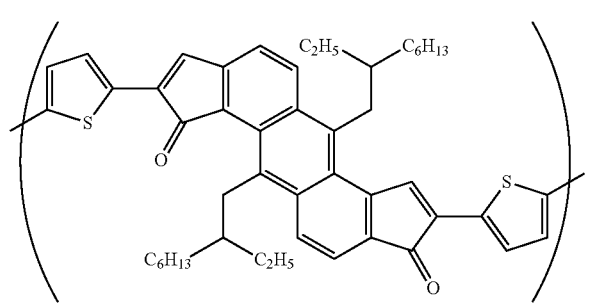
Compound 60

Compound 61
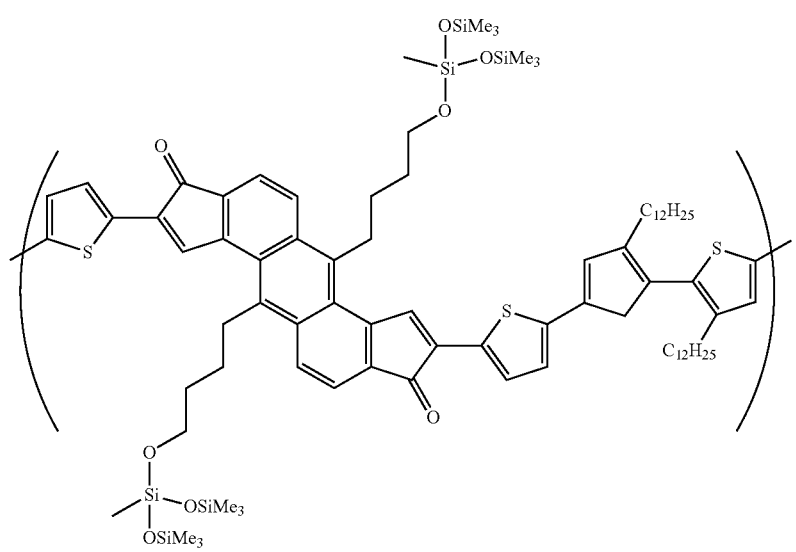
Compound 62
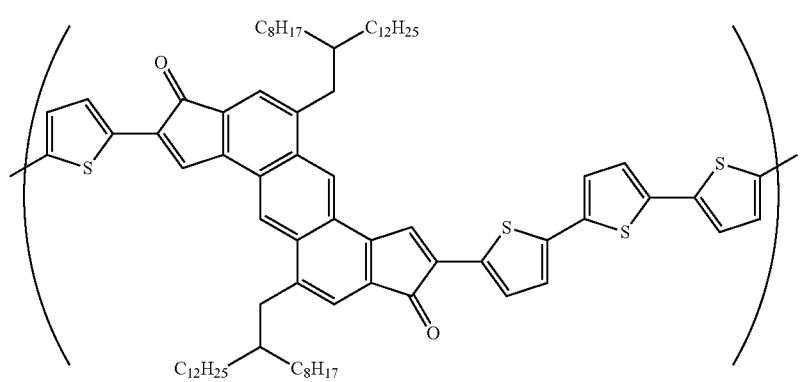
Compound 63
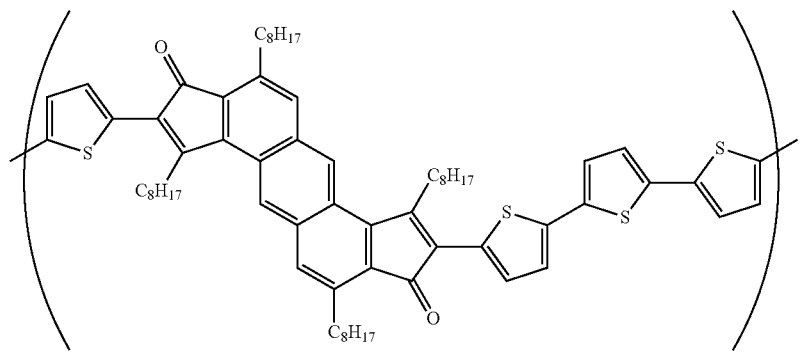
Compound 64
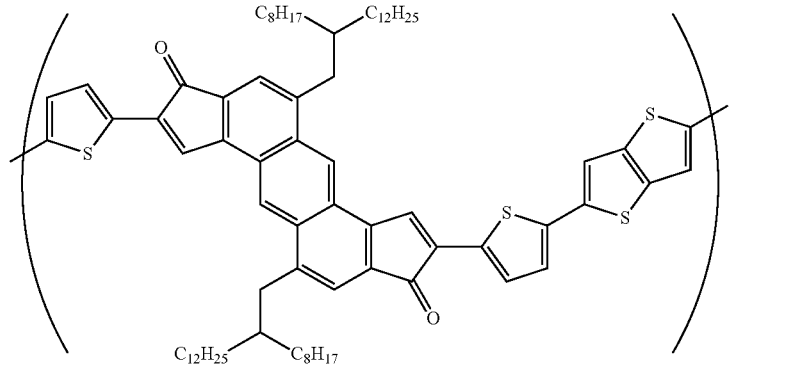

The compound composed of n repeating units represented by Formula (1-1) or (1-2) is a compound having two or more repeating units. The compound may be an oligomer in which the number n of the repeating units is 2 to 9 or a polymer in which the number n of the repeating units is equal to or greater than 10.

When the compound represented by Formula (1-1) or (1-2) is an oligomer having 2 to 9 repeating units, the molecular weight thereof is preferably equal to or greater than 2,000 and more preferably equal to or greater than 5,000.

When the compound represented by Formula (1-1) or (1-2) is a polymer compound, the weight average molecular weight thereof is preferably equal to or greater than 30,000, more preferably equal to or greater than 50,000, and particularly preferably equal to or greater than 100,000. The upper limit of the weight average molecular weight is not particularly limited, but it is preferably equal to or less than 1,000,000 and more preferably equal to or less than 750,000. It is preferable that the molecular weight is equal to or less than the upper limit described above, because the intermolecular interaction can be improved, the improved intermolecular interaction favors the transport of carriers, and the solubility in a solvent can also be maintained.

In the present invention, the weight average molecular weight is a value measured by gel permeation chromatography (GPC) using high-performance GPC (HLC-8220GPC) manufactured by TOSOH CORPORATION by means of dissolving a polymer in tetrahydrofuran (THF). In the present invention, the weight average molecular weight is a value expressed by using polystyrene as a standard substance.

The compound composed of n repeating units represented by Formula (1-1) or (1-2) can be synthesized with reference to U.S. Pat. No. 7,928,249B or the like.

For synthesizing the compound of the present invention, any reaction condition may be used. As a reaction solvent, any solvent may be used. Furthermore, in order to accelerate a ring-forming reaction, an acid or a base may be preferably used, and a base is particularly preferably used. The optimal reaction condition varies with the intended structure of the condensed cyclopentadienone, but can be set with reference to the specific reaction conditions described in the aforementioned document.

The synthetic intermediate having various substituents can be synthesized by using known reactions in combination. Furthermore, various substituents may be introduced at any stage of the intermediate. After the intermediate is synthesized, it is preferable to purify the intermediate by column chromatography, recrystallization, and the like.

<Compound Composed of n Repeating Unit Represented by Formula (101)>

A second preferred embodiment of the compound of the present invention is preferably composed of n repeating units represented by the following Formula (101). The compound of the present invention is contained in a semiconductor active layer, which will be described later, in the organic film transistor of the present invention. That is, the compound of the present invention can be used as a material for an organic film transistor.

The compound composed of n repeating units represented by Formula (101) is represented by the following Formula.

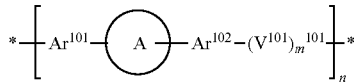

Formula (101)

In Formula (101), each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; n represents an integer of equal to or greater than 2; and A represents a divalent linking group represented by the following Formula (101'); and

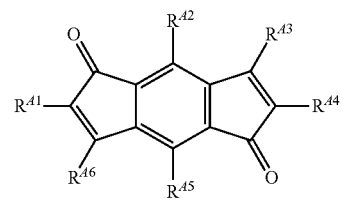

Formula (101')

in Formula (101'), each of $R^{41}$ to $R^{46}$ independently represents a hydrogen atom, a substituent, or a direct bond with $Ar^{101}$ or $Ar^{102}$ in Formula (101); and among the groups represented by $R^{41}$ to $R^{46}$, two different groups represent direct bonds with $Ar^{101}$ and $Ar^{102}$ in Formula (101) respectively.

In Formula (101'), each of $R^{41}$ to $R^{46}$ independently represents a hydrogen atom, a substituent, or a direct bond with $Ar^{101}$ or $Ar^{102}$ in Formula (101); and among the groups represented by $R^{41}$ to $R^{46}$, two different groups represent direct bonds with $Ar^{101}$ and $Ar^{102}$ in Formula (101) respectively. The substituent which can be adopted as $R^{41}$ to $R^{46}$ is not particularly limited, and examples thereof include a group represented by the following Formula ($W^{101}$) and the same substituents as the examples of the substituent which can be adopted as $R^5$ to $R^9$ in Formulae (102-1) to (102-3) which will be described later. The substituent which can be adopted as $R^{41}$ to $R^{46}$ is preferably a group represented by the following Formula ($W^{101}$). More preferably, any two groups represented by $R^{41}$ to $R^{46}$ are groups represented by the following Formula ($W^{101}$).

$$-L^{101}-R^{101}$$  Formula ($W^{101}$)

In Formula ($W^{101}$), $L^{101}$ represents a divalent linking group represented by any of the following Formulae (L-101) to (L-125) or a divalent linking group formed by bonding of two or more divalent linking groups represented by any of the following Formulae (L-101) to (L-125); $R^{101}$ represents a substituted or unsubstituted alkyl group, an oligo-oxyethylene group in which a repetition number v of an oxyethylene unit is equal to or greater than 2, an oligosiloxane group having two or more silicon atoms, or a substituted or unsubstituted silyl group; and $R^{101}$ represents a substituted or unsubstituted silyl group only when $L^{101}$ adjacent to $R^{101}$ is a divalent linking group represented by any of the following Formulae (L-101) to (L-103);

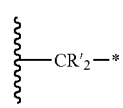

(L-101)

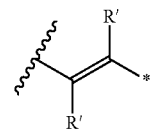

(L-102)

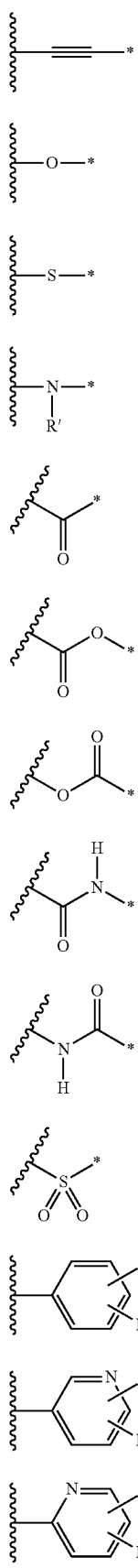
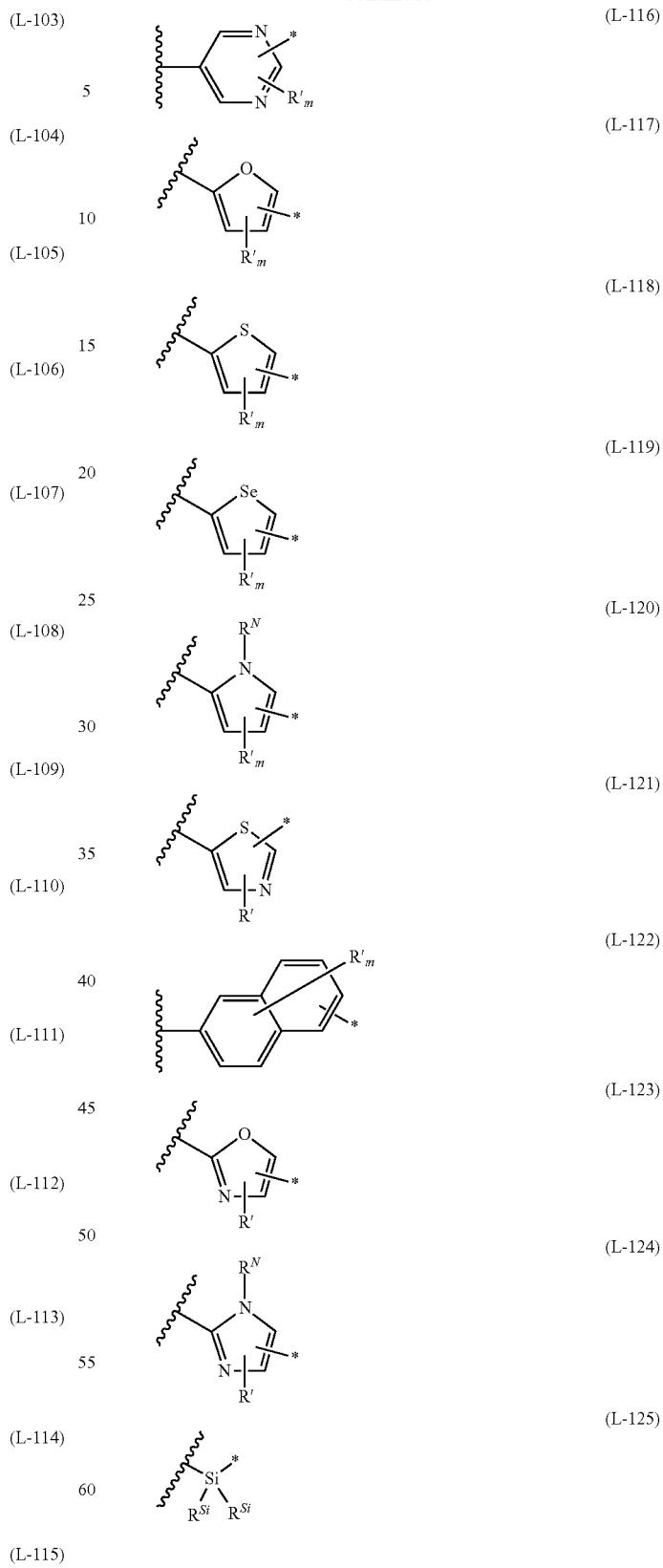
in Formulae (L-101) to (L-125), the portion of a wavy line represents a position where the divalent linking group is bonded to a cyclopentadienone skeleton; * represents a position where the divalent linking group is bonded to any of divalent linking groups represented by (L-101) to (L-125) and $R^{101}$; m in Formula (L-113) is 4; m in Formulae (L-114) and (L-115) is 3; m in Formulae (L-116) to (L-120) is 2; m in Formula (L-122) is 6; each R' in Formulae (L-101), (L-102), (L-106), and (L-113) to (L-124) independently represents a hydrogen atom or a substituent; $R^N$ represents a hydrogen atom or a substituent; and each $R^{si}$ independently represents a hydrogen atom, an alkyl group, an alkenyl group, or an alkynyl group.

Each R' in Formulae (L-101) and (L-102) may form a condensed ring by being bonded to R adjacent to L.

The divalent linking group represented by any of Formulae (L-119) to (L-121), (L-123), and (L-124) is more preferably a divalent linking group represented by any of the following Formulae (L-119A) to (L-121A), (L-123A), and (L-124A).

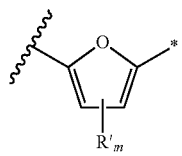
(L-117A)

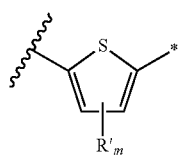
(L-118A)

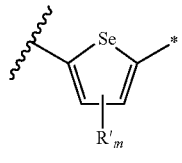
(L-119A)

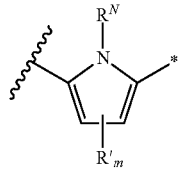
(L-120A)

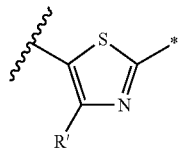
(L-121A)

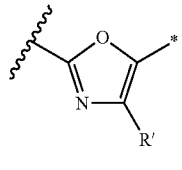
(L-123A)

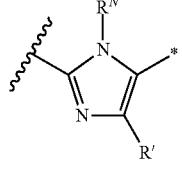
(L-124A)

In Formula ($W^{101}$), represents a divalent linking group represented by any of the following Formulae (L-101) to (L-125) or a divalent linking group formed by bonding of two or more divalent linking groups represented by any of the following Formulae (L-101) to (L-125). When $L^{101}$ represents a linking group formed by bonding of divalent linking groups represented by any of Formulae (L-101) to (L-125), the number of the bonded divalent linking groups represented by any of Formulae (L-101) to (L-125) is preferably 2 to 4 and more preferably 2 or 3.

Each W in Formulae (L-101), (L-102), (L-106), and (L-113) to (L-124) independently represents a hydrogen atom or a substituent. Examples of the substituent which can be adopted as R' include an alkyl group having 5 to 15 carbon atoms (preferably an alkyl group having 6 to 15 carbon atoms) and an alkoxy group having 5 to 15 carbon atoms (preferably an alkoxy group having 6 to 15 carbon atoms).

m in Formula (L-113) represents 4. m in Formulae (L-114) and (L-115) represents 3. m in Formulae (L-116) to (L-120) represents 2. m in Formula (L-122) represents 6.

$R^N$ represents a hydrogen atom or a substituent. Examples of $R^N$ include those exemplified above as the substituent which can be adopted as $R^{A1}$ to $R^{A6}$ in Formula (101). Among those, a hydrogen atom or a methyl group is preferable as $R^N$.

Each $R^{si}$ independently represents a hydrogen atom, an alkyl group, an alkenyl group, or an alkynyl group. $R^{si}$ is preferably an alkyl group. The alkyl group which can be adopted as $R^{si}$ is not particularly limited. However, the preferred range of the alkyl group which can be adopted as $R^{si}$ is the same as the preferred range of the alkyl group with which a silyl group can be substituted when R is the silyl group. The alkenyl group which can be adopted as $R^{si}$ is not particularly limited. However, it is preferably a substituted or unsubstituted alkenyl group and more preferably a branched alkenyl group. The alkenyl group preferably has 2 to 3 carbon atoms. The alkynyl group which can be adopted as $R^{si}$ is not particularly limited. However, it is preferably a substituted or unsubstituted alkynyl group, and more preferably a branched alkynyl group. The alkynyl group preferably has 2 to 3 carbon atoms.

$L^{101}$ is preferably a divalent linking group represented by any of Formulae (L-101), (L-104), and (L-109) or a divalent linking group formed by bonding of two or more divalent linking groups described above. $L^{101}$ is more preferably a divalent linking group represented by Formula (L-101) or (L-104) or a divalent linking group formed by bonding of two or more divalent linking groups described above, and particularly preferably a divalent linking group represented by Formula (L-101) or a divalent linking group formed by bonding of two or more divalent linking groups described above.

In Formula ($W^{101}$), $R^{101}$ represents a substituted or unsubstituted alkyl group, an oligo-oxyethylene group in which a repetition number v of an oxyethylene unit is equal to or greater than 2, an oligosiloxane group having two or more silicon atoms, or a substituted or unsubstituted silyl group. Here, $R^{101}$ represents a substituted or unsubstituted silyl group only when $L^{101}$ adjacent to $R^{101}$ is a divalent linking group represented by any of the following Formulae (L-101) to (L-103).

When $L^{101}$ is represented by Formula (L-101), the substituted or unsubstituted alkyl group which can be adopted as $R^{101}$ is preferably an alkyl group having 3 or more carbon atoms, more preferably an alkyl group having 3 to 40 carbon atoms, even more preferably an alkyl group having 10 to 30 carbon atoms from the viewpoint of the chemical stability and the carrier transport properties, and particularly preferably an alkyl group having 15 to 30 carbon atoms. Furthermore, when $L^{101}$ is represented by Formula (L-101), the substituted or unsubstituted alkyl group which can be adopted as $R^{101}$ is preferably a linear or branched alkyl group, and more preferably a branched alkyl group from the viewpoint of improving the carrier mobility and the solubility in a solvent without deteriorating the intramolecular hydrogen bonding properties.

When $L^{101}$ is represented by any of Formulae (L-102) and (L-103), the main chain of the alkyl group represented by $R^{101}$ preferably has 2 or more carbon atoms. The alkyl group preferably has 3 to 18 carbon atoms, more preferably has 3 to 12 carbon atoms, and particularly preferably has 4 to 10 carbon atoms.

When $L^{101}$ is represented by any of Formulae (L-104) to (L-125), the main chain of the alkyl group represented by $R^{101}$ preferably has 4 or more carbon atoms. The alkyl group preferably has 4 to 18 carbon atoms, more preferably has 4 to 12 carbon atoms, and particularly preferably has 4 to 10 carbon atoms.

When an alkyl group is contained in -$L^{101}$-$R^{101}$ in the group represented by Formula ($W^{101}$), if the number of carbon atoms of the alkyl group represented by $R^{101}$ is equal to or greater than the lower limit of the aforementioned range, the carrier mobility is improved. Furthermore, when $L^{101}$ contains an alkylene group represented by Formula (L-101) adjacent to $R^{101}$, if the number of carbon atoms of the alkyl group formed by bonding of the alkylene group represented by Formula (L-101) and the alkyl group represented by $R^{101}$ is equal to or greater than the lower limit of the aforementioned range, the carrier mobility is improved.

When $R^{101}$ is an alkyl group having a substituent, examples of the substituent include a halogen atom and the like, and as the halogen atom, a fluorine atom is preferable. When $R^{101}$ is an alkyl group having a fluorine atom, a perfluoroalkyl group may be formed by substituting all the hydrogen atoms of the alkyl group with fluorine atoms.

In the present specification, when $R^{101}$ is an oligo-oxyethylene group in which a repetition number v of an oxyethylene unit is equal to or greater than 2, the "oxyethylene group" represented by $R^{101}$ is a group represented by —$(CH_2CH_2)_vOY$ (the repetition number v of an oxyethylene unit represents an integer of equal to or greater than 2, and Y on the terminal represents a hydrogen atom or a substituent). When Y on the terminal of the oligo-oxyethylene group is a hydrogen atom, the terminal becomes a hydroxy group. The repetition number v of an oxyethylene unit is preferably 2 to 4, and more preferably 2 or 3. It is preferable that the hydroxy group on the terminal of the oligo-oxyethylene group is blocked. That is, Y preferably represents a substituent. In this case, the hydroxy group is preferably blocked by an alkyl group having 1 to 3 carbon atoms. That is, Y is preferably an alkyl group having 1 to 3 carbon atoms, more preferably a methyl group or an ethyl group, and particularly preferably a methyl group.

When $R^{101}$ is an oligosiloxane group having 2 or more silicon atoms, the repetition number of a siloxane unit is preferably 2 to 4, and more preferably 2 or 3. Furthermore, the Si atom is preferably bonded to a hydrogen atom or an alkyl group. When the Si atom is bonded to an alkyl group, the number of carbon atoms of the alkyl group is preferably 1 to 3. For example, the Si atom is preferably bonded to a methyl group or an ethyl group. The Si atom may be bonded to the same alkyl groups or may be bonded to different alkyl groups or hydrogen atoms. The siloxane units constituting the oligosiloxane group may be the same as or different from each other, but it is preferable that they are the same as each other.

When $R^{101}$ is a substituted or unsubstituted silyl group, as the silyl group which can be adopted as $R^{101}$, a trialkylsilyl group having 3 to 15 carbon atoms and silyl groups substituted with 1 to 3 trialkylsilyloxy groups (a monoalkyl di(trialkylsilyloxy)silyl group, a dialkyl mono(trialkylsilyloxy)silyl group, and a tri(trialkylsilyloxy)silyl group) are preferable.

Examples of the group represented by Formula ($W^{101}$) include a 2,6-dimethyloctyl group, a 2-decyltetradecyl group, a 2-hexyldodecyl group, a 2-ethyloctyl group, a 2-butyldecyl group, a 2-octylnonyl group, a 2-octyltetradecyl group, a 2-hexyldecyloxy group, a ditrimethylsiloxy methylbutoxy group, a hexyl group, a heptyl group, an octyl group, a nonyl group, a decyl group, an undecyl group, a dodecyl group, a tridecyl group, a tetradecyl group, a pentadecyl group, and the like.

The substituent which can be adopted as $R^{41}$ to $R^{46}$ is preferably a branched substituent in which a linear substituent further has a substituent.

At least one of $R^{41}$ to $R^{46}$ in Formula (101') is preferably a group represented by Formula ($W^{101}$).

Each of $Ar^{101}$ and $Ar^{102}$ independently represents a heteroarylene group or an arylene group. The heterocyclic aromatic ring or the aromatic ring which can be adopted as $Ar^{101}$ and $Ar^{102}$ is not particularly limited. However, the heterocyclic aromatic ring or the aromatic ring is preferably a compound represented by the following Formula (102-1), (102-2), or (102-3), and more preferably a compound represented by the following Formula (102-1) or (102-2).

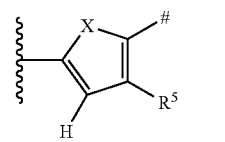

Formula (102-1)

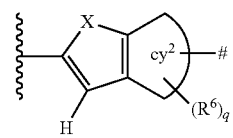

Formula (102-2)

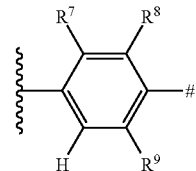

Formula (102-3)

In Formulae (102-1) to (102-3), X represents a S atom, an O atom, or a Se atom; $cy^2$ represents a structure in which 1 to 4 rings are condensed; each of $R^5$ to $R^9$ independently represents a hydrogen atom or a substituent; q represents an integer of 0 to 6; when q is equal to or greater than 2, two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^{101}$.

In Formulae (102-1) to (102-3), X represents a S atom, an O atom, or a Se atom. X is preferably a S atom or a Se atom, and more preferably a S atom.

In Formulae (102-1) to (102-3), each of $R^5$ to $R^9$ independently represents a hydrogen atom or a substituent. The substituent which can be adopted as $R^5$ to $R^9$ is not particularly limited, and examples thereof include a halogen atom, an alkyl group (including an alkyl group having 1 to 40 carbon atoms such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, or a pentadecyl group (preferably an alkyl group having 3 to 40 carbon atoms and more preferably an alkyl group having 10 to 30 carbon atoms), a 2,6-dimethyloctyl group, a 2-decyltetradecyl group, a 2-hexyldodecyl group, a 2-ethyloctyl group, a 2-butyldecyl group, a 1-octylnonyl group, a 2-octyltetradecyl group, and the like), an alkenyl group (including a 1-pentenyl group, a cycloalkenyl group, a bicycloalkenyl group, and the like), an alkynyl group (including a 1-pentynyl group, a trimethylsilylethynyl group, a triethylsilylethynyl group, a tri-i-propylsilylethynyl group, a 2-p-propylphenylethynyl group, and the like), an aryl group (including an aryl group having 6 to 20 carbon atoms such as a phenyl group, a naphthyl group, a p-pentylphenyl group, a 3,4-dipentylphenyl group, a p-heptoxyphenyl group, a 3,4-diheptoxyphenyl group, and the like), a hetero ring group (may also be referred to as a heterocyclic group, including a 2-hexylfuranyl group and the like), a cyano group, a hydroxyl group, a nitro group, an acyl group (including a hexanoyl group, a benzoyl group, and the like), an aryloxy group, a silyloxy group, a heterocyclic oxy group, an acyloxy group, a carbamoyloxy group, an amino group (including an anilino group), an acylamino group, an aminocarbonylamino group (including a ureide group), an alkoxy group (including an alkoxy group having 1 to 40 carbon atoms such as a methoxy group, an ethoxy group, a propoxy group, a butoxy group, a pentoxy group, a hexyloxy group, a heptoxy group, an octoxy group, a nonyloxy group, a decyloxy group, a 2-hexyldecyloxy group, an undecyloxy group, a dodecyloxy group, a tridecyloxy group, a tetradecyloxy group, and a pentadecyloxy group (preferably an alkoxy group having 3 to 40 carbon atoms and more preferably an alkoxy group having 10 to 30 carbon atoms)), an aryloxycarbonylamino group, alkyl and aryl sulfonylamino groups, a mercapto group, alkyl and arylthio groups (including a methylthio group, an octylthio group, and the like), a heterocyclic thio group, a sulfamoyl group, a sulfo group, alkyl and aryl sulfinyl groups, alkyl and aryl sulfonyl groups, alkyloxy and aryloxy carbonyl groups, a carbamoyl group, an arylazo group, a heterocyclic azo group, an imide group, a phosphino group, a phosphinyl group, a phosphinyloxy group, a phosphinylamino group, a phosphono group, a silyl group (a ditrimethylsiloxy methylbutoxy group), a hydrazino group, and other known substituents. Among these, an alkyl group and an alkoxy group are preferable.

The alkyl group which can be adopted as $R^5$ to $R^9$ is more preferably an alkyl group having 3 to 40 carbon atoms, even more preferably an alkyl group having 10 to 30 carbon atoms from the viewpoint of the chemical stability and the carrier transport properties, and particularly preferably an alkyl group having 15 to 30 carbon atoms. Furthermore, the alkyl group which can be adopted as $R^5$ to $R^9$ is preferably a linear or branched alkyl group, and more preferably a branched alkyl group from the viewpoint of improving the carrier mobility and the solubility in a solvent without deteriorating the intramolecular hydrogen bonding properties.

The alkoxy group which can be adopted as $R^5$ to $R^9$ is more preferably an alkoxy group having 3 to 40 carbon atoms, even more preferably an alkoxy group having 10 to 30 carbon atoms from the viewpoint of the chemical stability and the carrier transport properties, and particularly preferably an alkoxy group having 15 to 30 carbon atoms. Furthermore, the alkoxy group which can be adopted as $R^5$ to $R^9$ is preferably a linear or branched alkoxy group, and more preferably a branched alkoxy group from the viewpoint of improving the carrier mobility and the solubility in a solvent without deteriorating the intramolecular hydrogen bonding properties.

These substituents may further have a substituent.

In addition, these substituents may have a group derived from a polymerizable group.

In Formula (102-2), q represents an integer of 0 to 6. q is preferably an integer of 0 to 3, more preferably an integer of 0 to 2, and even more preferably an integer of 0 or 1.

In Formula (102-2), $cy^2$ represents a structure in which 1 to 4 rings are condensed. $cy^2$ is preferably a structure in which 1 to 4 aromatic rings or heterocyclic aromatic rings are condensed, more preferably a structure in which 1 to 4 aromatic rings having 6 to 10 carbon atoms or 1 to 4 heterocyclic aromatic rings having 4 to 6 carbon atoms are condensed, and particularly preferably a structure in which 1 to 4 benzene rings or thiophene rings are condensed.

The divalent linking group represented by Formula (102-2) is preferably a divalent linking group represented by any of the following Formulae (5-1) to (5-8), and more preferably a divalent linking group represented by Formula (5-1).

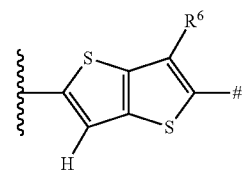

Formula (5-1)

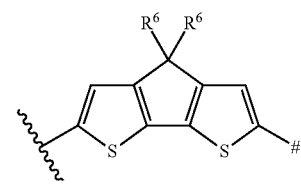

Formula (5-2)

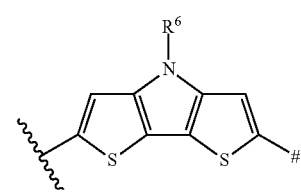

Formula (5-3)

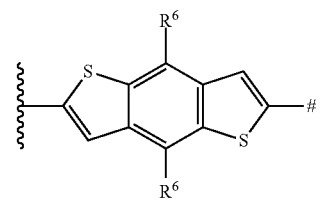

Formula (5-4)

Formula (5-5)
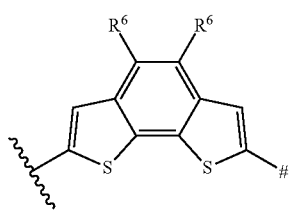

Formula (5-6)
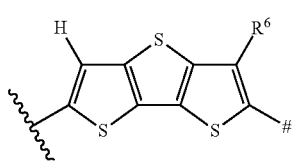

Formula (5-7)
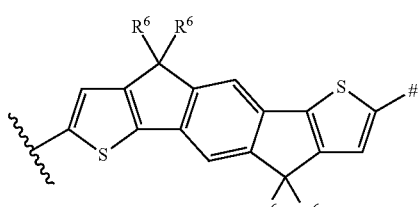

Formula (5-8)
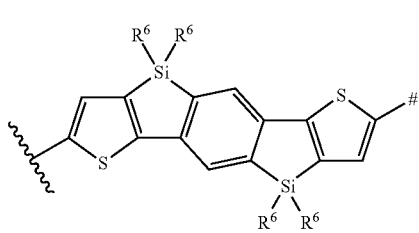

(In Formulae (5-1) to (5-8), each $R^6$ independently represents a hydrogen atom or a substituent; two or more groups represented by $R^6$ may be the same as or different from each other; the wavy line represents a position where the divalent linking group is bonded to a cyclopentadienone ring-condensed site; and # represents a position where the divalent linking group is bonded to $V^{101}$.)

In Formulae (5-1) to (5-8), each $R^6$ independently represents a hydrogen atom or a substituent, and two or more groups represented by $R^6$ may be the same as or different from each other. Examples of the substituent which can be adopted as $R^6$ include those exemplified above as the substituent which can be adopted as $R^5$ to $R^9$ in Formulae (102-1) to (102-3), and the preferred range thereof is also the same.

In Formula (101), $V^{101}$ represents a divalent linking group. From the viewpoint of improving the solubility, it is preferable that $V^{101}$ does not form a condensed ring together with $Ar^{101}$ or $Ar^{102}$.

$V^{101}$ is preferably a divalent linking group represented by any of the following Formulae (V-101) to (V-117).

(V-101)
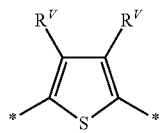

(V-102)
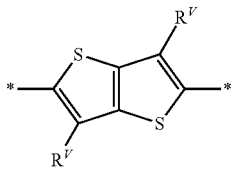

(V-103)

(V-104)
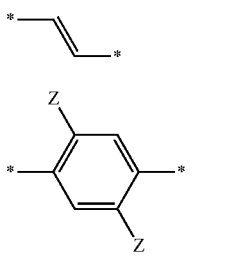

(V-105)

(V-106)
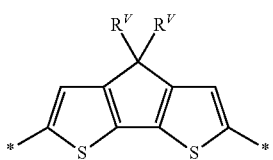

(V-107)
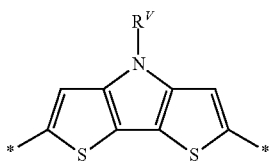

(V-108)
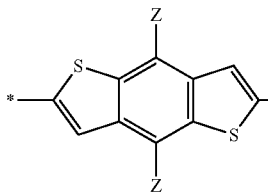

(V-109)
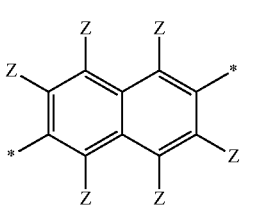

(V-110)
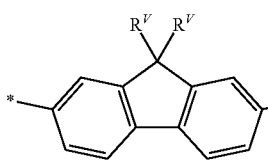

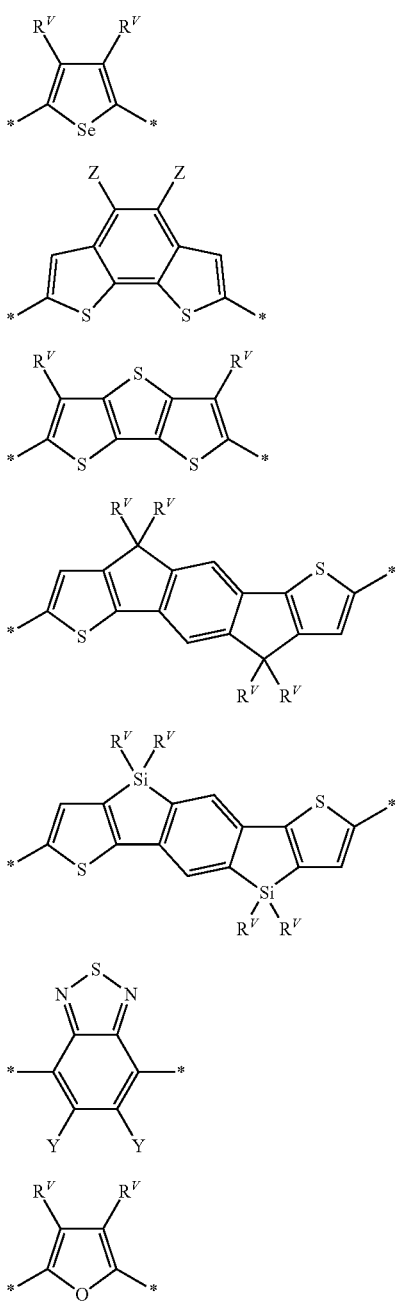

other; each Y in Formula (V-116) independently represents a hydrogen atom, an alkyl group, an alkoxy group, a CN group, or a F atom; and the groups adjacent to each other represented by Y may form a ring by being bonded to each other.

Each $R^V$ in Formulae (V-101), (V-102), (V-105), (V-106), (V-109) to (V-111), (V-113) to (V-115), and (V-117) independently represents a hydrogen atom or an alkyl group, and the groups adjacent to each other represented by $R^V$ may form a ring by being bonded to each other. Examples of the alkyl group which can be adopted as $R^V$ include the alkyl group which can be adopted as $R^5$ to $R^9$ in Formulae (102-1) to (102-3). The preferred range of the alkyl group which can be adopted as $R^V$ is also the same as the preferred range of the alkyl group which can be adopted as $R^5$ to $R^9$.

Each Z in Formulae (V-104), (V-107), (V-108), and (V-112) independently represents a hydrogen atom, an alkyl group, or an alkoxy group, and the groups adjacent to each other represented by Z may form a ring by being bonded to each other. Examples of the alkyl group or the alkoxy group which can be adopted as Z include the alkyl group and the alkoxy group which can be adopted as $R^5$ to $R^9$ in Formulae (102-1) to (102-3). The preferred range of the alkyl group and the alkoxy group which can be adopted as Z is also the same as the preferred range of the alkyl group and the alkoxy group which can be adopted as $R^5$ to $R^9$.

Each Y in Formula (V-116) independently represents a hydrogen atom, an alkyl group, an alkoxy group, a CN group, or a F atom, and the groups adjacent to each other represented by Y may form a ring by being bonded to each other. Y is preferably an alkyl group or an alkoxy group. Examples of the alkyl group or the alkoxy group which can be adopted as Y include the alkyl group and the alkoxy group exemplified above as the substituent which can be adopted as $R^5$ to $R^9$ in Formulae (102-1) to (102-3), and the preferred range thereof is also the same.

When the compound represented by Formula (101) is a compound represented by any of Formulae (101-1) to (101-3) which will be described later, among the divalent linking groups represented by Formulae (V-101) to (V-117), the divalent linking groups represented by Formulae (V-101) to (V-108) and (V-111) to (V-115) are preferable as $V^{101}$.

When the compound represented by Formula (101) is a compound represented by Formula (101-1) which will be described later, if each of $Ar^{101}$ and $Ar^{102}$ is a divalent linking group represented by Formula (2-1), $V^{101}$ is more preferably a divalent linking group represented by any of Formulae (V-102) to (V-107), and particularly preferably a divalent linking group represented by Formula (V-102), (V-103), or (V-107).

When the compound represented by Formula (101) is a compound represented by Formula (101-1) which will be described later, if each of $Ar^{101}$ and $Ar^{102}$ is a divalent linking group represented by Formula (2-2) or (2-3), $V^{101}$ is more preferably a divalent linking group represented by any of Formulae (V-101) to (V-107), and particularly preferably a divalent linking group represented by any of Formulae (V-101) to (V-103).

When the compound represented by Formula (101) is a compound represented by Formula (101-2) or (101-3) which will be described later, if each of $Ar^{101}$ and $Ar^{101}$ is a divalent linking group represented by Formula (2-2) or (2-3), $V^{101}$ is more preferably a divalent linking group represented by any of Formulae (V-101) to (V-107), and particularly preferably a divalent linking group represented by any of Formulae (V-101) to (V-103).

In Formulae (V-101) to (V-117), * represents a position where the divalent linking group is bonded to any of $Ar^{101}$ and $Ar^{102}$ when $m^{101}$, $p^{101}$, or $r^{101}$ is 1 and represents a position where the divalent linking group is bonded to any of $Ar^{101}$, $Ar^{102}$, and divalent linking groups represented by Formulae (V-101) to (V-117) when $m^{101}$, $p^{101}$, or $r^{101}$ is equal to or greater than 2; each $R^V$ in Formulae (V-101), (V-102), (V-105), (V-106), (V-109) to (V-111), (V-113) to (V-115), and (V-117) independently represents a hydrogen atom or an alkyl group; the groups adjacent to each other represented by $R^V$ may form a ring by being bonded to each other; each Z in Formulae (V-104), (V-107), (V-108), and (V-112) independently represents a hydrogen atom, an alkyl group, or an alkoxy group; the groups adjacent to each other represented by Z may form a ring by being bonded to each In Formula (101), $m^{101}$ represents an integer of 1 to 6. When $m^{101}$ is equal to or greater than 2, two or more groups represented by $V^{101}$ may be the same as or different from each other. $m^{101}$ is preferably an integer of 1 to 5, and more preferably 1 to 3.

In Formula (101), n represents an integer of equal to or greater than 2. n is preferably equal to or greater than 10, more preferably equal to or greater than 30, and particularly preferably equal to or greater than 50. The greater the value of n, the further the interaction between π-conjugated polymer chains can be improved, and thus the carrier mobility can be improved. The upper limit of n is not particularly limited, but it is preferably equal to or less than 1,000 and more preferably equal to or less than 900.

The compound composed of n repeating units represented by Formula (101) is preferably a compound composed of n repeating units represented by any of the following Formulae (101-1) to (101-3), more preferably a compound composed of n repeating units represented by Formula (101-1) or (101-2) from the viewpoint of improving the carrier mobility, and particularly preferably a compound composed of n repeating units represented by Formula (101-1) from the viewpoint of especially improving the carrier mobility.

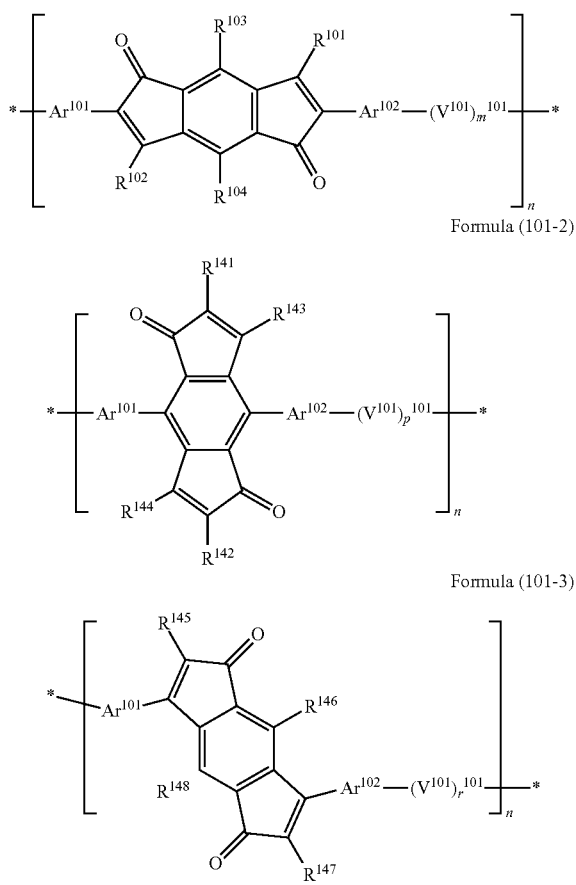

In Formulae (101-1), (101-2), and (101-3), each of $R^{101}$ to $R^{104}$ and $R^{141}$ to $R^{148}$ independently represents a hydrogen atom or a substituent; each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; each of $p^{101}$ and $r^{101}$ represents an integer of 0 to 6; when each of $p^{101}$ and $r^{101}$ is equal to or greater than 2, two or more groups represented by $V^{101}$ may be the same as or different from each other; and n represents an integer of equal to or greater than 2.

<Compound Composed of n Repeating Units Represented by Formula (101-1)>

First, a compound composed of n repeating units represented by Formula (101-1) will be described.

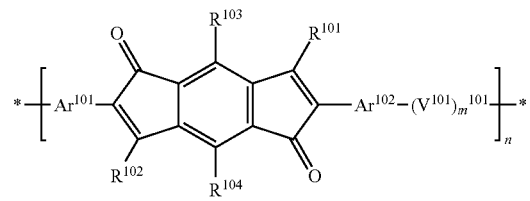

Formula (101-1)

In Formula (101-1), each of $R^{101}$ to $R^{104}$ independently represents a hydrogen atom or a substituent. When each of $R^{101}$ to $R^{104}$ in Formula (101-1) represents a substituent, as the substituent, the same substituent as those which can be adopted as $R^{41}$ to $R^{46}$ in Formula (101) can be used, and the preferred range thereof is also the same. Especially, it is preferable that at least one of $R^{101}$ to $R^{104}$ is a group represented by Formula ($W^{101}$) described above. More preferably, at least one of $R^{103}$ and $R^{104}$ is a group represented by Formula ($W^{101}$) described above. Particularly preferably, each of $R^{103}$ and $R^{104}$ is a group represented by Formula ($W^{101}$).

In Formula (101-1), each of $Ar^{101}$ and $Ar^{102}$ independently represents a heteroarylene group or an arylene group. $Ar^{101}$ and $Ar^{102}$ in Formula (101-1) are the same as Arm and $Ar^{102}$ in Formula (101), and the preferred range thereof is also the same.

In Formula (101-1), $V^{101}$ represents a divalent linking group. $V^{101}$ in Formula (101-1) is the same as $V^{101}$ in Formula (101), and the preferred range thereof is also the same. Particularly, $V^{101}$ is preferably a divalent linking group represented by any of Formulae (V-101) to (V-108) and (V-111) to (V-115).

When each of $Ar^{101}$ and $Ar^{102}$ is a divalent linking group represented by Formula (2-1) described above, $V^{101}$ is more preferably a divalent linking group represented by any of Formulae (V-102) to (V-107) described above, and particularly preferably a divalent linking group represented by Formula (V-102), (V-103), or (V-107).

When each of $Ar^{101}$ and $Ar^{102}$ is a divalent linking group represented by Formula (2-2) or (2-3) described above, $V^{101}$ is more preferably a divalent linking group represented by any of Formulae (V-101) to (V-107) described above, and particularly preferably a divalent linking group represented by any of Formulae (V-101) to (V-103).

In Formula (101-1), $m^{101}$ represents an integer of 1 to 6. When $m^{101}$ is equal to or greater than 2, two or more groups represented by $V^{101}$ may be the same as or different from each other. $m^{101}$ is preferably an integer of 1 to 5, and more preferably 1 to 3.

In Formula (101-1), n represents an integer of equal to or greater than 2. n is preferably equal to or greater than 10, more preferably equal to or greater than 30, and particularly preferably equal to or greater than 50. The greater the value of n, the further the interaction between π-conjugated polymer chains can be improved, and thus the carrier mobility can be improved. The upper limit of n is not particularly limited, but it is preferably equal to or less than 1,000 and more preferably equal to or less than 900.

<Compound Composed of n Repeating Units Represented by Formula (101-2)>

Next, a compound composed of n repeating units represented by Formula (101-2) will be described.

Formula (101-2)

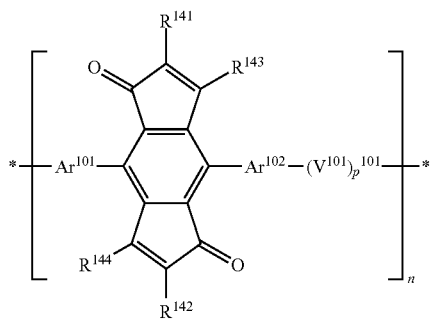

In Formula (101-2), each of $R^{141}$ to $R^{144}$ independently represents a hydrogen atom or a substituent. When each of $R^{141}$ to $R^{144}$ in Formula (101-2) represents a substituent, as the substituent, the same substituent as those which can be adopted as $R^{41}$ to $R^{46}$ in Formula (101) can be used, and the preferred range thereof is also the same. Especially, it is preferable that at least one of $R^{141}$ to $R^{144}$ is a group represented by Formula ($W^{101}$) described above. More preferably, at least one of $R^{141}$ and $R^{142}$ is a group represented by Formula ($W^{101}$) described above. Particularly preferably, each of $R^{141}$ and $R^{142}$ is a group represented by Formula ($W^{101}$).

In Formula (101-2), each of $Ar^{101}$ and $Ar^{102}$ independently represents a heteroarylene group or an arylene group. $Ar^{101}$ and $Ar^{102}$ in Formula (101-2) are the same as $Ar^{101}$ and $Ar^{102}$ in Formula (101), and the preferred range thereof is also the same.

In Formula (101-2), $V^{101}$ represents a divalent linking group. $V^{101}$ in Formula (101-2) is the same as $V^{101}$ in Formula (101), and the preferred range thereof is also the same. Particularly, $V^{101}$ is preferably a divalent linking group represented by any of Formulae (V-101) to (V-108) and (V-111) to (V-115) described above.

When each of $Ar^{101}$ and $Ar^{102}$ is a divalent linking group represented by Formula (2-2) or (2-3) described above, $V^{101}$ is more preferably a divalent linking group represented by any of Formulae (V-101) to (V-107) described above, and particularly preferably a divalent linking group represented by any of Formulae (V-101) to (V-103).

In Formula (101-2), represents an integer of 1 to 6. When is equal to or greater than 2, two or more groups represented by $V^{101}$ may be the same as or different from each other. $p^{101}$ is preferably an integer of 1 to 5, and more preferably 1 to 3.

In Formula (101-2), n represents an integer of equal to or greater than 2. n is preferably equal to or greater than 10, more preferably equal to or greater than 30, and particularly preferably equal to or greater than 50. The greater the value of n, the further the interaction between π-conjugated polymer chains can be improved, and thus the carrier mobility can be improved. The upper limit of n is not particularly limited, but it is preferably equal to or less than 1,000 and more preferably equal to or less than 900.

<Compound Composed of n Repeating Units Represented by Formula (101-3)>

Next, a compound composed of n repeating units represented by Formula (101-3) will be described.

Formula (101-3)

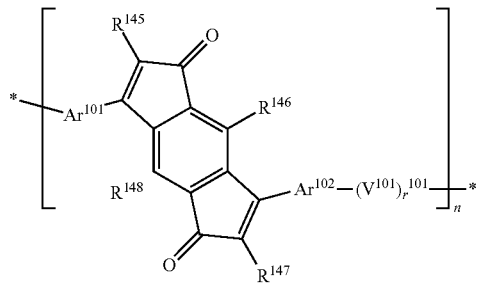

In Formula (101-3), each of $R^{145}$ to $R^{148}$ independently represents a hydrogen atom or a substituent. When each of $R^{145}$ to $R^{148}$ in Formula (101-3) represents a substituent, as the substituent, the same substituent as those which can be adopted as $R^{41}$ to $R^{46}$ in Formula (101) can be used, and the preferred range thereof is also the same. Especially, at least one of $R^{145}$ to $R^{148}$ is preferably a group represented by Formula ($W^{101}$) described above. Particularly preferably, all of $R^{145}$ to $R^{148}$ are groups represented by Formula ($W^{101}$).

In Formula (101-3), each of $Ar^{101}$ and $Ar^{102}$ independently represents a heteroarylene group or an arylene group. $Ar^{101}$ and $Ar^{102}$ in Formula (101-3) are the same as $Ar^{101}$ and $Ar^{102}$ in Formula (101), and the preferred range thereof is also the same.

In Formula (101-3), $V^{101}$ represents a divalent linking group. $V^{101}$ in Formula (101-3) is the same as $V^{101}$ in Formula (101), and the preferred range thereof is also the same. Particularly, $V^{101}$ is preferably a divalent linking group represented by any of Formulae (V-101) to (V-108) and (V-111) to (V-115) described above.

When each of $Ar^{101}$ and $Ar^{102}$ is a divalent linking group represented by Formula (2-2) or (2-3) described above, $V^{101}$ is more preferably a divalent linking group represented by any of Formulae (V-101) to (V-107) described above, and particularly preferably a divalent linking group represented by any of Formulae (V-101) to (V-103).

In Formula (101-3), $r^{101}$ represents an integer of 1 to 6. When $r^{101}$ is equal to or greater than 2, two or more groups represented by $V^{101}$ may be the same as or different from each other. $r^{101}$ is preferably an integer of 1 to 5, and more preferably 1 to 3.

In Formula (101-3), n represents an integer of equal to or greater than 2. n is preferably equal to or greater than 10, more preferably equal to or greater than 30, and particularly preferably equal to or greater than 50. The greater the value of n, the further the interaction between π-conjugated polymer chains can be improved, and thus the carrier mobility can be improved. The upper limit of n is not particularly limited, but it is preferably equal to or less than 1,000 and more preferably equal to or less than 900.

Specific examples of the compound composed of n repeating units represented by Formula (101) will be shown below. However, the compound composed of n repeating units represented by Formula (101) that can be used in the present invention is not limited to the specific examples. In the following specific examples of the compound, the number n of the repeating units is not described, and only the repeating units are illustrated.

101
Compound 101
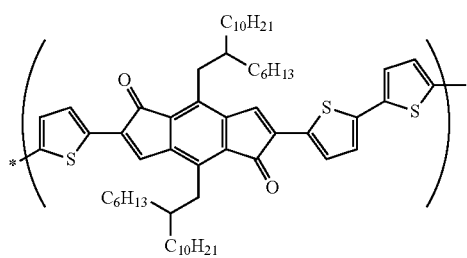
102
Compound 102
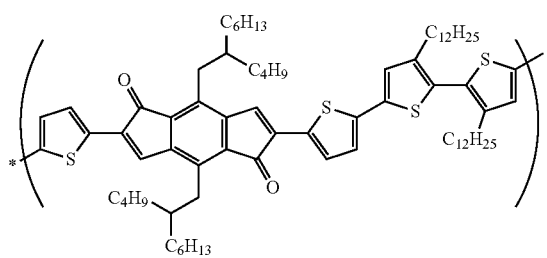
Compound 103
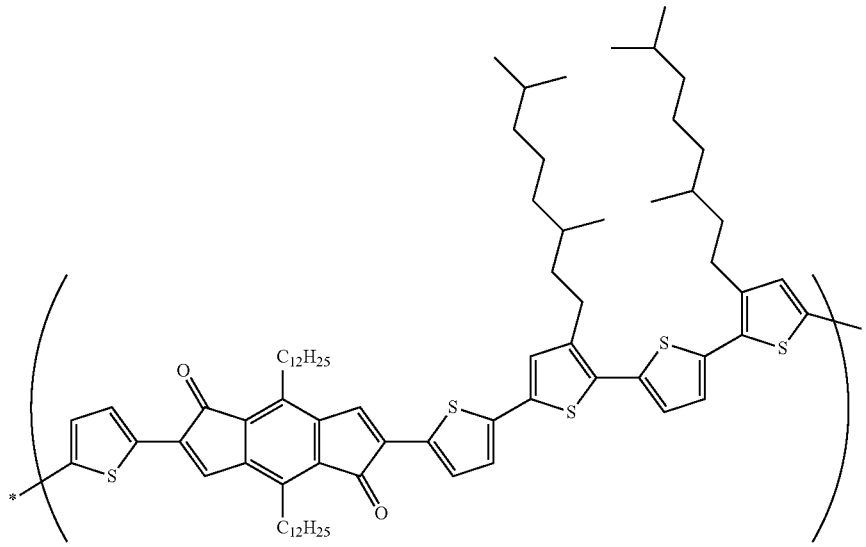
Compound 104
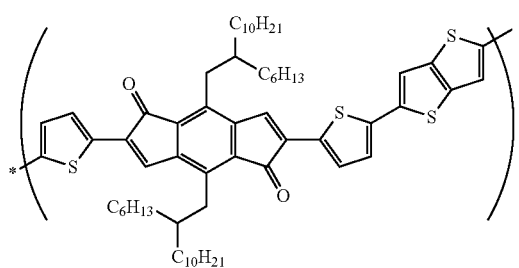
Compound 105
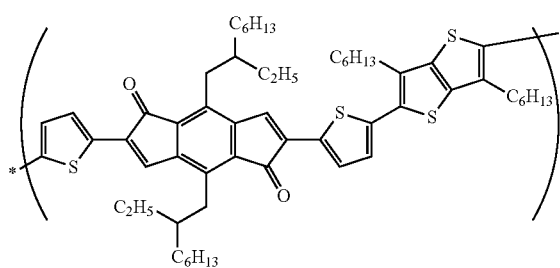
Compound 106
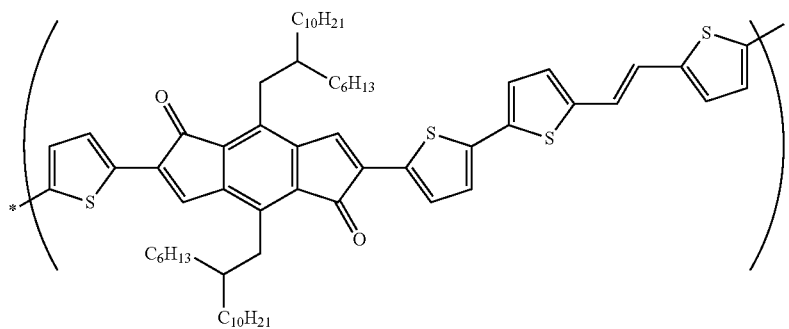

Compound 107
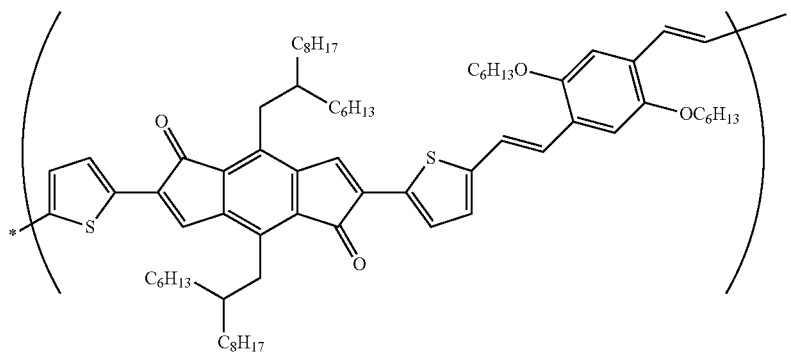
Compound 108
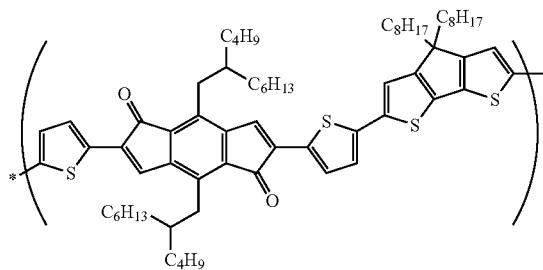
Compound 109
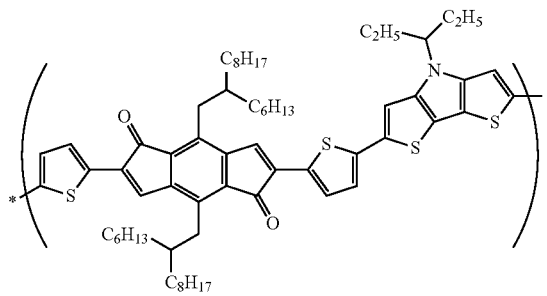
Compound 110
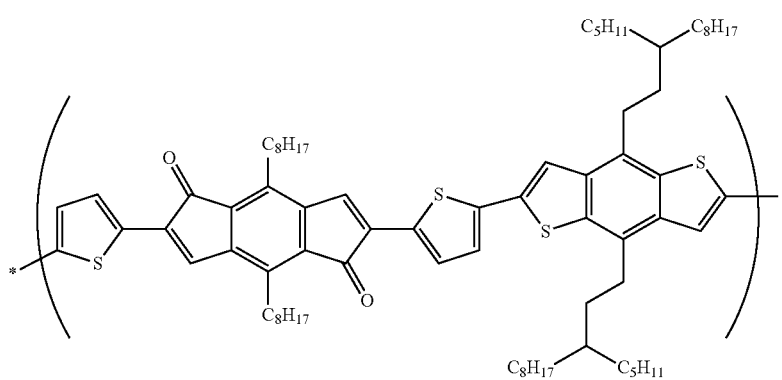
Compound 111
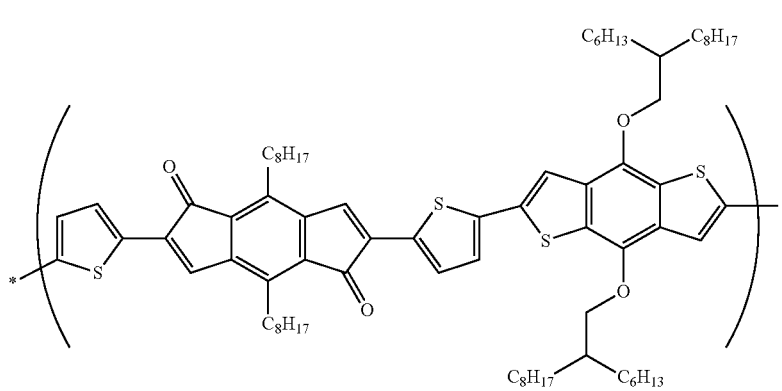

-continued
Compound 112
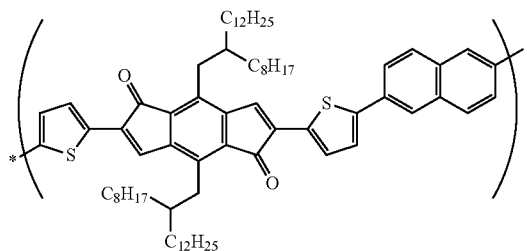
Compound 113
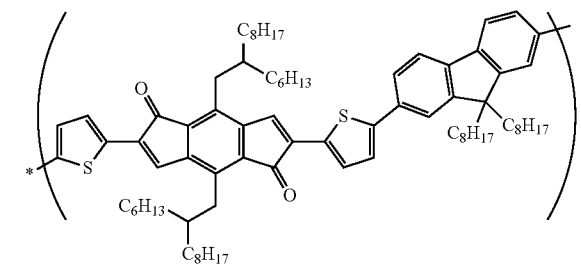
Compound 114
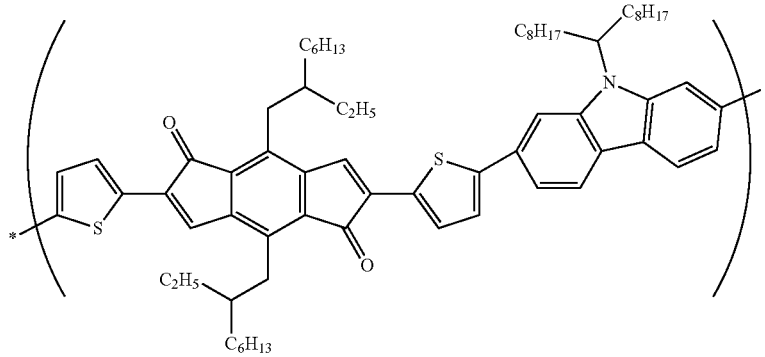
Compound 115
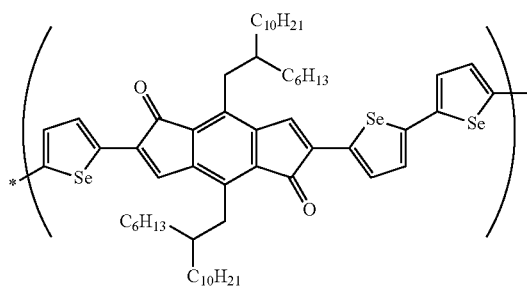
Compound 116
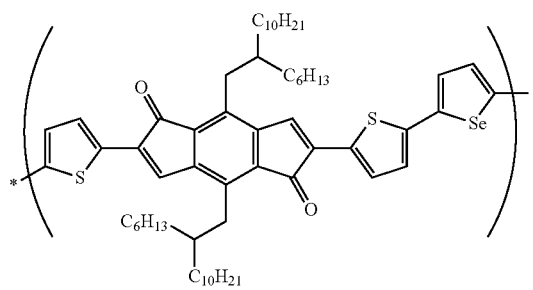
Compound 117
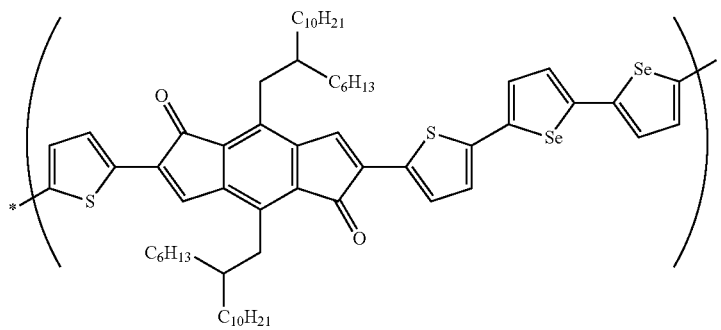
Compound 118
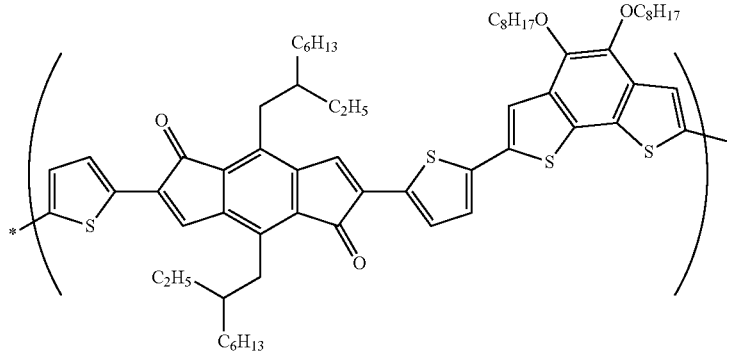

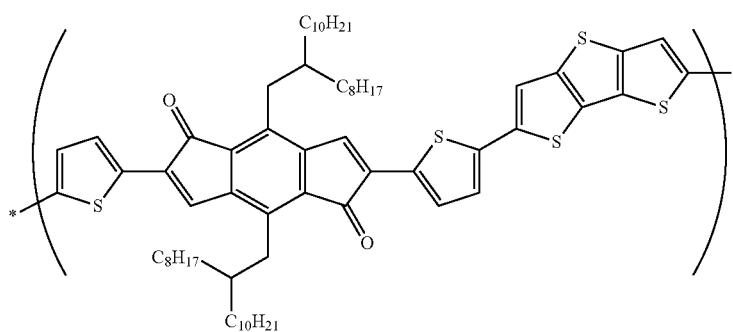
Compound 119
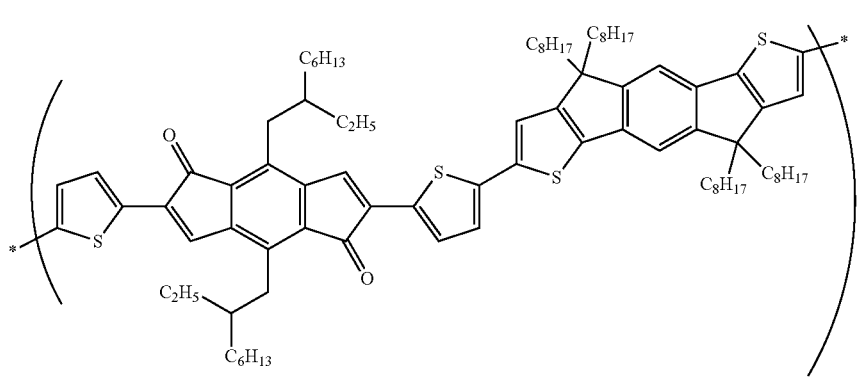
Compound 120
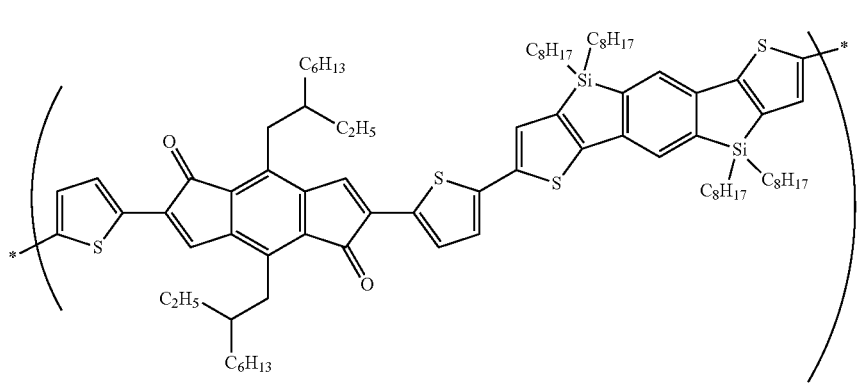
Compound 121
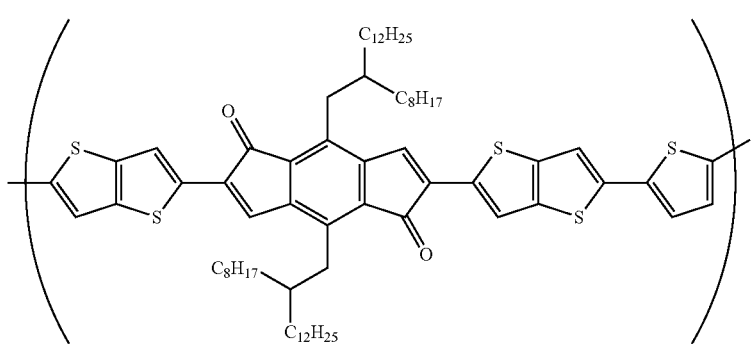
Compound 122

Compound 123
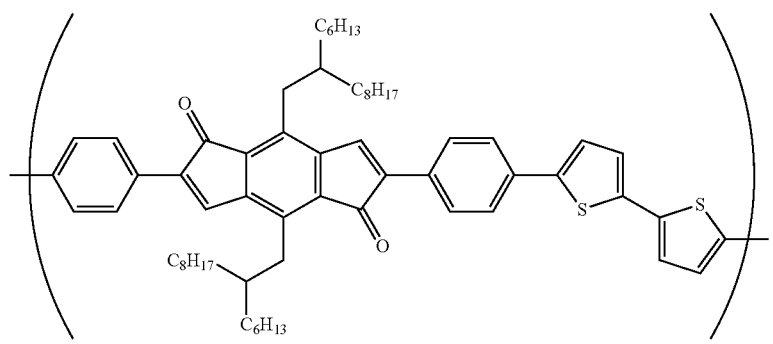
(124)
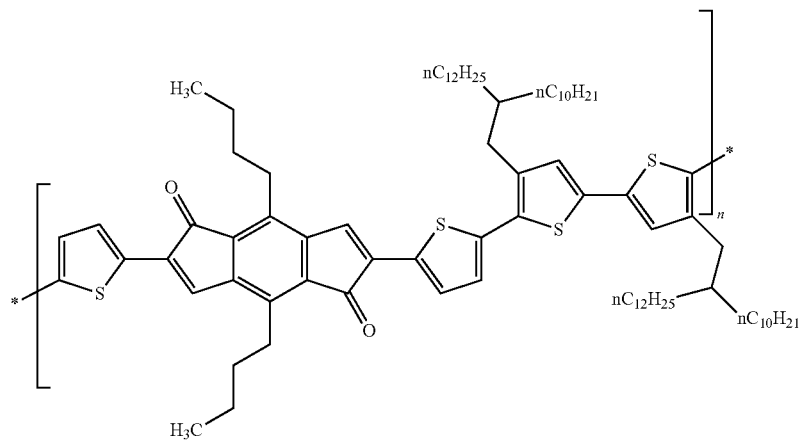
(125)
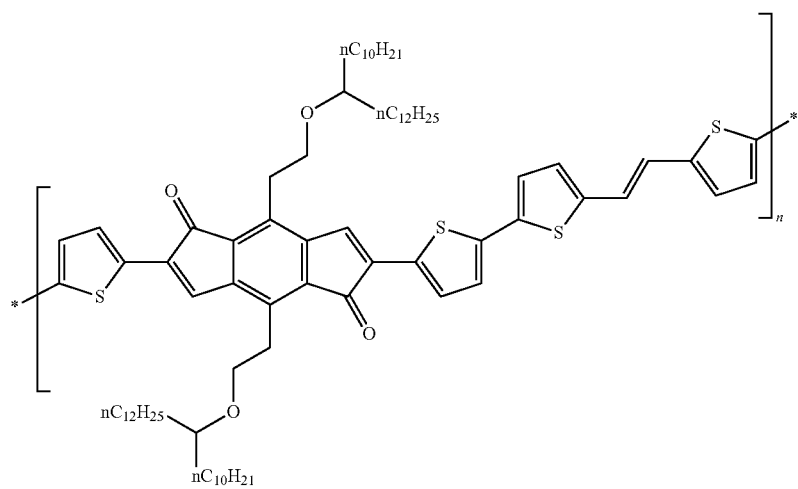
(126)
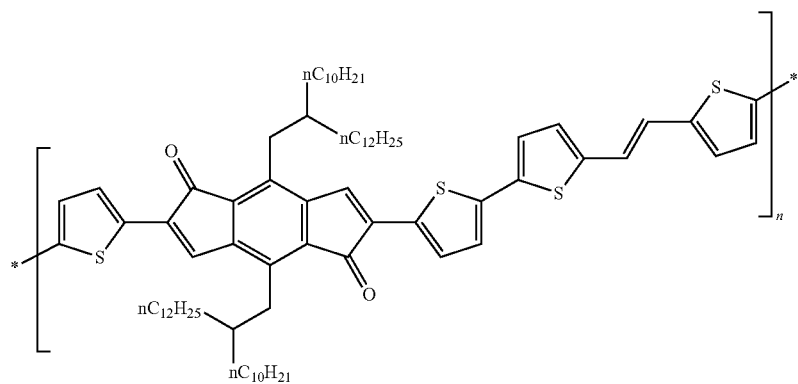

-continued
(127)
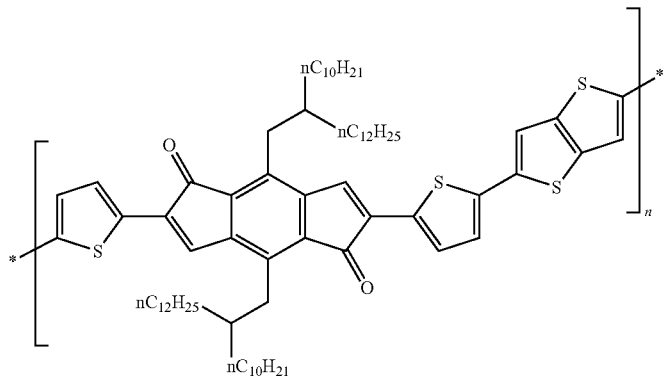
(128)
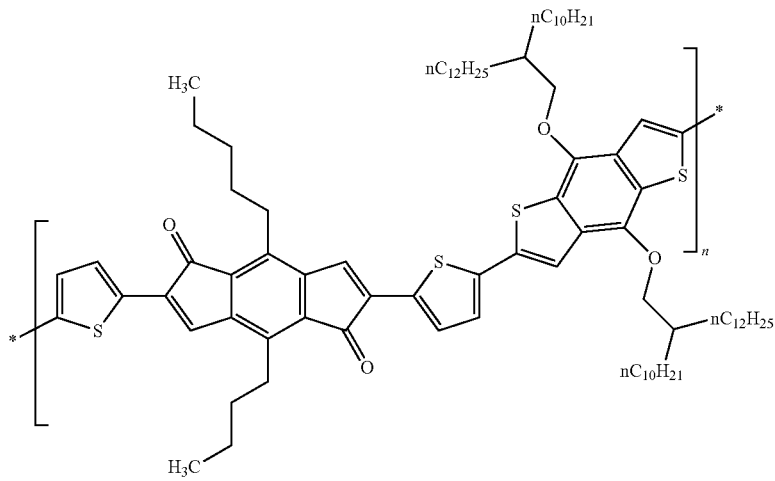
(129)
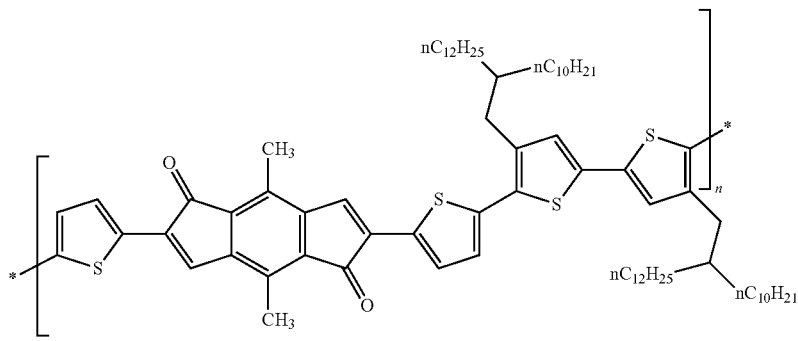
(130)
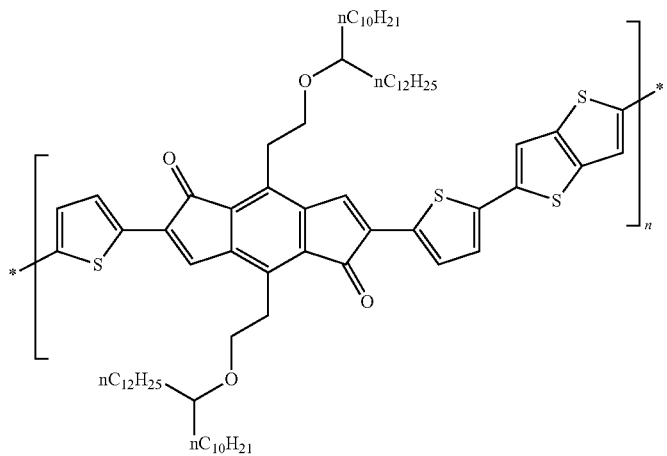

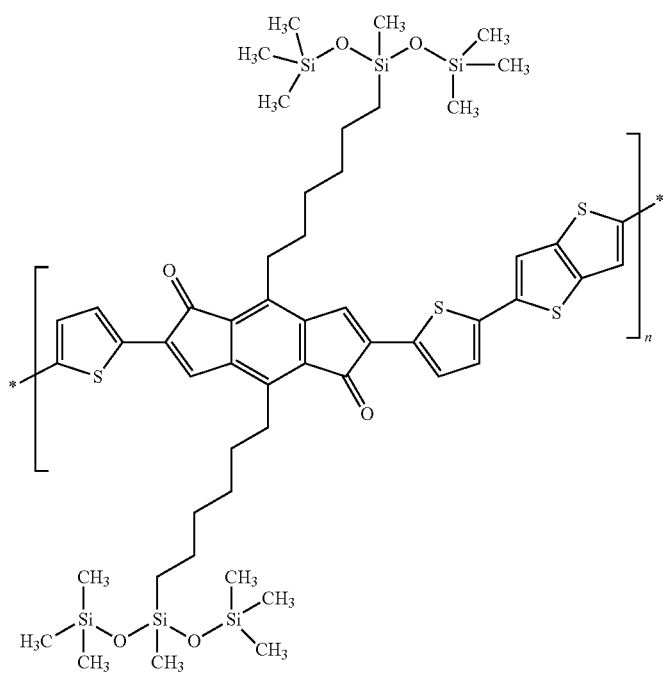
(131)
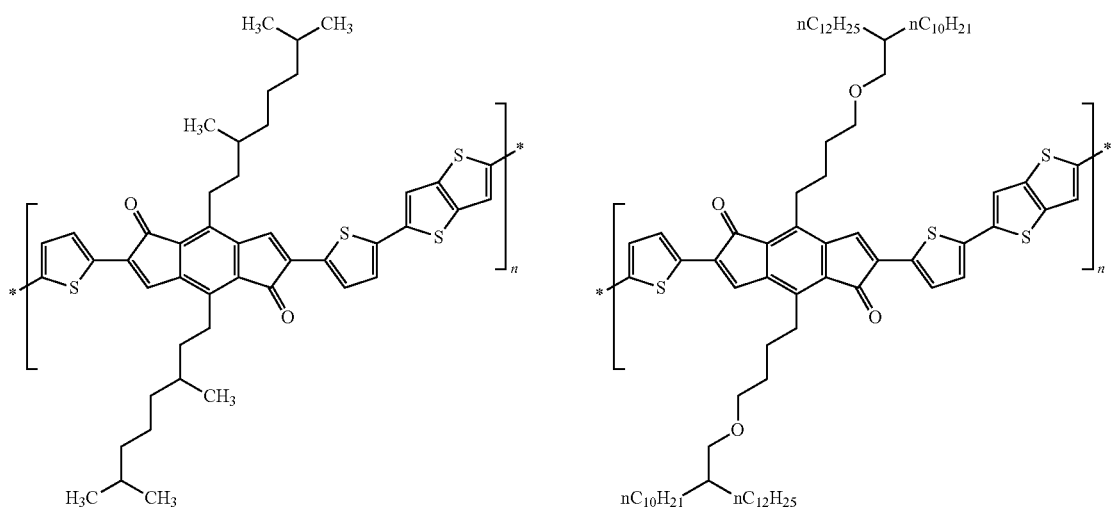
(132) (133)

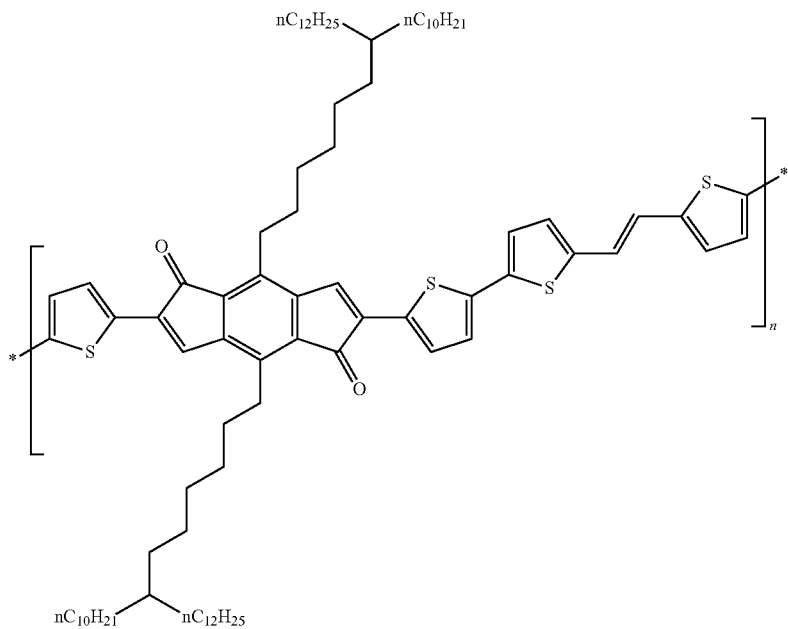
(134)
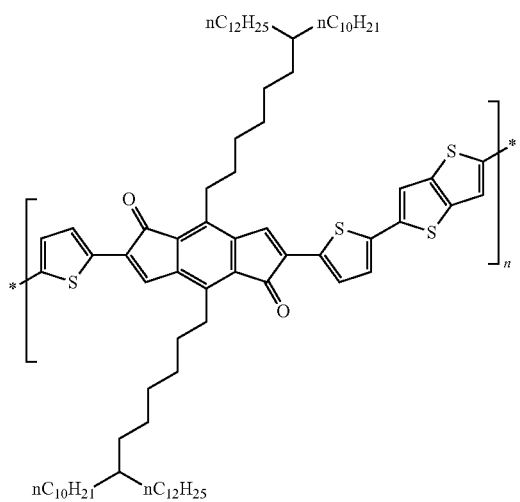
(135)
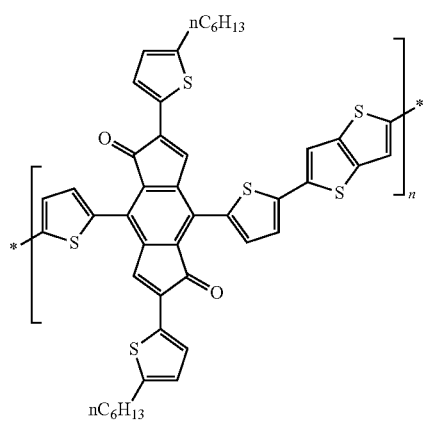
(136)

-continued
(137)
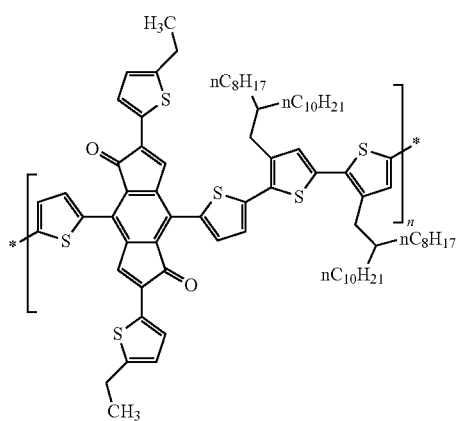
(138)
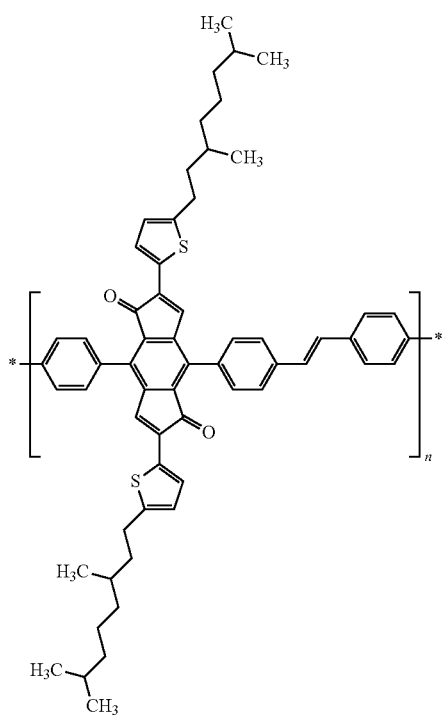
(139)
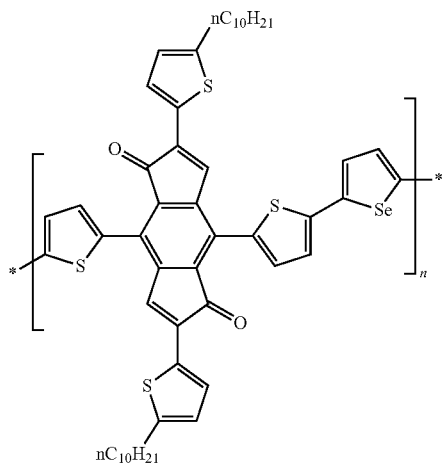
(140)
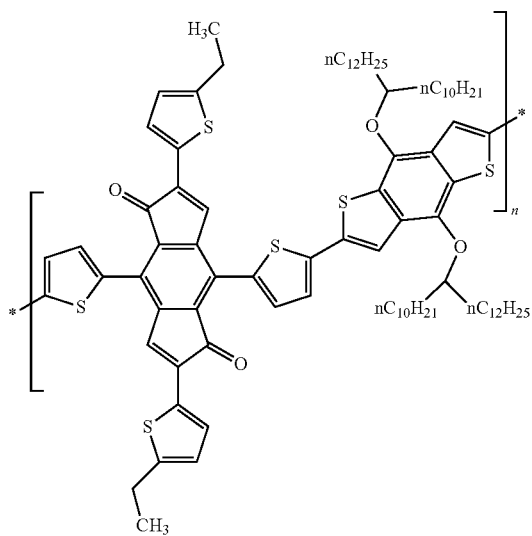

-continued
(141)
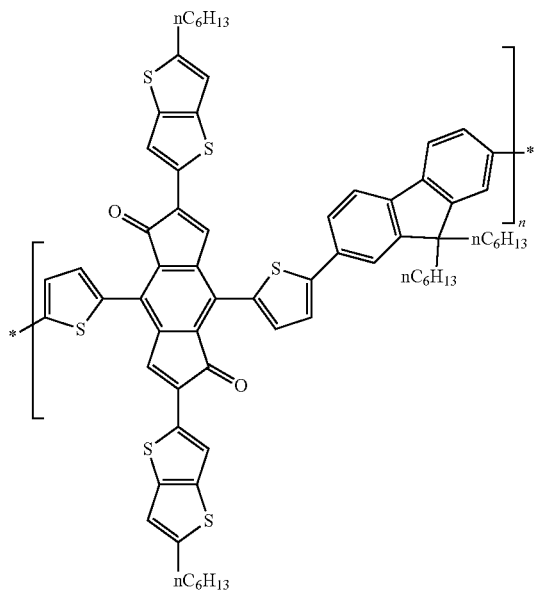
(142)
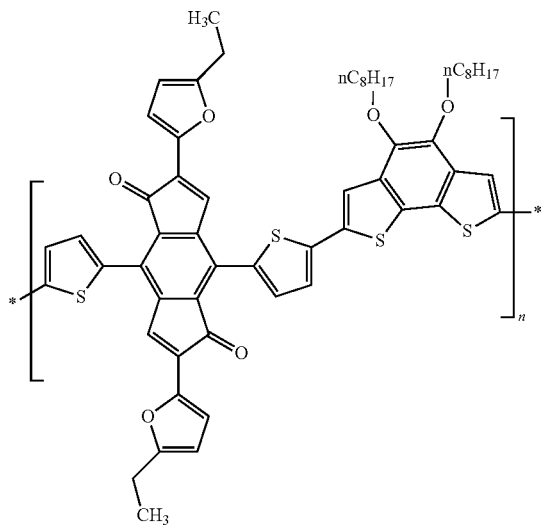
(143)
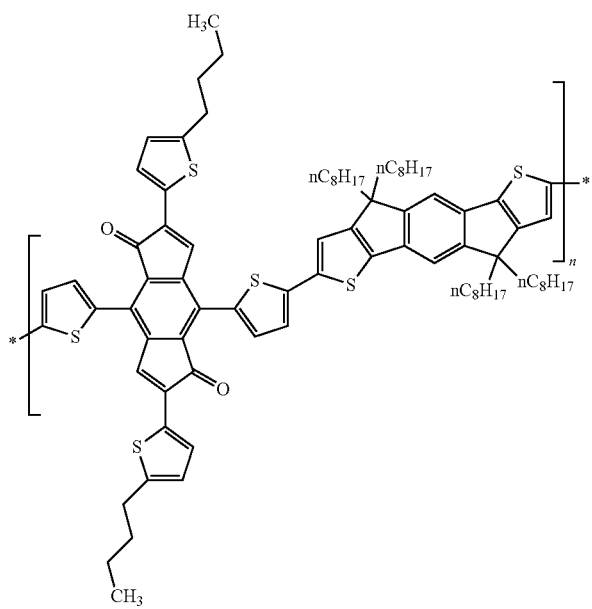

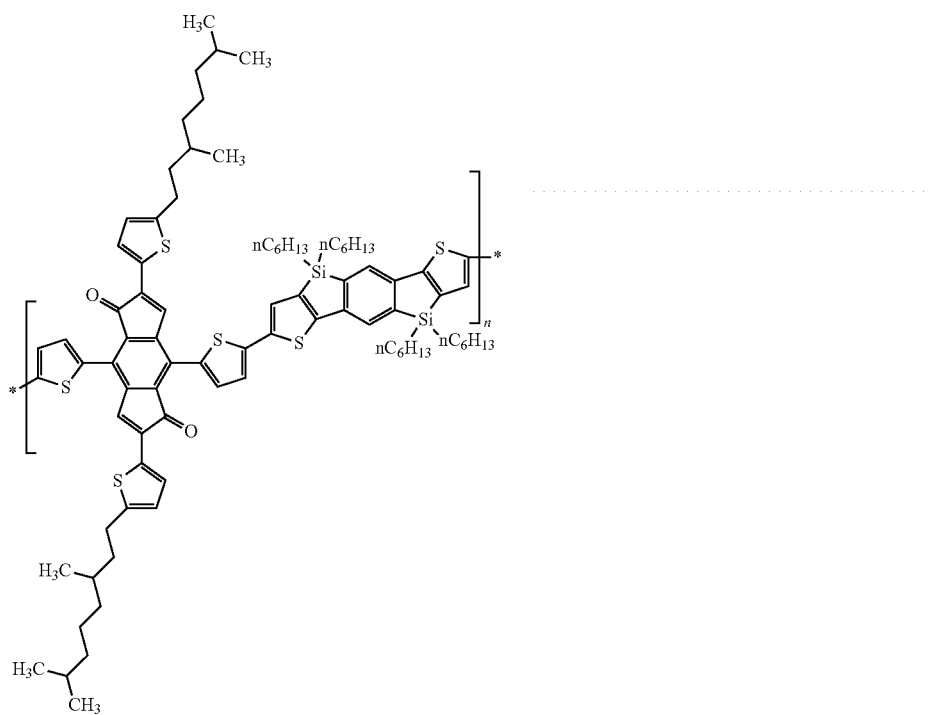
(144)
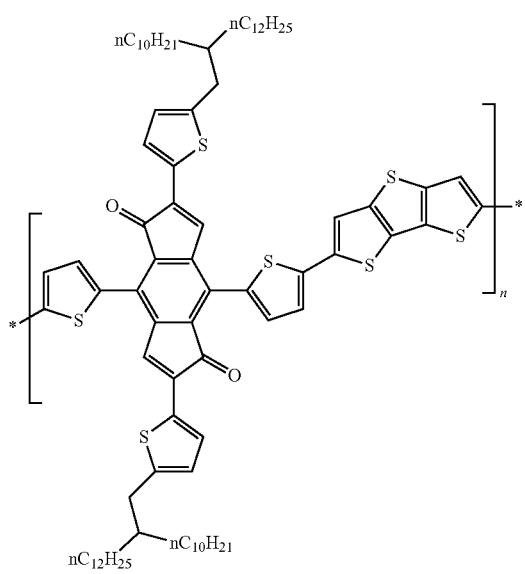
(145)
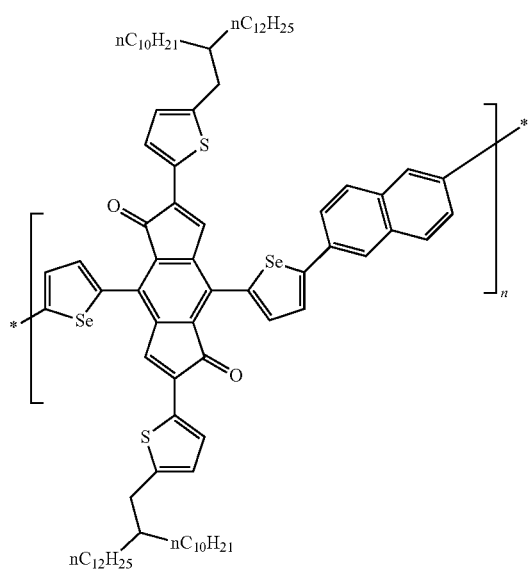
(146)

-continued
(147)
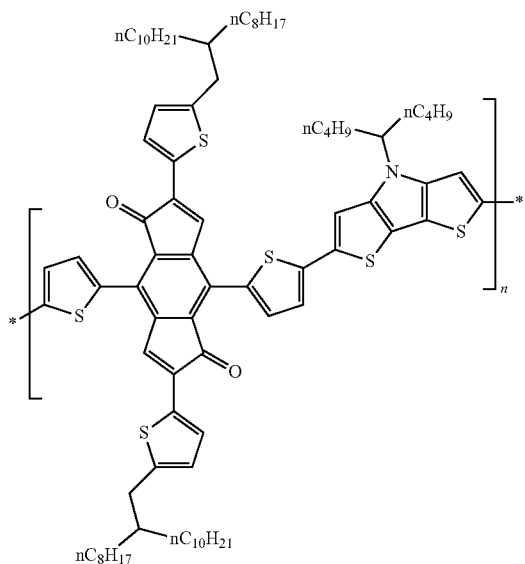
(148)
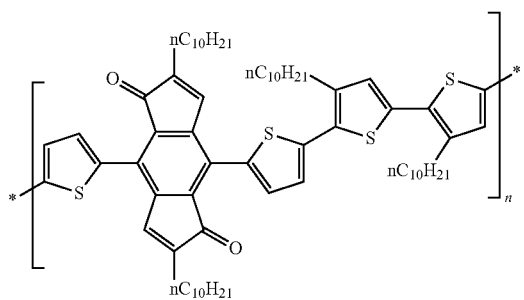
(149)
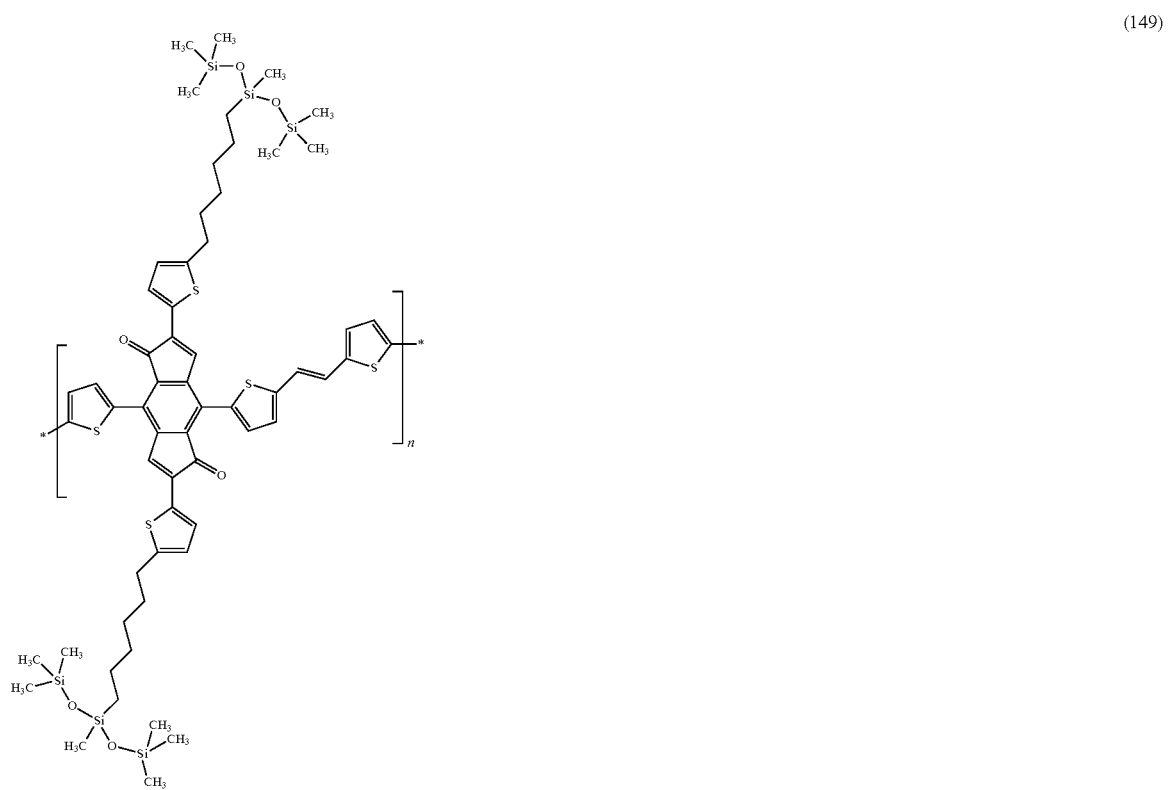

(150)
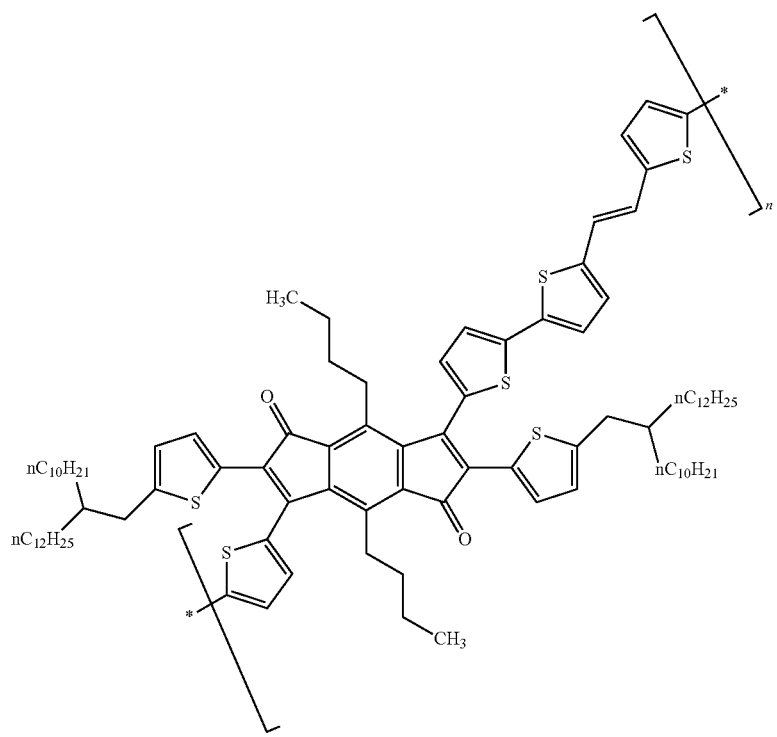
(151)
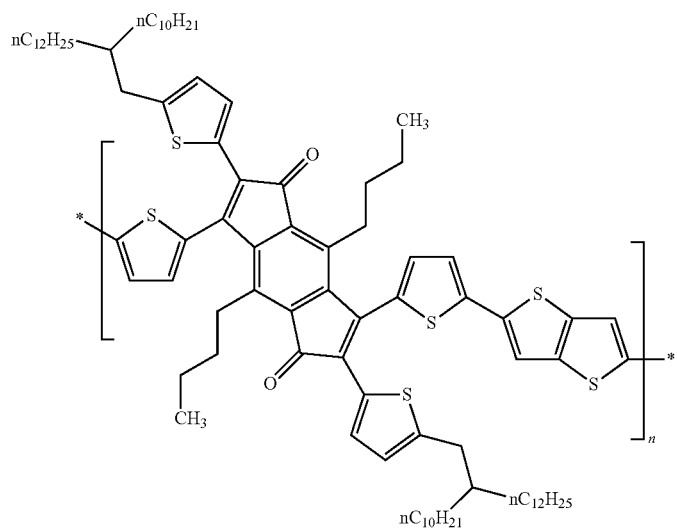

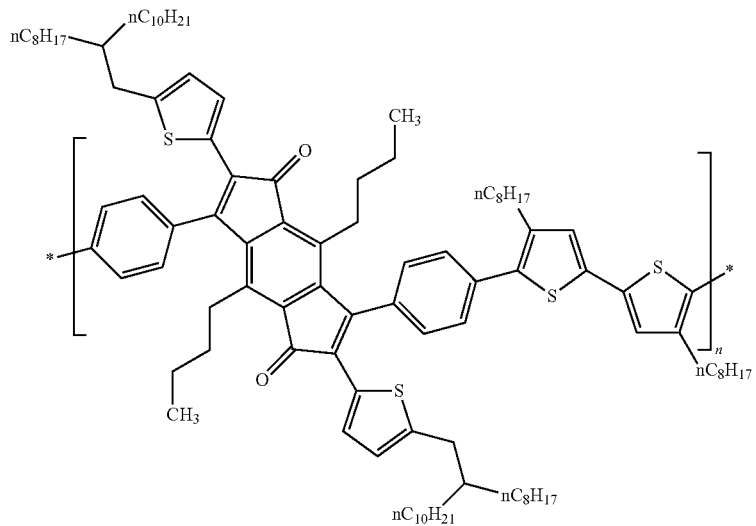
(152)
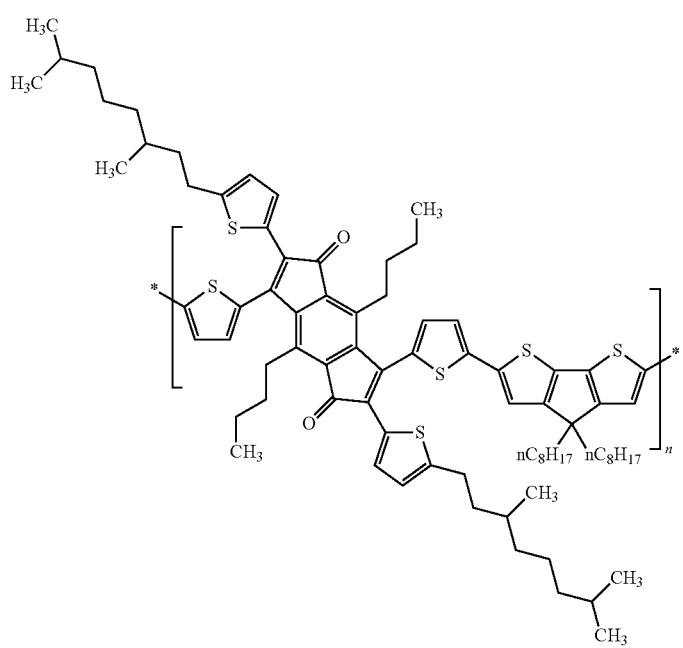
(153)

(154)
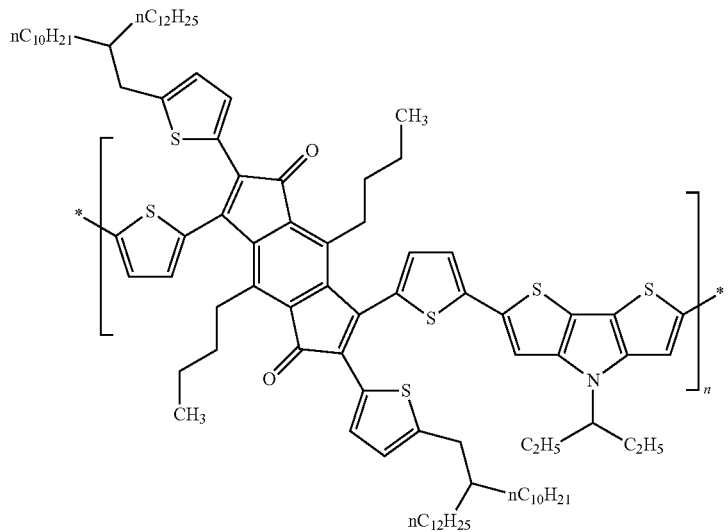
(155)
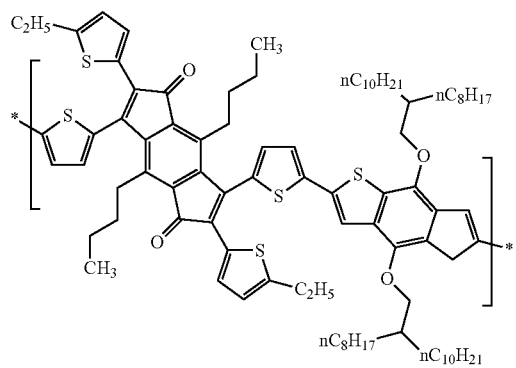
(156)
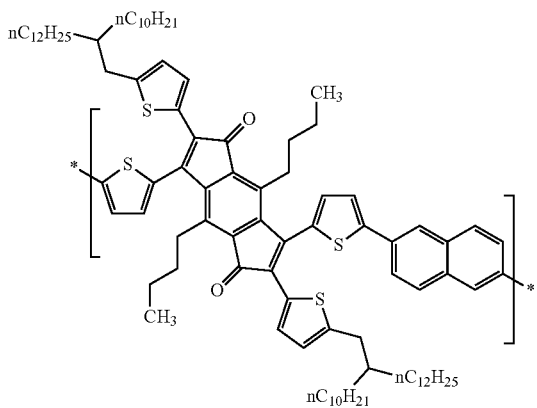
(157)
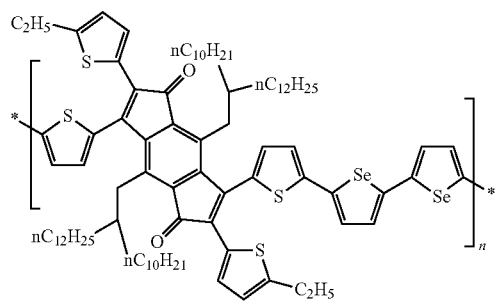
(158)
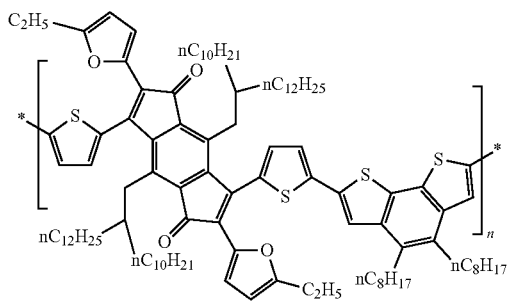

-continued
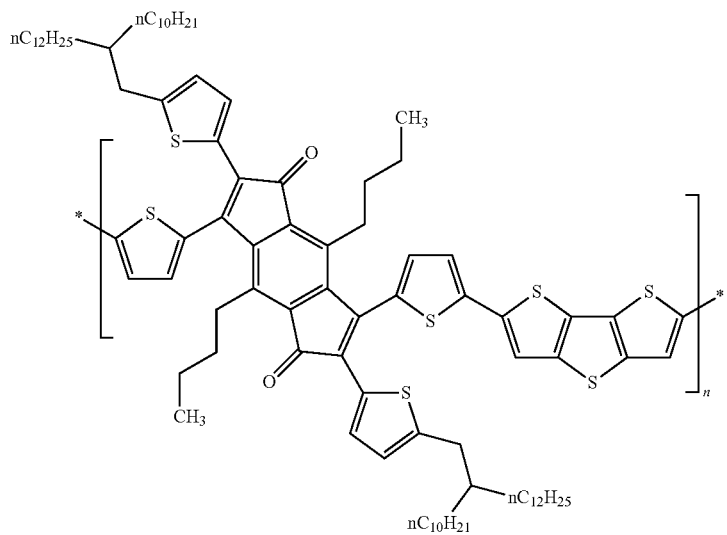
(159)
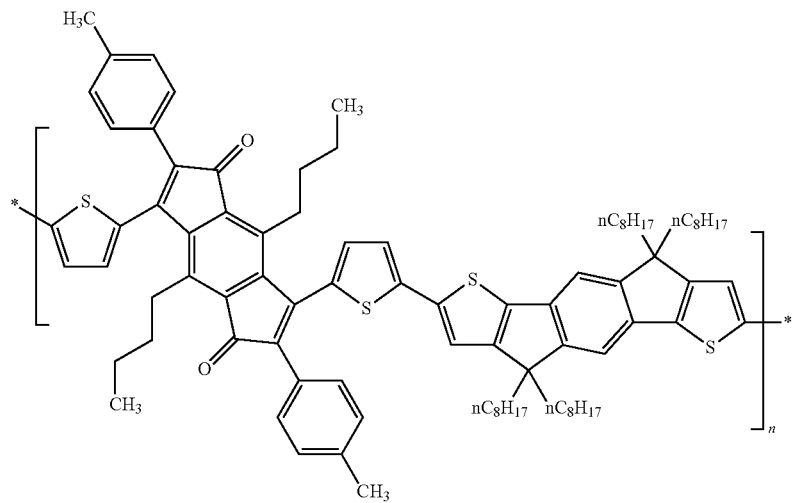
(160)
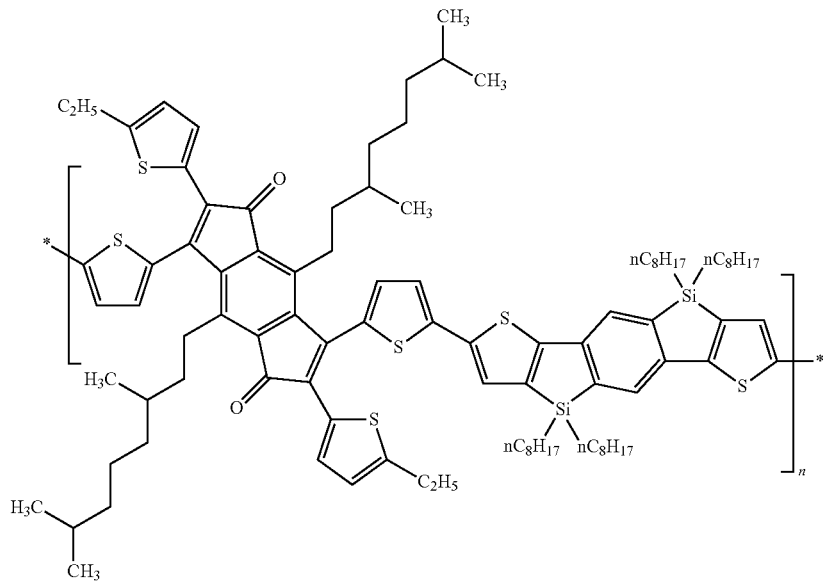
(161)

-continued

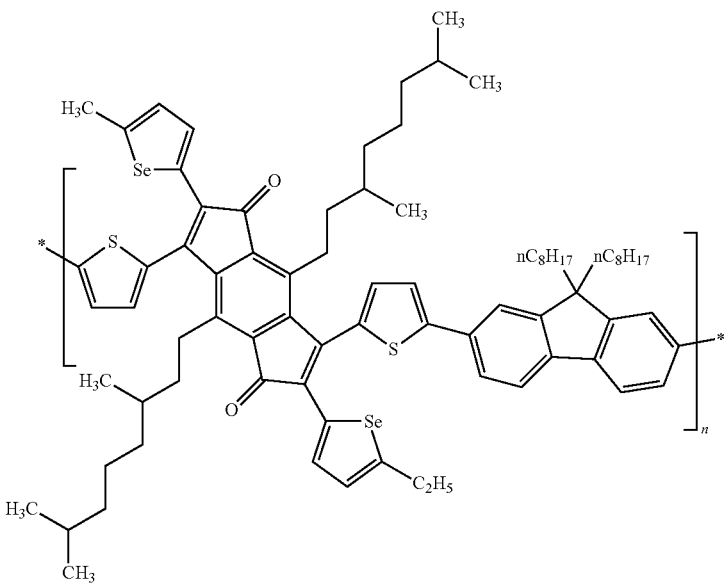

(162)

The compound composed of n repeating units represented by Formula (101) is a compound having two or more repeating structures. The compound may be an oligomer in which the number n of the repeating unit is 2 to 9 or a polymer in which the number n of the repeating unit is equal to or greater than 10.

The weight average molecular weight of the compound composed of n repeating units represented by Formula (101) is preferably equal to or greater than 2,000, more preferably equal to or greater than 5,000, even more preferably equal to or greater than 30,000, particularly preferably equal to or greater than 50,000, and still more preferably equal to or greater than 60,000. The upper limit of the weight average molecular weight is not particularly limited, but it is preferably equal to or less than 1,000,000 and more preferably equal to or less than 750,000. It is preferable that the weight average molecular weight is equal to or less than the aforementioned upper limit, because the intermolecular interaction can be improved, the improved intermolecular interaction favors the transport of carriers, and the solubility in a solvent can be maintained.

In the present invention, the weight average molecular weight is a value measured by gel permeation chromatography (GPC) using high-performance GPC (HLC-8220GPC) manufactured by TOSOH CORPORATION by means of dissolving a polymer in tetrahydrofuran (THF). In the present invention, the weight average molecular weight is a value expressed by using polystyrene as a standard substance.

The compound composed of n repeating units represented by Formula (101) can be synthesized with reference to U.S. Pat. No. 7,928,249B or the like.

For synthesizing the compound of the present invention, any reaction condition may be used. As a reaction solvent, any solvent may be used. Furthermore, in order to accelerate a ring-forming reaction, an acid or a base is preferably used, and a base is particularly preferably used. The optimal reaction condition varies with the intended structure of the condensed cyclopentadienone, but can be set with reference to the specific reaction conditions described in the aforementioned document.

<Intermediate Compound>

The synthetic intermediate having various substituents can be synthesized by using known reactions in combination. Furthermore, various substituents may be introduced at any stage of the intermediate. After the intermediate is synthesized, it is preferable to purify the intermediate by column chromatography, recrystallization, or the like and then further purify it by sublimation. By the sublimation purification, it is possible to separate organic impurities and to effectively remove an inorganic salt, a residual solvent, and the like.

The present invention also relates to a compound represented by the following Formula (6) and a compound represented by the following Formula (7).

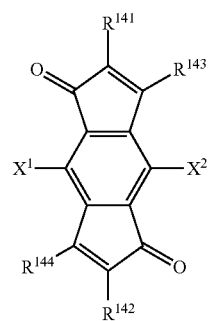

Formula (6)

In Formula (6), each of $R^{141}$ to $R^{144}$ independently represents a hydrogen atom or a substituent; each of $X^1$ and $X^2$ independently represents a halogen atom, —$OSO_2R^i$, —$Sn(R^j)_3$, —$Si(R^j)_3$, or —$B(R^k)_s$; $R^i$ represents a substituted or unsubstituted alkyl group or a hydrogen atom; $R^j$ represents a substituted or unsubstituted alkyl group; $R^k$ represents a substituted or unsubstituted alkoxy group, a hydroxyl group, or a halogen atom; s represents an integer of 2 or 3; the groups represented by $R^k$ may form a ring by being bonded to each other; and when s is 3, —$B(R^k)_s$ is accompanied by a cation $(X^3)^+$ and represents a salt of —$B^-(R^k)_s(X^3)^+$.

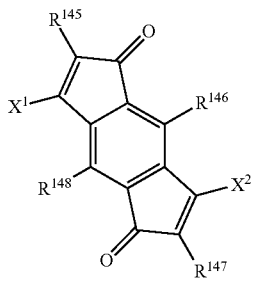

Formula (7)

In Formula (7), each of $R^{145}$ to $R^{148}$ independently represents a hydrogen atom or a substituent; each of $X^1$ and $X^2$ independently represents a halogen atom, $-OSO_2R^i$, $-Sn(R^J)_3$, $-Si(R^J)_3$, or $-B(R^k)_s$; $R^i$ represents a substituted or unsubstituted alkyl group or a hydrogen atom; $R^J$ represents a substituted or unsubstituted alkyl group; $R^k$ represents a substituted or unsubstituted alkoxy group, a hydroxyl group, or a halogen atom; s represents an integer of 2 or 3; the groups represented by $R^k$ may form a ring by being bonded to each other; and when s is 3, $-B(R^k)_s$ is accompanied by a cation $(X^3)^+$ and represents a salt of $-B^-(R^k)_s(X^3)^+$.

Each of the compound represented by Formula (6) and the compound represented by Formula (7) is preferably an intermediate compound of the compound represented by Formula (101).

First, the compound represented by Formula (6) will be described. This compound can be synthesized according to Scheme 2 which will be described later. From the compound represented by Formula (6), the compounds represented by Formula (101) described above can be synthesized. Particularly, among the compounds, the compound represented by Formula (101-2) described above can be synthesized.

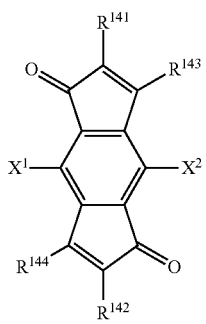

Formula (6)

Each of $R^{141}$ to $R^{144}$ in Formula (6) independently represents a hydrogen atom or a substituent. $R^{141}$ to $R^{144}$ in Formula (6) are the same as $R^{141}$ to $R^{144}$ in Formula (101-2) described above, and the preferred range thereof is also the same.

Each of $X^1$ and $X^2$ in Formula (6) independently represents a halogen atom, $-OSO_2R^i$, $-Sn(R^J)_3$, $-Si(R^J)_3$, or $-B(R^k)_s$. $R^i$ represents a substituted or unsubstituted alkyl group or a hydrogen atom. $R^J$ represents a substituted or unsubstituted alkyl group. $R^k$ represents a substituted or unsubstituted alkoxy group, a hydroxyl group, or a halogen atom. s represents an integer of 2 or 3. The groups represented by $R^k$ may form a ring by being bonded to each other. When s is 3, $-B(R^k)_s$ is accompanied by a cation $(X^3)^+$ and represents a salt of $-B^-(R^k)_s(X^3)^+$.

$R^i$ is preferably a fluorine-substituted alkyl group, and more preferably a perfluoroalkyl group having 1 to 10 carbon atoms.

$R^J$ is preferably an alkyl group having 1 to 6 carbon atoms.

When $R^k$ represents a substituted or unsubstituted alkoxy group, the alkoxy group is preferably an alkoxy group having 1 to 10 carbon atoms. Furthermore, the groups represented by $R^k$ may form a ring having 4 to 10 carbon atoms by being bonded to each other.

Next, the compound represented by Formula (7) will be described. From the compound represented by Formula (7), the compounds represented by Formula (101) described above can be synthesized. Particularly, among the compounds, the compound represented by Formula (101-3) described above can be synthesized.

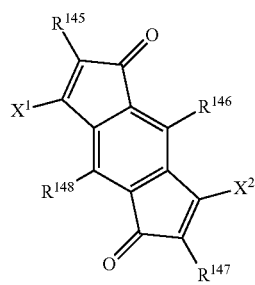

Formula (7)

In Formula (7), each of $R^{145}$ to $R^{148}$ independently represents a hydrogen atom or a substituent. $R^{145}$ to $R^{148}$ in Formula (7) are the same as $R^{145}$ to $R^{148}$ in Formula (3) described above, and the preferred range thereof is also the same.

Each of $X^1$ and $X^2$ in Formula (7) independently represents a halogen atom, $-OSO_2R^i$, $-Sn(R^J)_3$, $-Si(R^J)_3$, or $-B(R^k)_s$. $R^i$ represents a substituted or unsubstituted alkyl group or a hydrogen atom. $R^J$ represents a substituted or unsubstituted alkyl group. $R^k$ represents a substituted or unsubstituted alkoxy group, a hydroxyl group, or a halogen atom. s represents an integer of 2 or 3. The groups represented by $R^k$ may form a ring by being bonded to each other. When s is 3, $-B(R^k)_s$ is accompanied by a cation $(X^3)^+$ and represents a salt of $-B^-(R^k)_s(X^3)^+$.

$R^i$ is preferably a fluorine-substituted alkyl group, and more preferably a perfluoroalkyl group having 1 to 10 carbon atoms.

$R^J$ is preferably an alkyl group having 1 to 6 carbon atoms.

When $R^k$ represents a substituted or unsubstituted alkoxy group, it is preferably an alkoxy group having 1 to 10 carbon atoms. Furthermore, the groups represented by $R^k$ may form a ring having 4 to 10 carbon atoms by being bonded to each other.

<Structure of Organic Film Transistor>

The organic film transistor of the present invention has a semiconductor active layer containing the compound composed of n repeating units represented by Formula (1-1), (1-2), or (101).

The organic film transistor of the present invention may further have layers other than the semiconductor active layer.

The organic film transistor of the present invention is preferably used as an organic field effect transistor (FET), and is more preferably used as an insulated gate-type FET in which gate channels are insulated from each other.

Hereinafter, preferred structural embodiments of the organic film transistor of the present invention will be specifically described by using drawings, but the present invention is not limited to the embodiments.

(Lamination Structure)

The lamination structure of the organic field effect transistor is not particularly limited, and various known structures can be adopted.

For example, the organic film transistor of the present invention can adopt a structure (bottom gate-top contact type) in which an electrode, an insulating layer, a semiconductor active layer (organic semiconductor layer), and two electrodes are arranged in this order on the upper surface of a substrate as a lower most layer. In this structure, the electrode on the upper surface of the substrate as the lower most layer is provided in a portion of the substrate, and the insulating layer is disposed to come into contact with the substrate in a portion other than the electrode. The two electrodes provided on the upper surface of the semiconductor active layer are arranged in a state of being separated from each other.

FIG. 1 shows the constitution of a bottom gate-top contact-type element. FIG. 1 is a schematic view showing the cross-section of an exemplary structure of the organic film transistor of the present invention. In the organic film transistor shown in FIG. 1, a substrate 11 is disposed as a lower most layer, an electrode 12 is provided in a portion of the upper surface thereof, and an insulating layer 13 is provided such that it covers the electrode 12 and comes into contact with the substrate 11 in a portion other than the electrode 12. On the upper surface of the insulating layer 13, a semiconductor active layer 14 is provided, and in a portion of the upper surface thereof, two electrodes 15a and 15b separated from each other are arranged.

In the organic film transistor shown in FIG. 1, the electrode 12 is a gate, and the electrode 15a and the electrode 15b are a drain and a source respectively. The organic film transistor shown in FIG. 1 is an insulated gate-type FET in which a channel as a path of electric currents between the drain and the source is insulated from the gate.

As an example of the structure of the organic film transistor of the present invention, a bottom gate•bottom contact-type element can be exemplified.

Figure 2:
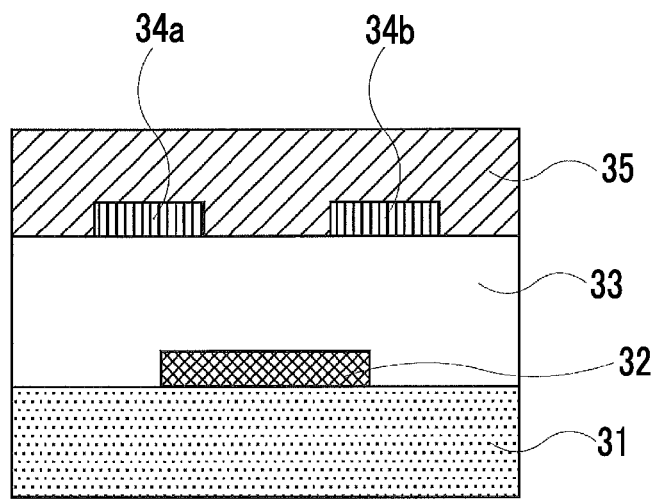
FIG. 2 is a schematic view showing the cross-section of a structure of an organic film transistor manufactured as a substrate for measuring FET characteristics in examples of the present invention.

FIG. 2 shows the constitution of the bottom gate•bottom contact-type element. FIG. 2 is a schematic view showing the cross-section of the structure of an organic film transistor manufactured as a substrate for measuring FET characteristics in examples of the present invention. In the organic film transistor of FIG. 2, a substrate 31 is disposed as a lower most layer, an electrode 32 is provided in a portion of the upper surface thereof, and an insulating layer 33 is provided such that it covers the electrode 32 and comes into contact with the substrate 31 in a portion other than the electrode 32. Furthermore, a semiconductor active layer 35 is provided on the upper surface of the insulating layer 33, and electrodes 34a and 34b are in a lower portion of the semiconductor active layer 35.

In the organic film transistor shown in FIG. 2, the electrode 32 is a gate, and the electrode 34a and the electrode 34b are a drain and a source respectively. The organic film transistor shown in FIG. 2 is an insulated gate-type FET in which a channel as a path of electric currents between the drain and the source is insulated from the gate.

As the structure of the organic film transistor of the present invention, a top gate-top contact-type element in which an insulator and a gate electrode are in the upper portion of a semiconductor active layer or a top gate•bottom contact-type element can also be preferably used.

(Thickness)

When the organic film transistor of the present invention needs to be a thinner transistor, the total thickness of the transistor is preferably, for example, within a range of 0.1 µm to 0.5 µm.

(Sealing)

In order to improve the storage stability of the organic film transistor element by blocking the organic film transistor element from the atmosphere or moisture, the entirety of the organic film transistor element may be sealed with a metal sealing can, glass, an inorganic material such as silicon nitride, a polymer material such as parylene, a low-molecular weight material, or the like.

Hereinafter, preferred embodiments of the respective layers of the organic film transistor of the present invention will be described, but the present invention is not limited to the embodiments.

<Substrate>

(Material)

The organic film transistor of the present invention preferably includes a substrate.

The material of the substrate is not particularly limited, and known materials can be used. Examples of the material include a polyester film such as polyethylene naphthalate (PEN) or polyethylene terephthalate (PET), a cycloolefin polymer film, a polycarbonate film, a triacetylcellulose (TAC) film, a polyimide film, a material obtained by bonding these polymer films to extremely thin glass, ceramics, silicon, quartz, glass, and the like. Among these, silicon is preferable.

<Electrode>

(Material)

The organic film transistor of the present invention preferably includes an electrode.

As the material constituting the electrode, known conductive materials such as a metal material like Cr, Al, Ta, Mo, Nb, Cu, Ag, Au, Pt, Pd, In, Ni, or Nd, an alloy material of these, a carbon material, and a conductive polymer can be used without particular limitation.

(Thickness)

The thickness of the electrode is not particularly limited, but is preferably within a range of 10 nm to 50 nm A gate width (or a channel width) W and a gate length (or a channel length) L are not particularly limited. However, a ratio of W/L is preferably equal to or greater than 10, and more preferably equal to or greater than 20.

<Insulating Layer>

(Material)

The material constituting the insulating layer is not particularly limited as long as an insulating effect is obtained as required. Examples of the material include silicon dioxide, silicon nitride, a fluorine polymer-based insulating material such as PTFE or CYTOP, a polyester insulating material, a polycarbonate insulating material, an acrylic polymer-based insulating material, an epoxy resin-based insulating material, a polyimide insulating material, a polyvinyl phenol resin-based insulating material, a poly p-xylylene resin-based insulating material, and the like.

A surface treatment may be performed on the upper surface of the insulating layer. For example, it is possible to preferably use an insulating layer in which the silicon dioxide surface thereof is subjected to the surface treatment by being coated with hexamethyldisilazane (HMDS) or octadecyltrichlorosilane (OTS).

(Thickness)

The thickness of the insulating layer is not particularly limited. However, when the thickness of the film is required to be reduced, the thickness of the insulating layer is preferably within a range of 10 nm to 400 nm, more preferably within a range of 20 nm to 200 nm, and particularly preferably within a range of 50 nm to 200 nm.

<Semiconductor Active Layer>

(Material)

In the organic film transistor of the present invention, the semiconductor active layer contains a compound which is composed of n repeating units represented by Formula (1-1), (1-2), or (101) described above. That is, the organic film transistor contains the compound of the present invention.

The semiconductor active layer may be a layer composed of the compound of the present invention or a layer further containing a polymer binder, which will be described later, in addition to the compound of the present invention. Furthermore, the semiconductor active layer may contain a residual solvent used at the time of forming a film.

The content of the polymer binder in the semiconductor active layer is not particularly limited. However, the content of the polymer binder used is preferably within a range of 0% by mass to 95% by mass, more preferably within a range of 10% by mass to 90% by mass, even more preferably within a range of 20% by mass to 80% by mass, and particularly preferably within a range of 30% by mass to 70% by mass.

(Thickness)

The thickness of the semiconductor active layer is not particularly limited. However, when the thickness of the film is required to be reduced, the thickness of the semiconductor active layer is preferably within a range of 10 nm to 400 nm, more preferably within a range of 10 nm to 200 nm, and particularly preferably within a range of 10 nm to 100 nm.

[Organic Semiconductor Material for Non-Light-Emitting Organic Semiconductor Device]

The present invention also relates to an organic semiconductor material for a non-light-emitting organic semiconductor device containing the compound composed of n repeating units represented by Formula (1-1), (1-2), or (101) described above, that is, an organic semiconductor material for a non-light-emitting organic semiconductor device containing the compound of the present invention.

(Non-Light-Emitting Organic Semiconductor Device)

In the present specification, a "non-light-emitting organic semiconductor device" refers to a device which is not used for the purpose of emitting light. The non-light-emitting organic semiconductor device preferably uses an electronic element having a structure composed of films layered on each other. The non-light-emitting organic semiconductor device includes an organic film transistor (also referred to as an organic thin film transistor), an organic photoelectric conversion element (a solid-state imaging element used for a photosensor, a solar cell used for energy conversion, or the like), a gas sensor, an organic rectifying element, an organic inverter, an information recording element, and the like. The organic photoelectric conversion element can be used for a photosensor (solid-state imaging element) and for energy conversion (a solar cell). Among these, an organic photoelectric conversion element and an organic film transistor are preferable, and an organic film transistor is more preferable. That is, the organic semiconductor material for a non-light-emitting organic semiconductor device of the present invention is preferably a material for an organic film transistor as described above.

(Organic Semiconductor Material)

In the present specification, the "organic semiconductor material" is an organic material showing characteristics of a semiconductor. Just like the semiconductor composed of an inorganic material, the organic semiconductor is classified into a p-type (hole-transporting) organic semiconductor conducting holes as carriers and an n-type (electron transporting) organic semiconductor conducting electrons as carriers.

The compound of the present invention may be used as both the p-type organic semiconductor material and the n-type organic semiconductor material, but is preferably used as the p-type. The ease with which the carriers flow in the organic semiconductor is represented by a carrier mobility $\mu$. The higher the carrier mobility $\mu$, the more preferable. The carrier mobility $\mu$ is preferably equal to or greater than $1\times10^{-2}$ cm$^2$/Vs, more preferably equal to or greater than $5\times10^{-2}$ cm$^2$/Vs, particularly preferably equal to or greater than $1\times10^{-1}$ cm$^2$/Vs, and further particularly preferably equal to or greater than $2\times10^{-1}$ cm$^2$/Vs. The carrier mobility $\mu$ can be determined by the characteristics of the prepared field effect transistor (FET) element or by a time-of-flight (TOF) measurement method.

[Organic Semiconductor Film for Non-Light-Emitting Organic Semiconductor Device]

(Material)

The present invention also relates to an organic semiconductor film for a non-light-emitting organic semiconductor device containing the compound composed of n repeating units represented by Formula (1-1), (1-2), or (101), that is, the present invention also relates to an organic semiconductor film for a non-light-emitting organic semiconductor device containing the compound of the present invention.

As the organic semiconductor film for a non-light-emitting organic semiconductor device of the present invention, an embodiment is preferable in which the organic semiconductor film contains the compound composed of n repeating units represented by Formula (1-1), (1-2), or (101), that is, the compound of the present invention, and does not contain a polymer binder.

Furthermore, the organic semiconductor film for a non-light-emitting organic semiconductor device of the present invention may contain the compound composed of n repeating units represented by Formula (1-1), (1-2), or (101), that is, the compound of the present invention, and a polymer binder.

Examples of the polymer binder include an insulating polymer such as polystyrene, polycarbonate, polyarylate, polyester, polyamide, polyimide, polyurethane, polysiloxane, polysulfone, polymethyl methacrylate, polymethyl acrylate, cellulose, polyethylene, or polypropylene, a copolymer of these, a photoconductive polymer such as polyvinylcarbazole or polysilane, a conductive polymer such as polythiophene, polypyrrole, polyaniline, or poly p-phenylenevinylene, and a semiconductor polymer.

One kind of the aforementioned polymer binder may be used singly, or plural kinds thereof may be used concurrently.

The organic semiconductor material may be uniformly mixed with the polymer binder. Alternatively, the organic semiconductor material and the polymer binder may be totally or partially in a phase separation state. From the viewpoint of the charge mobility, a structure, in which the organic semiconductor and the binder are in a phase separation state in the film thickness direction within the film, is the most preferable because the binder does not hinder the organic semiconductor from moving a charge.

Considering the mechanical strength of the film, a polymer binder having a high glass transition temperature is preferable. Furthermore, considering the charge mobility, a polymer binder having a structure not containing a polar group, a photoconductive polymer, and a conductive polymer are preferable.

The amount of the polymer binder used is not particularly limited. However, in the organic semiconductor film for a non-light-emitting organic semiconductor device of the present invention, the amount of the polymer binder used is preferably within a range of 0% by mass to 95% by mass, more preferably within a range of 10% by mass to 90% by mass, even more preferably within a range of 20% by mass to 80% by mass, and particularly preferably within a range of 30% by mass to 70% by mass.

If the compound of the present invention has the structure described above, an organic film having excellent quality can be obtained. Specifically, because the compound obtained in the present invention has excellent crystallinity, a sufficient film thickness can be obtained, and the obtained organic semiconductor film for a non-light-emitting organic semiconductor device of the present invention has excellent quality.

(Film Forming Method)

The compound of the present invention may be formed into a film on a substrate by any method.

At the time of forming the film, the substrate may be heated or cooled. By changing the temperature of the substrate, it is possible to control the film quality or the packing of molecules in the film. The temperature of the substrate is not particularly limited. However, it is preferably between 0° C. to 200° C., more preferably between 15° C. to 100° C., and particularly preferably between 20° C. to 95° C.

The compound of the present invention can be formed into a film on a substrate by a vacuum process or a solution process, and both of the processes are preferable.

Specific examples of the film forming method by a vacuum process include a physical vapor deposition method such as a vacuum vapor deposition method, a sputtering method, an ion plating method, or a molecular beam epitaxy (MBE) method and a chemical vapor deposition (CVD) method such as plasma polymerization, and it is particularly preferable to use a vacuum vapor deposition method.

Herein, the film forming method by a solution process refers to a method of dissolving an organic compound in a solvent which can dissolve the compound and forming a film by using the solution. Specifically, a substrate is coated with the composition of the present invention containing the compound, which is composed of n repeating units represented by Formula (1-1), (1-2), or (101), and an organic solvent. Concretely, it is possible to use general methods like a coating method such as a casting method, a dip coating method, a die coating method, a roll coating method, a bar coating method, or a spin coating method, various printing methods such as an inkjet method, a screen printing method, a gravure printing method, a flexographic printing method, an offset printing method, or a micro-contact printing method, and a Langmuir-Blodgett (LB) method. It is particularly preferable to use a casting method, a spin coating method, an inkjet method, a gravure printing method, a flexographic printing method, an offset printing method, or a micro-contact printing method.

The organic semiconductor film for a non-light-emitting organic semiconductor device of the present invention is preferably prepared by a solution coating method. When the organic semiconductor film for a non-light-emitting organic semiconductor device of the present invention contains a polymer binder, it is preferable to prepare a coating solution by dissolving or dispersing a material, which will be formed into a layer, and a polymer binder in an appropriate solvent and to form the organic semiconductor film by various coating methods.

Hereinafter, a coating solution for a non-light-emitting organic semiconductor device of the present invention that can be used for forming a film by a solution process will be described.

[Composition and Coating Solution for Non-Light-Emitting Organic Semiconductor Device]

The present invention also relates to a composition containing the compound composed of n repeating units represented by Formula (1-1), (1-2), or (101), that is, a composition containing the compound of the present invention and a coating solution for a non-light-emitting organic semiconductor device.

When a film is formed on a substrate by using a solution process, a material which will be formed into a layer is dissolved or dispersed in either or both of an appropriate organic solvent (for example, a hydrocarbon-based solvent such as hexane, octane, decane, toluene, xylene, mesitylene, ethylbenzene, decalin, or 1-methylnaphthalene, a ketone-based solvent such as acetone, methyl ethyl ketone, methyl isobutyl ketone, or cyclohexanone, a halogenated hydrocarbon-based solvent such as dichloromethane, chloroform, tetrachloromethane, dichloroethane, trichloroethane, tetrachloroethane, chlorobenzene, dichlorobenzene, or chlorotoluene, an ester-based solvent such as ethyl acetate, butyl acetate, or amyl acetate, an alcohol-based solvent such as methanol, propanol, butanol, pentanol, hexanol, cyclohexanol, methyl cellosolve, ethyl cellosolve, or ethylene glycol, an ether-based solvent such as dibutylether, tetrahydrofuran, dioxane, or anisole, an amide-imide-based solvent such as N,N-dimethylformamide, N,N-dimethylacetamide, 1-methyl-2-pyrrolidone, or 1-methyl-2-imidazolidinone, a sulfoxide-based solvent such as dimethyl sulfoxide, or a nitrile-based solvent such as acetonitrile) and/or water so as to obtain a coating solution, and a film can be formed by various coating methods by using the coating solution. One kind of the solvent may be used singly, or plural kinds thereof may be used in combination. Among these, an aromatic hydrocarbon-based solvent, a halogenated hydrocarbon-based solvent, an ether-based solvent, or a ketone-based solvent is preferable, and an aromatic hydrocarbon-based solvent, an ether-based solvent, or a ketone-based solvent is more preferable. Specifically, toluene, xylene, mesitylene, tetralin, chlorobenzene, dichlorobenzene, anisole, isophorone, diisopropylbenzene, and s-butylbenzene are more preferable, and toluene, xylene, tetralin, chlorobenzene, dichlorobenzene, diisopropylbenzene, and s-butylbenzene are particularly preferable. The concentration of the compound, which is composed of n repeating units represented by Formula (1-1), (1-2), or (101), in the coating solution is preferably 0.1% by mass to 80% by mass, more preferably 0.1% by mass to 10% by mass, and particularly preferably 0.5% by mass to 10% by mass. The thickness of the formed film can be arbitrarily set.

Among the above solvents, from the viewpoint of improving the solubility of the compound, which is composed of n repeating units represented by Formula (1-1), (1-2), or (101), and the carrier mobility, an active hydrogen-free aromatic solvent having a boiling point of equal to or greater than 150° C. is preferable as the organic solvent. Examples of such a solvent include tetralin, dichlorobenzene, anisole, isophorone, diisopropylbenzene, s-butylbenzene, and the like. As the organic solvent used in the present invention, dichlorobenzene, tetralin, diisopropylbenzene, and s-butylbenzene are preferable, and tetralin, diisopropylbenzene, and s-butylbenzene are more preferable.

In order to form a film by a solution process, the material needs to dissolve in the solvent exemplified above, but simply dissolving in a solvent is not good enough. Generally, even the material formed into a film by a vacuum process can dissolve in a solvent to some extent. The solution process includes a step of coating a substrate with a material by dissolving the material in a solvent and then forming a film by evaporating the solvent, and many of the materials not suitable for being formed into a film by the solution process have high crystallinity. Therefore, the material is inappropriately crystallized (aggregated) in the step, and hence it is difficult to form an excellent film. The compound composed of n repeating units represented by Formula (1-1), (1-2), or (101) is also excellent in the respect that it is not easily crystallized (aggregated).

As the coating solution for a non-light-emitting organic semiconductor device of the present invention, an embodiment is also preferable in which the coating solution contains the compound composed of n repeating units represented by Formula (1-1), (1-2), or (101), that is, the compound of the present invention, and does not contain a polymer binder.

Furthermore, the coating solution for a non-light-emitting organic semiconductor device of the present invention may contain the compound composed of n repeating units represented by Formula (1-1), (1-2), or (101), that is, the compound of the present invention, and a polymer binder. In this case, a material, which will be formed into a layer, and a polymer binder are dissolved or dispersed in an appropriate solvent described above so as to prepare a coating solution, and by using the coating solution, a film can be formed by various coating methods. The polymer binder can be selected from those described above.

EXAMPLES

Hereinafter, the characteristics of the present invention will be more specifically explained by describing examples and comparative examples. The materials, the amount thereof used, the proportion thereof, the content of treatment, the treatment procedure, and the like described in the following examples can be appropriately modified within a range that does not depart from the gist of the present invention. Accordingly, the scope of the present invention is not limited to the following specific examples.

Example 1

Synthesis Example 1

Synthesis of Compound 2

According to a specific synthesis procedure shown in the following scheme, a compound composed of n repeating units represented by Formula (1-1) was synthesized as Compound 2.

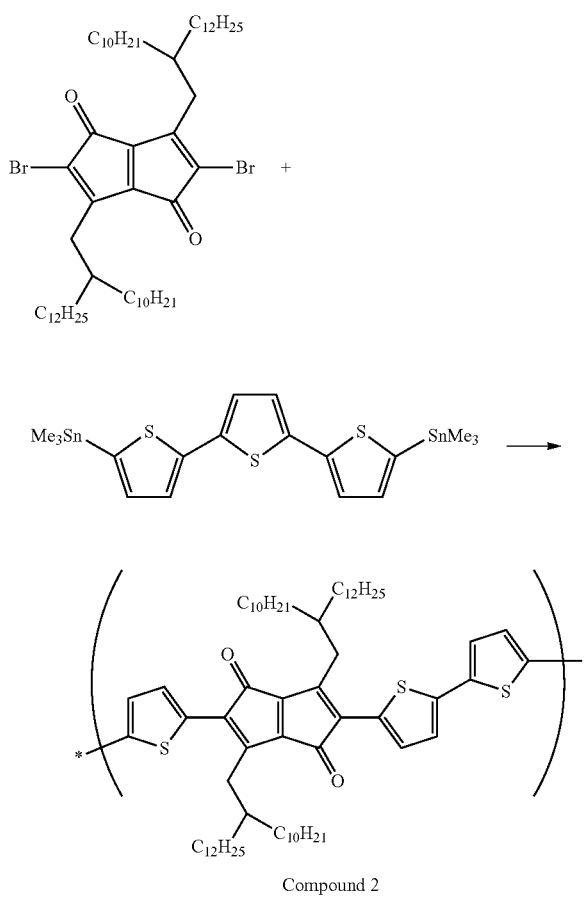

Compound 2

The obtained compound was identified by elemental analysis and NMR.

The compound composed of n repeating units represented by Formula (1-1) that was used in other examples was synthesized in the same manner as Compound 2.

Example 2

Synthesis Example 2

Synthesis of Compound 34

According to the specific synthesis procedure shown in the following scheme, a compound represented by Formula (1-2) was synthesized as Compound 34.

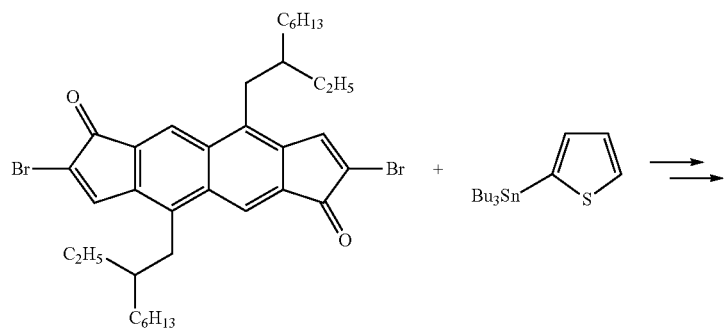

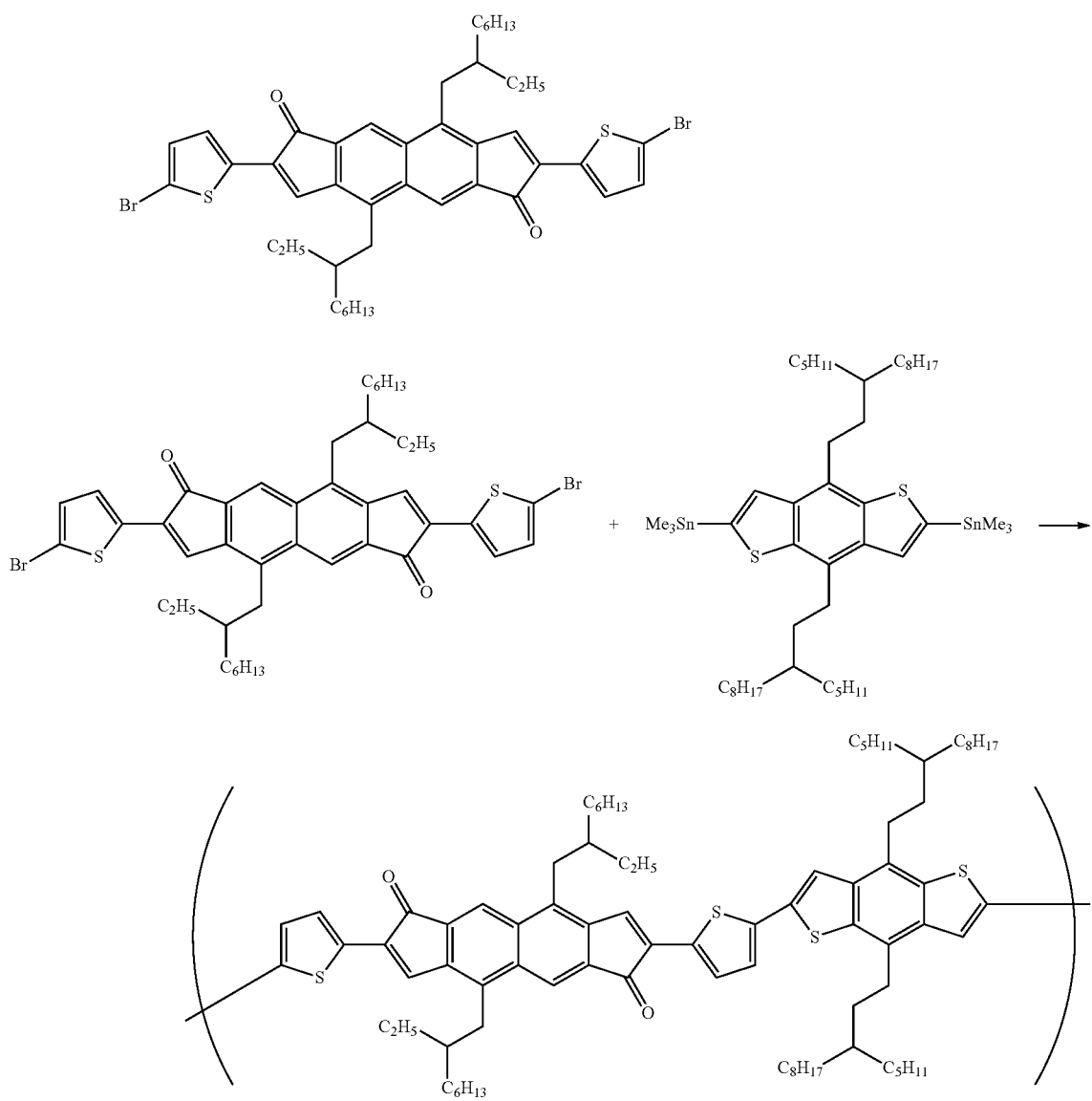

Compound 34

The obtained compound was identified by elemental analysis and NMR.

As a result of measuring the molecular weight of each compound by the method described in the present specification, it was found that the weight average molecular weight of each compound was within a range of 50,000 to 200,000. That is, it was found that the number n of the repeating unit of each compound represented by Formula (1-1) or (1-2) was within a range of 50 to 200.

The compound represented by Formula (1-2) used in other examples was synthesized in the same manner as Compound 34.

Comparative Compound 1 described in JP2012-177104A and Comparative Compound 2 described in THEOCHEM, (2002), 589-590, 459-464 that were used in a semiconductor active layer (organic semiconductor layer) of a comparative element were synthesized respectively with reference to each of the aforementioned documents. The structures of Comparative Compounds 1 and 2 are as below.

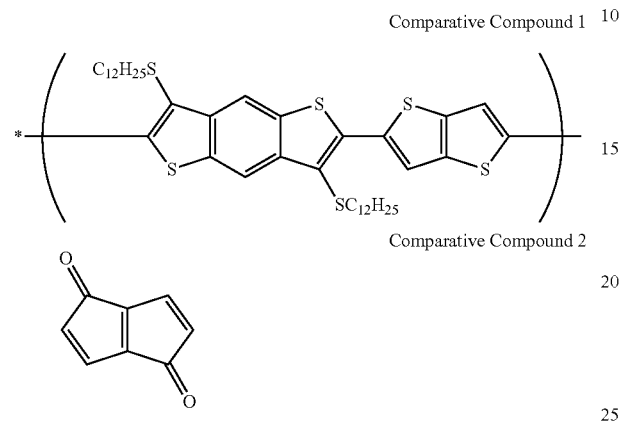

Comparative Compound 1

Comparative Compound 2

<Preparation•Evaluation of Element>

Example 3

Preparation of Coating Solution for
Non-Light-Emitting Organic Semiconductor Device The compound of the present invention or the comparative compound (10 mg each) was mixed with toluene (1 mL), and the mixture was heated to 100° C., thereby preparing a coating solution for a non-light-emitting organic semiconductor device. The coating solution in which the compound was not completely dissolved was filtered through a 0.2 μm filter.

<Formation of Semiconductor Active Layer (Organic Semiconductor Layer) by Using Compound Alone>

By performing spin coating of the coating solution for a non-light-emitting organic semiconductor device in the atmosphere, an organic semiconductor film for a non-light-emitting organic semiconductor device was formed, thereby obtaining an organic film transistor element of Example 3 that was for measuring FET characteristics. As a substrate for measuring FET characteristics, a silicon substrate having a bottom contact structure was used which included chromium/gold (gate width W=100 mm, gate length L=100 μm) arranged to form a comb pattern as source and drain electrodes and included $SiO_2$ (film thickness: 200 nm) as an insulating layer (the structure is schematically shown in FIG. 2).

By using a semiconductor parameter analyzer (4156C manufactured by Agilent Technologies) connected to a semi-automatic prober (AX-2000 manufactured by Vector Semiconductor Co., Ltd.), the FET characteristics of the organic film transistor element of Example 3 were evaluated in a normal pressure•nitrogen atmosphere, from the viewpoint of the carrier mobility, the threshold voltage shift after repeated driving, and the film formability.

Furthermore, the coating solution for a non-light-emitting organic semiconductor device of Example 3 was evaluated from the viewpoint of the solubility.

The obtained results are shown in the following table.

(a) Solubility Evaluation

The compound of the present invention or the comparative compound (10 mg each) was mixed with toluene (1 mL), and the mixture was heated to 100° C. Thereafter, the mixture was left for 30 minutes at room temperature. From the amount of the precipitated solid, the solubility was evaluated based into 3 levels below.

A: No solid precipitated.

B: The amount of the precipitated solid was less than 30%.

C: The amount of the precipitated solid was equal to or greater than 30%.

(b) Carrier Mobility

Between the source electrode and the drain electrode of each organic film transistor element (FET element), a voltage of −50 V was applied, and the gate voltage was varied within a range of 20 V to −100 V. In this way, by using Equation $I_d=(w/2L)\mu C_i(V_g-V_{th})^2$, a carrier mobility μ was calculated (in the equation, $I_d$ represents a drain current; L represents a gate length; W represents a gate width; $C_i$ represents a capacity of the insulating layer per unit area; $V_g$ represents a gate voltage; and $V_{th}$ represents a threshold voltage). Herein, because the characteristics of the element having a carrier mobility of less than $1\times10^{-5}$ cm$^2$/Vs were too poor, the element was not subjected to the evaluation of (c) Threshold voltage shift after repeated driving described below.

(c) Threshold Voltage Shift after Repeated Driving

Between the source electrode and the drain electrode of each organic film transistor element (FET element), a voltage of −80 V was applied, and the element was repeatedly driven 100 times by varying the gate voltage within a range of +20 V to −100 V. In this way, the element was measured in the same manner as in the section (a), and a difference between a threshold voltage $V_{before}$ before the repeated driving and a threshold voltage $V_{after}$ after the repeated driving ($V_{after}-V_{before}$) was evaluated into 3 levels below. The smaller the difference, the higher the stability of the element against repeated driving. Therefore, the smaller the difference, the more preferable.

A: $|V_{after}-V_{before}| \leq 5$ V

B: $5 V < |V_{after}-V_{before}| \leq 10$ V

C: $|V_{after}-V_{before}| > 10$ V (d) Film Formability Evaluation

Each of the obtained organic film transistor elements was observed with unaided eyes and with an optical microscope. By the method described above, 10 elements were prepared, and the ratio of film cissing that occurred on the source and drain electrodes was evaluated.

The results were evaluated into 3 levels as below.

A: Less than 10%.

B: Equal to or greater than 10% and less than 30%

C: Equal to or greater than 30%

(e) Element Variation

The mobility of the prepared 30 elements was measured, and a coefficient of variation was calculated. The results were evaluated into 3 levels as below.

A: Less than 30%

B: Equal to or greater than 30% and less than 50%

C: Equal to or greater than 50%

TABLE 1

| Element No. | Organic semiconductor material | Solubility | Carrier mobility (cm²/Vs) | Threshold voltage shift after repeated driving | Film formability | Element variation | Note |
|---|---|---|---|---|---|---|---|
| Element 1 | Compound 2 | A | 0.08 | A | A | A | Present invention |
| Element 2 | Compound 5 | A | 0.16 | A | A | A | Present invention |
| Element 3 | Compound 7 | A | 0.21 | A | A | A | Present invention |
| Element 4 | Compound 22 | A | 0.14 | A | A | A | Present invention |
| Element 5 | Compound 26 | A | 0.25 | A | A | A | Present invention |
| Element 6 | Compound 34 | A | 0.09 | A | A | A | Present invention |
| Element 7 | Compound 38 | A | 0.17 | A | A | A | Present invention |
| Element 8 | Compound 50 | A | 0.08 | A | A | A | Present invention |
| Element 9 | Compound 59 | A | 0.1 | A | A | A | Present invention |
| Element 10 | Compound 62 | A | 0.12 | A | A | A | Present invention |
| Comparative element 1 | Comparative Compound 1 | C | 0.005 | C | B | B | Comparative example |
| Comparative element 2 | Comparative Compound 2 | B | $<1 \times 10^{-5}$ | C | C | C | Comparative example |

From the above table, it was understood that the compound of the present invention exhibits excellent solubility in an organic solvent, and the organic film transistor element using the compound of the present invention has high carrier mobility. It was also understood that accordingly, the compound of the present invention can be preferably used as an organic semiconductor material for a non-light-emitting organic semiconductor device.

In contrast, the organic film transistor elements using Comparative Compounds 1 and 2 exhibited low carrier mobility.

In the organic film transistor element using the compound of the present invention, the threshold voltage shift occurred to a small extent after the repeating driving. Furthermore, it was understood that in all of the organic film transistor elements using the compound of the present invention, the smoothness-homogeneity of the film are extremely high, and the film formability is excellent.

Example 4

Formation of Semiconductor Active Layer (Organic Semiconductor Layer)

The surface of a silicon wafer, which contained SiO₂ (film thickness: 370 nm) as a gate insulating film, was treated with octyltrichlorosilane.

The compound of the present invention or the comparative compound (1 mg each) was mixed with toluene (1 mL), and the mixture was heated to 100° C., thereby preparing a coating solution for a non-light-emitting organic semiconductor device. In a nitrogen atmosphere, the coating solution was cast onto the silicon wafer which had been heated to 90° C. and undergone surface treatment with octylsilane, thereby forming an organic semiconductor film for a non-light-emitting organic semiconductor device.

Furthermore, gold was deposited onto the surface of the film through a mask so as to prepare source and drain electrodes, thereby obtaining an organic film transistor element having a bottom gate-top contact structure with a gate width W=5 mm and a gate length L=80 μm (the structure is schematically shown in FIG. 1).

By using a semiconductor parameter analyzer (4156C manufactured by Agilent Technologies) connected to a semi-automatic prober (AX-2000 manufactured by Vector Semiconductor Co., Ltd.), the FET characteristics of the organic film transistor element of Example 4 were evaluated in a normal pressure•nitrogen atmosphere, from the viewpoint of the carrier mobility, the threshold voltage shift after repeated driving, and the film formability.

Furthermore, the coating solution for a non-light-emitting organic semiconductor device of Example 4 was evaluated from the viewpoint of the solubility.

The obtained results are shown in the following table.

TABLE 2

| Element No. | Organic semiconductor material | Carrier mobility (cm²/Vs) | Threshold voltage shift after repeated driving | Film formability | Element variation | Note |
|---|---|---|---|---|---|---|
| Element 11 | Compound 5 | 0.22 | A | A | A | Present invention |
| Element 12 | Compound 26 | 0.31 | A | A | A | Present invention |
| Element 13 | Compound 38 | 0.24 | A | A | A | Present invention |

TABLE 2-continued

| Element No. | Organic semiconductor material | Carrier mobility (cm²/Vs) | Threshold voltage shift after repeated driving | Film formability | Element variation | Note |
|---|---|---|---|---|---|---|
| Element 14 | Compound 59 | 0.15 | A | A | A | Present invention |
| Element 15 | Compound 62 | 0.18 | A | A | A | Present invention |
| Comparative element 1 | Comparative Compound 1 | 0.01 | C | B | B | Comparative example |
| Comparative element 2 | Comparative Compound 2 | <1 × 10⁻⁵ | C | C | C | Comparative example |

From the above table, it was understood that the compound of the present invention exhibits excellent solubility in an organic solvent, and the organic film transistor element using the compound of the present invention has high carrier mobility. It was also understood that accordingly, the compound of the present invention can be preferably used as an organic semiconductor material for a non-light-emitting organic semiconductor device.

In contrast, the organic film transistor elements using Comparative Compounds 1 and 2 exhibited low carrier mobility.

In the organic film transistor element using the compound of the present invention, the threshold voltage shift occurred to a small extent after the repeated driving. Furthermore, it was understood that in all of the organic film transistor elements using the compound of the present invention, the smoothness-homogeneity of the film are extremely high, and the film formability is excellent.

Example 101

Synthesis Example

Synthesis of Intermediate Compounds A7 and A9

An acceptor portion A7 was synthesized according to the following scheme 1.

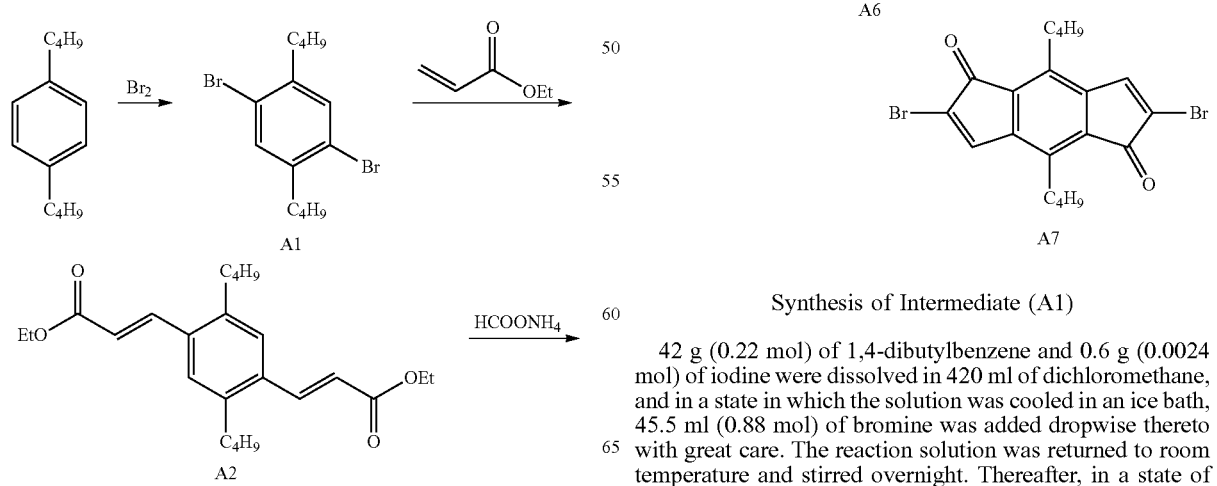

Synthesis of Intermediate (A1)

42 g (0.22 mol) of 1,4-dibutylbenzene and 0.6 g (0.0024 mol) of iodine were dissolved in 420 ml of dichloromethane, and in a state in which the solution was cooled in an ice bath, 45.5 ml (0.88 mol) of bromine was added dropwise thereto with great care. The reaction solution was returned to room temperature and stirred overnight. Thereafter, in a state of being cooled in an ice bath, the reaction solution was added with great care to 2,000 ml of a 3% aqueous sodium hydrogen sulfite solution. Then, a liquid separation/extraction using dichloromethane was performed twice, and the organic layer was washed twice with water. After being dried over magnesium sulfate, the resultant was separated by filtration, and the solvent of the organic layer was distilled away under reduced pressure. The obtained oily substance was purified by silica gel column chromatography (n-hexane), thereby obtaining 60 g of an intermediate (A1) (yield: 78%).

The obtained intermediate (A1) was identified by NMR. The results are as below.

$^1$H NMR (CDCl$_3$) δ 7.38 (s, 2H), 2.66 (t, 4H), 1.58 (m, 4H), 1.39 (m, 4H), 0.95 (t, 6H) ppm Synthesis of Intermediate (A2)

10 g (0.029 mol) of the intermediate (A1), 25 ml (0.23 mol) of ethyl acrylate, 15 g (0.12 mol) of N,N-diisopropylethylamine, 18 g (0.056 mol) of tetrabutylammonium bromide, 1.1 g (0.0023 mol) of 2-dicyclohexylphosphino-2',4',6'-triisopropylphenyl, and 0.32 g (0.0014 mol) of palladium acetate were dissolved in 100 ml of N,N-dimethylformamide, and the solution was stirred overnight at a temperature of 100° C. in a nitrogen atmosphere. The solution was then filtered through celite, and to the obtained filtrate, 500 ml of a 1 N aqueous hydrochloric acid solution and 500 ml of ethyl acetate were added. The resultant solution was subjected to liquid separation, and the organic layer was washed with a 3% aqueous sodium hydrogen carbonate solution and saturated saline. After being dried over magnesium sulfate, the resultant was separated by filtration, and the solvent of the organic layer was distilled away under reduced pressure. The obtained solid was recrystallized over ethanol, thereby obtaining 6.8 g of an intermediate (A2) (yield: 61%).

The obtained intermediate (A2) was identified by NMR. The results are as below.

$^1$H NMR (CDCl$_3$) δ 7.97 (d, 2H), 7.41 (s, 2H), 6.40 (d, 2H), 4.28 (q, 4H), 2.70 (t, 4H), 1.58 (m, 4H), 1.34 (m, 10H), 0.95 (t, 6H) ppm Synthesis of Intermediate (A3)

200 ml of tetrahydrofuran was added to 20 g (0.052 mol) of the intermediate (A2) and 32 g (0.51 mol) of ammonium formate, and then 11.2 g (0.0053 mol) of palladium carbon (Pd: 10%, moistened with water at about 50%) was further added thereto. The solution was heated under reflux for 2 hours in a nitrogen gas flow. The resultant was filtered through celite, and the solvent of the obtained filtrate was distilled away under reduced pressure, thereby obtaining 20 g of an intermediate (A3) (yield: 99%).

The obtained intermediate (A3) was identified by NMR. The results are as below.

$^1$H NMR (CDCl$_3$) δ 6.91 (s, 2H), 4.15 (q, 4H), 2.90 (t, 4H), 2.55 (m, 8H), 1.52 (m, 4H), 1.30 (m, 4H), 1.22 (t, 6H), 0.95 (t, 6H) ppm Synthesis of Intermediate (A4)

200 ml of methanol was added to 20 g (0.051 mol) of the intermediate (A3). In a state in which the solution was cooled in an ice bath, 43 g (0.77 mol) of potassium hydroxide was added thereto with great care, and the solution was returned to room temperature and then heated under reflux for 2 hours. The reaction solution was added to a 2 N aqueous hydrochloric acid solution with great care, the resultant was then filtered, and the obtained crystal was washed with toluene, thereby obtaining 17 g of an intermediate (A4) (yield: 99%).

The obtained intermediate (A4) was identified by NMR. The results are as below.

$^1$H NMR (DMSO-d6) δ 6.90 (s, 2H), 2.74 (t, 4H), 2.43 (m, 8H), 1.48 (m, 4H), 1.32 (m, 4H), 0.91 (t, 6H) ppm Synthesis of Intermediate (A5)

100 ml of dichloromethane was added to 10 g (0.03 mol) of the intermediate (A4), 7.7 ml (0.09 mol) of oxalyl chloride and N,N-dimethylformamide in a catalytic amount were then added thereto, and the solution was stirred for 3 hours at room temperature. After the dichloromethane and excess oxalyl chloride were distilled away under reduced pressure, 100 ml of dichloromethane and 15.2 g (0.114 mol) of aluminum chloride were added thereto, and the solution was heated under reflux for 4 hours. After being returned to room temperature, the reaction solution was added with great care to 300 ml of a 1 N aqueous hydrochloric acid solution cooled in an ice bath. By using dichloromethane, liquid separation/extraction was performed twice, and the organic layer was washed with a 3% aqueous sodium hydrogen carbonate solution and saturated saline. After being dried over magnesium sulfate, the resultant was separated by filtration, and the solvent of the organic layer was distilled away under reduced pressure. The obtained solid was purified by silica gel column chromatography (n-hexane/ethyl acetate=10/1), thereby obtaining 5.6 g of an intermediate (A5) (yield: 63%).

The obtained intermediate (A5) was identified by NMR. The results are as below.

$^1$H NMR (CDCl$_3$) δ 3.08 (m, 8H), 2.76 (t, 4H), 1.40-1.60 (m, 8H), 0.98 (t, 6H) ppm Synthesis of Intermediate (A6)

180 ml of acetic acid was added to 7 g (0.023 mol) of the intermediate (A5), 5.5 ml (0.11 mol) of bromine was then added thereto, and the solution was heated and stirred for 2 hours at a temperature of 100° C. As a result of returning the solution to room temperature, crystals were precipitated. The reaction solution was filtered, and the obtained crystals were washed with a 3% aqueous sodium hydrogen sulfite solution and ethanol, thereby obtaining 10.4 g of an intermediate (A6) (yield: 72%).

The obtained intermediate (A6) was identified by NMR. The results are as below.

$^1$H NMR (CDCl$_3$) δ 4.21 (s, 4H), 3.02 (t, 4H), 1.42-1.60 (m, 8H), 0.97 (m, 6H) ppm Synthesis of Intermediate (A7)

3 g (0.0049 mol) of the intermediate (A6) was dissolved in 30 ml of dichloromethane, 2.2 ml (0.016 mol) of triethylamine was added thereto, and the solution was heated under reflux for 4 hours. After the solution was returned to room temperature, 30 ml of water was added thereto to perform liquid separation. After being dried over sodium sulfate, the resultant was separated by filtration, and the solvent of the organic layer was distilled away under reduced pressure. The obtained solid was washed with 2-propanol, thereby obtaining 1.6 g of an intermediate (A7) (yield: 73%).

The obtained intermediate (A7) was identified by NMR. The results are as below.

$^1$H NMR (CDCl$_3$) δ 7.68 (s, 2H), 2.88 (t, 4H), 1.35-1.60 (m, 8H), 0.95 (t, 6H) ppm

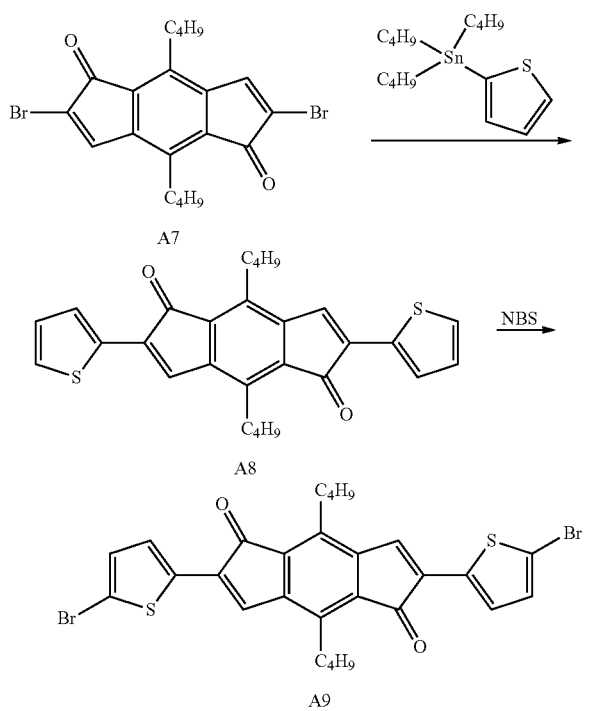

A7

A8

A9

Synthesis of Intermediate (A8)

0.5 g (1.1 mmol) of the intermediate (A7), 0.9 g (2.4 mmol) of 2-thienyltin, 22.8 mg (0.022 mmol) of a tris(dibenzylideneacetone)dipalladium-chloroform adduct, and 53.5 mg (0.18 mmol) of tris(2-methylphenyl)phosphine were put into a reaction container for a microwave, 6 ml of chlorobenzene was added thereto, and nitrogen purging was performed. In a microwave reaction device, the solution was reacted for 1 hour at a temperature of 90° C. and returned to room temperature. Thereafter, the reaction solution was added to 60 ml of methanol. The precipitated solid was collected by filtration and purified by silica gel chromatography, thereby obtaining 0.3 g of an intermediate (A8) (yield: 60%).

The obtained intermediate (A8) was identified by NMR. The results are as below.

$^1$H NMR (CDCl$_3$) δ 7.68 (d, 2H), 7.52 (s, 2H), 7.36 (d, 2H), 7.08 (m, 2H), 2.93 (t, 4H), 1.35-1.60 (m, 8H), 0.95 (t, 6H) ppm

Synthesis of Intermediate (A9)

0.3 g (0.65 mmol) of the intermediate (A8) was dissolved in 5 ml of chloroform, 0.25 g (1.4 mmol) of N-bromosuccinimide was added thereto, and the solution was stirred overnight at room temperature in a nitrogen atmosphere. The reaction solution was added to 40 ml of methanol, the precipitated solid was collected by filtration, and crystals were repeatedly precipitated in a dichloromethane/methanol solvent mixture, thereby obtaining 0.26 g of an intermediate (A9) (yield: 65%).

The obtained intermediate (A9) was identified by NMR. The results are as below.

$^1$H NMR (CDCl$_3$) δ 7.51 (d, 2H), 7.38 (s, 2H), 7.03 (d, 2H), 2.88 (t, 4H), 1.35-1.60 (m, 8H), 0.95 (t, 6H) ppm

Synthesis Example

Synthesis of Compound 101

According to the following scheme, Example Compound 101 was synthesized. An intermediate (D1) was synthesized according to the method described in "Macromolecules, vol. 45 (2012), p. 7806". Furthermore, an intermediate (A10) was synthesized in substantially the same manner as the intermediate (A7).

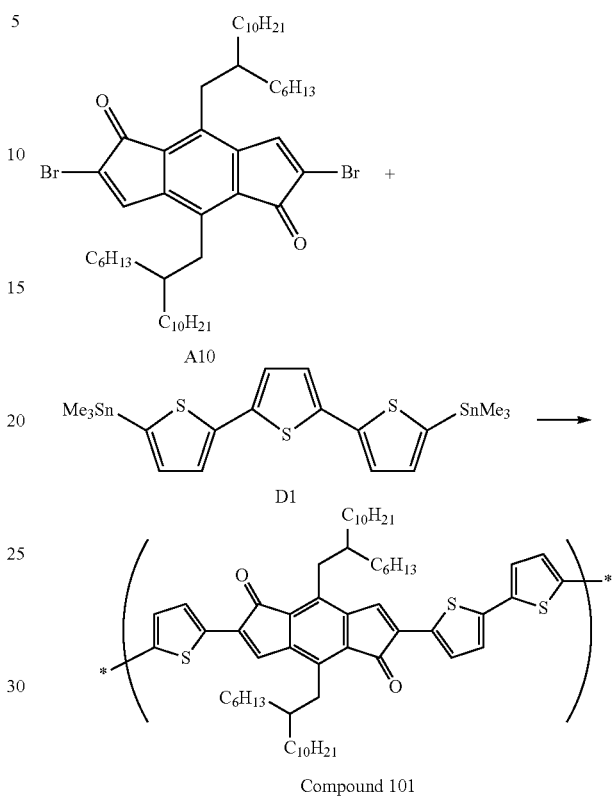

A10

D1

Compound 101

Synthesis of Example Compound (101)

0.37 g (0.44 mmol) of the intermediate (A10), 0.25 g (0.44 mmol) of the intermediate (D1), 9.1 mg (0.0088 mmol) of a tris(dibenzylideneacetone)dipalladium-chloroform adduct, and 21.4 mg (0.07 mmol) of tris(2-methylphenyl)phosphine were put into a reaction container for a microwave, 2.4 ml of chlorobenzene was added thereto, and then nitrogen purging was performed. In a microwave reaction device, the solution was reacted for 1 hour at a temperature of 140° C. and then returned to room temperature. Thereafter, 20 ml of methanol was added to the reaction solution. The precipitated solid was collected by filtration, and Soxhlet extraction was performed for 3 hours by using methanol, n-hexane, and acetone respectively. Thereafter, Soxhlet extraction was performed by using chlorobenzene, and the obtained chlorobenzene solution of a polymer was concentrated until it became a saturated solution. The solution was added to 20 ml of methanol, and the precipitated solid was collected by filtration and dried in a vacuum (80° C.), thereby obtaining 0.39 g of an example compound (101) (yield: 94%).

GPC (o-dichlorobenzene) Mw=78×10$^3$, Mn=40×10$^3$

Synthesis Example

Synthesis of Compound 108

According to the following scheme, an example compound (108) was synthesized. An intermediate (A11) was synthesized in substantially the same method as the intermediate (A9). Furthermore, an intermediate (D2) was synthesized with reference to the method described in U.S. Pat. No. 7,772,485B2.

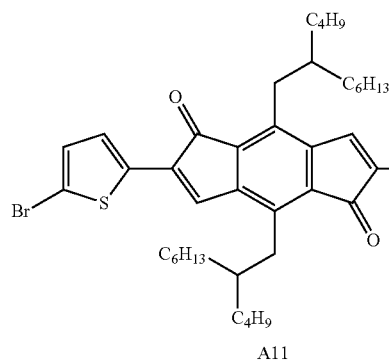

A11

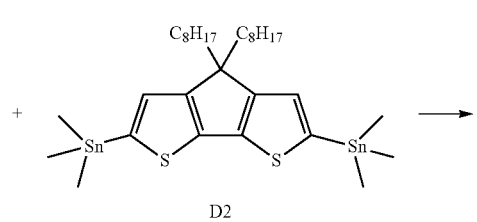

D2

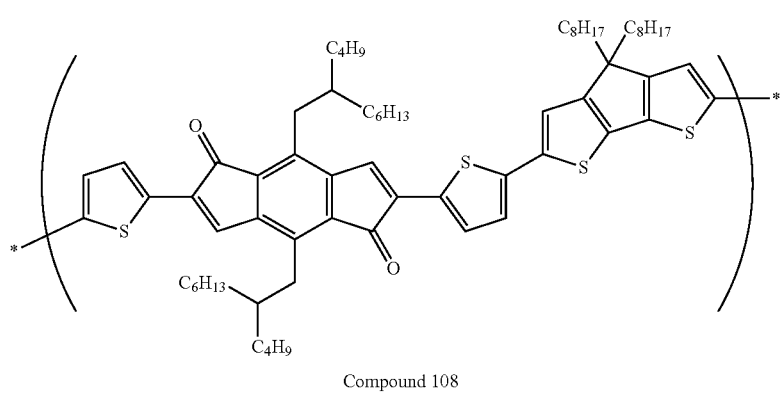

Compound 108

Synthesis of Example Compound (108)

The example compound (108) was synthesized in substantially the same manner as the example compound (101), except that in the synthesis of the example compound (101), the intermediate (D2) was used instead of the intermediate (D1), and the intermediate (A11) was used instead of the intermediate (A10).

GPC (o-dichlorobenzene) Mw=77×10³, Mn=31×10³

Synthesis Example

Synthesis of Compound 124

According to the following scheme, Example Compound 124 was synthesized. An intermediate (D3) was synthesized with reference to the method described in "Journal of American Chemical Society, vol. 133 (2011), p. 1405".

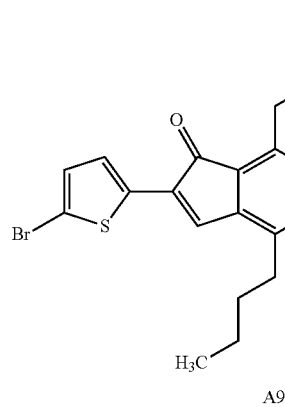

A9

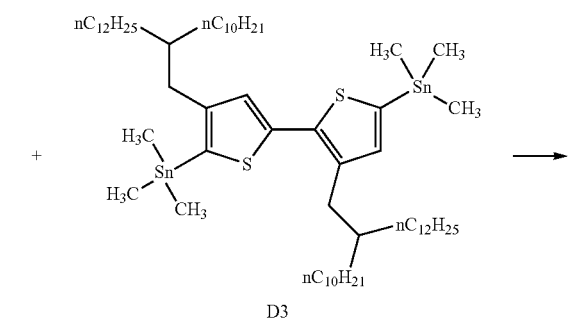

D3

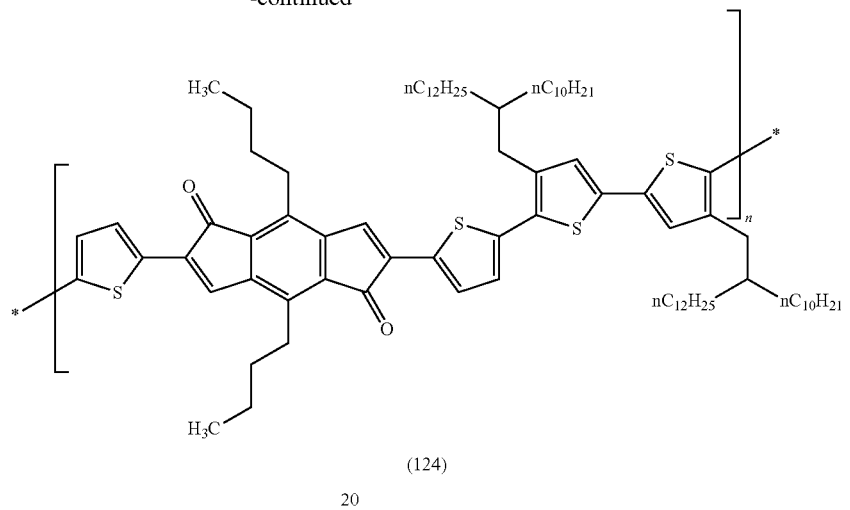

(124)

Synthesis of Example Compound (124)

The example compound (124) was synthesized in substantially the same manner as the example compound (101), except that in the synthesis of the example compound (101), the intermediate (D3) was used instead of the intermediate (D1), and the intermediate (A9) was used instead of the intermediate (A10).

GPC (o-dichlorobenzene) Mw=64×10³, Mn=36×10³

Synthesis Example

Synthesis of Compound 127

According to the following scheme, an example compound (127) was synthesized. An intermediate (A12) was synthesized by substantially the same method as the intermediate (A9).

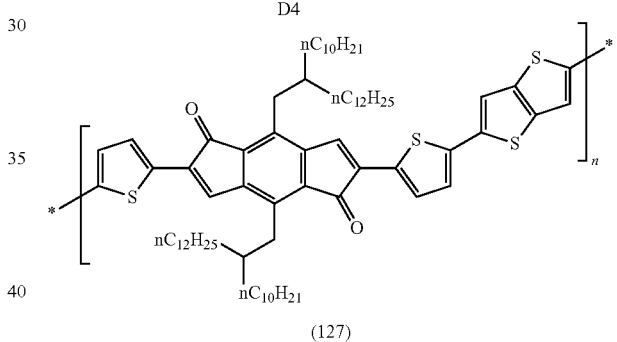

(127)

Synthesis of Example Compound (127)

The example compound (127) was synthesized in substantially the same manner as the example compound (101), except that in the synthesis of the example compound (101), an intermediate (D4) was used instead of the intermediate (D1), and the intermediate (A12) was used instead of the intermediate (A10).

GPC (o-dichlorobenzene) Mw=85×10³, Mn=38×10³

Synthesis Example

Synthesis of Compound 137

According to the following scheme 2, an acceptor portion B1 was synthesized through an intermediate compound b1.

Scheme 2

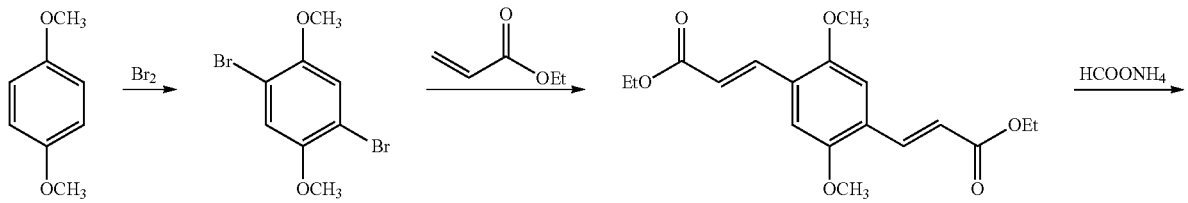

161
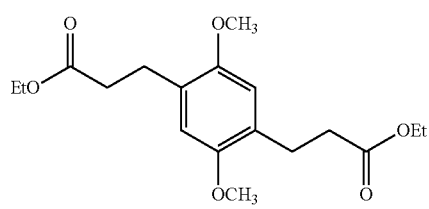
162
-continued
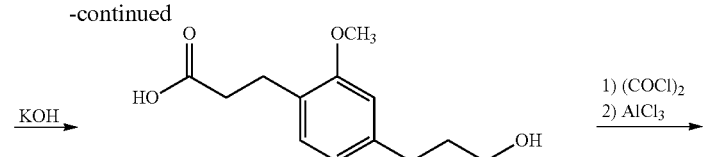
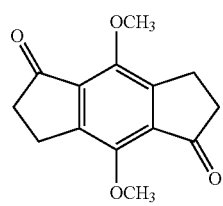
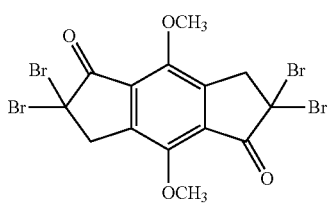
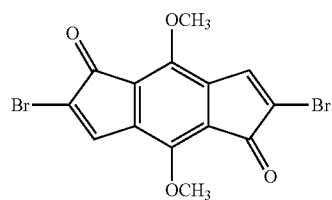
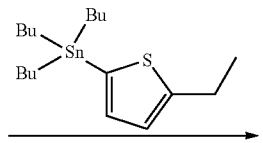
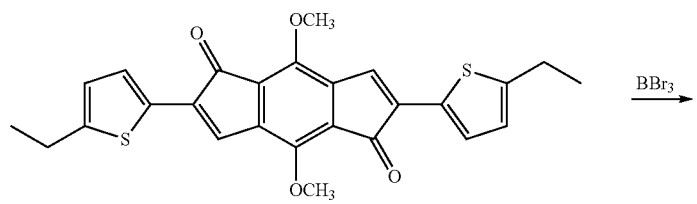
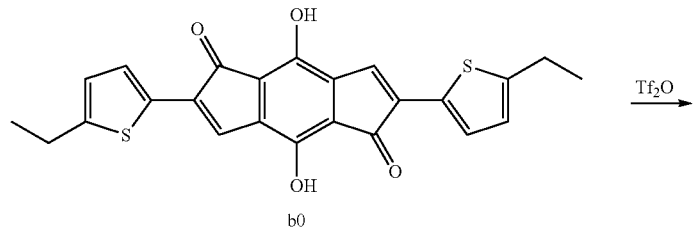
b0
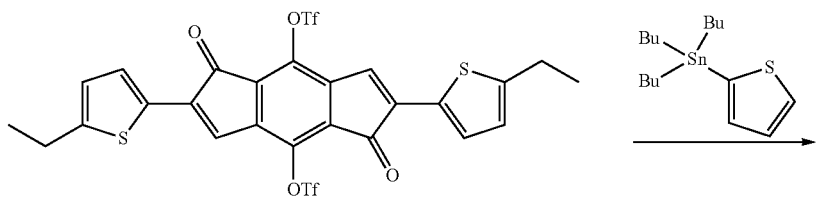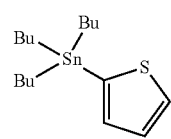
b1
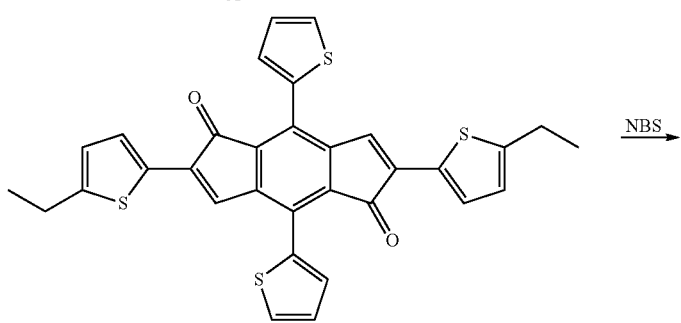

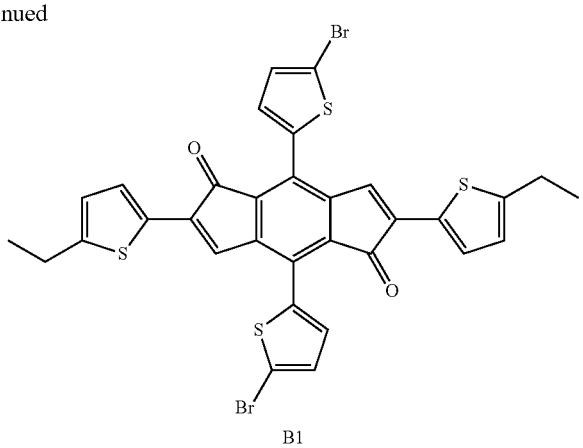

B1

According to the following scheme, Example Compound 137 was synthesized. An intermediate (D20) was synthesized by substantially the same method as the intermediate (D3).

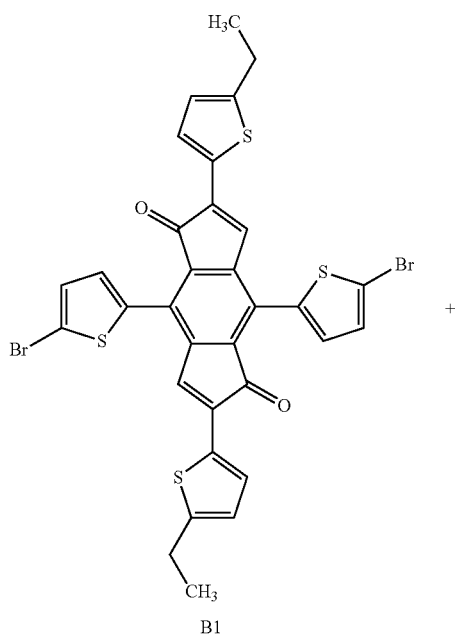

B1

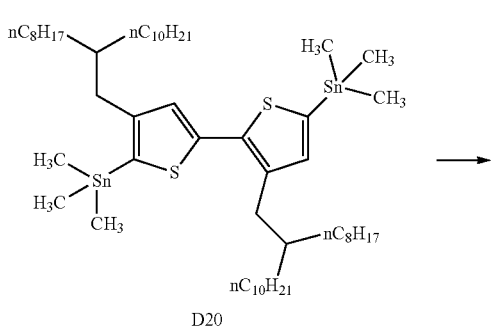

D20

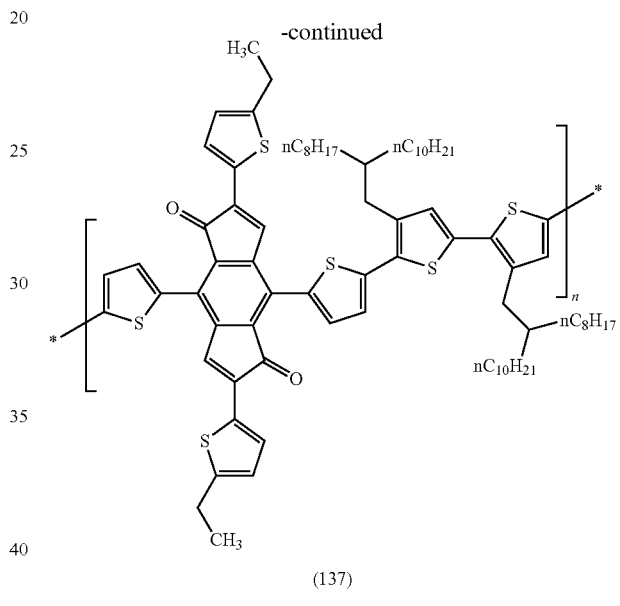

(137)

Synthesis of Example Compound (137)

The example compound (137) was synthesized by substantially the same method as the example compound (101), except that in the synthesis of the example compound (101), the intermediate (D20) was used instead of the intermediate (D1), and the intermediate (B1) was used instead of the intermediate (A10).

The obtained compound was identified by elemental analysis, NMR, or gel permeation chromatography (GPC).

The molecular weight of each compound was measured by the method described in the present specification. As a result, it was found that the weight average molecular weight of each compound is within a range of 50,000 to 200,000. That is, it was found that the number n of the repeating unit of each compound represented by Formula (101) is within a range of 40 to 200.

The compound composed of n repeating units represented by Formula (101) that was used in other examples was synthesized in the same manner as Compound 101 or the like.

Comparative Compounds 101, 102, and 103 described in JP2010-535270A and Comparative Compound 104 described in JP2012-177104A that were used in the semiconductor active layer (organic semiconductor layer) of the comparative elements were synthesized with reference to the respective documents. The structures of Comparative Compounds 101 to 104 are as below.

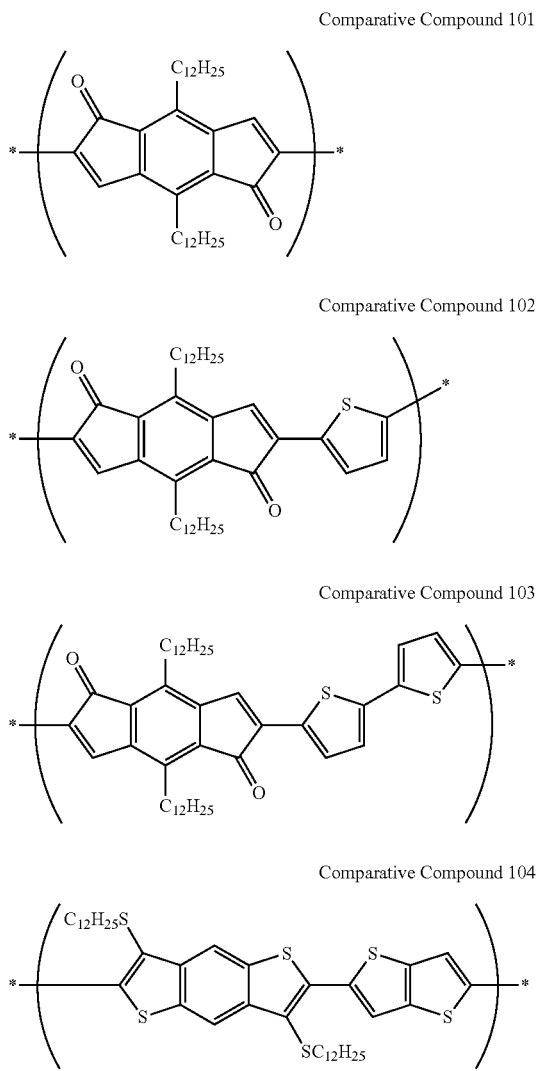

Comparative Compound 101

Comparative Compound 102

Comparative Compound 103

Comparative Compound 104

<Preparation•Evaluation of Element>

Example 102

Preparation of Coating Solution for Non-Light-Emitting Organic Semiconductor Device The compound of the present invention or the comparative compound (10 mg each) was mixed with toluene (1 mL) and heated to 100° C., thereby obtaining a coating solution for a non-light-emitting organic semiconductor device. The solution in which the compound was not completely dissolve was filtered through a 0.2 μm filter.

<Formation of Semiconductor Active Layer (Organic Semiconductor Layer) by Using Compound Alone>

By performing spin coating of the coating solution for a non-light-emitting organic semiconductor device in the atmosphere, an organic semiconductor film for a non-light-emitting organic semiconductor device was formed, thereby obtaining an organic film transistor element of Example 102 that was for measuring FET characteristics. As a substrate for measuring FET characteristics, a silicon substrate having a bottom contact structure was used which included chromium/gold (gate width W=100 mm, gate length L=100 μm) arranged to form a comb pattern as source and drain electrodes and included $SiO_2$ (film thickness: 200 nm) as an insulating layer (the structure is schematically shown in FIG. 2).

By using a semiconductor parameter analyzer (4156C manufactured by Agilent Technologies) connected to a semi-automatic prober (AX-2000 manufactured by Vector Semiconductor Co., Ltd.), the FET characteristics of the organic film transistor element of Example 102 were evaluated in a normal pressure•nitrogen atmosphere, from the viewpoint of the carrier mobility, the threshold voltage shift after repeated driving, and the film formability.

Furthermore, the coating solution for a non-light-emitting organic semiconductor device of Example 102 was evaluated from the viewpoint of the solubility.

The obtained results are shown in the following table.

(a) Solubility Evaluation

The compound of the present invention or the comparative compound (10 mg each) was mixed with toluene (1 mL), and the mixture was heated to 100° C. Thereafter, the mixture was left for 30 minutes at room temperature. From the amount of the precipitated solid, the solubility was evaluated into 3 levels as below.

A: No solid precipitated.

B: The amount of the precipitated solid was less than 30%.

C: The amount of the precipitated solid was equal to or greater than 30%.

(b) Carrier mobility

Between the source electrode and the drain electrode of each organic film transistor element (FET element), a voltage of −50 V was applied, and the gate voltage was varied within a range of 20 V to −100 V. In this way, by using Equation $I_d=(w/2L)\mu C_i(V_g-V_{th})^2$, a carrier mobility μ was calculated (in the equation, $I_d$ represents a drain current; L represents a gate length; W represents a gate width; $C_i$ represents a capacity of the insulating layer per unit area; $V_g$ represents a gate voltage; and $V_{th}$ represents a threshold voltage). Herein, because the characteristics of the element having a carrier mobility of less than $1\times10^{-5}$ cm²/Vs were too poor, the element was not subjected to the evaluation of (c) Threshold voltage shift after repeated driving described below.

A: Equal to or greater than 0.11 cm²/Vs

B: Greater than 0.005 cm²/Vs and less than 0.11 cm²/Vs

C: Equal to or less than 0.005 cm²/Vs (c) Threshold Voltage Shift After Repeated Driving Between the source electrode and the drain electrode of each organic film transistor element (FET element), a voltage of −80 V was applied, and the element was repeatedly driven 100 times by varying the gate voltage within a range of +20 V to −100 V. In this way, the element was measured in the same manner as in the section (a), and a difference between a threshold voltage $V_{before}$ before the repeated driving and a threshold voltage $V_{after}$ after the repeated driving ($|V_{after}-V_{before}|$) was evaluated into 3 levels as below. The smaller the difference, the higher the stability of the element against repeated driving. Therefore, the smaller the difference, the more preferable.

A: $|V_{after}-V_{before}| \leq 5$ V
B: $5$ V $< |V_{after}-V_{before}| \leq 10$ V
C: $|V_{after}-V_{before}| > 10$ V (d) Film Formability Evaluation Each of the obtained organic film transistor elements was observed with unaided eyes and with an optical microscope. By the method described above, 10 elements were prepared, and the ratio of film cissing that occurred on the source and drain electrodes was evaluated.

The results were evaluated into 3 levels as below.
A: Less than 10%.
B: Equal to or greater than 10% and less than 30%
C: Equal to or greater than 30%

(e) Element Variation

The mobility of the prepared 30 elements was measured, and a coefficient of variation was calculated. The results were evaluated into 3 levels as below.
A: Less than 30%
B: Equal to or greater than 30% and less than 50%
C: Equal to or greater than 50%

From the above table, it was understood that the compound of the present invention exhibits excellent solubility in an organic solvent, and the organic film transistor element using the compound of the present invention has high carrier mobility. It was also understood that accordingly, the compound of the present invention can be preferably used as an organic semiconductor material for a non-light-emitting organic semiconductor device.

In contrast, the organic film transistor elements using Comparative Compounds 101 to 104 exhibited low carrier mobility.

In the organic film transistor element using the compound of the present invention, the threshold voltage shift occurred to a small extent after the repeated driving. Furthermore, it was understood that in all of the organic film transistor elements using the compound of the present invention, the smoothness-homogeneity of the film are extremely high, and the film formability is excellent.

TABLE 3

| | Organic semiconductor material | Solubility | Carrier mobility (cm2/Vs) | Threshold voltage shift after repeated driving | Film formability | Element variation | Note |
|---|---|---|---|---|---|---|---|
| Element 101 | Compound 101 | A | 0.09 | B | A | A | A | Present invention |
| Element 102 | Compound 102 | A | 0.1 | B | A | A | A | Present invention |
| Element 103 | Compound 104 | A | 0.16 | A | A | A | A | Present invention |
| Element 104 | Compound 106 | A | 0.24 | A | A | A | A | Present invention |
| Element 105 | Compound 108 | A | 0.11 | A | A | A | A | Present invention |
| Element 106 | Compound 109 | A | 0.12 | A | A | A | A | Present invention |
| Element 107 | Compound 115 | A | 0.21 | A | A | A | A | Present invention |
| Element 108 | Compound 117 | A | 0.24 | A | A | A | A | Present invention |
| Element 109 | Compound 119 | A | 0.13 | A | A | A | A | Present invention |
| Element 110 | Compound 122 | A | 0.18 | A | A | A | A | Present invention |
| Element 111 | Compound 124 | A | 0.09 | B | A | A | A | Present invention |
| Element 112 | Compound 125 | A | 0.2 | A | A | A | A | Present invention |
| Element 113 | Compound 126 | A | 0.22 | A | A | A | A | Present invention |
| Element 114 | Compound 127 | A | 0.22 | A | A | A | A | Present invention |
| Element 115 | Compound 128 | A | 0.15 | A | A | A | A | Present invention |
| Element 116 | Compound 137 | A | 0.16 | A | A | A | A | Present invention |
| Element 117 | Compound 150 | A | 0.08 | B | A | A | A | Present invention |
| Element 118 | Compound 131 | A | 0.2 | A | A | A | A | Present invention |
| Comparative element 101 | Comparative Compound 101 | C | $<1 \times 10^{-5}$ | C | B | C | C | Comparative example |
| Comparative element 102 | Comparative Compound 102 | C | $4 \times 10^{-4}$ | C | B | C | C | Comparative example |
| Comparative element 103 | Comparative Compound 103 | C | $4 \times 10^{-3}$ | C | B | C | C | Comparative example |
| Comparative element 104 | Comparative Compound 104 | C | 0.005 | C | C | C | C | Comparative example |

Example 103

Formation of Semiconductor Active Layer (Organic Semiconductor Layer)

The surface of a silicon wafer, which contained $SiO_2$ (film thickness: 370 nm) as a gate insulating film, was treated with octyltrichlorosilane.

The compound of the present invention or the comparative compound (1 mg each) was mixed with toluene (1 mL), and the mixture was heated to 100° C., thereby preparing a coating solution for a non-light-emitting organic semiconductor device. In a nitrogen atmosphere, the coating solution was cast onto the silicon wafer which had been heated to 90° C. and undergone surface treatment with octylsilane, thereby forming an organic semiconductor film for a non-light-emitting organic semiconductor device.

Furthermore, gold was deposited onto the surface of the film through a mask so as to prepare source and drain electrodes, thereby obtaining an organic film transistor element having a bottom gate-top contact structure with a gate width W=5 mm and a gate length L=80 μm (the structure is schematically shown in FIG. 1).

By using a semiconductor parameter analyzer (4156C manufactured by Agilent Technologies) connected to a semi-automatic prober (AX-2000 manufactured by Vector Semiconductor Co., Ltd.), the FET characteristics of the organic film transistor element of Example 3 were evaluated in a normal pressure•nitrogen atmosphere, from the viewpoint of the carrier mobility, the threshold voltage shift after repeated driving, and the film formability.

In Example 3, the carrier mobility was evaluated according to the following criteria.

A: Equal to or greater than 0.15 $cm^2/Vs$

B: Greater than 0.01 $cm^2/Vs$ and less than 0.15 $cm^2/Vs$

C: Equal to or less than 0.01 $cm^2/Vs$

Furthermore, the coating solution for a non-light-emitting organic semiconductor device of Example 4 was evaluated from the viewpoint of solubility.

The obtained results are shown in the following table.

TABLE 4

| | Organic semiconductor material | Solubility | Carrier mobility ($cm^2/Vs$) | | Threshold voltage shift after repeated driving | Film formability | Element variation | Note |
|---|---|---|---|---|---|---|---|---|
| Element 119 | Compound 101 | A | 0.13 | B | A | A | A | Present invention |
| Element 120 | Compound 104 | A | 0.22 | A | A | A | A | Present invention |
| Element 121 | Compound 106 | A | 0.27 | A | A | A | A | Present invention |
| Element 122 | Compound 117 | A | 0.26 | A | A | A | A | Present invention |
| Element 123 | Compound 122 | A | 0.21 | A | A | A | A | Present invention |
| Element 124 | Compound 124 | A | 0.12 | B | A | A | A | Present invention |
| Element 125 | Compound 125 | A | 0.24 | A | A | A | A | Present invention |
| Element 126 | Compound 127 | A | 0.24 | A | A | A | A | Present invention |
| Element 127 | Compound 128 | A | 0.19 | A | A | A | A | Present invention |
| Element 128 | Compound 137 | A | 0.21 | A | A | A | A | Present invention |
| Comparative element 105 | Comparative Compound 101 | C | $3 \times 10^{-4}$ | C | B | C | C | Comparative example |
| Comparative element 106 | Comparative Compound 102 | C | $1 \times 10^{-3}$ | C | B | C | C | Comparative example |
| Comparative element 107 | Comparative Compound 103 | C | $9 \times 10^{-3}$ | C | B | C | C | Comparative example |
| Comparative element 108 | Comparative Compound 104 | C | 0.01 | C | C | C | C | Comparative example |

From the above table, it was understood that the compound of the present invention exhibits excellent solubility in an organic solvent, and the organic film transistor element using the compound of the present invention has high carrier mobility. It was also understood that accordingly, the compound of the present invention can be preferably used as an organic semiconductor material for a non-light-emitting organic semiconductor device.

In contrast, the organic film transistor elements using Comparative Compounds 101 to 104 exhibited low carrier mobility.

In the organic film transistor element using the compound of the present invention, the threshold voltage shift occurred to a small extent after the repeated driving. Furthermore, it was understood that in all of the organic film transistor elements using the compound of the present invention, the smoothness-homogeneity of the film are extremely high, and the film formability is excellent.

EXPLANATION OF REFERENCES

11: substrate

12: electrode

13: insulating layer
14: semiconductor active layer (organic substance layer, organic semiconductor layer)
15a, 15b: electrode
31: substrate
32: electrode
33: insulating layer
34a, 34b: electrode
35: semiconductor active layer (organic substance layer, organic semiconductor layer)

What is claimed is:

1. An organic film transistor comprising a compound, which is composed of n repeating units represented by the following Formula (1-1), (1-2), or (101), in a semiconductor active layer;

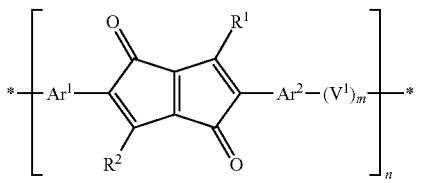

Formula (1-1)

in Formula (1-1), each of $R^1$ and $R^2$ independently represents a hydrogen atom or a substituent; each of $Ar^1$ and $R^2$ independently represents a heteroarylene group or an arylene group; $V^1$ represents a divalent linking group; m represents an integer of 0 to 6; when m is equal to or greater than 2, two or more groups represented by $V^1$ may be the same as or different from each other; and n represents an integer of equal to or greater than 2;

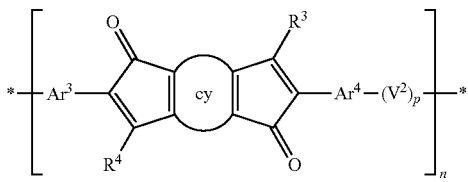

Formula (1-2)

in Formula (1-2), cy represents a naphthalene ring or an anthracene ring; each of $R^3$ and $R^4$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2;

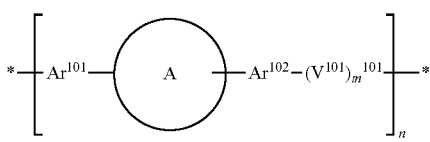

Formula (101)

in Formula (101), each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; n represents an integer of equal to or greater than 2; and A represents a divalent linking group represented by the following Formula (101'); and

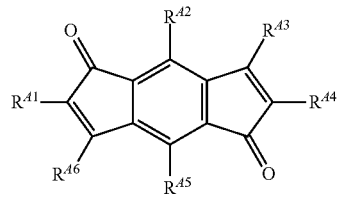

Formula (101')

in Formula (101'), each of $R^{A1}$ to $R^{A6}$ independently represents a hydrogen atom, a substituent, or a direct bond with $Ar^{101}$ or $Ar^{102}$ in Formula (101); and among the groups represented by $R^{A1}$ to $R^{A6}$, two different groups represent direct bonds with $Ar^{101}$ and $Ar^{102}$ in Formula (101) respectively, the transistor further comprising a compound, which is composed of n repeating units represented by Formula (101), in the semiconductor active layer;

in Formula (101), each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; n represents an integer of equal to or greater than 2; and A represents a divalent linking group represented by Formula (101'); and in Formula (101'), each of $R^{A1}$ to $R^{A6}$ independently represents a hydrogen atom, a substituent, or a direct bond with $Ar^{101}$ or $Ar^{102}$ in Formula (101); and among the groups represented by $R^{A1}$ to $R^{A6}$, two different groups represent direct bonds with $Ar^{101}$ and $Ar^{102}$ in Formula (101) respectively, wherein the compound composed of n repeating units represented by Formula (101) is a compound composed of n repeating units represented by any of the following Formulae (101-1) to (101-3);

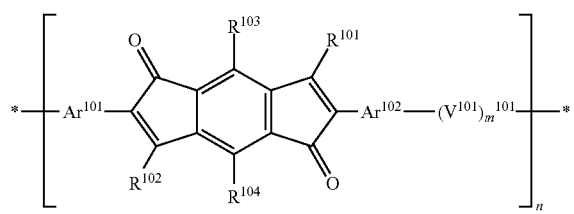

Formula (101-1)

Formula (101-2)

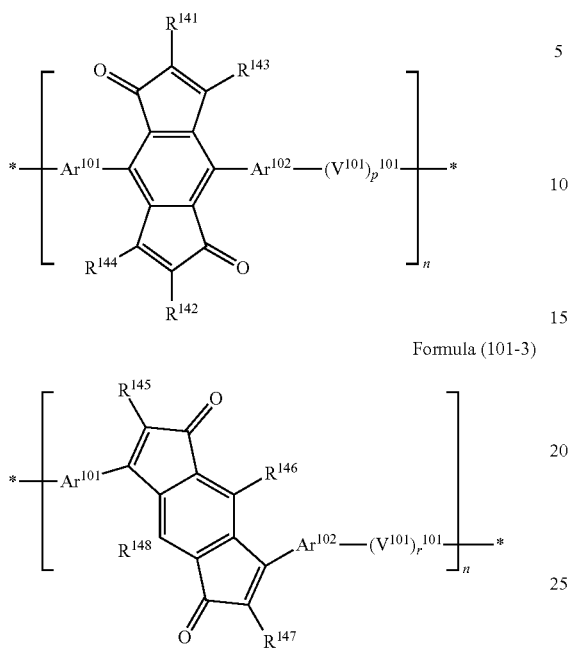

Formula (101-3)

in Formulae (101-1), (101-2), and (101-3), each of $R^{101}$ to $R^{104}$ and $R^{141}$ to $R^{148}$ independently represents a hydrogen atom or a substituent; each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; each of $p^{101}$ and $r^{101}$ represents an integer of 0 to 6; when each of $p^{101}$ and $r^{101}$ is equal to or greater than 2, two or more groups represented by $V^{101}$ may be the same as or different from each other; and n represents an integer of equal to or greater than 2, wherein in Formulae (101-1) to (101-3), $V^{101}$ is a divalent linking group represented by any of the following Formulae (V-101) to (V-117);

(V-101)
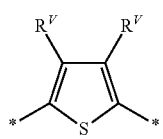

(V-102)
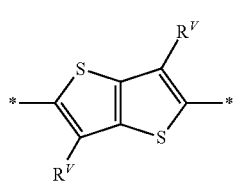

(V-103)
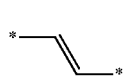

(V-104)
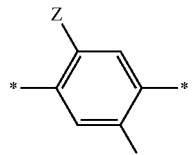

(V-105)
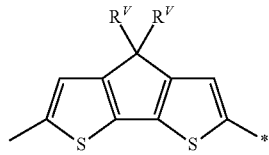

(V-106)
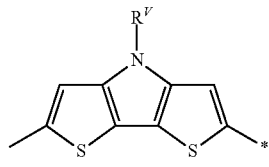

(V-107)
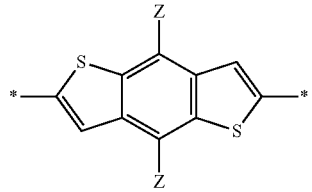

(V-108)
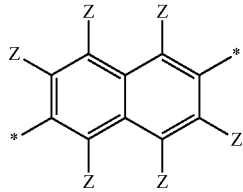

(V-109)
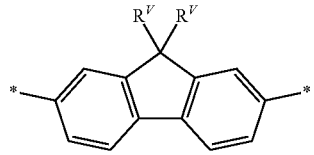

(V-110)
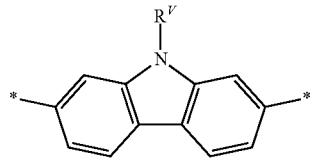

(V-111)
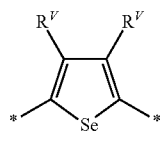

(V-112)
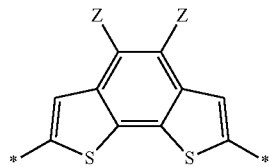

-continued

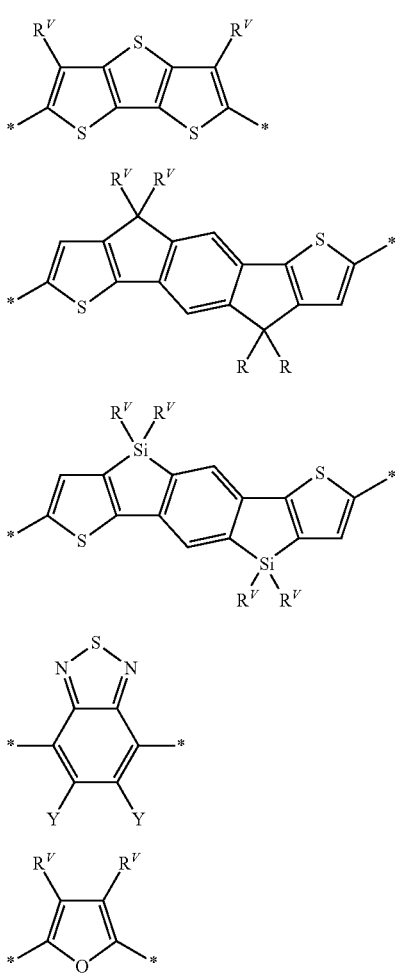

in Formulae (V-101) to (V-117), * represents a position where the divalent linking group is bonded to any of $Ar^{101}$ and $Ar^{102}$ when $m^{101}$, $p^{101}$, or $r^{101}$ is 1 and represents a position where the divalent linking group is bonded to an of $Ar^{101}$, $Ar^{102}$, and divalent linking groups represented by Formulae (V-101) to (V-117) $m^{101}$, $p^{101}$, or $r^{101}$ is equal to or greater than 2; each $R^V$ in Formulae (V-101), (V-102), (V-105), (V-106), (V-109) to (V-111), (V-113) to (V-115), and (V-117) independently represents a hydrogen atom or an alkyl group; the groups adjacent to each other represented by $R^V$ may form a ring by being bonded to each other; each Z in Formulae (V-104), (V-107), (V-108), and (V-112) independently represents a hydrogen atom, an alkyl group, or an alkoxy group; the groups adjacent to each other represented by Z may form a ring by being bonded to each other; each Y in Formula (V-116) independently represents a hydrogen atom, an alkyl group, an alkoxy group, a CN group, or a F atom; and the groups adjacent to each other represented by Y may form a ring by being bonded to each other, and in Formulae (101-1) to (101-3), $V^{101}$ represents a divalent linking group represented by any of Formulae (V-101) to (V-108) and (V-111) to (V-115).

2. The organic film transistor according to claim 1, comprising a compound, which is composed of n repeating units represented by the following Formula (1-1) or (1-2), in the semiconductor active layer;

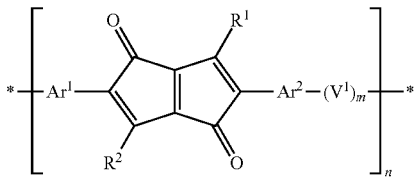

in Formula (1-1), each of $R^1$ and $R^2$ independently represents a hydrogen atom or a substituent; each of $Ar^1$ and $Ar^2$ independently represents a heteroarylene group or an arylene group; $V^1$ represents a divalent linking group; m represents an integer of 0 to 6; when m is equal to or greater than 2, two or more groups represented by $V^1$ may be the same as or different from each other; and n represents an integer of equal to or greater than 2; and

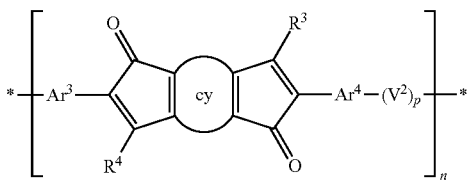

in Formula (1-2), cy represents a naphthalene ring or an anthracene ring; each of $R^3$ and $R^4$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2.

3. The organic film transistor according to claim 1, wherein Formula (1-2) represents a compound composed of n repeating units represented by the following Formula (2-1), (2-2), (2-3), (2-4), or (2-5);

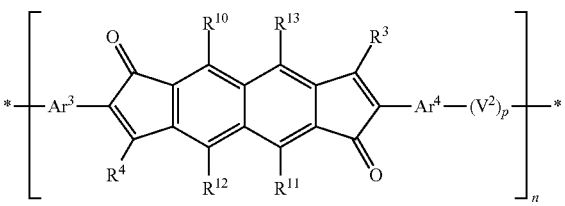

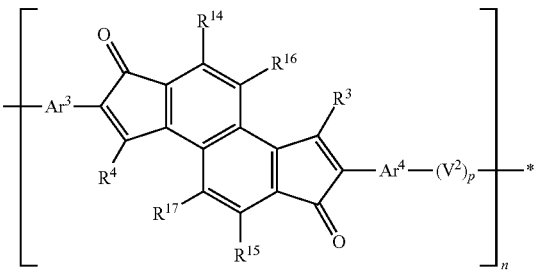

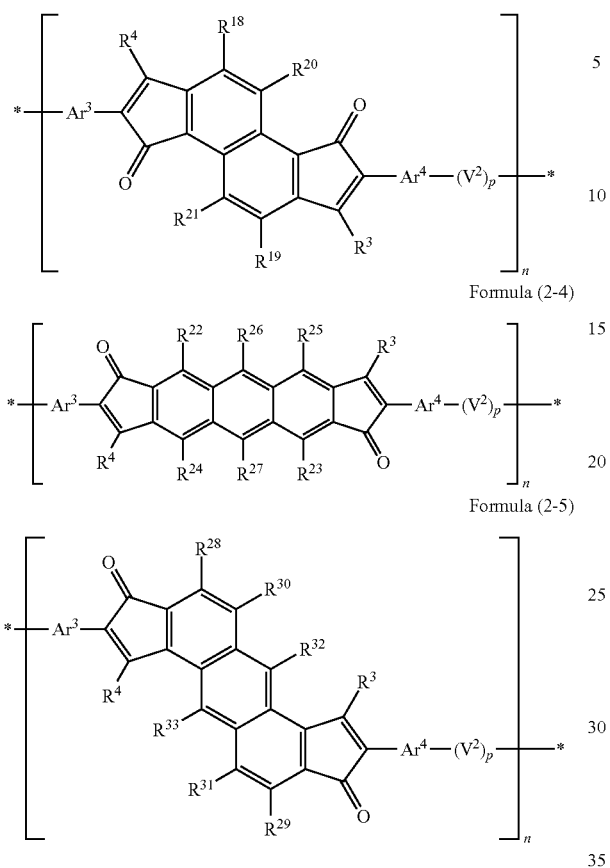

Formula (2-3)

Formula (2-4)

Formula (2-5)

in Formulae (2-1) to (2-5), each of $R^3$, $R^4$, and $R^{10}$ to $R^{33}$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2.

4. The organic film transistor according to claim 1, wherein in Formulae (1-1) and (1-2), each of $V^1$ and $V^2$ is independently a divalent linking group represented by any of the following Formulae (V-1) to (V-17),

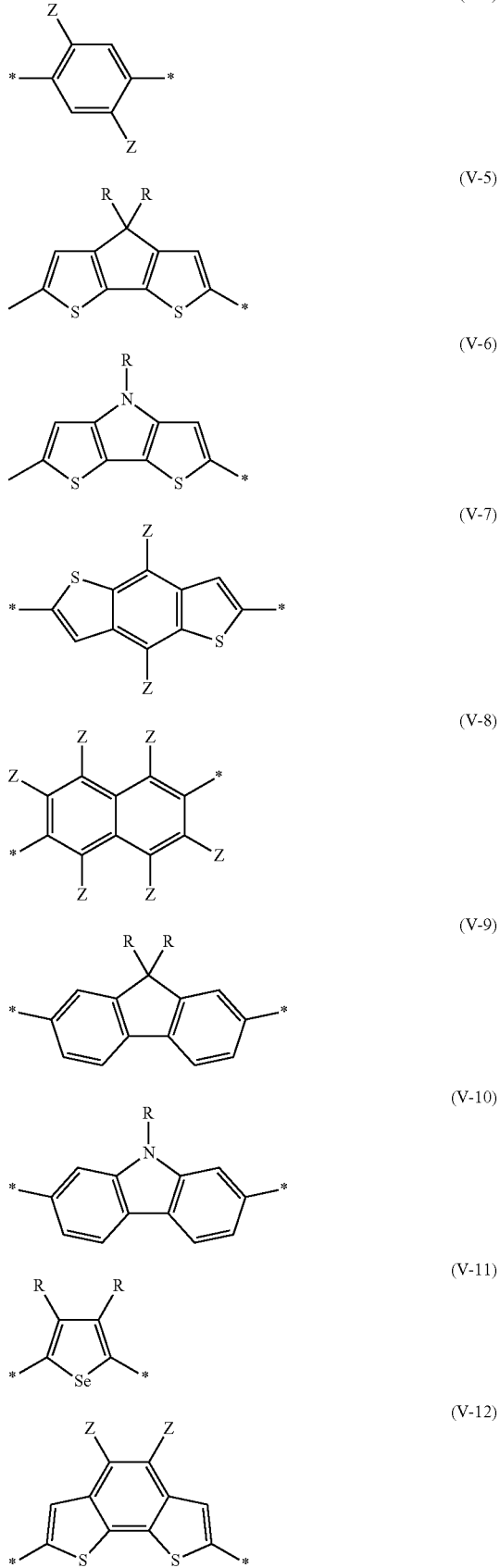

-continued

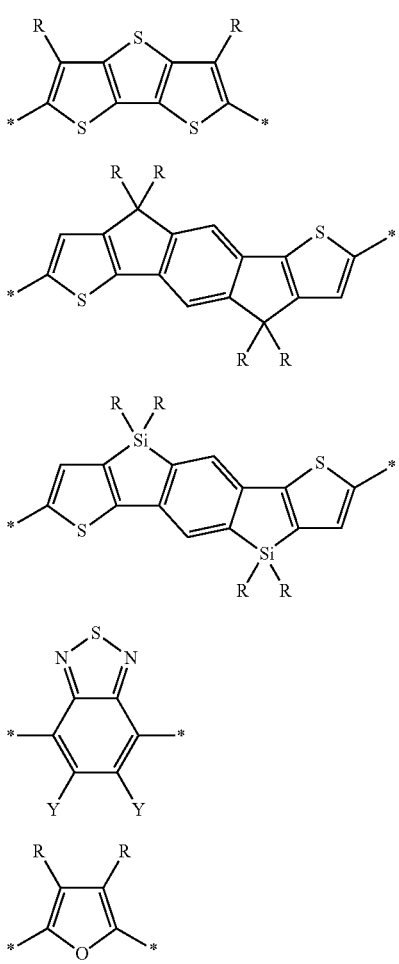

(V-13)
(V-14)
(V-15)
(V-16)
(V-17)

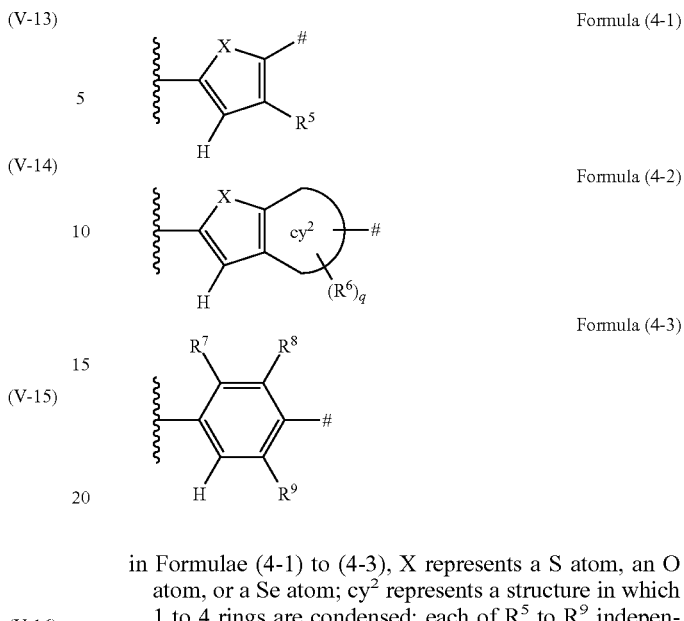

Formula (4-1)
Formula (4-2)
Formula (4-3)

in Formulae (4-1) to (4-3), X represents a S atom, an O atom, or a Se atom; $cy^2$ represents a structure in which 1 to 4 rings are condensed; each of $R^5$ to $R^9$ independently represents a hydrogen atom or a substituent; q represents an integer of 0 to 6; when q is equal to or greater than 2, two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^1$ or $V^2$.

7. The organic film transistor according to claim 6, wherein in Formulae (1-1) and (1-2), each of $Ar^1$ to $Ar^4$ is independently a divalent linking group represented by Formula (4-1) or (4-2).

8. The organic film transistor according to claim 6, wherein the divalent linking group represented by Formula (4-2) is a divalent linking group represented by any of the following Formulae (5-1) to (5-8);

in Formulae (V-1) to (V-17), * represents a position where the divalent linking group is bonded to any of $Ar^1$ to $Ar^4$ when m or p is 1, and represents a position where the divalent linking group is bonded to any of $Ar^1$ to $Ar^4$ and the divalent linking groups represented by Formulae (V-1) to (V-17) when m or p is equal to or greater than 2; each R in Formulae (V-1), (V-2), (V-5), (V-6), (V-9) to (V-11), (V-13) to (V-15), and (V-17) independently represents a hydrogen atom or an alkyl group; the groups adjacent to each other represented by R may form a ring by being bonded to each other; each Z in Formulae (V-4), (V-7), (V-8), and (V-12) independently represents a hydrogen atom, an alkyl group, or an alkoxy group; the groups adjacent to each other represented by Z may form a ring by being bonded to each other; each Y in Formula (V-16) independently represents a hydrogen atom, an alkyl group, an alkoxy group, a CN group, or a F atom; and the groups adjacent to each other represented by Y may form a ring by being bonded to each other.

5. The organic film transistor according to claim 4, wherein in Formulae (1-1) and (1-2), each of $V^1$ and $V^2$ is a divalent linking group represented by any of Formulae (V-1) to (V-8) and (V-11) to (V-15).

6. The organic film transistor according to claim 1, wherein in Formulae (1-1) and (1-2), each of $Ar^1$ to $Ar^4$ is independently a divalent linking group represented by the following Formula (4-1), (4-2), or (4-3),

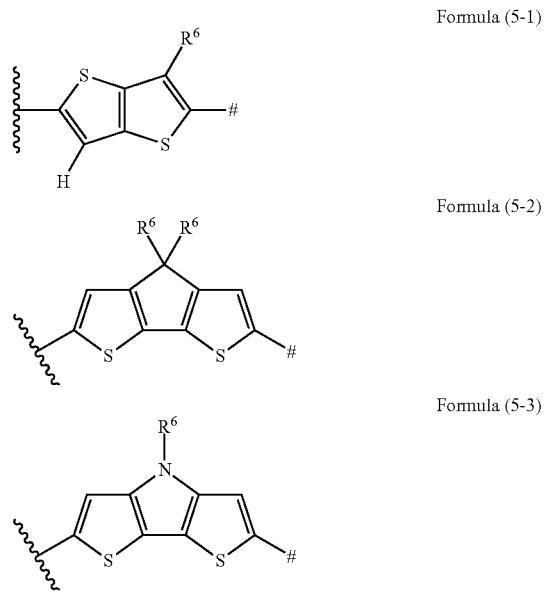

Formula (5-1)
Formula (5-2)
Formula (5-3)

-continued

Formula (5-4)

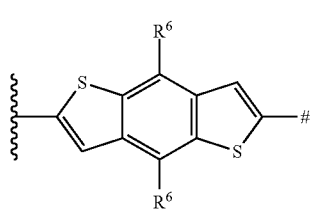

Formula (5-5)

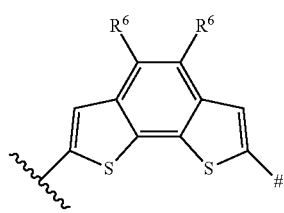

Formula (5-6)

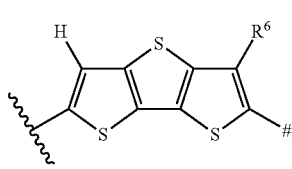

Formula (5-7)

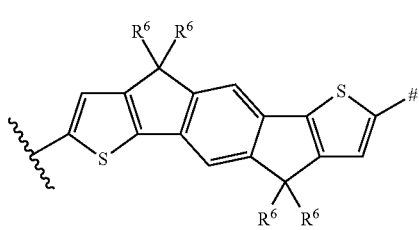

Formula (5-8)

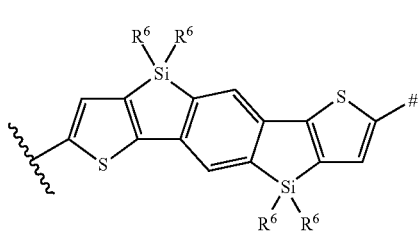

in Formulae (5-1) to (5-8), each $R^6$ independently represents a hydrogen atom or a substituent; two or more groups represented by $R^6$ may be the same as or different from each other; the wavy line represents a position where the divalent linking group is bonded to a cyclopentadienone ring-condensed site; and # represents a position where the divalent linking group is bonded to $V^1$ or $V^2$.

9. The organic film transistor according to claim 1, wherein each of at least one of $R^1$ and $R^2$ in Formula (1-1) and at least one of $R^3$ and $R^4$ in Formula (1-2) is a group represented by the following Formula (W);

-L-R              Formula (W)

in Formula (W), L represents a divalent linking group represented by any of the following Formulae (L-1) to (L-12) or a divalent linking group formed by bonding of two or more divalent linking groups represented by any of the following Formulae (L-1) to (L-12); R represents a substituted or unsubstituted alkyl group, an oligo-oxyethylene group in which a repetition number v of an oxyethylene unit is equal to or greater than 2, an oligosiloxane group having two or more silicon atoms, or a substituted or unsubstituted silyl group; and R represents a substituted or unsubstituted silyl group only when L adjacent to R is a divalent linking group represented by any of the following Formulae (L-1) to (L-3); and (L-1)
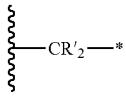

(L-2)
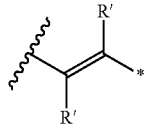

(L-3)
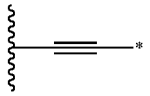

(L-4)
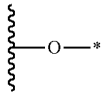

(L-5)
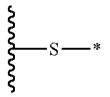

(L-6)
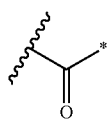

(L-7)
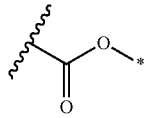

(L-8)
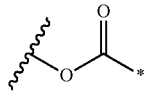

(L-9)
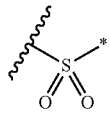

(L-10)
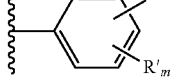

(L-11)
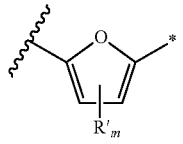

-continued (L-12)

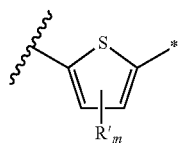

in Formulae (L-1) to (L-12), the portion of a wavy line represents a position where the divalent linking group is bonded to a cyclopentadienone skeleton; * represents a position where the divalent linking group is bonded to any of the divalent linking groups represented by (L-1) to (L-12) and R; m in Formula (L-10) is 4; m in Formulae (L-11) and (L-12) is 2; and each R' in Formulae (L-1), (L-2), (L-10), (L-11), and (L-12) independently represents a hydrogen atom or a substituent.

10. The organic film transistor according to claim 9, wherein in Formula (W), L is a divalent linking group represented by any of Formulae (L-1), (L-4), and (L-8) or a divalent linking group formed by bonding of two or more divalent linking groups described above.

11. The organic film transistor according to claim 1, wherein in Formulae (1-1) and (1-2), n is equal to or greater than 10.

12. The organic film transistor according to claim 1, wherein the compound composed of n repeating units represented by Formula (101) is a compound composed of n repeating units represented by the following Formula (101-1);

Formula (101-1)

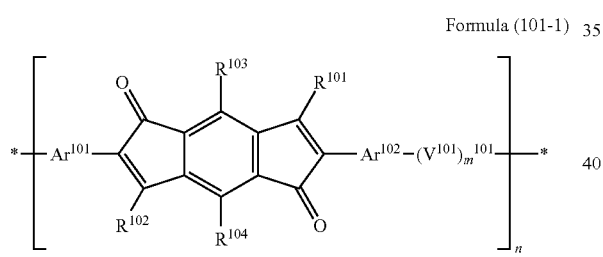

in Formula (101-1), each of $R^{101}$ to $R^{104}$ independently represents a hydrogen atom or a substituent; each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; and n represents an integer of equal to or greater than 2.

13. The organic film transistor according to clam 1, wherein in Formulae (101-1) to (101-3), each of $Ar^{101}$ and $Ar^{102}$ is a divalent linking group represented by the following Formula (102-1), (102-2), or (102-3);

Formula (102-1)

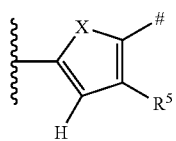

Formula (102-2)

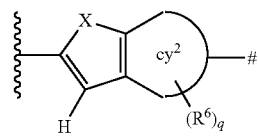

Formula (102-3)

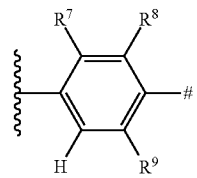

in Formulae (102-1) to (102-3), X represents a S atom, an O atom, or a Se atom; $cy^2$ represents a structure in which 1 to 4 rings are condensed; each of $R^5$ to $R^9$ independently represents a hydrogen atom or a substituent; q represents an integer of 0 to 6; when q is equal to or greater than 2, two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^{101}$.

14. The organic film transistor according to claim 13, wherein in Formula (101-1), each of $Ar^{101}$ and $Ar^{102}$ is a divalent linking group represented by Formula (102-1), and $V^{101}$ is a divalent linking group represented by any of Formulae (V-102) to (V-107).

15. The organic film transistor according to claim 13, wherein in Formulae (101-1) to (101-3), each of $Ar^{101}$ and $Ar^{102}$ is independently a divalent linking group represented by Formula (102-1) or (102-2).

16. The organic film transistor according to claim 13, wherein the divalent linking group represented by Formula (102-2) is a divalent linking group represented by any of the following Formulae (5-1) to (5-8);

Formula (5-1)

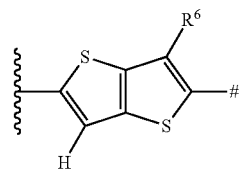

Formula (5-2)

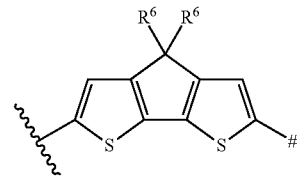

Formula (5-3)

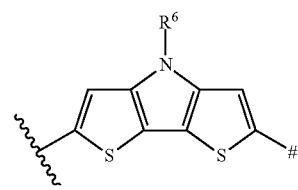

Formula (5-4)
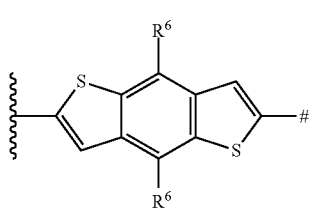

Formula (5-5)
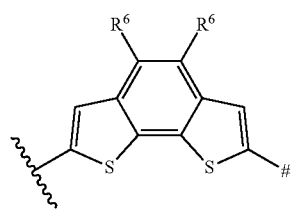

Formula (5-6)
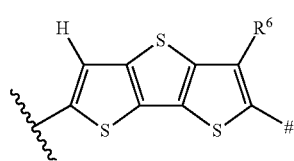

Formula (5-7)
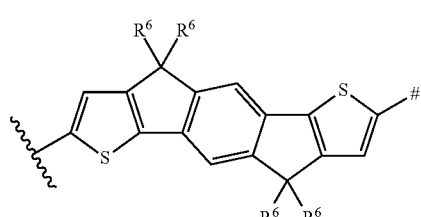

Formula (5-8)
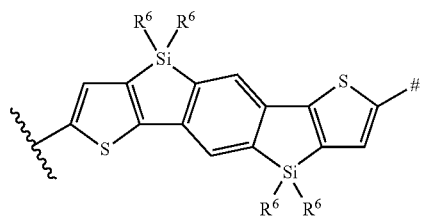

in Formulae (5-1) to (5-8), each $R^6$ independently represents a hydrogen atom or a substituent; two or more groups represented by $R^6$ may be the same as or different from each other; the wavy line represents a position where the divalent linking group is bonded to a cyclopentadienone ring-condensed site; and # represents a position where the divalent linking group is bonded to $V^{101}$.

17. The organic film transistor according to claim 1, wherein at least one of $R^{101}, R^{102}, R^{103}$, and $R^{104}$ in Formulae (101-1) to (101-3), at least one of $R^{141}, R^{142}, R^{143}$, and $R^{144}$ in the same formulae, or at least one of $R^{145}, R^{146}, R^{147}$, and $R^{148}$ in the same formulae is a group represented by the following Formula ($W^{101}$);

-$L^{101}$-$R^{101}$      Formula ($W^{101}$)

in Formula ($W^{101}$), $L^{101}$ represents a divalent linking group represented by any of the following Formulae (L-101) to (L-125) or a divalent linking group formed by bonding of two or more divalent linking groups represented by any of the following Formulae (L-101) to (L-125); $R^{101}$ represents a substituted or unsubstituted alkyl group, an oligo-oxyethylene group in which a repetition number v of an oxyethylene unit is equal to or greater than 2, an oligosiloxane group having two or more silicon atoms, or a substituted or unsubstituted silyl group; and $R^{101}$ represents a substituted or unsubstituted silyl group only when $L^{101}$ adjacent to $R^{101}$ is a divalent linking group represented by any of the following Formulae (L-101) to (L-103); and (L-101)
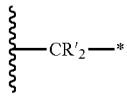

(L-102)
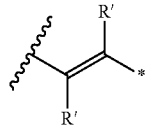

(L-103)
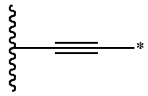

(L-104)
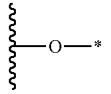

(L-105)
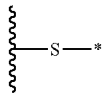

(L-106)
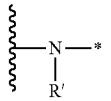

(L-107)
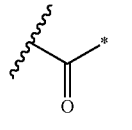

(L-108)
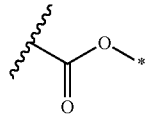

(L-109)
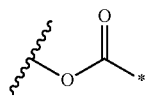

(L-110)
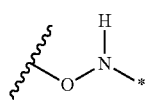

(L-111)
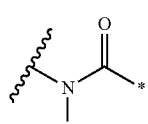

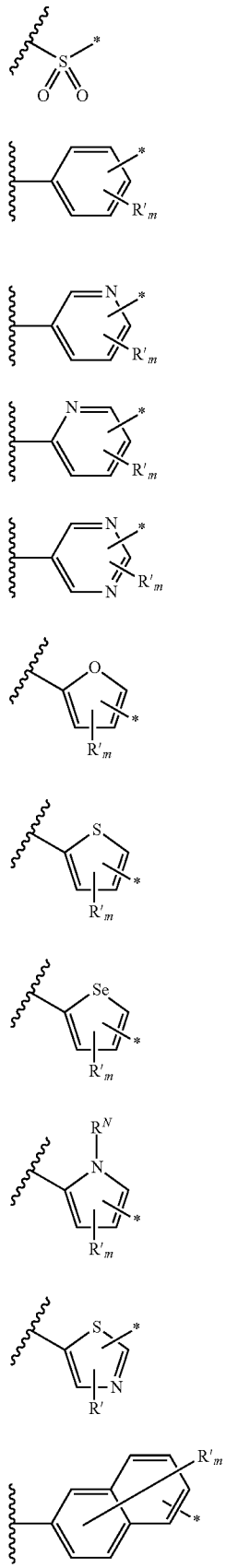
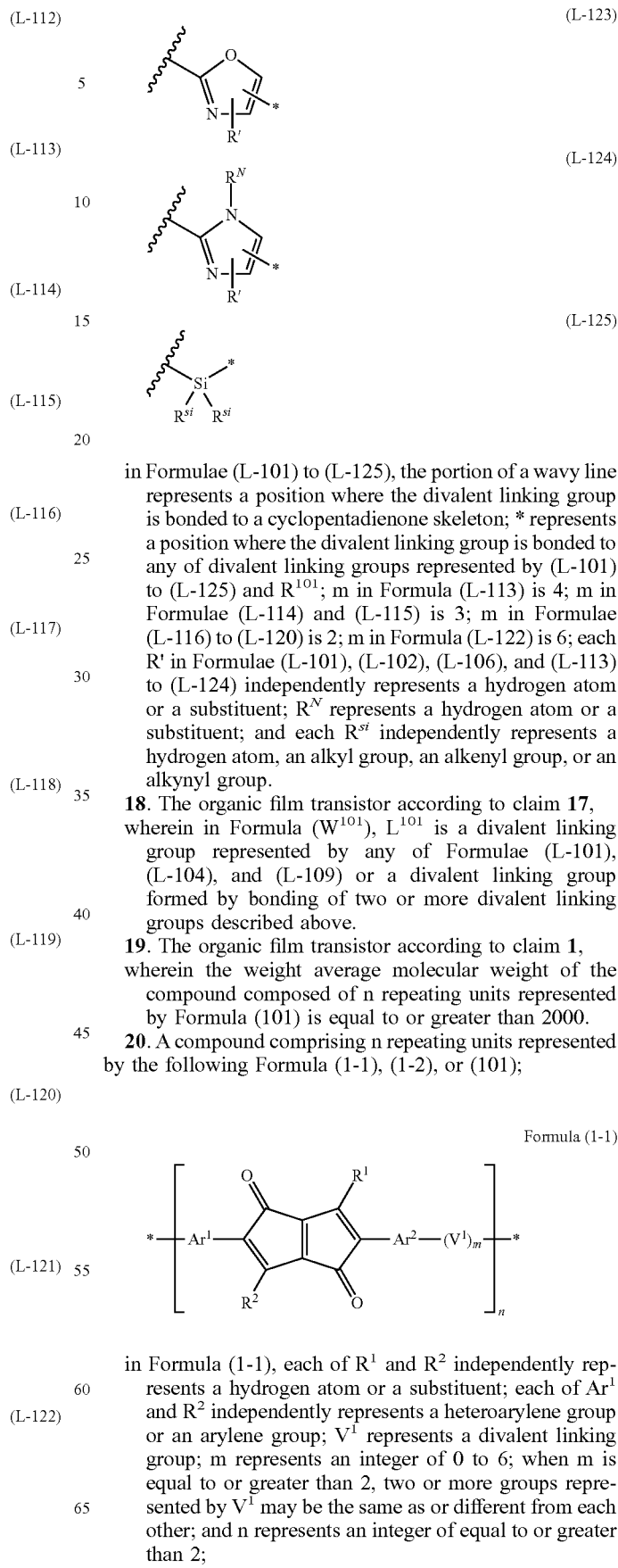

in Formulae (L-101) to (L-125), the portion of a wavy line represents a position where the divalent linking group is bonded to a cyclopentadienone skeleton; * represents a position where the divalent linking group is bonded to any of divalent linking groups represented by (L-101) to (L-125) and $R^{101}$; m in Formula (L-113) is 4; m in Formulae (L-114) and (L-115) is 3; m in Formulae (L-116) to (L-120) is 2; m in Formula (L-122) is 6; each R' in Formulae (L-101), (L-102), (L-106), and (L-113) to (L-124) independently represents a hydrogen atom or a substituent; $R^N$ represents a hydrogen atom or a substituent; and each $R^{si}$ independently represents a hydrogen atom, an alkyl group, an alkenyl group, or an alkynyl group.

18. The organic film transistor according to claim 17, wherein in Formula ($W^{101}$), $L^{101}$ is a divalent linking group represented by any of Formulae (L-101), (L-104), and (L-109) or a divalent linking group formed by bonding of two or more divalent linking groups described above.

19. The organic film transistor according to claim 1, wherein the weight average molecular weight of the compound composed of n repeating units represented by Formula (101) is equal to or greater than 2000.

20. A compound comprising n repeating units represented by the following Formula (1-1), (1-2), or (101);

in Formula (1-1), each of $R^1$ and $R^2$ independently represents a hydrogen atom or a substituent; each of $Ar^1$ and $R^2$ independently represents a heteroarylene group or an arylene group; $V^1$ represents a divalent linking group; m represents an integer of 0 to 6; when m is equal to or greater than 2, two or more groups represented by $V^1$ may be the same as or different from each other; and n represents an integer of equal to or greater than 2;

Formula (1-2)

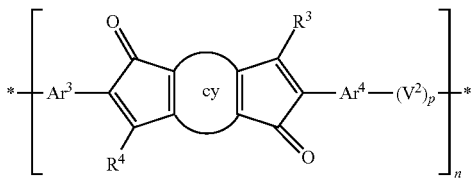

in Formula (1-2), cy represents a naphthalene ring or an anthracene ring; each of $R^3$ and $R^4$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2;

Formula (101)

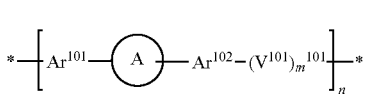

in Formula (101), each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; n represents an integer of equal to or greater than 2; and A represents a divalent linking group represented by the following Formula (101'); and Formula (101')

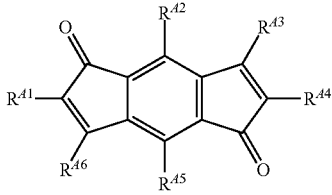

in Formula (101'), each of $R^{A1}$ to $R^{A6}$ independently represents a hydrogen atom, a substituent, or a direct bond with $Ar^{101}$ or $Ar^{102}$ in Formula (101); and among the groups represented by $R^{A1}$ to $R^{A6}$, two different groups represent direct bonds with $Ar^{101}$ and $Ar^{102}$ in Formula (101) respectively, the transistor comprising a compound, which is composed of n repeating units represented by Formula (101), in the semiconductor active layer;
in Formula (101), each of Ar101 and Ar102 independently represents a heteroarylene group or an arylene group; V101 represents a divalent linking group; m101 represents an integer of 1 to 6; when m101 is equal to or greater than 2, two or more groups represented by V101 may be the same as or different from each other; n represents an integer of equal to or greater than 2; and A represents a divalent linking group represented by Formula (101'); and in Formula (101'), each of RA1 to RA6 independently represents a hydrogen atom, a substituent, or a direct bond with Ar101 or Ar102 in Formula (101); and among the groups represented by RA1 to RA6, two different groups represent direct bonds with Ar101 and Ar102 in Formula (101) respectively; wherein the compound composed of n repeating units represented by Formula (101) is a compound composed of n repeating units represented by any of the following Formulae (101-1) to (101-3);

Formula (101-1)

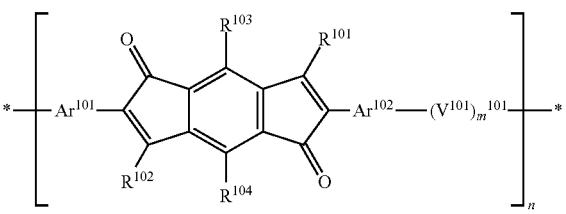

Formula (101-2)

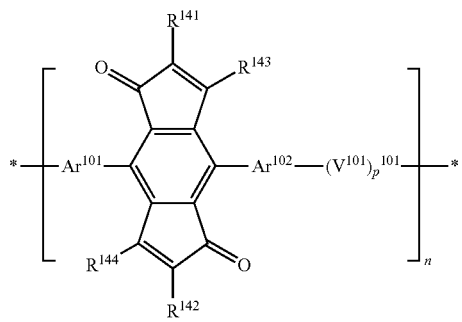

Formula (101-3)

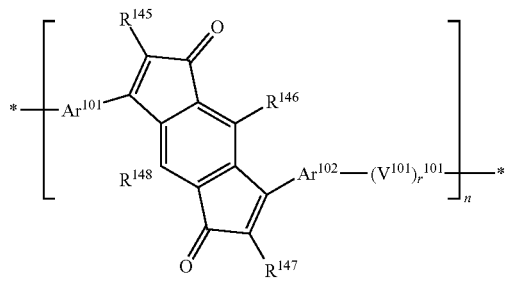

in Formulae (101-1), (101-2), and (101-3), each of R101 to R104 and R141 to R148 independently represents a hydrogen atom or a substituent; each of Ar101 and Ar102 independently represents a heteroarylene group or an arylene group; V101 represents a divalent linking group; m101 represents an integer of 1 to 6; when m101 is equal to or greater than 2, two or more groups represented by V101 may be the same as or different from each other; each of p101 and r101 represents an integer of 0 to 6; when each of p101 and r101 is equal to or greater than 2, two or more groups represented by V101 may be the same as or different from each other; and n represents an integer of equal to or greater than 2;

in Formulae (101-1) to (101-3), V101 is a divalent linking group represented by any of the following Formulae (V-101) to (V-117);

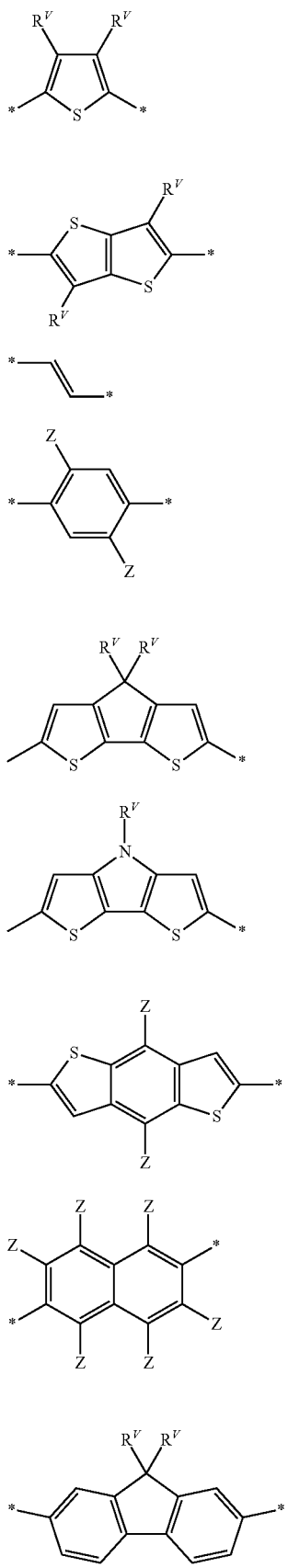
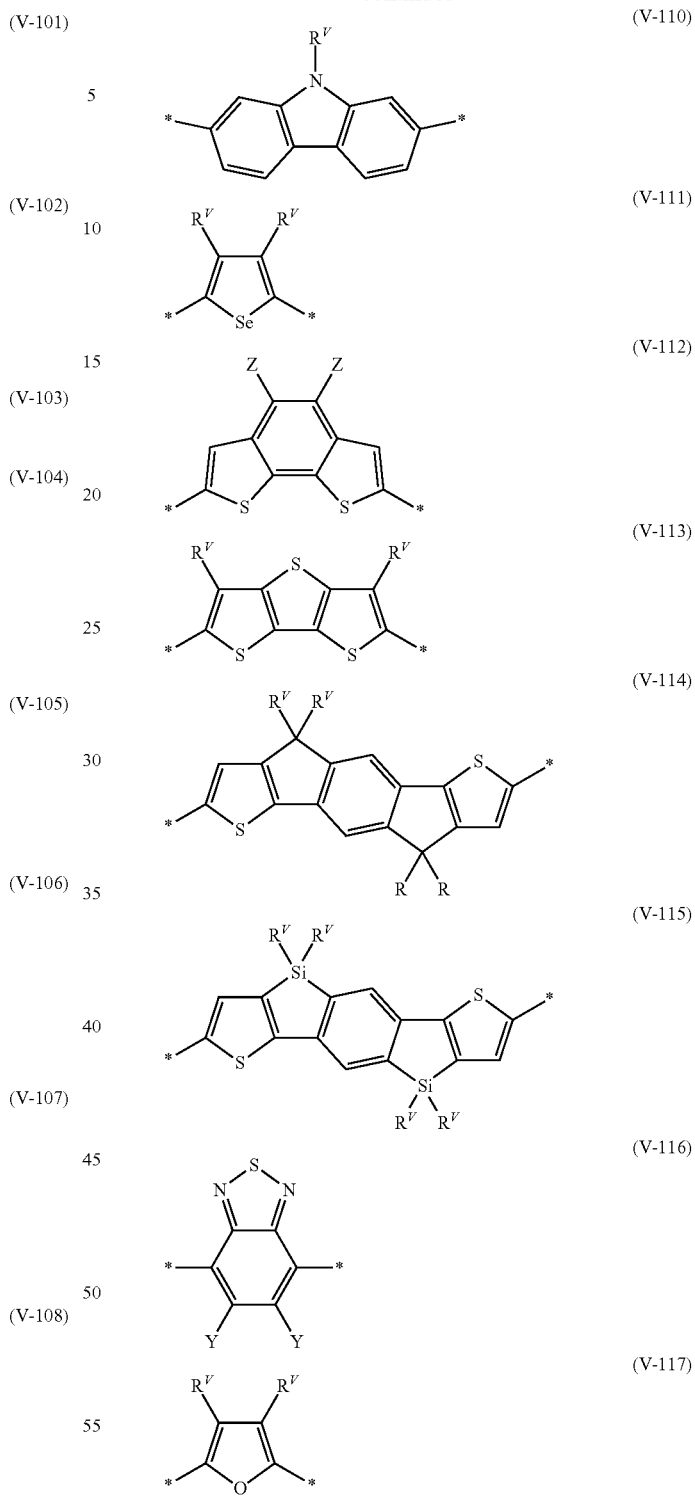
in Formulae (V-101) to (V-117), * represents a position where the divalent linking group is bonded to any of Ar101 and Ar102 when m101, p101, or r101 is 1 and represents a position where the divalent linking group is bonded to any of Ar101 Ar102 and divalent linking groups represented by Formulae (V-101) to (V-117) when m101, p101, or r101 is equal to or greater than 2; each RV in Formulae (V-101), (V-102), (V-105), (V-106), (V-109) to (V-111), (V-113) to (V-115), and (V-117) independently represents a hydrogen atom or an alkyl group; the groups adjacent to each other represented by RV may form a ring by being bonded to each other; each Z in Formulae (V-104), (V-107), (V-108), and (V-112) independently represents a hydrogen atom, an alkyl group, or an alkoxy group; the groups adjacent to each other represented by Z may form a ring by being bonded to each other; each Y in Formula (V-116) independently represents a hydrogen atom, an alkyl group, an alkoxy group, a CN group, or a F atom; and the groups adjacent to each other represented by Y may form a ring by being bonded to each other, and in Formulae (101-1) to (101-3), V101 is a divalent linking group represented by any of Formulae (V-101) to (V-108) and (V-111) to (V-115).

21. The compound according to claim 20, comprising n repeating units represented by the following Formula (1-1) or (1-2);

Formula (1-1)
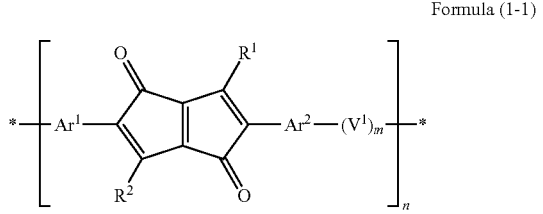

in Formula (1-1), each of $R^1$ and $R^2$ independently represents a hydrogen atom or a substituent; each of $Ar^1$ and $R^2$ independently represents a heteroarylene group or an arylene group; $V^1$ represents a divalent linking group; m represents an integer of 0 to 6; when m is equal to or greater than 2, two or more groups represented by $V^1$ may be the same as or different from each other; and n represents an integer of equal to or greater than 2; and Formula (1-2)
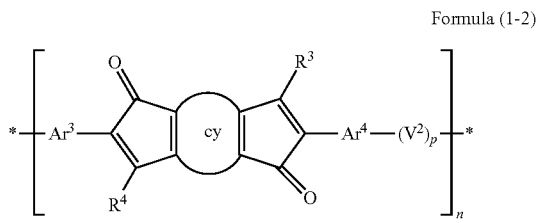

in Formula (1-2), cy represents a naphthalene ring or an anthracene ring; each of $R^3$ and $R^4$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2.

22. The compound according to claim 20, wherein Formula (1-2) represents a compound composed of n repeating units represented by the following Formula (2-1), (2-2), (2-3), (2-4), or (2-5);

Formula (2-1)
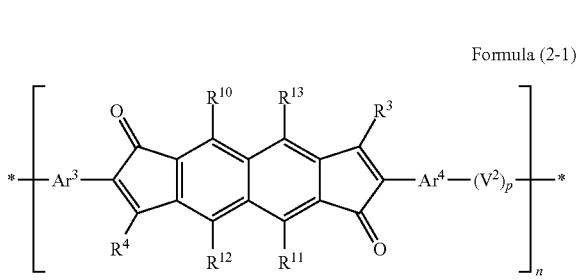

Formula (2-2)
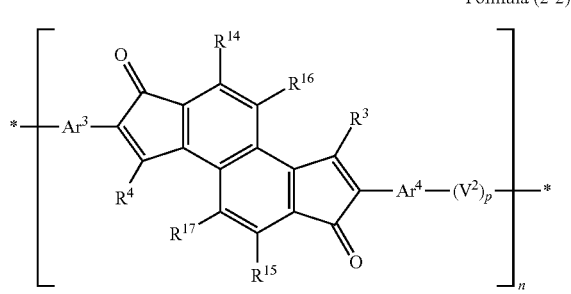

Formula (2-3)
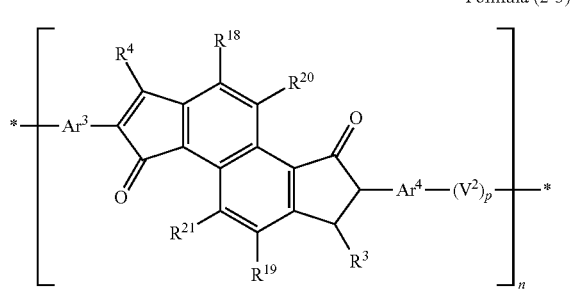

Formula (2-4)
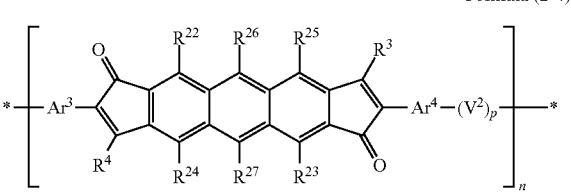

Formula (2-5)
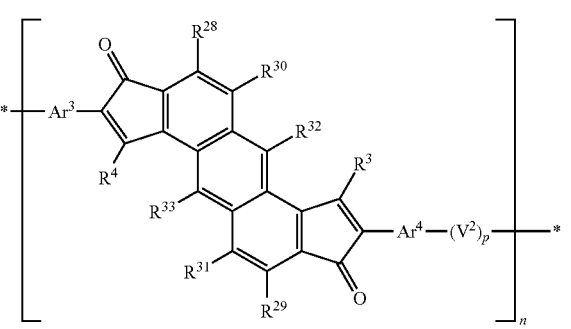

in Formulae (2-1) to (2-5), each of $R^3$, $R^4$, and $R^{10}$ to $R^{33}$ independently represents a hydrogen atom or a substituent; each of $Ar^3$ and $Ar^4$ independently represents a heteroarylene group or an arylene group; $V^2$ represents a divalent linking group; p represents an integer of 0 to 6; when p is equal to or greater than 2, two or more groups represented by $V^2$ may be the same as or different from each other; and n represents an integer of equal to or greater than 2.

23. The compound according to claim 20, wherein in Formulae (1-1) and (1-2), each of $V^1$ and $V^2$ is independently a divalent linking group represented by any of the following Formulae (V-1) to (V-17);

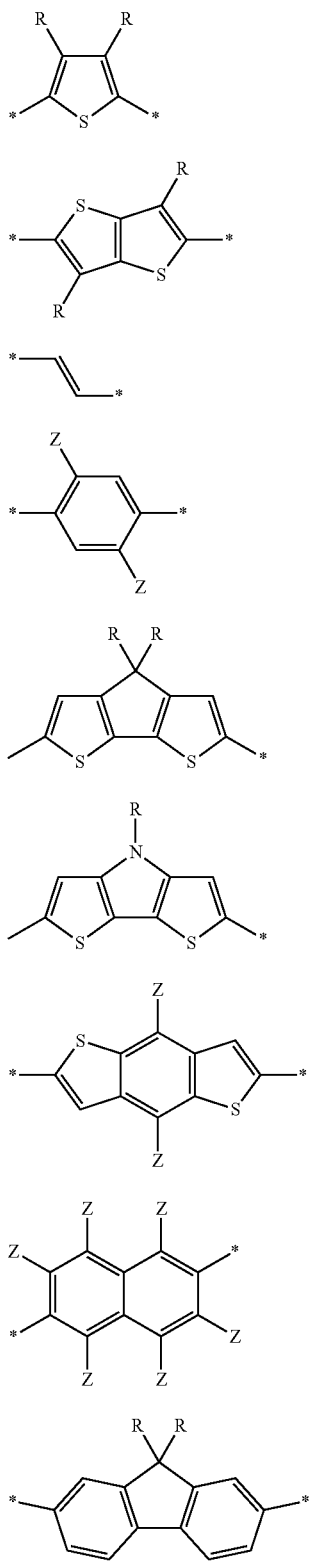

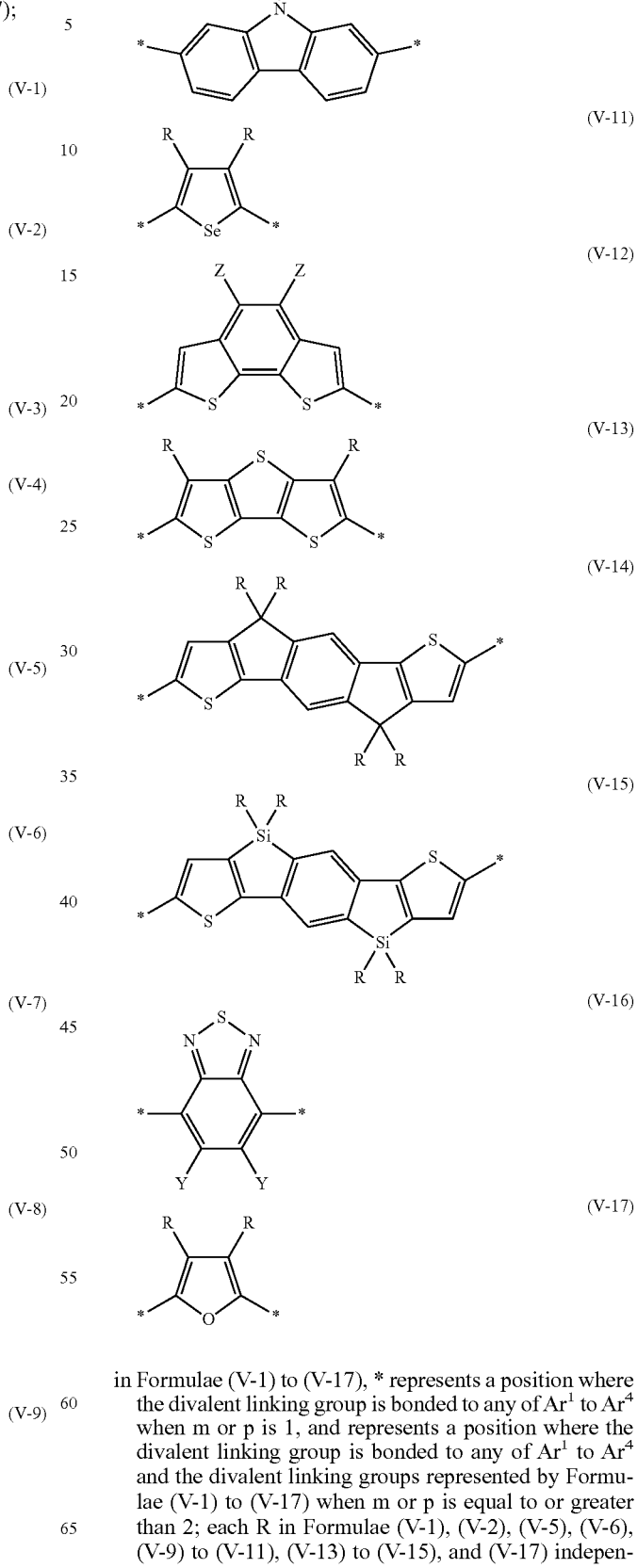

in Formulae (V-1) to (V-17), * represents a position where the divalent linking group is bonded to any of $Ar^1$ to $Ar^4$ when m or p is 1, and represents a position where the divalent linking group is bonded to any of $Ar^1$ to $Ar^4$ and the divalent linking groups represented by Formulae (V-1) to (V-17) when m or p is equal to or greater than 2; each R in Formulae (V-1), (V-2), (V-5), (V-6), (V-9) to (V-11), (V-13) to (V-15), and (V-17) independently represents a hydrogen atom or an alkyl group;

the groups adjacent to each other represented by R may form a ring by being bonded to each other; each Z in Formulae (V-4), (V-7), (V-8), and (V-12) independently represents a hydrogen atom, an alkyl group, or an alkoxy group; the groups adjacent to each other represented by Z may form a ring by being bonded to each other; each Y in Formula (V-16) independently represents a hydrogen atom, an alkyl group, an alkoxy group, a CN group, or a F atom; and the groups adjacent to each other represented by Y may form a ring by being bonded to each other.

24. The compound according to claim 23,
wherein in Formulae (1-1) and (1-2), each of $V^1$ and $V^2$ is a divalent linking group represented by any of Formulae (V-1) to (V-8) and (V-11) to (V-15).

25. The compound according to claim 20,
wherein in Formulae (1-1) and (1-2), each of $Ar^1$ to $Ar^4$ is independently a divalent linking group represented by the following Formula (4-1), (4-2), or (4-3);

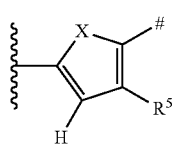

Formula (4-1)

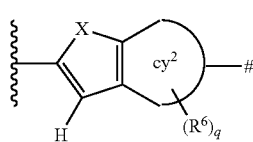

Formula (4-2)

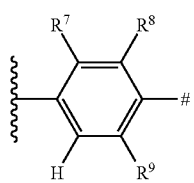

Formula (4-3)

in Formulae (4-1) to (4-3), X represents a S atom, an O atom, or a Se atom; $cy^2$ represents a structure in which 1 to 4 rings are condensed; each of $R^5$ to $R^9$ independently represents a hydrogen atom or a substituent; q represents an integer of 0 to 6; when q is equal to or greater than 2, two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^1$ or $V^2$.

26. The compound according to claim 25,
wherein in Formulae (1-1) and (1-2), each of $Ar^1$ to $Ar^4$ is independently a divalent linking group represented by Formula (4-1) or (4-2).

27. The compound according to claim 25,
wherein the divalent linking group represented by Formula (4-2) is a divalent linking group represented by any of the following Formulae (5-1) to (5-8);

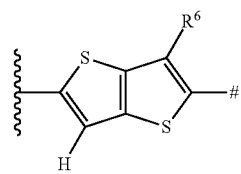

Formula (5-1)

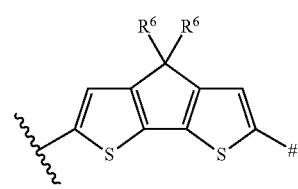

Formula (5-2)

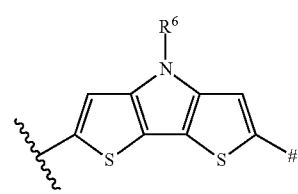

Formula (5-3)

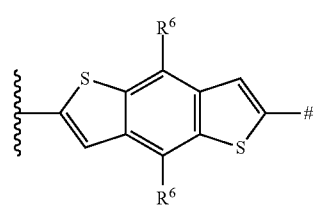

Formula (5-4)

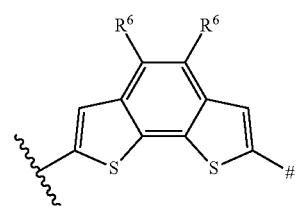

Formula (5-5)

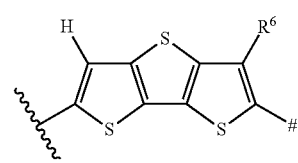

Formula (5-6)

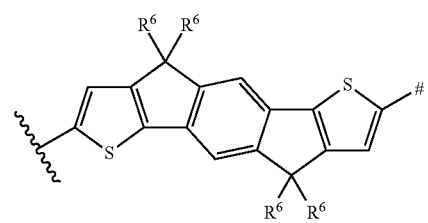

Formula (5-7)

Formula (5-8)

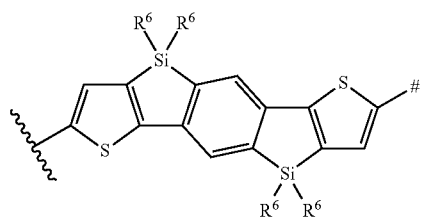

in Formulae (5-1) to (5-8), each $R^6$ independently represents a hydrogen atom or a substituent; two or more groups represented by $R^6$ may be the same as or different from each other; the wavy line represents a position where the divalent linking group is bonded to a cyclopentadienone ring-condensed site; and # represents a position where the divalent linking group is bonded to $V^1$ or $V^2$.

28. The compound according to claim 20, wherein each of at least one of $R^1$ and $R^2$ in Formula (1-1) and at least one of $R^3$ and $R^4$ in Formula (1-2) is a group represented by the following Formula (W);

-L-R    Formula (W)

in Formulae (L-1) to (L-12), the portion of a wavy line represents a position where the divalent linking group is bonded to a cyclopentadienone skeleton; * represents a position where the divalent linking group is bonded to any of the divalent linking groups represented by (L-1) to (L-12) and R; m in Formula (L-10) is 4; m in Formulae (L-11) and (L-12) is 2; and each R' in Formulae (L-1), (L-2), (L-10), (L-11), and (L-12) independently represents a hydrogen atom or a substituent: and (L-1)

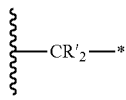

(L-2)

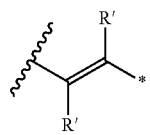

(L-3)

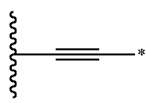

(L-4)

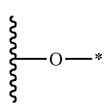

(L-5)

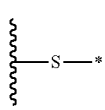

(L-6)

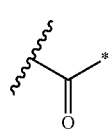

(L-7)

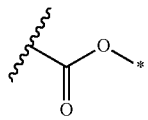

(L-8)

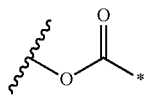

(L-9)

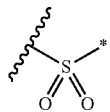

(L-10)

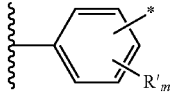

(L-11)

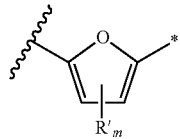

(L-12)

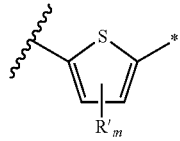

in Formulae (L-1) to (L-12), the portion of a wavy line represents a position where the divalent linking group is bonded to a cyclopentadienone skeleton; * represents a position where the divalent linking group is bonded to any of the divalent linking groups represented by (L-1) to (L-12) and R; m in Formula (L-10) is 4; m in Formulae (L-11) and (L-12) is 2; and each R' in Formulae (L-1), (L-2), (L-10), (L-11), and (L-12) independently represents a hydrogen atom or a substituent.

29. The compound according to claim 28, wherein in Formula (W), L is a divalent linking group represented by any of Formulae (L-1), (L-4), and (L-8) or a divalent linking group formed by bonding of two or more divalent linking groups described above.

30. The compound according to claim 20, wherein in Formulae (1-1) and (1-2), n is equal to or greater than 10.

31. The organic film transistor according to claim 20, wherein the compound composed of n repeating units represented by Formula (101) is a compound composed of n repeating units represented by the following Formula (101-1);

Formula (101-1)

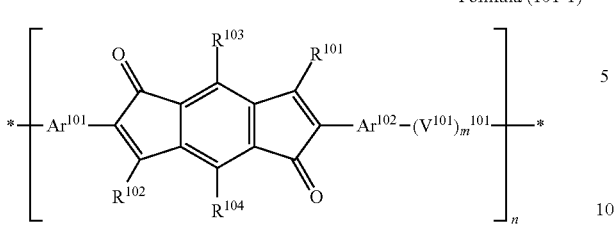

in Formula (101-1), each of $R^{101}$ to $R^{104}$ independently represents a hydrogen atom or a substituent; each of $Ar^{101}$ and $Ar^{102}$ independently represents a heteroarylene group or an arylene group; $V^{101}$ represents a divalent linking group; $m^{101}$ represents an integer of 1 to 6; when $m^{101}$ is equal to or greater than 2, two or more groups represented by $V^{101}$ may be the same as or different from each other; and n represents an integer of equal to or greater than 2.

32. The organic film transistor according to claim 20, wherein in Formulae (101-1) to (101-3), each of $Ar^{101}$ and $Ar^{102}$ is a divalent linking group represented by the following Formula (102-1), (102-2), or (102-3);

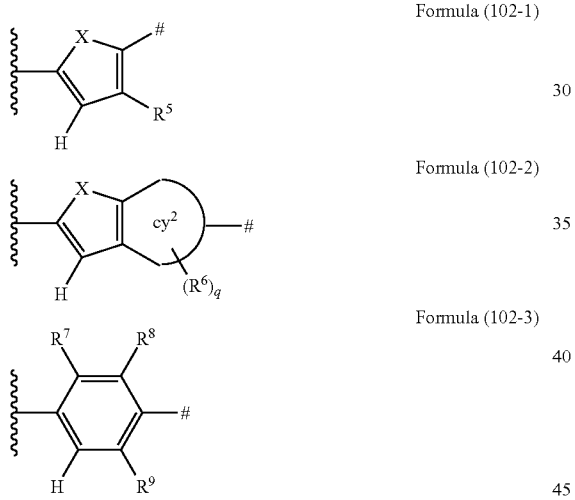

Formula (102-1)

Formula (102-2)

Formula (102-3)

in Formulae (102-1) to (102-3), X represents a S atom, an O atom, or a Se atom; $cy^2$ represents a structure in which 1 to 4 rings are condensed; each of $R^5$ to $R^9$ independently represents a hydrogen atom or a substituent; q represents an integer of 0 to 6; when q is equal to or greater than 2, two or more groups represented by $R^6$ may be the same as or different from each other; the portion of a wavy line represents a position where the divalent linking group is bonded to a cyclopentadienone ring-condensed site; and # represents a position where the divalent linking group is bonded to $V^{101}$.

33. The organic film transistor according to claim 32, wherein in Formula (101-1), each of $Ar^{101}$ and $Ar^{102}$ is a divalent linking group represented by Formula (102-1), and $V^{101}$ is a divalent linking group represented by any of Formulae (V-102) to (V-107).

34. The organic film transistor according to claim 32, wherein in Formulae (101-1) to (101-3), each of $Ar^{101}$ and $Ar^{102}$ is independently a divalent linking group represented by Formula (102-1) or (102-2).

35. The organic film transistor according to claim 32, wherein the divalent linking group represented by Formula (102-2) is a divalent linking group represented by any of the following Formulae (5-1) to (5-8);

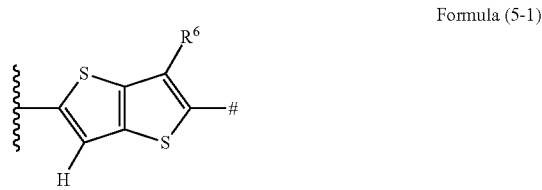

Formula (5-1)

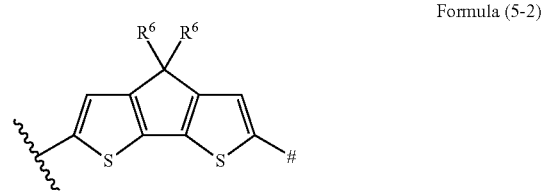

Formula (5-2)

Formula (5-3)

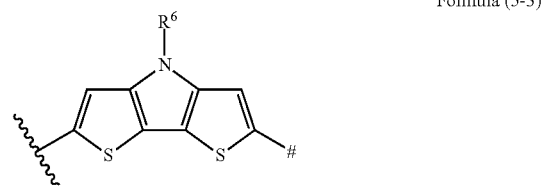

Formula (5-4)

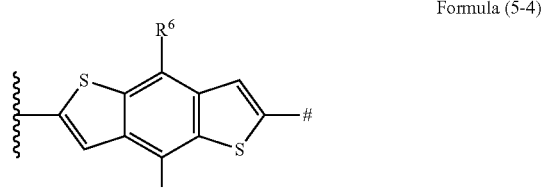

Formula (5-5)

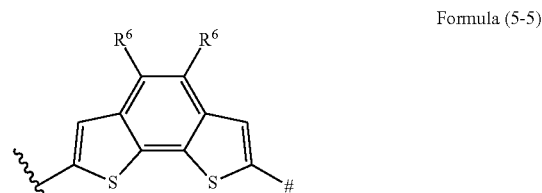

Formula (5-6)

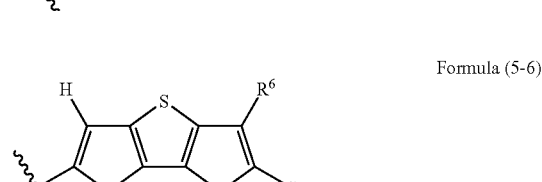

Formula (5-7)

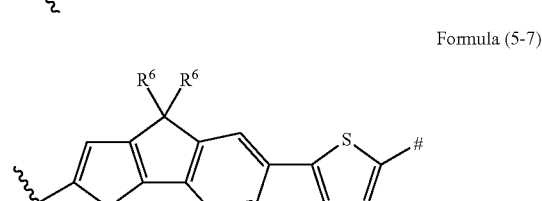

Formula (5-8)

[structure with R⁶ groups, Si, S atoms]

in Formulae (5-1) to (5-8), each R⁶ independently represents a hydrogen atom or a substituent; two or more groups represented by R⁶ may be the same as or different from each other; the wavy line represents a position where the divalent linking group is bonded to a cyclopentadienone ring-condensed site; and # represents a position where the divalent linking group is bonded to $V^{101}$.

36. The organic film transistor according to claim 20, wherein at least one of $R^{101}$, $R^{102}$, $R^{103}$, and $R^{104}$ in Formulae (101-1) to (101-3), at least one of $R^{141}$, $R^{142}$, $R^{143}$, and $R^{144}$ in the same formulae, or at least one of $R^{145}$, $R^{146}$, $R^{147}$, and $R^{148}$ in the same formulae is a group represented by the following Formula ($W^{101}$);

$$-L^{101}-R^{101} \quad \text{Formula (W}^{101}\text{)}$$

in Formula ($W^{101}$), $L^{101}$ represents a divalent linking group represented by any of the following Formulae (L-101) to (L-125) or a divalent linking group formed by bonding of two or more divalent linking groups represented by any of the following Formulae (L-101) to (L-125); $R^{101}$ represents a substituted or unsubstituted alkyl group, an oligo-oxyethylene group in which a repetition number v of an oxyethylene unit is equal to or greater than 2, an oligosiloxane group having two or more silicon atoms, or a substituted or unsubstituted silyl group; and $R^{101}$ represents a substituted or unsubstituted silyl group only when $L^{101}$ adjacent to $R^{101}$ is a divalent linking group represented by any of the following Formulae (L-101) to (L-103); and (L-101) $-CR'_2-*$ (L-102) [C=C with R' groups]

(L-103) [C≡C—*]

(L-104) $-O-*$ (L-105) $-S-*$ (L-106) [N with R']

(L-107) [C(=O)—*]

(L-108) [—O—C(=O)—*]

(L-109) [—C(=O)—O—*]

(L-110) [—O—N(H)—*]

(L-111) [—N(H)—C(=O)—N(H)—*]

(L-112) [—S(=O)₂—*]

(L-113) [phenylene with R'ₘ]

(L-114) [pyridine with R'ₘ]

(L-115) [pyridine with R'ₘ]

(L-116) [pyrazine/pyrimidine with R'ₘ]

(L-117) [oxazole with R'ₘ]

(L-118) [thiazole with R'ₘ]

-continued

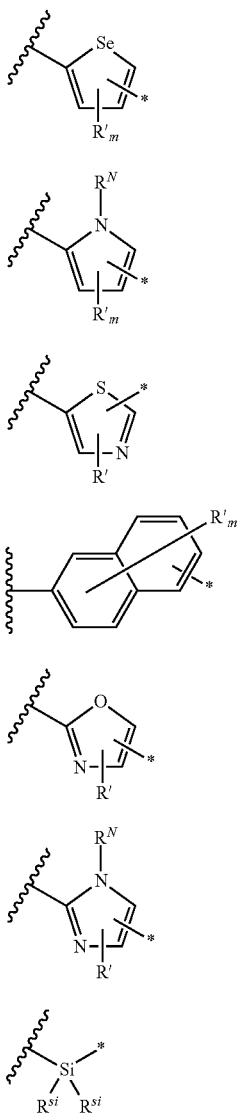

in Formulae (L-101) to (L-125), the portion of a wavy line represents a position where the divalent linking group is bonded to a cyclopentadienone skeleton; * represents a position where the divalent linking group is bonded to any of divalent linking groups represented by (L-101) to (L-125) and $R^{101}$; m in Formula (L-113) is 4; m in Formulae (L-114) and (L-115) is 3; m in Formulae (L-116) to (L-120) is 2; m in Formula (L-122) is 6; each R' in Formulae (L-101), (L-102), (L-106), and (L-113) to (L-124) independently represents a hydrogen atom or a substituent; $R^N$ represents a hydrogen atom or a substituent; and each $R^{si}$ independently represents a hydrogen atom, an alkyl group, an alkenyl group, or an alkynyl group.

37. The organic film transistor according to claim 36, wherein in Formula ($W^{101}$), $L^{101}$ is a divalent linking group represented by any of Formulae (L-101), (L-104), and (L-109) or a divalent linking group formed by bonding of two or more divalent linking groups described above.

38. The organic film transistor according to claim 20, wherein the weight average molecular weight of the compound composed of n repeating units represented by Formula (101) is equal to or greater than 2,000.

39. A composition comprising:
the compound according to claim 20; and
an organic solvent.

40. The composition according to claim 39,
wherein the organic solvent is an aromatic hydrocarbon-based solvent, an ether-based solvent, or a ketone-based solvent.

41. An organic semiconductor material for a non-light-emitting organic semiconductor device, comprising:
the compound according to claim 20.

42. A material for an organic film transistor, comprising:
the compound according to claim 20.

43. A coating solution for a non-light-emitting organic semiconductor device, comprising:
the compound according to claim 20.

44. A coating solution for a non-light-emitting organic semiconductor device, comprising:
the compound according to claim 20; and
a polymer binder.

45. An organic semiconductor film for a non-light-emitting organic semiconductor device, comprising:
the compound according to claim 20.

46. An organic semiconductor film for a non-light-emitting organic semiconductor device, comprising:
the compound according to claim 20; and
a polymer binder.

47. The organic semiconductor film for a non-light-emitting organic semiconductor device according to claim 45 that is prepared by a solution coating method.

* * * * *